US012680074B2

(12) United States Patent
Fowler

(10) Patent No.: US 12,680,074 B2
(45) Date of Patent: *Jul. 14, 2026

(54) ANTIGEN PRESENTING T CELLS, SENSITIZED, MANUFACTURED T CELLS AND METHODS OF TREATMENT USING THE SAME

(71) Applicant: RAPA THERAPEUTICS, LLC, Rockville, MD (US)

(72) Inventor: Daniel Harding Fowler, Bethesda, MD (US)

(73) Assignee: RAPA THERAPEUTICS, LLC, Rockville, MD (US)

( * ) Notice: Subject to any disclaimer, the term of this patent is extended or adjusted under 35 U.S.C. 154(b) by 785 days.

This patent is subject to a terminal disclaimer.

(21) Appl. No.: 17/984,810

(22) Filed: Nov. 10, 2022

(65) Prior Publication Data

US 2023/0159893 A1      May 25, 2023

Related U.S. Application Data

(63) Continuation of application No. PCT/US2021/032351, filed on May 13, 2021.

(60) Provisional application No. 63/024,435, filed on May 13, 2020.

(51) Int. Cl.

| | |
|---|---|
| *C12N 15/74* | (2006.01) |
| *A61K 40/11* | (2025.01) |
| *A61K 40/42* | (2025.01) |
| *C12N 5/0783* | (2010.01) |
| *C12N 15/00* | (2006.01) |
| *A61K 48/00* | (2006.01) |

(52) U.S. Cl.
CPC ............ *C12N 5/0636* (2013.01); *A61K 40/11* (2025.01); *A61K 40/4267* (2025.01); *A61K 2239/31* (2023.05); *A61K 2239/38* (2023.05); *A61K 2239/48* (2023.05); *C12N 2501/2302* (2013.01); *C12N 2501/2307* (2013.01); *C12N 2501/2315* (2013.01); *C12N 2501/24* (2013.01)

(58) Field of Classification Search
CPC .......... C12N 5/0636; C12N 2501/2302; C12N 2501/2307; C12N 2501/2315; C12N 2501/24; A61K 40/11; A61K 2239/38
See application file for complete search history.

(56) References Cited

U.S. PATENT DOCUMENTS

| | | | |
|---|---|---|---|
| 8,075,921 | B2 | 12/2011 | Fowler |
| 9,644,179 | B2 | 5/2017 | Riley et al. |
| 2004/0175827 | A1 | 9/2004 | Fowler et al. |
| 2004/0241153 | A1 | 12/2004 | Fowler et al. |
| 2008/0050341 | A1 | 2/2008 | Morgan et al. |
| 2010/0068192 | A1 | 3/2010 | Enoki et al. |
| 2011/0052547 | A1 | 3/2011 | Fowler et al. |
| 2012/0114623 | A1 | 5/2012 | Zhang |
| 2014/0154228 | A1 | 6/2014 | Volk et al. |
| 2014/0275257 | A1 | 9/2014 | Perl |
| 2015/0301058 | A1 | 10/2015 | Schettini et al. |
| 2016/0000789 | A1 | 1/2016 | Shokat et al. |
| 2017/0043009 | A1 | 2/2017 | Lundemose |
| 2017/0117418 | A1 | 4/2017 | Bhalla et al. |
| 2017/0218337 | A1 | 8/2017 | Friedman |
| 2017/0274058 | A1 | 9/2017 | Bergstein et al. |
| 2017/0356917 | A1 | 12/2017 | Hideshima et al. |
| 2019/0307856 | A1 | 10/2019 | Geiger et al. |

FOREIGN PATENT DOCUMENTS

| | | | |
|---|---|---|---|
| EP | 2532740 | A1 | 12/2012 |
| KR | 1020180087423 | A | 8/2018 |
| WO | 2003004625 | A1 | 1/2003 |
| WO | 2010068923 | A2 | 6/2010 |
| WO | 2010151517 | A2 | 12/2010 |
| WO | 2012171882 | | 12/2012 |
| WO | 2013049307 | A2 | 4/2013 |
| WO | 2016090034 | A2 | 6/2016 |
| WO | 2017093969 | A1 | 6/2017 |
| WO | 2017117418 | A1 | 7/2017 |
| WO | 2017177137 | A1 | 10/2017 |

(Continued)

OTHER PUBLICATIONS

Cieri et al. IL-7 and IL-15 instruct the generation of human memory stem T cells from naive precursors. Blood 121:573-584; (Year: 2013).*

Alvarez-Fernandez et al. A short CD3/CD28 costimulation combined with IL-21 enhance the generation of human memory stem T cells for adoptive immunotherapy. J Transl Med 14:214; DOI 10.1186/s 12967-016-0973-y, 10 pages; (Year: 2016).*

Kaartinen et al. Low interleukin-2 concentration favors generation of early memory T cells over effector phenotypes during chimeric antigen receptor T-cell expansion. Cytotherapy 19:689-702; (Year: 2017).*

International Search Report mailed Feb. 18, 2020 for PCT/US2019/061777.

(Continued)

*Primary Examiner* — Quang Nguyen
(74) *Attorney, Agent, or Firm* — Hogan Lovells US LLP

(57) ABSTRACT

The present disclosure provides methods for treating cancer and infectious disease using manufactured T cells or other cell types including antigen-presenting T cells, loaded, antigen-presenting T cells, sensitized, manufactured T cells and combinations thereof which can be co-administered with the manufactured T cells or without. Methods of treatment can include administration of pentostatin and cyclophosphamide followed by administration of T cells. The present disclosure also provides methods to produce antigen-presenting T cells from the manufactured T cells, load antigen-presenting T cells and to sensitize the manufactured T cells using the loaded, antigen-presenting T cells. Methods of treatment using the antigen-presenting T cells and/or sensitized, manufactured T cells are also provided which can be performed in vivo or ex vivo.

13 Claims, 93 Drawing Sheets

(56) References Cited

FOREIGN PATENT DOCUMENTS

| | | | |
|---|---|---|---|
| WO | 2018005712 A1 | 1/2018 | |
| WO | 2018007263 A1 | 1/2018 | |
| WO | WO-2018064976 A1 * | 4/2018 | ........... C12N 5/0656 |
| WO | 2018085690 A1 | 5/2018 | |
| WO | 2018106732 A1 | 6/2018 | |
| WO | 2018106885 | 6/2018 | |
| WO | 2018106958 A1 | 6/2018 | |
| WO | 2018175636 | 9/2018 | |
| WO | 2018183927 | 10/2018 | |
| WO | 2019090004 | 11/2018 | |
| WO | 2019222513 A1 | 11/2019 | |
| WO | 2020102708 A1 | 5/2020 | |
| WO | 2020102731 A1 | 5/2020 | |

OTHER PUBLICATIONS

International Preliminary Report on Patentability mailed May 18, 2021 for PCT/US2019/061777.

Jacobsohn, et al. "Phase II study of pentostatin in patients with corticosteroid-refractory chronic graft-versus-host disease," Journal of Clinical Oncology, Sep. 20, 2017, vol. 25, No. 27, pp. 4255-4261.

International Search Report mailed Feb. 12, 2020 for PCT/US2019/061768.

International Preliminary Report on Patantability mailed May 18, 2021 for PCT/US2019/061768.

Saito, et al. "Anti-leukemic potency of pibbyBac-meidated CD19-specific T cells against refractory Philadelphia chromosome-positive acute lymphoblastic leukemia," Cytotherapy, Sep. 30, 2014, vol. 16, No. 9, pp. 1257-1269.

Kamphorst, et al. "Rescue of exhausted CD8 T cells by PD-1 targeted therapies is CD28-dependent," Science, Mar. 9, 2017, vol. 355, No. 6332, pp. 1423-1427.

Comin-Anduix et al. "Modulation of Cell Signaling Networkds after CTLA4 Blockade in Patients with Metastatic Melanoma," PLoS One, Sep. 15, 2015, vol. 5, Issue 9:e12711, pp. 1-12.

Pollizzi et al., "mTORC1 and mTORC2 selectively regulate CD8+ T cell differentiation," Journal of Clinical Investigation, Apr. 20, 2015, vol. 125, No. 5, pp. 2090-2108.

Zeng, et al. "mTORC1 couple immune signals and metabolic programming to establish Treg cell function," Nature, Jun. 30, 2013, vol. 499, No. 7459, pp. 485-490.

Triana E, Ortega S, Azqueta C, et al. "Thawing of cryopreserved hematopoietic progenitor cells from apheresis will be with using a new drywarming device," Transfusion. 2013; 53(1), pp. 85-90.

Zhang et al. "In vitro cultivation of dendritic cells with serum-free medium," Zhongguo shi yan xue ye xue za zhi.2006; 14(5), pp. 985-989.

Brown et al. "Ammonium-Chloride-Potassium Lysing Buffer Treatment of Fully Differentiated Cells Increases CellPurity and Resulting Neotissue Functional Properties," Tissue Engineering 22(9): 895-903 (2016).

Stroncek et al. "Counter-flow elutriation of clinical peripheral blood mononuclear cell concentrates for the production ofdendritic and T cell therapies," J. Transl. Med. 12:241 (2014).

Bajgain et al. "Optimizing the production of suspension cells using the G-Rex "M" series, "Mol. Ther. 1:14015 (2014).

Hunt, CJ. "Cryopreservation of Human Stem Cells for Clinical Application: A Review," Transfus Med Hemother 38:107-123 (2011).

Xiao et al. "Flow Cytometry-Based Assessment of Mitophagy Using MitoTracker" Frontiers in Cellular Neuroscience10:76 (2016).

Robert et al. "Distinct immunological mechanisms of CTLA-4 and PD-1 blockade revealed by analyzing TCR usage inblood lymphocytes" OncoImmunology 3:6, e29244 (2014).

Chen et al. "Safety and efficacy of selinexor in relapsed or refractory multiple myeloma and Waldenstrommacroglobulinemia," Blood 131(8):855-863 (2018).

Mfarrej, et al. "Pre-clinical assessment of the Lovo device for dimethyl sulfoxide removal and cell concentration inthawed hematopoietic progenitor cell grafts," Cytotherapy 19:1501-1508 (2017).

Examination Report issued in European Application No. 19884558.8 on May 22, 2023.

Stanzani, Marta et al.; "CD25 expression on donor DC4+ or CD8+ T cells is associated with an increased risk for graftversus-host disease after HLA-identical stem cell transplantation in humans", Blood, vol. 103, No. 3, Feb. 1, 2004(Feb. 1, 2004), pp. 1140-1146, XP093046776.

Chattopadhyay, Subhasis et al.; "Effect of CD4+CD25+ and CD4+ CD25– T Regulatory Cells on the Generation ofCytolytic T Cell Response to a Self but Human Tumor-Associated Epitope in Vitro," The Journal of Immunology, vol. 176, No. 2, Jan. 15, 2006 (Jan. 15, 2006), pp. 984-990, XP093046779.

European Search Report issued in European Application No. 19884558.8 on Jul. 12, 2022.

Office Action mailed Oct. 24, 2023 for JP Patent Application No. 2021-526728.

Extended European Search Report mailed May 27, 2024 in European Application No. 21805213.2.

Talarico, Leeann, et al. "Engineering antigen presenting T cells for treatment of solid tumor cancers," Proceedings of the AACR Special Conference on Tumor Immunology and Immunotherapy, XP055595759 (Sep. 1, 2028).

Melenhorst, Jan Joseph, t al. "Robust Expansion of Viral Antigen-specific CD4+ and CD8+ T Cells for Adoptive T Cell Therapy Using Gene-modified Activated T cells as Antigen Presenting Cells," Journal of Immunotherapy, vol. 29, No. 4, XP093161439 (Jul. 1, 2006).

Wyss-Coray, Tony, et al. "Antigen-presenting human T cells and antigen-presenting B cells induce a similar cytokine profile in specific T cell clones," European Journal of Immunology, vol. 23, No. 12, XP093161448 (Dec. 1, 1993).

Arnold, Paula, et al. "Antigen presentation by T cells: T cell receptor litigation promotes antigen acquisition from professional antigen-presenting cells," European Journal of Immunology, vol. 27, No. 12, XP071219069 (Dec. 6, 2005).

Wyss-Coray, et al. "Discrimination of Human CD4 T Cell Clones Based on their Reactivity with Antigen-Presenting T Cells," European Journal of Immunology, vol. 22, No. 9, XP008007512 (Jan. 1, 1992).

Mannie, Mark, et al. "Feedback activation of T-cell antigen-presenting cells during interactions with T-cell responders," Journal of Leukocyte Biology, vol. 70, No. 2, XP093161441 (Aug. 1, 2001).

International Search Report and Written Opinion issued by the International Searching Authority on Oct. 27, 2021 In International Patent Application No. PCT/US2021/032351.

Office Action issued in Canadian Patent Application No. 3,119,603, dated Dec. 16, 2024.

Yang and Rosenberg, "Adoptive T-Cell Therapy for Cancer", Adv Immunol, 130, pp. 279-294, 2016.

Examination Report No. 1 issued in Australian Application No. 2019379815, dated Jul. 28, 2025.

First Office Action issued in Chinese Patent Application No. 201980089257.X, dated Dec. 27, 2023.

Second Office Action issued in Chinese Patent Application No. 201980089257.X, dated Aug. 31, 2024.

First Office Action issued in Japanese Patent Application No. 2021-526728, dated Oct. 24, 2023.

Second Office Action issued in Japanese Patent Application No. 2021-526728, dated Jul. 16, 2024.

Third Office Action issued in Japanese Patent Application No. 2021-526728, dated Dec. 17, 2024.

First Office Action issued in Korean Patent Application No. 10-2021-7018420, dated Jun. 16, 2025.

Non-Final Office Action issued in U.S. Appl. No. 17/320,712, dated Jan. 29, 2025.

Non-Final Office Action issued in U.S. Appl. No. 17/320,712, dated Dec. 2, 2025.

Feng, X et al. Rapamycin is highly effective in murine models of immune-mediated bone marrow failure. Haematologica 2017; 102( 10): 1691-1703. (Year: 2017).

Ramos, H. J. et al., Reciprocal responsiveness to interleukin-12 and interferon-I± specifies human CDS+ effector versus central memory T-cell fates. Blood 2009; 113 (22): 5516a5525. (Year: 2009).

(56)                    References Cited

OTHER PUBLICATIONS

Beziaud L. et al. Rapalogs Efficacy Relies on the Modulation of Antitumor T-cell Immunity. Cancer Res Jul. 15, 2016; 76 (14): 4100a-4112. (Year: 2016).

Delgoffe GM, Powell JD. mTOR: taking cues from the immune microenvironment. Immunology. Aug. 2009;127 (4):459-65. (Year: 2009).

Wang Y. et al., Temsirolimus, an mTOR inhibitor, enhances anti-tumour effects of heat shock protein cancer vaccines. British journal of cancer. Feb. 2011;104(4):643-52. (Year: 2011).

Zaza et al., mTOR inhibition role in cellular mechanisms. Transplantation. Feb. 1, 2018;102(2S):S3-16. (Year: 2018).

* cited by examiner

Fig. 8B

DAY 13 TNF-alpha Secretion
(pg/ml per million cells per 24 hr)

| Bead-to-T Cell Ratio | mTOR Inhibitor | Daclizumab | IFN-alpha | Overnight Pre-Incubation |
|---|---|---|---|---|
| 1:1 | TEM 0.1 | YES | NO | YES |
| 1:1 | TEM 0.1 | NO +IL-2 | YES | YES |
| 1:1 | TEM 0.1 | NO | YES | YES |
| 1:1 | TEM 0.1 | YES | YES | NO |
| 1:1 | TEM 0.1 | YES | YES | YES |
| 3:1 | RAPA | NO | YES | NO |
| 3:1 | NO | NO | YES | NO |

Fig. 25G

GITR$^+$

Fig. 25H

LAG3⁺

IL-2 Secretion: T-RAPA Cells

Fig. 31

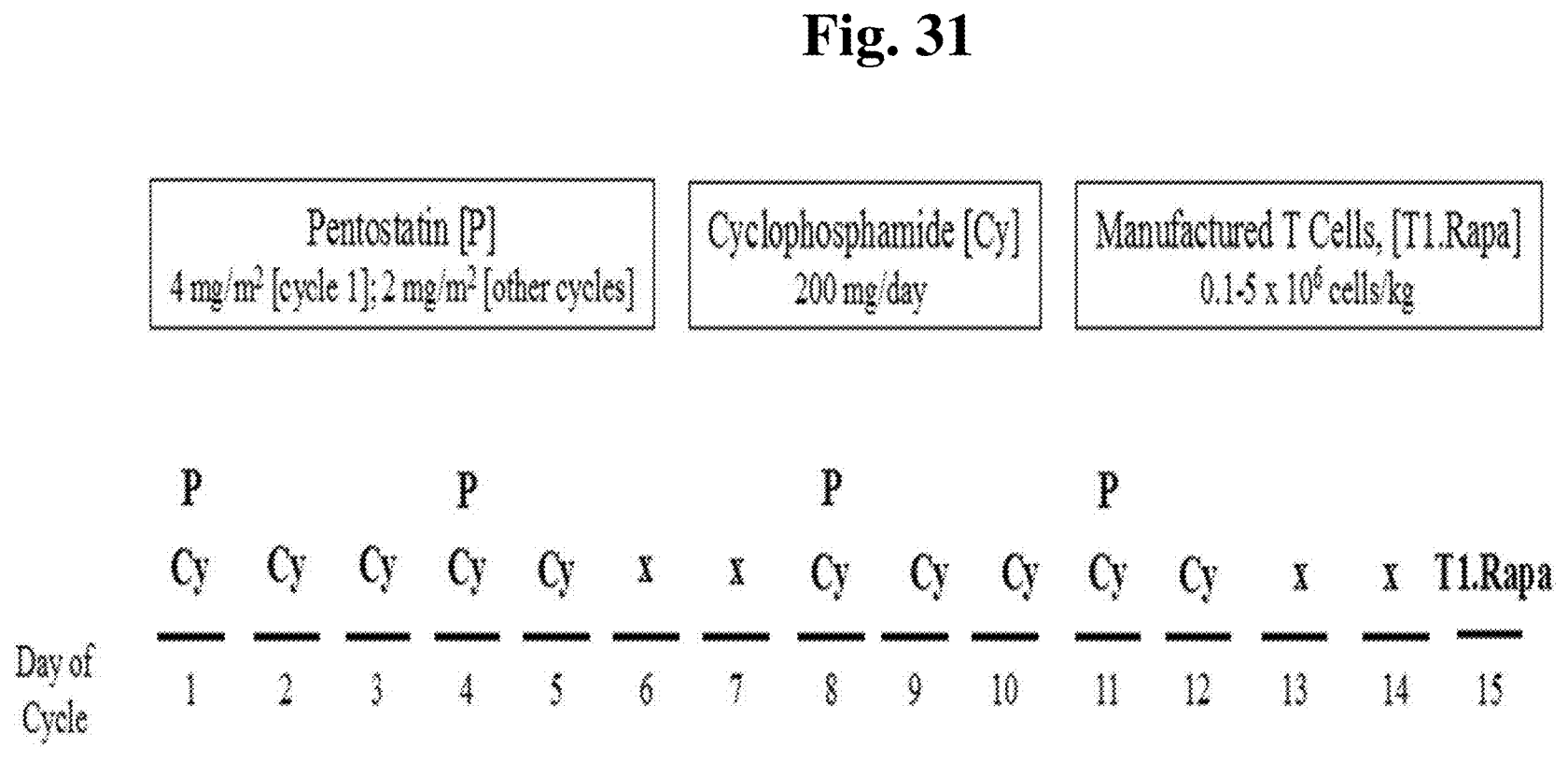

| Pentostatin [P] 4 mg/m² [cycle 1]; 2 mg/m² [other cycles] | Cyclophosphamide [Cy] 200 mg/day | Manufactured T Cells, [T1.Rapa] 0.1-5 x 10⁶ cells/kg |
| --- | --- | --- |

| | P | | P | | x | | P | | | | P | | x | x | T1.Rapa |
| Cy | Cy | Cy | Cy | Cy | x | x | Cy | Cy | Cy | Cy | Cy | x | x | T1.Rapa |
| 1 | 2 | 3 | 4 | 5 | 6 | 7 | 8 | 9 | 10 | 11 | 12 | 13 | 14 | 15 |

Day of Cycle

Culture Input
T Cells

CD45RO

FATE

TBET          FOXP3
RORγ          GATA3

EFFECTOR MEMORY    CHECK POINTS

PD1
CTLA4
TIM3
LAG3

STEP 1

STARVATION
AUTOPHAGY
DE-DIFFERENTIATION
mTORC1 Inhibited
mTORC2 Preserved

Diffuse Fate
Senescent

RAPA-201 Product
(culture day 6)

Pure Th1/Tc1 Fate
Pro-engraftment
Pro-Memory

(pancreatic CA cells)

Fig. 37 (continued)

Lung Cancer Cells (H23 Line)

ANTIGEN PRESENTING T CELLS, SENSITIZED, MANUFACTURED T CELLS AND METHODS OF TREATMENT USING THE SAME

CROSS-REFERENCE TO RELATED APPLICATIONS

This application is a continuation of International Patent Application PCT/US2021/032351, filed May 13, 2021, entitled Antigen Presenting T Cells, Sensitized, Manufactured T Cells and Methods of Treatment Using the Same, the entire contents of which are hereby incorporated by reference in their entirety. International Patent Application PCT/US2021/032351 claims priority to U.S. Provisional Application No. 63/024,435, filed May 13, 2020, the entirety of which is incorporated herein by reference.

BACKGROUND

CD4$^+$ and CD8$^+$ T cells of type I cytokine profile (Th1 and Tc1 cells, respectively) are candidate T cell populations for adoptive T cell therapy efforts. This Th1-type T cell is promoted by polarizing cytokines such as IL-12 and IFN-α, which stimulate STAT1 and STAT4 transcription factors, which in-turn promote TBET transcription factor that defines in part Th1-type differentiation status.

The success of adoptive T cell therapy is dependent in-part upon the in vivo persistence of the T cell population in the host. T cell persistence is a balance determined by both an increase in T cell ability to proliferate and maintain T cell memory and by reduction in T cell propensity to apoptotic cell death. In previous research, it has been demonstrated that ex vivo manufacture of T cells in the pharmacologic agent rapamycin (which inhibits the mammalian target of rapamycin, mTOR) yielded T cells that manifested these characteristics, namely: an increased ability to undergo antigen-driven clonal expansion in vivo after adoptive transfer; an improved memory status, as exemplified by a T central memory (T$_{CM}$) differentiation state; and a multi-faceted anti-apoptotic phenotype characterized by induction of autophagy, including mitochondrial autophagy, and by preferential expression of anti-apoptotic members of the bcl-2 family of genes relative to the pro-apoptotic members. Taken together, these properties of the ex vivo manufactured, rapamycin-resistant cells was associated with enhanced in vivo modulation of transplantation responses, including the prevention of graft-versus-host disease (GVHD) and graft rejection and the mediation of human-into-mouse xenogeneic GVHD; of note, these cells were successfully translated into clinical trials in the autologous and allogeneic settings for the treatment of multiple myeloma and were shown to be safe and effective for relapsed, refractory multiple myeloma. For these clinical trial efforts, the manufacturing process included the following elements: co-stimulation with anti-CD3, anti-CD28 coated magnetic beads (3/28 beads) at the relatively high ratio of 3 beads: 1 T cell; simultaneous addition of T cells and 3/28 beads to ex vivo culture; addition of a high-dose of the orally-administered mTOR inhibitor rapamycin (1 μM); and use of IL-2 addition to culture during cytokine polarization (IFN-α addition). The cells produced by this method are referred to herein as T-Rapa cells which are more specifically defined later in the present disclosure.

Cancer development can be associated with alterations in immune functions. Such alterations include suppressed cell mediated immunity (CMI) associated with failure to reject tumors, as well as enhanced humoral immunity that can potentiate tumor promotion and progression. CD4$^+$ T cell subsets, Th1 and Th2 T cells, have distinctive function and regulate each other. Th1 cells produce interleukin (IL-2) and interferon (IFN-γ) and direct CMI responses, whereas Th2 cells produce IL-4 and IL-10, and facilitate local humoral immune responses.

There is evidence of Th1/Th2 imbalance in certain cancers, where the proportion of Th2 cells is significantly elevated at the expense of Th1 cell number. Chronic Th1/Th2 imbalance in favor of Th2 potentially leads to suppressed cell mediated immunity, thereby providing a propitious environment for decreased effective immunosurveillance and development of malignancy.

Idiotype specific T cell responses are found in most patients with early stage multiple myeloma. These include Th1 responses with IL-2 and IFN-γ production. For example, Th1-type immunity is found preferentially in cases of indolent disease and Th2-type responses predominate in cases of advanced multiple myeloma. Defective Th1 immune responses (mediated by IL-6) as well as dysregulated cytokine network are found in multiple myeloma patients. Myeloma idiotype-specific T helper cells derived from MM patients are consistently of non-Th1 phenotype.

Despite advances in the treatment of multiple myeloma and the recent FDA-approval of new pharmaceutical agents and monoclonal antibodies, multiple myeloma is nearly universally fatal. As such, patients with relapsed, refractory multiple myeloma (RRMM) who are refractory to the top five drugs against multiple myeloma ("penta-refractory") have limited survival of a few months and few therapeutic options. Multiple myeloma is a disease that is susceptible to immune therapy, as evidenced by the long-observed curative role of allogeneic stem cell transplantation and by numerous other approaches, including monoclonal antibody therapy, vaccines, and T cell receptor (TCR-) and CAR-modified T cell therapy. As such, this penta-refractory patient population is suitable for a novel T cell therapy. In addition, patients with less refractory disease are also in great need of novel therapy; that is, even at the second or third relapse of disease, the median progression-free survival is typically less than two years.

For certain cancers, there is a need for novel and innovative immune therapy approaches. There is likewise a need for novel and innovative immune therapy approaches for infectious diseases.

SUMMARY

The present disclosure is directed to methods for treating cancer and infectious disease in a subject. Methods and compositions disclosed can include manufactured T cells, sensitized, manufactured T cells, antigen-presenting T cells, and loaded, antigen-presenting T cells as described herein. Methods provided include methods to generate antigen-presenting T cells (loaded and unloaded) from manufactured T cells and methods for treating cancer and infectious disease.

In some embodiments, a method for generating antigen-presenting T cells is provided which includes inoculating manufactured T cells or populations thereof of the present disclosure in a culture medium which includes IL-7 and IL-15 and incubating the manufactured T cells or population thereof for a period of time to yield a population of antigen-presenting T cells.

In some embodiments, an antigen-presenting T cell or population thereof is provided, including from the methods of the present disclosure. In some embodiments compositions are provided of manufactured T cells and antigen-presenting T cells or manufactured T cells, IL-7 and IL-15.

In some embodiments, a method for generating loaded, antigen-presenting T cells is provided that can include inoculating manufactured T cells or a population thereof of the present disclosure in a culture medium including IL-7 and IL-15, adding an immunogenic composition comprising an antigen to the culture medium, and incubating the manufactured T cells for a period of time to yield a population of loaded, antigen-presenting T cells which comprise the antigen or a portion thereof.

In some embodiments, a method for generating loaded, antigen-presenting T cells comprising an antigen or portion thereof can include, after the steps in the method to produce antigen-presenting T cells, adding an immunogenic composition comprising the antigen to the culture medium and incubating for an additional period of time to yield the loaded, antigen-presenting T cells which include the antigen or a portion thereof.

In some embodiments, a method for producing loaded, antigen-presenting T cells can include adding an immunogenic composition comprising an antigen and antigen-presenting T cells of the present disclosure in a culture medium and incubating the culture for an additional period of time to yield loaded, antigen-presenting T cells that include the antigen or a portion thereof.

In some embodiments, loaded, antigen-presenting T cells and populations thereof are provided. In some embodiments, compositions of manufactured T cells of the present disclosure and loaded, antigen-presenting T cells of the present disclosure are provided. In some embodiments, compositions of sensitized, manufactured T cells and loaded, antigen-presenting T cells of the present disclosure are provided.

In some embodiments, a method for producing sensitized, manufactured T cells are provided which can include co-incubating a population of loaded, antigen-presenting T cells of the present disclosure and manufactured T cells of the present disclosure at a ratio for a period of time to yield sensitized, manufactured T cells.

In some embodiments, a method for producing sensitized, manufactured T cells are provided which can include co-incubating a population of antigen-presenting T cells of the present disclosure and manufactured T cells of the present disclosure at a ratio, adding an immunogenic composition of the present disclosure, and incubating for a period of time to yield sensitized, manufactured T cells.

In some embodiments, a sensitized, manufactured T cell or population thereof is provided. In some embodiments, compositions including sensitized, manufactured T cells are provided.

In some embodiments, method for treating cancer or an infectious disease in a subject are provided, where manufactured T cells, antigen-presenting T cells, loaded, antigen-presenting T cells, sensitized, manufactured T cells, or sensitized T cells, or any combination thereof are administered to the subject and, in some aspects, where an agent sufficient to produce an immunogenic composition, e.g. immunogenic cell death, in the subject, an agent to cause IL-7 or IL-15 expression in the subject, exogenous IL-7, exogenous IL-15, or a combination is also administered to the subject.

BRIEF DESCRIPTION OF THE DRAWINGS

FIG. 8B depicts day 13 TNF-alpha secretion after culturing CD4$^+$ and CD8$^+$ T cells under various conditions.

Figure 25G:
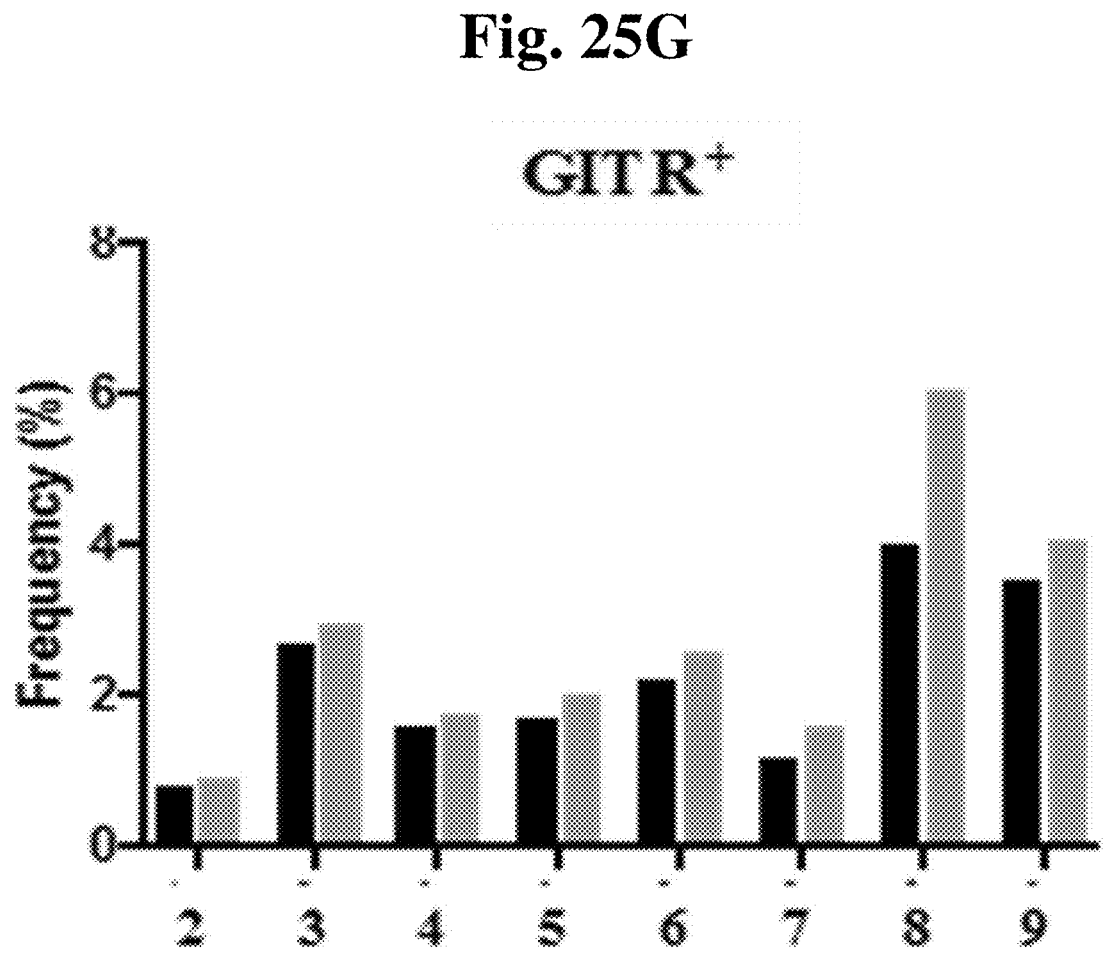
Figure 25H:
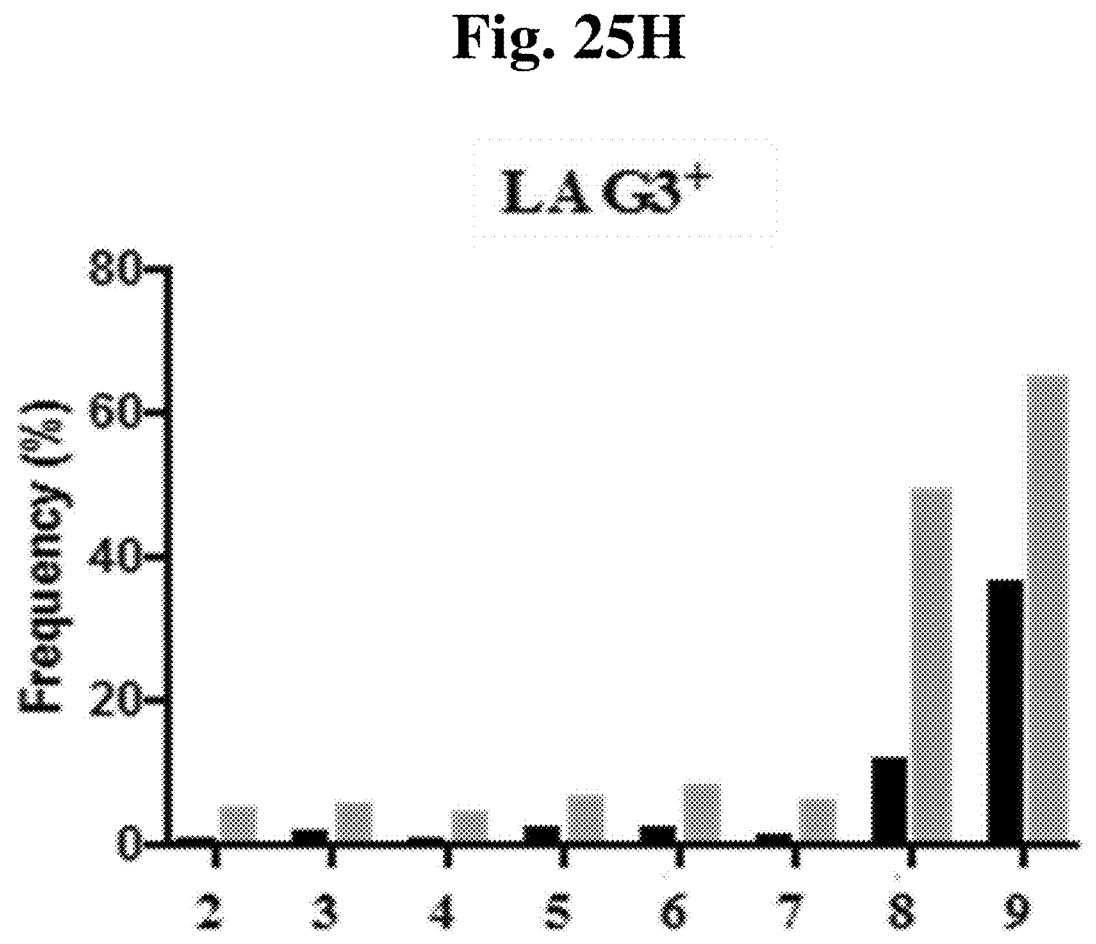
Figure 25I:
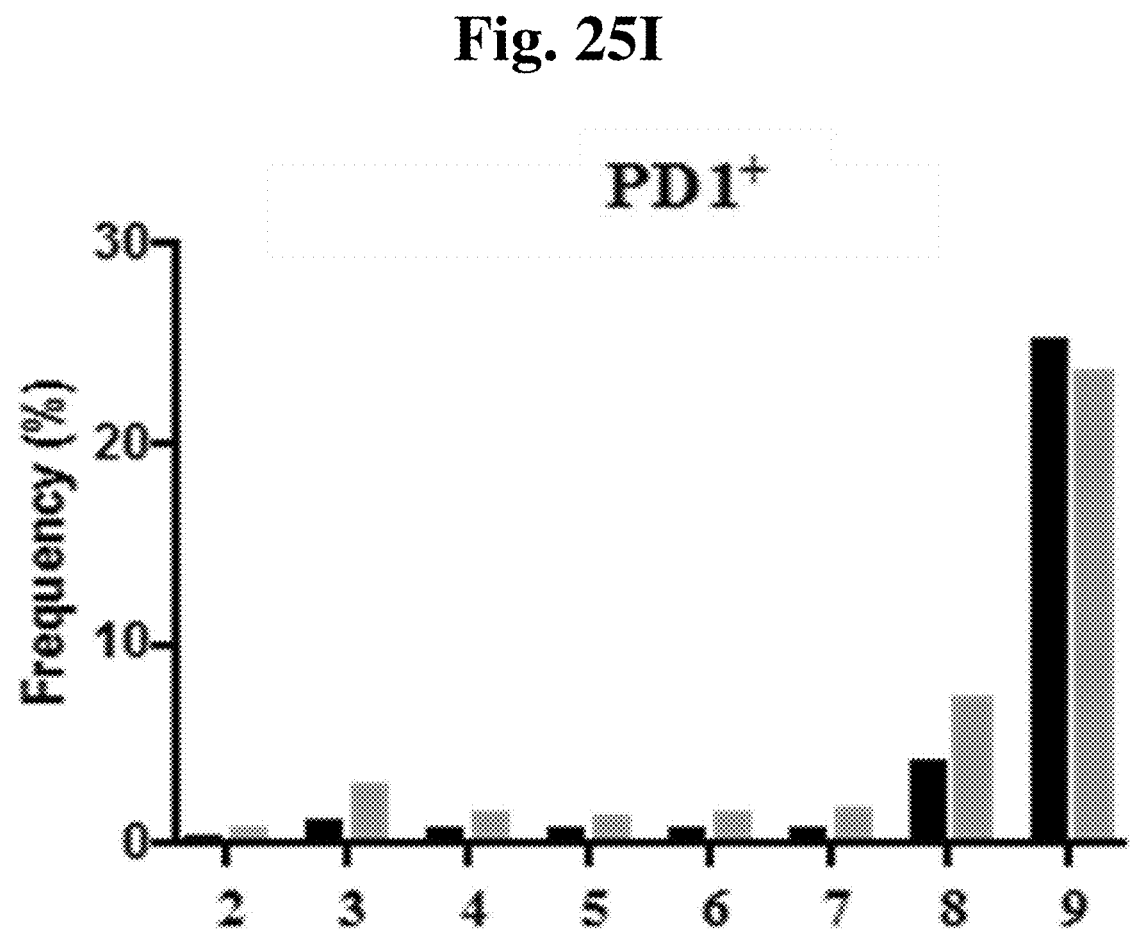
Figure 25J:
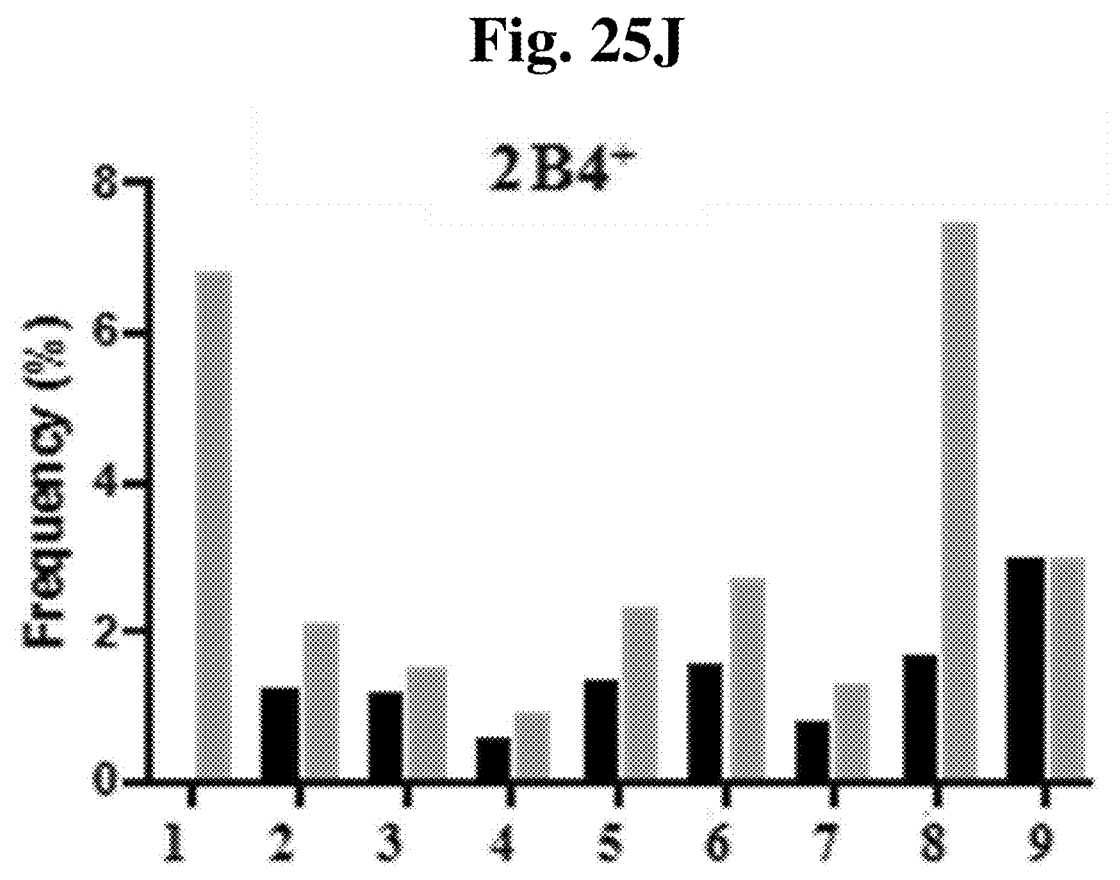

FIG. 25G depicts flow cytometry data measurements for GITR+ for T cells under various culture conditions.

FIG. 25H depicts flow cytometry data measurements for LAG3+ for T cells under various culture conditions.

FIG. 25I depicts flow cytometry data measurements for PD1+ for T cells under various culture conditions.

FIG. 25J depicts flow cytometry data measurements for 2B4+ for T cells under various culture conditions.

FIG. 31 depicts a Pentostatin/Cyclophosphamide regimen followed by manufactured T cell infusion.

DETAILED DESCRIPTION

Figure 1A:
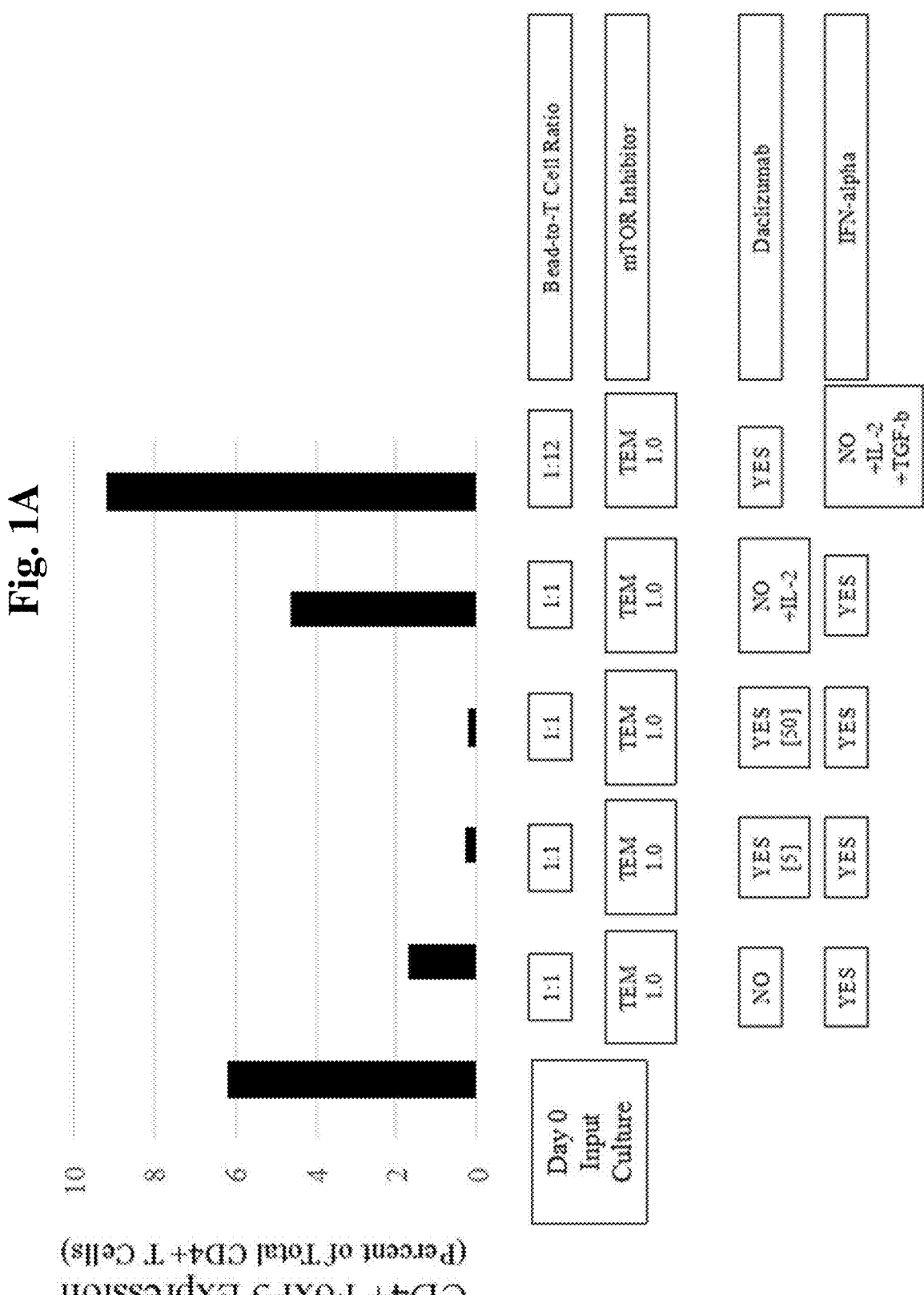
FIG. 1A depicts the percentage of CD4$^+$ T cells expressing FoxP3 at day 0 and after various culture conditions.

The present disclosure provides methods for producing manufactured T cells, antigen-presenting T cells (APTCs), loaded APTCs, and sensitized, manufactured T cells, each of these cells types as produced by the methods disclosed herein, populations and compositions of the same, including compositions of combinations of cell types, and methods for treating cancer or infectious disease in a subject using such cell types, populations and compositions.

Definitions

The following definitions are provided:

As used herein, the singular forms "a", "an" and "the" include plural referents unless the context clearly dictates otherwise. The use of the term "or" in the claims and the present disclosure is used to mean "and/or" unless explicitly indicated to refer to alternatives only or the alternatives are mutually exclusive.

Use of the term "about", when used with a numerical value, is intended to include +/−10%. By way of example but not limitation, if a number of amino acids is identified as about 200, this would include 180 to 220 (plus or minus 10%).

The terms "subject," "patient," and "individual" are used interchangeably herein, and refer to a mammalian subject to be treated, with human patients being preferred. In some cases, the methods of the invention find use in experimental animals, in veterinary application, and in the development of animal models for disease, including, but not limited to, rodents including mice, rats, and hamsters; and primates.

"Sample" is used herein in its broadest sense. A sample comprising cells, polynucleotides, polypeptides, peptides, antibodies and the like may comprise a bodily fluid; a soluble fraction of a cell preparation, or media in which cells were grown; a chromosome, an organelle, or membrane isolated or extracted from a cell; genomic DNA, RNA, or cDNA, polypeptides, or peptides in solution or bound to a substrate; a cell; a tissue; a tissue print; a fingerprint, skin or hair; and the like.

"Treatment" is an intervention performed with the intention of preventing the development or altering the pathology or symptoms of a disorder. Accordingly, "treatment" refers to both therapeutic treatment and prophylactic or preventative measures. Those in need of treatment include those already with the disorder as well as those in which the disorder is to be prevented. For example, in tumor (e.g. cancer) treatment, a therapeutic agent may directly decrease the pathology of tumor cells, or render the tumor cells more susceptible to treatment by other therapeutic agents, e.g., radiation and/or chemotherapy. As used herein, "ameliorated" refers to a symptom which approaches a normalized value (by way of example but not limitation, a value obtained in a healthy patient or individual), e.g., is less than 50% different from a normalized value, preferably is less than about 25% different from a normalized value, more preferably, is less than 10% different from a normalized value, and still more preferably, is not significantly different from a normalized value as determined using routine statistical tests. By way of example but not limitation, amelioration or treatment of a patient suffering from an infectious disease organism, such as for example, Hepatitis B Virus, may be determined by a decrease of viral particles in a sample taken from a patient, as measured by, for example, a decrease in plaque forming units (p.f.u.).

"Treatment cycle" as used herein can generally refer to any of the primary treatment cycles, a first treatment cycle, a second treatment cycle or one or more additional treatment cycles.

As used herein, the term "therapeutically effective dose" or "therapeutically effective amount" is meant an amount of a compound of the present invention effective to yield the desired therapeutic response. By way of example but not limitation, a dose effective to delay the growth of or to cause the cancer to shrink or prevent metastasis can be a "therapeutically effective dose." The specific therapeutically effective dose will vary with such factors as the particular condition being treated, the physical condition of the patient, the type of mammal or animal being treated, the duration of the treatment, the nature of concurrent therapy (if any), and the specific formulations employed and the structure of the compounds or its derivatives.

"Immune cells" as used herein is meant to include any cells of the immune system that may be assayed, including, but not limited to, B lymphocytes, also called B cells, T lymphocytes, also called T cells, natural killer (NK) cells, natural killer T (NKT) cells, lymphokine-activated killer (LAK) cells, monocytes, macrophages, neutrophils, granulocytes, mast cells, platelets, Langerhans cells, stem cells, dendritic cells, peripheral blood mononuclear cells, tumor-infiltrating (TIL) cells, gene modified immune cells including hybridomas, drug modified immune cells, and derivatives, precursors or progenitors of the above cell types.

As used herein, an "immunogenic composition" should be understood as a composition that includes at least one antigen and is able to stimulate an immune response in a T cell population when presented to the T cell population by a cell with antigen-presenting capacity.

"T cells" are a subset of lymphocytes originating in the thymus and having heterodimeric receptors associated with proteins of the CD3 complex (e.g., a rearranged T cell receptor, the heterodimeric protein on the T cell surfaces responsible for antigen/MHC specificity of the cells). T cell responses may be detected by assays for their effects on other cells (e.g., target cell killing, activation of other immune cells, such as B-cells) or for the cytokines they produce.

As used herein, the term "anti-CD3/anti-CD28" should be understood to refer to anti-CD3/anti-CD28 antibodies. For example, "anti-CD3/anti-CD28 magnetic beads" should be understood to refer to magnetic beads having anti-CD3/anti-CD28 antibody moieties associated therewith. In instances where it is disclosed that no anti-CD3/anti-CD28 co-stimulation is provided even by a specific form such as anti-CD3/anti-CD28 magnetic beads, it should be understood that this can also exclude co-stimulation with other forms of anti-CD3/anti-CD28.

As used herein, the term "T-Rapa cell(s)" refers to T cell(s) produced by co-stimulation with anti-CD3/anti-CD28 coated magnetic beads at a ratio of 3:1 (bead:T cell ratio) without a delay between culture initiation and co-stimulation, where the cells are grown in X-Vivo or the equivalent media containing IFN-α (10,000 IU/mL), IL-2 (20 IU/mL) and rapamycin (1 μM), supplemented with 5% AB serum, but no IL-2 signaling inhibitor, where the cells are cultured for 6 days at 37° C. and are initiated into culture at a concentration of $1.5 \times 10^6$ cells/mL. As used in reference to methods "T-Rapa" refers to the method of producing T-Rapa cells as defined above unless otherwise noted.

As used herein, the term "manufactured T cells" and "Rapa-T cells" are used interchangeably to refer to T cells produced by the methods of the present disclosure. "Manufactured T cells" can include CD4$^+$, CD8$^+$ T cells or both. "Manufactured T cells" do not include T cells as collected from a patient, i.e. naturally occurring T cells.

It should be understood that as used herein "level of expression," "expression level" or an equivalent reference, when used to refer to results measured by flow cytometry refers to the frequency of positive cells of the specified type in the population. To the extent that the "level of expression" or equivalent refers to that of a specific cell type, it should be understood, that any reduction or increased referenced is relative to the corresponding specified cell type unless otherwise noted.

As will be recognized by those in the art, the term "autologous" cells means cells that are of the same or similar haplotype as that of the subject or "host" to which the cells are administered, such that no significant immune response against these cells occurs when they are transplanted into a host.

"CD4" is a cell surface protein important for recognition by the T cell receptor of antigenic peptides bound to MHC class II molecules on the surface of an APC. Upon activation, naive CD4 T cells differentiate into one of at least two cell types, Th1 cells and Th2 cells, each type being characterized by the cytokines it produces. "Th1 cells" are primarily involved in activating macrophages with respect to cellular immunity and the inflammatory response, whereas "Th2 cells" or "helper T cells" are primarily involved in stimulating B cells to produce antibodies (humoral immunity). CD4 is the receptor for the human immunodeficiency virus (HIV). Effector molecules for Th1 cells include, but are not limited to, IFN-γ, GM-CSF, TNF-α, CD40 ligand, Fas ligand, IL-3, TNF-β, and IL-2. Effector molecules for Th2 cells include, but are not limited to, IL-4, IL-5, IL-13, CD40 ligand, IL-3, G-CSF, IL-10, TGF-β, and eotaxin. Activation of the Th1 type cytokine response can suppress the Th2 type cytokine response, and reciprocally, activation of the Th2 type cytokine response can suppress the Th1 type response.

A "cytokine" is a protein made by a cell that affects the behavior of other cells through a "cytokine receptor" on the surface of the cells the cytokine effects. Cytokines manufactured by lymphocytes are sometimes termed "lymphokines." Cytokines are also characterized as Type I (e.g. IL-2 and IFN-gamma) and Type II (e.g. IL-4 and IL-10).

By the term "modulate," it is meant that any of the mentioned activities, are, e.g., increased, enhanced, increased, agonized (acts as an agonist), promoted, decreased, reduced, suppressed blocked, or antagonized (acts as an agonist). Modulation can increase activity more than 1-fold, 2-fold, 3-fold, 5-fold, 10-fold, 100-fold, etc., over baseline values. Modulation can also decrease its activity below baseline values.

"Substrate" refers to any rigid or semi-rigid support to which nucleic acid molecules or proteins are bound and includes membranes, filters, chips, slides, wafers, fibers, magnetic or nonmagnetic beads, gels, capillaries or other tubing, plates, polymers, and microparticles with a variety of surface forms including wells, trenches, pins, chamiels and pores.

Methods for Producing Manufactured T Cells, Manufactured T Cells Produced by the Methods Disclosed Herein, and Compositions Comprising a Population of Manufactured T Cells In methods of the present disclosure, IFN-α is utilized for the ex vivo polarization of a culture comprising T cells towards the Th1-type differentiation status phenotype. The Th1-type differentiation can be eroded by polarization towards a regulatory T (T$_{REG}$) cell phenotype, which is promoted by cytokines including IL-2, which signals through STAT5 to promote FoxP3 transcription factor that defines in part T$_{REG}$ differentiation status. In the methods of the present disclosure, T$_{REG}$ contamination is limited during Th1-type polarization by omitting exogenous use of IL-2 during cell culture and by preventing autocrine IL-2 signaling by culture addition of an IL-2 signaling inhibitor. In some aspects, the IL-2 signaling inhibitor is an anti-IL-2 receptor monoclonal antibody.

In the present disclosure, new methods for manufacturing are provided which incorporate the following interventions compared to other T cell manufacturing methods: (1) delayed or no addition of anti-CD3/CD28 beads (alternatively, one can provide any alternative source of anti-CD3/anti-CD28 co-stimulation such as nanoparticles or microparticles) to culture for improved T cell yield, where anti-CD3/CD28 beads or nanoparticles are used for co-stimulation; (2) use of a lower ratio of anti-CD3/CD28 beads for enhancement of the resistant T cell phenotype, or alternatively, no addition of bead, nanoparticle or microparticle artificial antibody-based co-stimulation; (3) use of the parenteral formulation of mTOR inhibition (temsirolimus) for increased manufacturing feasibility; and (4) avoidance of IL-2 signaling and resultant T$_{REG}$ cell contamination of Th1-type differentiation by omitting the typical use of exogenous IL-2 during T cell culture and by abrogating endogenous, autocrine IL-2 signaling, for example, through use of an anti-IL-2 receptor monoclonal antibody (daclizumab or basiliximab or other reagents that inhibit IL-2 receptor signaling) during T cell culture. In side-by-side culture experiments, T cells generated by this new combinatorial method, termed "manufactured T cells," manifested a more optimal cellular phenotype relative to previously described T cells produced in ex vivo culture.

Figure 33:
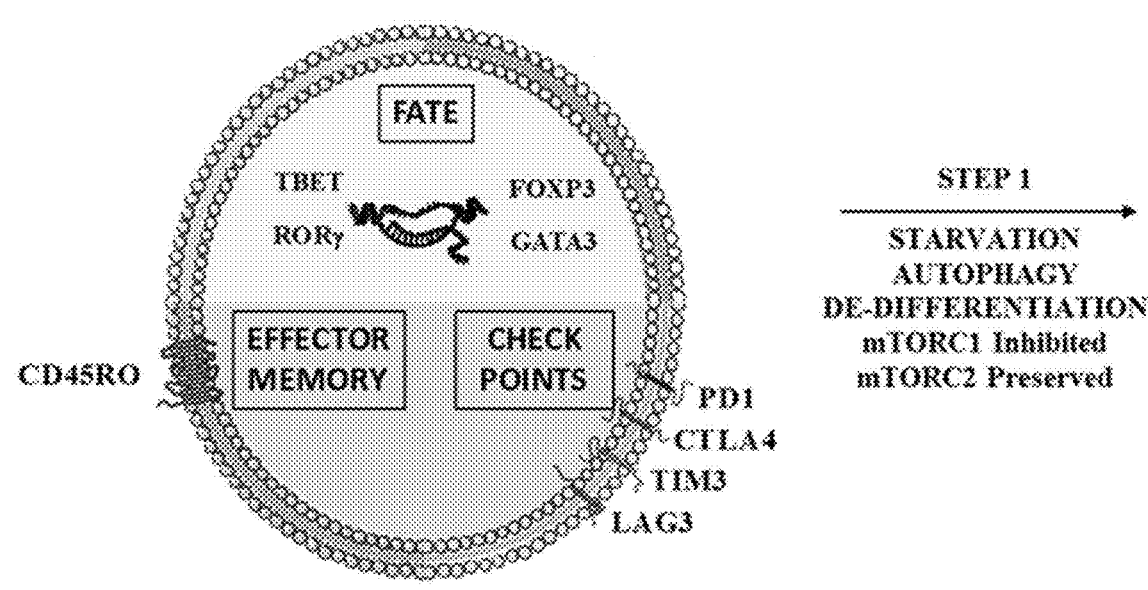
FIG. 33 depicts an exemplary workflow for generating manufactured T cells of the present disclosure.
Figure 33:
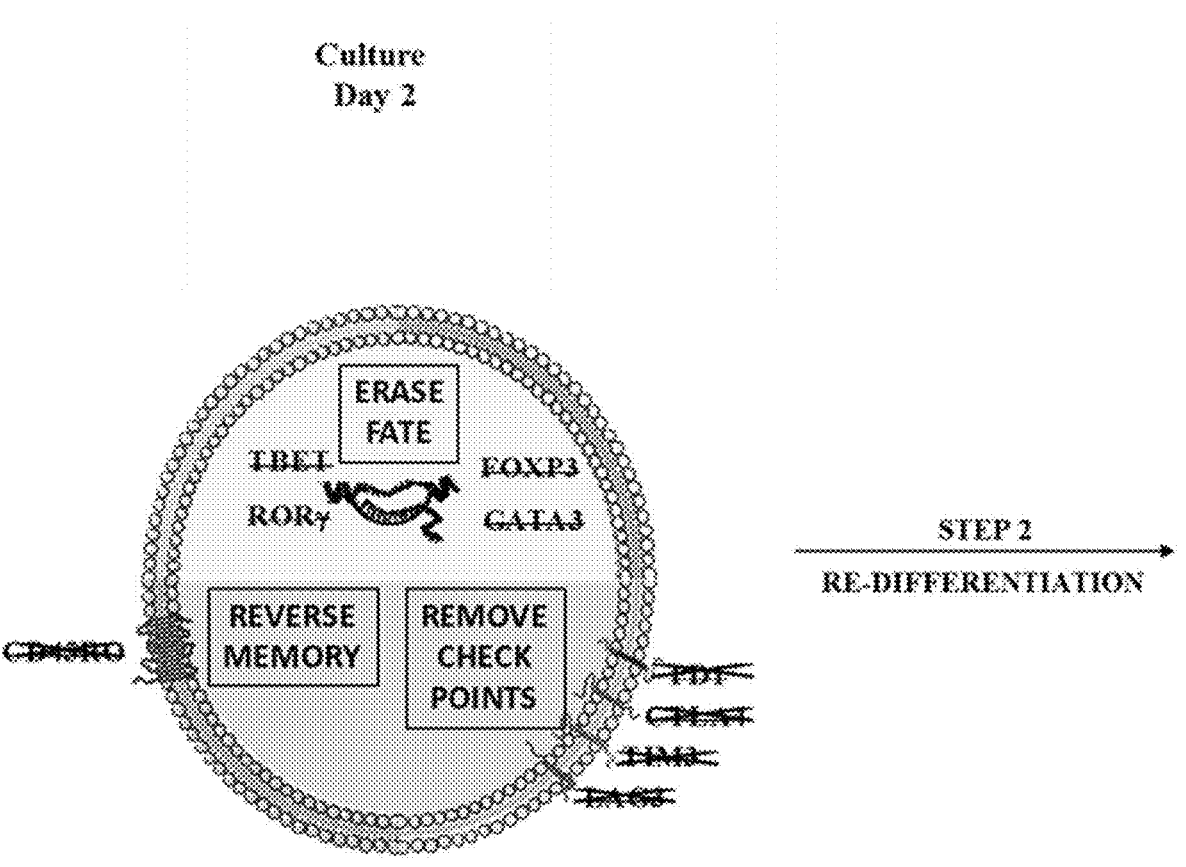
Figure 33:
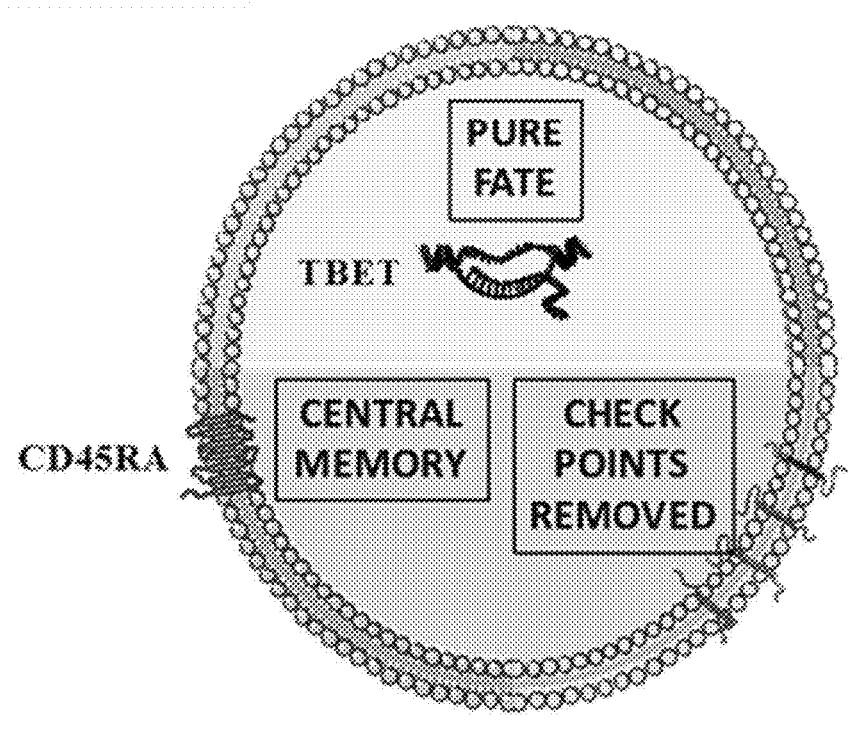

FIG. 33 provides an exemplary workflow for generating manufactured T cells of the present disclosure.

In some embodiments, a method for producing manufactured T cells includes the steps of inoculating a culture input population of cells comprising T cells from a subject at a cell density in a culture medium comprising temsirolimus and an IL-2 signaling inhibitor. In certain aspects, the culture medium does not already include temsirolimus and/or the IL-2 signaling inhibitor and these components can be added at or about the same time as the inoculation. The culture input population of cells is incubated for a first period of time without co-stimulation by anti-CD3/anti-CD28 antibodies, including, by way of example but not limitation, co-stimulation with anti-CD3/anti-CD28 coated magnetic beads, nanoparticles or microparticles. After the first period of time, the culture input population of cells can be stimulated by anti-CD3/anti-CD28 antibodies, for example, by adding anti-CD3/anti-CD28 coated magnetic beads, nanoparticles or microparticles. Where anti-CD3/anti-CD28 coated magnetic beads are used, these can be used at a bead ratio between 1:1 and 1:12. In addition, IFN-α is added to the culture medium. The culture input population of cells is then incubated for a second period of time to yield the manufactured T cells. In some aspects, there is no co-stimulation with anti-CD3/anti-CD28 coated magnetic beads, nanoparticles or microparticles. In some embodiments, no co-stimulation is performed.

In any of the foregoing embodiments, the method of producing manufactured T cells can further include after harvesting said manufactured T cells: packaging at least a portion of said manufactured T cells in a package; and freezing said package containing said portion of said manufactured T cells. Cryopreservation of said manufactured T cells can be performed by methods known in the art.

In any of the foregoing embodiments, the method can further include before inoculating T cells from said subject at a cell density in a culture medium: harvesting said culture input population of cells from said subject.

In any of the foregoing embodiments, said culture medium can not contain IL-2 and no IL-2 can be added to said culture medium. In any of the foregoing embodiments, no serum can added to the culture, e.g. the culture is serum-free. In any of the foregoing embodiments, the culture medium can be substantially free of serum.

In any of the foregoing embodiments, said IFN-α can be added at or about the same time as the anti-CD3/anti-CD28 coated magnetic beads are added. If no co-stimulation of the culture is performed, IFN-α can be added, for example, at culture initiation or within 48 hours of culture initiation. By way of example, but not limitation, IFN-α can be added at 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, or 48 hours after culture initiation.

In any of the foregoing embodiments, said cell density can be about $1 \times 10^6$ T cells per mL to $50 \times 10^6$ cells per mL. By way of example but not limitation, said cell density may be about $1 \times 10^6$ cells per mL to $5 \times 10^6$ cells per mL, $1 \times 10^6$ cells per mL to $10 \times 10^6$ cells per mL, $1 \times 10^6$ cells per mL to $15 \times 10^6$ cells per mL, $15 \times 10^6$ cells per mL to $22.5 \times 10^6$ cells per mL, $10 \times 10^6$ cells per mL to $22.5 \times 10^6$ cells per mL, $10 \times 10^6$ cells per mL to $22.5 \times 10^6$ cells per mL, $5 \times 10^6$ cells per mL to $22.5 \times 10^6$ cells per mL, $1 \times 10^6$ cell per mL to $50 \times 10^6$ cells per mL, $10 \times 10^6$ cells per mL to $40 \times 10^6$ cells per mL, $20 \times 10^6$ cells per mL to $40 \times 10^6$ cells per mL, $1 \times 10^6$ cells per mL, $2.5 \times 10^6$ cells per mL, $5 \times 10^6$ cells per mL, $7.5 \times 10^6$ cells per mL, $10 \times 10^6$ cells per mL, $12.5 \times 10^6$ cells per mL, $15 \times 10^6$ cells per mL, $17.5 \times 10^6$ cells per mL, $20 \times 10^6$ cells per mL, $22.5 \times 10^6$ cells per mL, $25 \times 10^6$ T cells per mL, $30 \times 10^6$ cells per mL, $35 \times 10^6$ cells per mL, $40 \times 10^6$ cells per mL, $45 \times 10^6$ cells per mL, or $50 \times 10^6$ cells per mL.

In any of the foregoing embodiments, said temsirolimus can be present in said culture medium at a concentration of 0.1-5 µM. In some embodiments, temsirolimus can be present in said culture medium at a concentration of 0.1-1 µM. In any of the foregoing embodiments, temsirolimus can be present in said culture medium at a concentration of 1 µM. By way of example, but not limitation, temsirolimus can be present in said culture medium at a concentration of at least 0.1 µM, 0.2 µM, 0.3 µM, 0.4 µM, 0.5 µM, µM, 0.6 µM, 0.7 µM, 0.8 µM, 0.9 µM, 1.0 µM, 1.5 µM, 2.0 µM, 2.5 µM, 3.0 µM, 3.5 µM, 4.0 µM, 4.5 µM, 5.0 µM or more. By way of further example, but not limitation, temsirolimus can be present in said culture medium at a concentration of about 1-5 µM, 2-5 µM, 3-5 µM, 4-5 µM, 0.1 µM, 0.2 µM, 0.3 µM, 0.4 µM, 0.5 µM, µM, 0.6 µM, 0.7 µM, 0.8 µM, 0.9 µM, 1.0 µM, 1.5 µM, 2.0 µM, 2.5 µM, 3.0 µM, 3.5 µM, 4.0 µM, 4.5 µM, 5.0 µM, or more.

In any of the foregoing embodiments, said temsirolimus can be added to said culture medium one or more times during the second period of time to maintain a desired concentration. In any of the foregoing embodiments, temsirolimus can be added once to the culture medium. By way of non-limiting example, said temsirolimus can be added to said culture medium every 2 days during said second period of time. The desired concentration of temsirolimus can be between 0.1-5 µM. In any of the foregoing embodiments, the desired concentration of temsirolimus can be between 0.1-1 µM. In any of the foregoing embodiments, the desired concentration of temsirolimus can be 1 µM. By way of example but not limitation, the desired concentration of temsirolimus can be at least 0.1 µM, 0.2 µM, 0.3 µM, 0.4 µM, 0.5 µM, µM, 0.6 µM, 0.7 µM, 0.8 µM, 0.9 µM, 1.0 µM, 1.5 µM, 2.0 µM, 2.5 µM, 3.0 µM, 3.5 µM, 4.0 µM, 4.5 µM, 5.0 µM or more. By way of further example, but not limitation, the desired concentration of temsirolimus can be a concentration of about 1-5 µM, 2-5 µM, 3-5 µM, 4-5 µM, 0.1 µM, 0.2 µM, 0.3 µM, 0.4 µM, 0.5 µM, µM, 0.6 µM, 0.7 µM, 0.8 µM, 0.9 µM, 1.0 µM, 1.5 µM, 2.0 µM, 2.5 µM, 3.0 µM, 3.5 µM, 4.0 µM, 4.5 µM, 5.0 µM, or more.

The IL-2 signaling inhibitor can be any substance that inhibits IL-2 signaling and can be added in an amount sufficient to inhibit IL-2 signaling. In any of the foregoing embodiments, said IL-2 signaling inhibitor can be an anti-IL-2 receptor antibody or fragment thereof, such as basiliximab or daclizumab. Said IL-2 signaling inhibitor can be present in said culture medium at a concentration of 5 to 50 µg/mL. By way of non-limiting example, IL-2 signaling inhibitor can be present at a concentration of about 5 to 50 µg/mL, 5 to 40 µg/mL, 5 to 30 µg/mL, 5 to 20 µg/mL, 5 to 10 µg/mL, 40 to 50 µg/mL, 30 to 50 µg/mL, 20 to 50 µg/mL, 20 to 40 µg/mL, 20 to 30 µg/mL, 5 µg/mL, 10 µg/mL, 15 µg/mL, 20 µg/mL, 25 µg/mL, 30 µg/mL, 35 µg/mL, 40 µg/mL, 45 µg/mL, or 50 µg/mL.

In any of the foregoing embodiments, said first period of time can be about 8 hours to about 24 hours. By way of non-limiting example, said first period of time can be about 8 hours to about 20 hours, 8 hours to about 16 hours, 8 hours to about 12 hours, 20 hours to about 24 hours, 16 hours to about 24 hours, 12 hours to about 24 hours, 8 hours, 10 hours, 12 hours, 14 hours, 16 hours, 18 hours, 20 hours, 22 hours, or 24 hours.

In any of the foregoing embodiments, said bead:T cell ratio can be 1:3. In some embodiments, the bead:T cell ratio can be between 1:12 and 1:1, or in the most extreme example, no bead addition. By way of example but not limitation, ratios of 1:12, 1:11, 1:10, 1:9, 1:8, 1:7, 1:6, 1:5, 1:4, 1:3, 1:2, 1:1 or any range therebetween can be used. In some embodiments, co-stimulation of the culture input population of cells can be achieved using anti-CD3/anti-CD28 containing nanoparticles which can be used at a reduced concentration than recommended. By way of example, but not limitation, such nanoparticles can be used at about 0.01× to about 0.1×, about 0.025× to about 0.1×, about 0.05× to about 0.1×, about 0.075× to about 0.1×, about 0.01× to about 0.075×, about 0.01× to about 0.05×, about 0.01× to about 0.025×, about 0.025× to about 0.075×, about 0.025× to about 0.05×, about 0.05× to about 0.075×, or about 0.01×, about 0.025×, about 0.05×, about 0.075×, or about 0.01× the recommended dose. By way of example but not limitation, a reagent such as Miltenyi® T Cell TransAct™ could be used at a reduced dose compared to the recommended dose of 10 µL per 1×10⁶ T cells such as, by way of example but not limitation, 1.1 µL (a nine-fold decrease) or about 0.11×. Alternatively, if anti-CD3/anti-CD28 co-stimulation is to be used for producing manufactured T cells, the source of co-stimulation can be provided by dissolvable anti-CD3/anti-CD28 microparticles. By way of example, but not limitation, the dissolvable anti-CD3/anti-CD28 microparticles can be used at 20% of the strength recommended by the manufacturer (e.g. Cloudz®; Bio-Techne). By way of further example, the dissolvable anti-CD3-anti-CD28 microparticles can be used at 5%, 10%, 15%, 20%, 25% or 30% of the manufacturer's recommended strength. The specific amount of anti-CD3/anti-CD28 reagent to be added can be titrated based on the desired functional characteristics of the final Rapa-T cell product. Specifically, a sufficient amount of reagent can be added to maintain T cell viability in vitro in the presence of the inhibitory molecules described in the present disclosure. However, any specific anti-CD3/anti-CD28 reagent should not be added in excess, as defined by: inappropriately high level of T cell activation (increase in CD25 expression by flow cytometry relative to the T cell culture with the optimal, minimal amount of co-stimulation); inappropriately high level of T cell checkpoint inhibitor receptor expression by flow cytometry; and inappropriately altered expression of molecules associated with T cell effector memory cells by flow cytometry (such as reduction in levels of CD62L and CCR7; such as increase in levels of CD45RO and KLRG).

In any of the foregoing embodiments, said IFN-α can be added to said culture medium to a concentration of about 1,000 IU/mL to about 10,000 IU/mL. By way of example but not limitation, concentrations of 2,500 IU/mL to 10,000 IU/mL, 5,000 IU/mL to 10,000 IU/mL, 7,500 IU/mL to 10,000 IU/mL, 1,000 IU/mL to 7,500 IU/mL, 1,000 IU/mL to 5,000 IU/mL, 1,000 IU/mL to 2,500 IU/mL, 2,500 IU/mL to 7,500 IU/mL, 2,500 IU/mL to 5,000 IU/mL, 5,000 IU/mL to 7,500 IU/mL, 5,000 IU/mL to 10,000 IU/mL, 7,500 IU/mL to 10,000 IU/mL, or 1,000 IU/mL, 2,500 IU/mL, 5,000 IU/mL, 7,500 IU/mL, or 10,000 IU/mL can be used. Lower concentrations of IFN-α such as 1000 IU/mL may result in less marked shift towards a Th1 phenotype.

In any of the foregoing embodiments, said second period of time can be about 2 days to about 8 days, about 4 days to about 8 days, 4 days to about 6 days, or 6 days to about 8 days. By way of non-limiting example, said second period of time can be about 4 days, 5 days, 6 days, 7 days, or 8 days. Where no co-stimulation is performed, the period of time for incubation can be about 2 days to about 8 days, 4 days to about 8 days, 4 days to about 6 days, or 6 days to about 8 days. By way of non-limiting example, said second period of time can be about 4 days, 5 days, 6 days, 7 days, or 8 days.

In any of the foregoing embodiments, said culture medium can further comprise 5% human serum. In some embodiments, said culture medium can further comprise 1%-20% human serum. By way of example but not limitation, said culture medium may comprise about 1%, 2%, 3%, 4%, 5%, 6%, 7%, 8%, 9%, 10%, 11%, 12%, 13%, 14%, 15%, 16%, 17%, 18%, 19% or 20% human serum. In some embodiments, said culture medium can comprise at least 1%, 2%, 3%, 4%, 5%, 6%, 7%, 8%, 9%, 10%, 11%, 12%, 13%, 14%, 15%, 16%, 17%, 18%, 19% or 20% human serum. In any of the foregoing embodiments, no serum can be added to or present in the culture medium.

In any of the foregoing embodiments, said culture medium can further comprise X-Vivo 20 medium. In any of the foregoing embodiments, said culture medium can further comprise TexMACS (Miltenyi®) medium. Any suitable culture medium can be used for culturing T cells.

In any of the foregoing embodiments, additional culture medium can be added to the culture. By way of example but not limitation, additional culture medium can be added at about 12 hours, 24 hours, 36 hours, 48 hours, 60 hours, 72 hours, 84 hours, 96 hours, 108 hours, 120 hours or any range or time therebetween after the initial inoculation of the culture input population of cells into culture. By way of example, but not limitation, the amount of culture medium added relative to the initial amount of culture medium can be in a ratio of about 0.5, 0.75, 1, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0 or more, and any range therebetween. By way of example, but not limitation, the amount of culture medium added after the initial inoculation of the culture input population of cells into culture can be an amount sufficient to reduce the cell density in the culture to a target cell density. By way of example but not limitation, this target cell density can be about 1×10⁶, 2×10⁶, 3×10⁶, 4×10⁶, 5×10⁶, 6×10⁶, 7×10⁶, 8×10⁶, 9×10⁶, 1×10⁷, 2×10⁷, 3×10⁷, or 4×10⁷ and any range therebetween, provided that the initial cell density is greater than the target cell density.

In any of the foregoing embodiments, said culture input population of cells can comprise about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, about 90% to about 100%, about 5% to about 90%, about 5% to about 80%, about 5% to about 70%, about 5% to about 60%, about 5% to about 50%, about 5% to about 40%, about 5% to about 30%, about 5% to about 20%, or about 5% to about 10%, about T cells out of the total number of cells in the culture input population of cells. By way of non-limiting example, said culture input population of cells can comprise about 5%, 10%, 15%, 20%, 33%, 40%, 50%, 66%, 70%, 75%, 90%, 95%, 98%, or 99% or more T cells out of the total number of cells in said culture input population of cells.

In any of the foregoing embodiments, said culture input population of cells can further comprise monocytes. In any of the foregoing embodiments, the culture input population of cells can be enriched for T cells. By way of example, but not limitation, the culture input population of cells can be subjected to T cell enrichment using an automated Ficoll procedure. Methods to perform the Ficoll procedure are known in the art, and involve removing neutrophils and red blood cells from the sample. Any suitable method for enriching T cells in a population of cells can be used.

In any of the foregoing embodiments, the method can further comprise harvesting a sample comprising T cells from said subject; and isolating T cells from said sample to yield said culture input population of cells. Such samples can contain peripheral blood stem cells (PBSCs) and can be obtained, by way of example but not limitation, by mobilized collection, steady state apheresis or a simple blood draw. In any of the foregoing embodiments, the sample containing PBSCs and/or the culture input population of cells can be cryopreserved prior to manufactured T cell preparation. Steady state apheresis can be performed when the subject has a sufficient number of immune cells which, by way of example but not limitation can be characterized by a minimum absolute lymphocyte count (ALC). The minimum ALC can, for example, be 300 lymphocytes per microliter.

In any of the foregoing embodiments, said T cells can isolated by antibody-based purification.

In any of the foregoing embodiments, said enrichment of T cells can be performed by counter-flow centrifugal elutriation. Such a technique is well known in the art.

In any of the foregoing embodiments, said IFN-α can be added at or about the same time as the anti-CD3/anti-CD28 containing nanoparticles are added.

In any of the foregoing embodiments, the anti-CD3/anti-CD28 antibodies can be removed by any suitable method after culture. By way of example, but not limitation, anti-CD3/anti-CD28 magnetic beads can be removed by magnetic capture and dissolvable anti-CD3/anti-CD28 microparticles can be removed by adding release buffer and washing the manufactured T cells.

In some embodiments, a population of manufactured T cells exhibits increased IFN-γ secretion relative to T-Rapa cells after one week of incubation using stimulation with anti-CD3/anti-CD28 magnetic beads added at a bead:T cell ratio of 3:1.

In some embodiments, a population of manufactured T cells exhibits increased TNF-α secretion relative to T-Rapa cells after one week of incubation using stimulation with anti-CD3/anti-CD28 magnetic beads added at a bead:T cell ratio of 3:1.

In some embodiments, a population of manufactured T cells exhibits increased GM-CSF secretion relative to T-Rapa cells after one week of incubation using stimulation with anti-CD3/anti-CD28 magnetic beads added at a bead:T cell ratio of 3:1.

In some embodiments, a population of manufactured T cells exhibits increased IL-2 secretion relative to T-Rapa cells after one week of incubation using stimulation with anti-CD3/anti-CD28 magnetic beads added at a bead:T cell ratio of 3:1.

In some embodiments, a population of manufactured T cells comprises an increased percentage of cells positive for CD4, CD62L, CCR7 and CD127 relative to said control population of T cells and to T-Rapa cells.

In some embodiments, a population of manufactured T cells exhibits an increase in 4EBP1 phosphorylation relative to said control population of T cells. In some embodiments, a manufactured T cell exhibits increased 4EBP1 phosphorylation relative to a control T cell. By way of example but not limitation, the increase in phosphorylation of 4EBP1 relative to a control population of T cells characteristic of the T cells from which the T cell was produced, i.e. culture input T cells, or a control T cell is no more than 50%, no more than 45%, no more than 40%, no more than 35%, or no more than 30%. By way of further example but not limitation, the increase in 4EBP1 phosphorylation can be between 5-50%, 5-45%, 5-40%, 5-30%, 5-20%, 5-10%, 10-50%, 10-45%, 10-40%, 10-30%, 10-20%, 20-50%, 20-45%, 20-40%, 20-30%, 30-50%, 30-45%, 30-40%, 40-50%, or any value therebetween or ranges within these ranges. The phosphorylation of 4EBP1 is reduced (or blunted) as compared to T-Rapa cells. In some embodiments, the increase in 4EBP1 phosphorylation can be measured at 32 hours post-initiation of culture.

In some embodiments, a population of manufactured T cells exhibits reduced P70S6K expression relative to T-Rapa cells and increased relative to said control population of T cells characteristic of the cells form which the manufactured T cells were produced. By way of example, but not limitation, the increase can be by at least 10%, 20%, 30%, 40%, 50% or more and the reduction can be by 50%, 60%, 70%, 80% or more.

In some embodiments, a population of manufactured T cells exhibits reduced expression of the IL-2 receptor CD25 by flow cytometry relative to T-Rapa cells. By way of example, but not limitation, the reduction can be by at least 50%, 60%, 70%, 80%, 90% or more.

In some embodiments, a manufactured T cell can express a unique RNA expression profile relative to culture input T cells, characterized by a 50% or greater increase in RNA content of de-differentiation molecules such as KLF4, KLF10, Nanog and combinations thereof and a 50% or greater decrease in RNA content of differentiation molecules such as perforin, granzyme B, IFN-γ, and combinations thereof.

In some embodiments, a population of manufactured T cells exhibits reduced levels of the following molecules associated with immune suppressive effects relative to T-Rapa cells: CTLA4; and TIM3.

In some embodiments, a population of manufactured T cells can be characterized by 10% or less of the CD4+ or CD8+ manufactured T cells expressing CTLA4 as measured by flow cytometry. In some embodiments, the population of manufactured T cells can be characterized by 5% or less of the CD4+ or CD8+ manufactured T cells expressing CTLA4 as measured by flow cytometry. By way of example, but not limitation, 10%, 9%, 8%, 7%, 6%, 5%, 4%, 3%, 2%, 1% or less of the CD4+ or CD8+ T cells in the population of manufactured T cells can express CTLA4 as measured by flow cytometry. In some embodiments, the population of manufactured T cells can exhibit a reduced frequency of CD4+ or CD8+ T cells expressing CTLA4 relative to the corresponding frequency of CD4+ or CD8+ T-Rapa cells expressing CTLA4 as measured by flow cytometry. In some embodiments, the reduced frequency of CD4+ or CD8+ T cells expressing CTLA4 can be at least 50% less than the corresponding frequency of CD4+ or CD8+ T-Rapa cells expressing CTLA4. By way of example, but not limitation, the reduced frequency can be at least 50%, 60%, 70%, 80%, 90%, 95% or 99% less than the corresponding frequency. In some embodiments, the reduced frequency is 6 days after the cells resulting in the manufactured T cells were inoculated into culture.

In some embodiments, a population of manufactured T cells can be characterized by 10% or less of the CD4+ or CD8+ manufactured T cells expressing TIM3 as measured by flow cytometry. In some embodiments, the population of manufactured T cells can be characterized by 5% or less of the CD4+ or CD8+ manufactured T cells expressing TIM3 as measured by flow cytometry. By way of example, but not limitation, 10%, 9%, 8%, 7%, 6%, 5%, 4%, 3%, 2% 1% or less of the CD4+ or CD8+ T cells in the population of manufactured T cells can express TIM3 as measured by flow cytometry. In some embodiments, the population of manufactured T cells can exhibit a reduced frequency of CD4+ or CD8+ T cells expressing TIM3 relative to a corresponding frequency of CD4+ or CD8+ T cells expressing TIM3 in a control population of T cells characteristic of T cells from which the manufactured T cells were produced as measured by flow cytometry. In some embodiments, the reduced frequency of CD4+ or CD8+ T cells expressing TIM3 can be at least 50% less than the corresponding frequency of CD4+ or CD8+ T cells expressing TIM3 in the control population. By way of example, but not limitation, the reduced frequency of CD4+ or CD8+ T cells expressing TIM3 can be at least 50%, 60%, 70%, 80%, 90%, 95% or 99% less than the corresponding frequency of CD4+ or CD8+ T cells expressing TIM3 in the control population. In some embodiments, the reduced frequency is 6 days after the cells resulting in the manufactured T cells were inoculated into culture. In some embodiments, the population of manufactured T cells can exhibit a reduced frequency of CD4+ or CD8+ T cells expressing TIM3 relative to a corresponding frequency of CD4+ or CD8+ T-Rapa cells expressing TIM3 as measured by flow cytometry. In some embodiments, the reduced frequency of CD4+ or CD8+ T cells expressing TIM3 can be at least 50% less than the corresponding frequency of CD4+ or CD8+ T-Rapa cells expressing TIM3. By way of example, but not limitation, the reduced frequency of CD4+ or CD8+ T cells expressing TIM3 can be at least 50%, 60%, 70%, 80%, 90%, 95% or 99% less than the corresponding frequency of CD4+ or CD8+ T-Rapa cells expressing TIM3. In some embodiments, the reduced frequency is 6 days after the cells resulting in the manufactured T cells were inoculated into culture.

In some embodiments, a population of manufactured T cells can be characterized by 5% or less of the CD4+ or CD8+ manufactured T cells expressing PD1 as measured by flow cytometry. By way of example, but not limitation, 5%, 4%, 3%, 2%, 1% or less of the CD4+ or CD8+ T cells in the population of manufactured T cells can express PD1 as measured by flow cytometry. In some embodiments, the population of manufactured T cells can exhibit a frequency of CD4+ or CD8+ T cells expressing PD1 relative to a corresponding frequency of CD4+ and CD8+ T-Rapa cells expressing PD1 as measured by flow cytometry. In some embodiments, the reduced frequency of CD4+ or CD8+ T cells expressing PD1 can be at least 50% less than the corresponding frequency of CD4+ or CD8+ T-Rapa cells expressing PD1. By way of example, but not limitation, the reduced frequency of CD4+ or CD8+ T cells expressing PD1 can be at least 50%, 60%, 70%, 80%, 90%, 95% or 99% less than the corresponding frequency of CD4+ or CD8+ T-Rapa cells expressing PD1. In some embodiments, the reduced frequency is 6 days after the cells resulting in the manufactured T cells were inoculated into culture.

In some embodiments, a population of manufactured T cells can be characterized by 5% or less of the CD4+ and CD8+ manufactured T cells expressing 2B4 as measured by flow cytometry. By way of example, but not limitation, 5%, 4%, 3%, 2%, 1% or less of the CD4+ or CD8+ T cells in the population of manufactured T cells can express 2B4 as measured by flow cytometry. In some embodiments, at least 0.1% of the CD4+ T cells in the population of manufactured T cells express 2B4 as measured by flow cytometry. By way of example, but not limitation, at least 0.1%, 0.2%, 0.3%, 0.5%, 0.6%, 0.7%, 0.8%, 0.9%, 1% or more of the CD4+ T cells in the population of manufactured T cells can express 2B4 as measured by flow cytometry. In some embodiments, the population of manufactured T cells can exhibit a reduced frequency of CD8+ T cells expressing 2B4 relative to a corresponding frequency of CD8+ T cells expressing 2B4 in control population of T cells characteristic of T cells from which the manufactured T cells were produced as measured by flow cytometry. By way of example, but not limitation, the reduced frequency of CD8+ T cells expressing 2B4 can be by at least 50%, 60%, 70%, or 80% less than the corresponding frequency of CD8+ T cells expressing 2B4 in the control population of T cells. In some embodiments, the reduced frequency is 6 days after the cells resulting in the manufactured T cells were inoculated into culture. In some embodiments, the population of manufactured T cells can exhibit a reduced frequency of CD4+ or CD8+ T cells expressing 2B4 relative to a corresponding frequency of CD4+ or CD8+ T-Rapa cells expressing 2B4 as measured by flow cytometry. By way of example, but not limitation, the reduced frequency of CD4+ or CD8+ T cells expressing 2B4 can be by at least 20%, 30%, 40%, 50%, 60%, 70% or 80% less than the corresponding frequency of CD4+ or CD8+ T-Rapa cells expressing 2B4. In some embodiments, the reduction is 6 days after the cells resulting in the manufactured T cells were inoculated into culture.

In some embodiments, a population of manufactured T cells can be characterized by 10% or less of the CD4+ or CD8+ manufactured T cells expressing LAIR1 as measured by flow cytometry. By way of example, but not limitation, 10%, 9%, 8%, 7%, 6%, 5%, 4%, 3%, 2%, 1% or less of the CD4+ or CD8+ T cells in the population of manufactured T cells can express LAIR1 as measured by flow cytometry. In some embodiments, the population of manufactured T cells can exhibit a reduced frequency of CD4+ or CD8+ T cells expressing LAIR1 relative to a corresponding frequency of CD4+ or CD8+ T cells expressing LAIR1 in a control population of T cells characteristic of T cells from which the manufactured T cells were produced as measured by flow cytometry. By way of example, but not limitation, the reduced frequency of CD4+ or CD8+ T cells expressing LAIR1 can be by at least 50%, 60%, 70%, 80%, 90%, 95% or 99% less than the corresponding frequency of CD4+ or CD8+ T cells expressing LAIR1 in the control population of T cells. In some embodiments, the reduced frequency is 6 days after the cells resulting in the manufactured T cells were inoculated into culture. In some embodiments, the CD4+ or CD8+ T cells of the population of manufactured T cells can exhibit a reduced level of expression of LAIR1 relative to T-Rapa cells as measured by flow cytometry. By way of example, but not limitation, the reduction can be by at least 30%, 40%, 50%, or more.

In some embodiments, a population of manufactured T cells can be characterized by 10% or less of the CD4+ or CD8+ manufactured T cells expressing TIGIT as measured by flow cytometry. By way of example, but not limitation, 10%, 9%, 8%, 7%, 6%, 5%, 4%, 3%, 2%, 1% or less of the CD4+ or CD8+ T cells in the population of manufactured T cells can express TIGIT as measured by flow cytometry. In some embodiments, at least 0.1% of the CD4+ T cells in the population of manufactured T cells express 2B4 as measured by flow cytometry. By way of example, but not limitation, at least 0.1%, 0.2%, 0.3%, 0.5%, 0.6%, 0.7%, 0.8%, 0.9%, 1% or more of the CD4+ T cells in the population of manufactured T cells can express TIGIT as measured by flow cytometry. In some embodiments, the population of manufactured T cells can exhibit a reduced frequency of CD4+ or CD8+ T cells expressing TIGIT relative to a corresponding frequency of CD4+ or CD8+ T-Rapa cells expressing TIGIT as measured by flow cytometry. By way of example, but not limitation, the reduced frequency of CD4+ or CD8+ T cells expressing TIGIT can be at least 40%, 50%, 60%, 70%, 80% or 90% less than the corresponding frequency of CD4+ or CD8+ T-Rapa cells expressing TIGIT. In some embodiments, the reduced frequency is 6 days after the cells resulting in the manufactured T cells were inoculated into culture.

In some embodiments, a population of manufactured T cells can be characterized by 10% or less of the CD4+ or CD8+ manufactured T cells expressing LAG3 as measured by flow cytometry. By way of example, but not limitation, 10%, 9%, 8%, 7%, 6%, 5%, 4%, 3%, 2%, 1% or less of the CD4+ or CD8+ T cells in the population of manufactured T cells can express LAG3 as measured by flow cytometry. In some embodiments, the population of manufactured T cells can exhibit a reduced frequency of CD4+ or CD8+ T cells expressing LAG3 relative to a corresponding frequency of CD4+ or CD8+ T-Rapa cells expressing LAG3 as measured by flow cytometry. In some embodiments, the reduced frequency of CD4+ or CD8+ T cells expressing LAG3 can be by at least 50% less than the corresponding frequency of CD4+ or CD8+ T-Rapa cells expressing LAG3. By way of example, but not limitation, the reduced frequency of CD4+ or CD8+ T cells expressing LAG3 can be at least 50%, 60%, 70%, 80%, 90%, 95% or 99% less than the corresponding frequency of CD4+ or CD8+ T-Rapa cells expressing LAG3. In some embodiments, the reduced frequency is 6 days after the cells resulting in the manufactured T cells were inoculated into culture In some embodiments, a population of manufactured T cells can be characterized by a preserved level, i.e. substantially the same level, of positive co-stimulatory molecule CD28 relative to a control population of T cells characteristic of T cells from which the manufactured T cells were produced as measured by flow cytometry. In some embodiments, the frequency of CD28 expression in CD4+ or CD8+ T cells in the population of manufactured T cells can be within about 20% of the frequency of CD28 expression in CD4+ or CD8+ T cells in the control population, respectively. By way of example, but not limitation, the frequency of CD28 expression in CD4+ or CD8+ T cells in the population of manufactured T cells can be within 20%, 15%, 10%, 9%, 8%, 7%, 6%, 5%, 4%, 3%, 2%, or 1% of the frequency of CD28 expression in CD4+ or CD8+ T cells in the control population, respectively. In some embodiments, this preservation is 6 days after the cells resulting in the manufactured T cells were inoculated into culture.

In some embodiments, a population of manufactured T cells can be characterized by a preserved level, i.e. substantially the same level, of positive co-stimulatory molecule ICOS relative to a control population of T cells characteristic of T cells from which the manufactured T cells were produced as measured by flow cytometry. In some embodiments, the frequency of ICOS expression in CD4+ or CD8+ T cells in the population of manufactured T cells can be within about 20% of the frequency of ICOS expression in CD4+ or CD8+ T cells in the control population, respectively. By way of example, but not limitation, the frequency of ICOS expression in CD4+ or CD8+ T cells in the population of manufactured T cells can be within 20%, 15%, 10%, 9%, 8%, 7%, 6%, 5%, 4%, 3%, 2%, or 1% of the frequency of ICOS expression in CD4+ or CD8+ T cells in the control population, respectively. In some embodiments, this preservation is 6 days after the cells resulting in the manufactured T cells were inoculated into culture.

In some embodiments, a population of manufactured T cells can be characterized by a preserved level, i.e. substantially the same level, of CD45RA relative to a control population of T cells characteristic of T cells from which the manufactured T cells were produced as measured by flow cytometry. In some embodiments, the frequency of CD45RA expression in CD4+ or CD8+ T cells in the population of manufactured T cells can be within about 20% of the frequency of CD45RA expression in CD4+ or CD8+ T cells in the control population, respectively. By way of example, but not limitation, the frequency of CD45RA expression in CD4+ or CD8+ T cells in the population of manufactured T cells can be within 20%, 15%, 10%, 9%, 8%, 7%, 6%, 5%, 4%, 3%, 2%, or 1% of the frequency of CD45RA expression in CD4+ or CD8+ T cells in the control population, respectively. In some embodiments, this preservation is 6 days after the cells resulting in the manufactured T cells were inoculated into culture.

In some embodiments, a population of manufactured T cells can be characterized by 5% or less of the CD4+ or CD8+ manufactured T cells expressing CD25 as measured by flow cytometry. By way of example, but not limitation, 5%, 4%, 3%, 2%, 1% or less of the CD4+ or CD8+ T cells in the population of manufactured T cells can express CD25 as measured by flow cytometry. In some embodiments, the population of manufactured T cells can exhibit a reduced frequency of CD4+ or CD8+ T cells expressing CD25 relative to a corresponding frequency of CD4+ or CD8+ T-Rapa cells expressing CD25 as measured by flow cytometry. In some embodiments, the reduced frequency of CD4+ or CD8+ T cells expressing CD25 can be at least 50% less than the corresponding frequency of CD4+ or CD8+ T-Rapa cells expressing CD25. By way of example, but not limitation, the reduced frequency of CD4+ or CD8+ T cells expressing CD25 can be at least 50%, 60%, 70%, 80%, 90%, 95% or 99% less than the corresponding frequency of CD4+ or CD8+ T-Rapa cells expressing CD25. In some embodiments, the reduced frequency is 6 days after the cells resulting in the manufactured T cells were inoculated into culture.

In some embodiments, a population of manufactured T cells exhibits a quiescent and non-senescent phenotype characterized by a reduced level KLRG1, as measured by flow cytometry. In some embodiments, the reduction in the level of KLRG1 is 6 days after the cells resulting in the manufactured T cells were inoculated into culture. In some embodiments, a population of manufactured T cells can be characterized by 5% or less of the CD4+ or CD8+ manufactured T cells expressing KLRG1 as measured by flow cytometry. By way of example, but not limitation, 5%, 4%, 3%, 2%, 1% or less of the CD4+ or CD8+ T cells in the population of manufactured T cells can express KLRG1 as measured by flow cytometry. In some embodiments, the population of manufactured T cells can exhibit a reduced frequency of CD4+ or CD8+ T cells expressing KLRG1 relative to a corresponding frequency of CD4+ or CD8+ T-Rapa cells expressing KLRG1 as measured by flow cytometry. In some embodiments, the reduced frequency of CD4+ or CD8+ T cells expressing KLRG1 can be at least 50% less than the corresponding frequency of CD4+ or CD8+ T-Rapa cells expressing KLRG1. By way of example, but not limitation, the reduced frequency of CD4+ or CD8+ T cells expressing KLRG1 can be at least 50%, 60%, 70%, 80%, 90%, 95% or 99% less than the corresponding frequency of CD4+ or CD8+ T-Rapa cells expressing KLRG1.

In some embodiments, the reduced frequency is 6 days after the cells resulting in the manufactured T cells were inoculated into culture. In some embodiments, the reduced frequency is 6 days after the cells resulting in the manufactured T cells were inoculated into culture.

In some embodiments, a population of manufactured T cells exhibits reduced expression of the immune suppression molecule CD39 relative to a control population of T cells characteristic of the T cells from which the manufactured T cells were produced. In some embodiments, a population of manufactured T cells can be characterized by 20% or less of the CD4+ or CD8+ manufactured T cells expressing CD39 as measured by flow cytometry. By way of example, but not limitation, 20%, 19%, 18%, 17%, 16%, 15%, 14%, 13%, 12%, 11%, 10%, 9%, 8%, 7%, 6%, 5% or less of the CD4+ or CD8+ T cells in the population of manufactured T cells can express CD39 as measured by flow cytometry. In some embodiments, the population of manufactured T cells can exhibit a reduced frequency of CD4+ or CD8+ T cells expressing CD39 relative to a corresponding frequency of CD4+ or CD8+ T-Rapa cells expressing CD39 as measured by flow cytometry. In some embodiments, the reduced frequency of CD4+ or CD8+ T cells expressing CD39 can be at least 50% less than the corresponding frequency of CD4+ or CD8+ T-Rapa cells expressing CD39. By way of example, but not limitation, the reduced frequency of CD4+ or CD8+ T cells expressing CD39 can be at least 50%, 60%, 70%, 80%, 90%, 95% or 99% less than the corresponding frequency of CD4+ or CD8+ T-Rapa cells expressing CD39. In some embodiments, the reduced frequency is 6 days after the cells resulting in the manufactured T cells were inoculated into culture.

In some embodiments, a population of manufactured T cells exhibits reduced expression of the immune suppression molecule CD73 relative to a control population of T cells characteristic of the T cells from which the manufactured T cells were produced. In some embodiments, a population of manufactured T cells can be characterized by 20% or less of the CD4+ or CD8+ manufactured T cells expressing CD73 as measured by flow cytometry. By way of example, but not limitation, 20%, 19%, 18%, 17%, 16%, 15%, 14%, 13%, 12%, 11%, 10%, 9%, 8%, 7%, 6%, 5% or less of the CD4+ or CD8+ T cells in the population of manufactured T cells can express CD73 as measured by flow cytometry. In some embodiments, the population of manufactured T cells can exhibit a reduced frequency of CD4+ or CD8+ T cells expressing CD73 relative to a corresponding frequency of CD4+ or CD8+ T-Rapa cells expressing CD73 as measured by flow cytometry. In some embodiments, the reduced frequency of CD4+ or CD8+ T cells expressing CD73 can be at least 50% less than the corresponding frequency of CD4+ or CD8+ T-Rapa cells expressing CD73. By way of example, but not limitation, the reduced frequency of CD4+ or CD8+ T cells expressing CD73 can be at least 50%, 60%, 70%, 80%, 90%, 95% or 99% less than the corresponding frequency of CD4+ or CD8+ T-Rapa cells expressing CD73. In some embodiments, the reduced frequency is 6 days after the cells resulting in the manufactured T cells were inoculated into culture.

In some embodiments, a population of manufactured T cells exhibits reduced expression of the immune suppression molecule GITR relative to a control population of T cells characteristic of the T cells from which the manufactured T cells were produced. In some embodiments, a population of manufactured T cells can be characterized by 5% or less of the CD4+ or CD8+ manufactured T cells expressing GITR as measured by flow cytometry. By way of example, but not limitation, 5%, 4%, 3%, 2%, 1% or less of the CD4+ or CD8+ T cells in the population of manufactured T cells can express GITR as measured by flow cytometry. In some embodiments, the population of manufactured T cells can exhibit a reduced frequency of CD4+ or CD8+ T cells expressing GITR relative to a corresponding frequency of CD4+ or CD8+ T-Rapa cells expressing GITR as measured by flow cytometry. In some embodiments, the reduced frequency of CD4+ or CD8+ T cells expressing GITR can be at least 20% less than relative to the corresponding frequency of CD4+ or CD8+ T-Rapa cells expressing GITR. By way of example, but not limitation, the reduced frequency of CD4+ or CD8+ T cells expressing GITR can be at least 20%, 30%, 40%, 50%, 60%, 70%, 80%, 90%, 95% or 99% less than the corresponding frequency of CD4+ or CD8+ T-Rapa cells expressing GITR. In some embodiments, the reduced frequency is 6 days after the cells resulting in the manufactured T cells were inoculated into culture.

In some embodiments, a manufactured T cell can exhibit an early differentiation state of cytokine biology relative to a control T cell culture, as evidenced by an increase in secretion of the precursor cytokine IL-2 and increased responsiveness to the homeostatic cytokines IL-7 and IL-15. In this manner, the manufacturing method of the present disclosure describes a process for the manufacture of helper-independent T cells with increased reactivity to homeostatic cytokines.

In some embodiments, a population of manufactured T cells exhibits increased IL-2 secretion relative to a T-Rapa culture incubated under the same conditions. In some embodiments, this increase in IL-2 secretion is at least 1.1-fold. By way of example, but not limitation, the increase can be at least 1.1-, 1.5-, 2.0-, 2.5-, 3.0-, 3.5-, 4.0-, 4.5-, 5.0-fold or more. In some embodiments, the population of manufactured T cells secretes at least 500 pg/mL/1×10⁶ cells/day IL-2 after co-stimulation with anti-CD3/anti-CD28 coated magnetic beads at a ratio between 3:1 and 1:3 beads:T cells. By way of example, the population of manufactured T cells can secrete about 500, 600, 700, 800, 900, 1000 or more pg/mL/1×10⁶ cells/day of IL-2 under these conditions.

In some embodiments, the population of manufactured T cells can secrete an increased amount of IL-2 when exposed to IL-7 or IL-15. In some embodiments, the population of manufactured T cells is characterized by an increase in IL-2 secretion of at least 1.1-fold when the population of manufactured T cells is incubated in the presence of IL-7 or IL-15 relative to conditions without the presence of IL-7 or IL-15. By way of example, but not limitation, the increase can be at least 1.1-, 1.2-, 1.3-, 1.4-, 1.5-, 1.6-, 1.7-, 1.8-, 1.9-, 2.0-fold or more. In some embodiments, the population of manufactured T cells secretes at least 1000 pg/mL/1×10⁶ cells/day IL-2 after co-stimulation with anti-CD3/anti-CD28 coated magnetic beads at a ratio between 3:1 and 1:3 beads:T cells and exposure to IL-7, IL-15 or both IL-7 and IL-15 at a concentration of 10 ng/mL of IL-7 and 10 ng/mL IL-15 when present. By way of example, the population of manufactured T cells can secrete about 1000, 1100, 1200, 1300, 1400, 1500, 1600, 1700, 1800, 1900, 2000 or more pg/mL/1×10⁶ cells/day of IL-2 under these conditions. IL-2 secretion is associated with helper-independent T cells. The high IL-2 secretion of Rapa-T cells can be advantageous by obviating the need to administer exogenous IL-2 after T cell adoptive therapy. In some embodiments, the IL-7 or IL-15 is added at 10 ng/mL, if present.

In some embodiments, said population of manufactured T cells exhibits increased in vivo function relative to said control population T cells, said in vivo function characterized by increased human T cell engraftment in a model of human-into-mouse xenogeneic graft-versus-host-disease.

In some embodiments, said population of manufactured T cells exhibits a reduction in mTORC1 activation as measured by phosphor-P70S6K. Said reduction can be, by way of example but not limitation, at least 50%, at least 60%, at least 70%, at least 80%, at least 90%, at least 95%, or at least 99% relative to T-Rapa cells at 32 hours after culture initiation.

In some embodiments, said population of manufactured T cells exhibits decreased phosphor-STAT5 relative to T-Rapa cells. Said reduction can be, by way of example but not limitation, at least 50%, at least 60%, at least 70%, at least 80%, at least 90%, at least 95%, or at least 99% relative to T-Rapa cells at 32 hours after culture initiation.

In some embodiments, said population of manufactured T cells exhibits decreased phosphor-STAT5 relative to a control population of cultured T-Rapa cells. Said reduction can be, by way of example, but not limitation, at least 50% relative to the control population of cultured T-Rapa cells. In some embodiments, said reduction is at 48 hours after the manufactured T cells were inoculated into culture from an input population of cells comprising T cells. In some embodiments, the p-STAT5 level is as measured by Western blot.

In some embodiments, said population of manufactured T cells exhibits at least some detectable level of STAT1 and phosphor-STAT1. In some embodiments, said level is measured at 48 hours after the manufactured T cells were inoculated into culture from an input population of cells comprising T cells. In some embodiments, the population of manufactured T cells exhibits decreased phosphor-STAT5 relative to a control population of T cells and at least some level of STAT1 and phosphor-STAT1. In some embodiments, the level of STAT1 or p-STAT1 is as measured by Western blot.

In some embodiments, said population of manufactured T cells exhibits a reduction in mTORC1 activation as measured by p70S6K or Raptor expression relative to a control population of T cells characteristic of the T cells from which the population of manufactured T cells was obtained. Said reduction can be, by way of example, but not limitation, by 50%. In some embodiments, said reduction is at 48 hours after the manufactured T cells were inoculated into culture from an input population of cells comprising T cells. In some embodiments, the reduction is as measured by Western blot.

In some embodiments, said population of manufactured T cells exhibits approximately the same level of Rictor, SGK1 or phosphorylated SGK1 relative to a control population of T cells. By way of example, but not limitation, the level of Rictor, SGK1 or phosphorylated SGK1 can be within 50%, 40%, 30%, 20%, 10% or 5% or the corresponding level of Rictor, SGK1 or phosphorylated SGK1 in T-Rapa cells. In some embodiments, said level is at 48 hours after the manufactured T cells were inoculated into culture from an input population of cells comprising T cells. In some embodiments, the level of Rictor, SGK1 or pSGK1 is at least the level as measured in the control population of T cells. In some embodiments, the level is as measured by Western blot.

In some embodiments, a population of manufactured T cells exhibits an increase in secretion of at least one of IFN-γ, TNF-α, GM-CSF and IL-2 relative to T-Rapa cells after expansion in culture media for 6 days after manufacturing without inhibitors. Said increase can be, by way of example, but not limitation, at least 50%, at least 60%, at least 70%, at least 80%, at least 90%, at least 95%, at least 99% or more.

In some embodiments, a population of manufactured T cells at the end of manufacturing (day 6 in culture) can have an increased number of CD4+ T cells that express the T cell marker CD45RA relative to T-Rapa cells. Said increase can be, by way of example, but not limitation, at least 50%, at least 60%, at least 70%, at least 80%, at least 90%, at least 95%, at least 99% or more.

In some embodiments, a population of manufactured T cells can have reduced expression of one or more checkpoint inhibitor receptors selected from CD39, CD73, GITR, LAG3, PD1, 2B4, LAIR1, CTLA4, KLRG1, TIGIT, and TIM3. By way of example, but not limitation, the reduced expression can be at least 25% less than a corresponding level of expression in a T-Rapa cell. By way of further example, but not limitation, the reduced expression can be at least 25%, 50%, 75%, 80%, 85%, 90%, 95% or 99% less than a corresponding level of expression in a population of T-Rapa cells. In some embodiments, a population of manufactured T cells can have a level of expression of one or more checkpoint inhibitors selected from CD39, CD73, GITR, LAG3, PD1, 2B4, LAIR1, CTLA4, KLRG1, TIGIT and TIM3 that is within about 25% of a corresponding level of expression in a control T cell population characteristic of the T cells from which the population of manufactured T cells was produced. By way of example, but not limitation, the level of expression of the one or more checkpoint inhibitors selected from CD39, CD73, GITR, LAG3, PD1, 2B4, LAIR1, CTLA4, KLRG1, TIGIT and TIM3 can be within about 25%, 20%, 15%, 10%, or 5% of a corresponding level of expression in the control T cell population characteristic of the T cells from which the population of manufactured T cells was produced. It should be understood that the expression levels for the checkpoint inhibitors are compared between the same cell types, e.g. a CD4+ manufactured T cell would be compared to a CD4+ T-Rapa cell or CD4+ control T cell characteristic of the T cells from which the manufactured T cell was produced.

In some embodiments, a manufactured T cell can have reduced expression of one or more checkpoint inhibitor receptors selected from CD39, CD73, GITR, LAG3, PD1, 2B4, LAIR1, CTLA4, KLRG1, TIGIT and TIM3. By way of example, but not limitation, the reduced expression can be at least 25% less than a corresponding level of expression in a T-Rapa cell. By way of further example, but not limitation, the reduced expression can be at least 25%, 50%, 75%, 80%, 85%, 90%, 95% or 99% less than a corresponding level of expression in a T-Rapa cell. In some embodiments, a manufactured T cell can have a level of expression of one or more checkpoint inhibitors selected from CD39, CD73, GITR, LAG3, PD1, 2B4, LAIR1, CTLA4, KLRG1, TIGIT and TIM3 that is within about 25% of a corresponding level of expression in a control T cell characteristic of the T cells from which the manufactured T cell was produced. By way of example, but not limitation, the level of expression of the one or more checkpoint inhibitors selected from CD39, CD73, GITR, LAG3, PD1, 2B4, LAIR1, CTLA4, KLRG1, TIGIT and TIM3 can be within about 25%, 20%, 15%, 10%, or 5% of a corresponding level of expression in the control T cell characteristic of the T cells from which the manufactured T cell was produced. It should be understood that the expression levels for the checkpoint inhibitors are compared between the same cell types, e.g. a CD4+ manufactured T cell would be compared to a CD4+ T-Rapa cell or CD4+ control T cell characteristic of the T cells from which the manufactured T cell was produced.

In some embodiments, a manufactured T cell has increased expression of CD127 relative to a control T cell characteristic of the cells from which the manufactured T cell was produced. By way of example, but not limitation, this increase can be at least 10%, 20%, 30%, 40%, 50% or more.

In some embodiments a population of manufactured T cells can have at least 5% of CD4+ T cells that express CD127 as measured by flow cytometry. By way of example, the population of manufactured T cells can have at least 5%, 6%, 7%, 8%, 9%, 10% or more of CD4+ T cells that express CD127 as measured by flow cytometry. In some embodiments a population of manufactured T cells can have an increased frequency of CD4+ T cells that express CD127 relative to a control population of T cells characteristic of the cells from which the population of manufactured T cells was produced. By way of example, but not limitation, the increase can be at least 50%, 100%, 150%, 200%, 300% or more.

To the extent that any of the foregoing properties associated with populations of manufactured T cells can be associated with a single cell, a manufactured T cell can be characterized by said properties. In any of the foregoing embodiments, a manufactured T cell or population of manufactured T cells can have more than one of the recited properties.

Methods of Making Antigen-Presenting T Cells, Sensitized, Manufactured T Cells, Loaded, Antigen-Presenting T Cells and Compositions Thereof Methods of Making Antigen-Presenting T Cells In some embodiments, a method for producing antigen-presenting T cells is provided that can include: inoculating manufactured T cells or a population thereof of any of the foregoing embodiments and of the present disclosure in a culture medium comprising IL-7 and IL-15; optionally, adding anti-CD3/anti-CD28 co-stimulation to the culture medium; and incubating the manufactured T cells or population thereof for a period of time to yield a population of antigen-presenting T cells. It should be understood that the IL-7 and IL-15 can be present in the culture medium prior to inoculating the at least a portion of the manufactured T cells or population thereof in the culture medium or can be added to the culture medium after inoculating the at least a portion of manufactured T cells or population thereof. In some embodiments, anti-CD3/anti-CD28 co-stimulation, as understood herein, is added to the culture. Thus, the foregoing methods of producing manufactured T cells can comprise these and any other steps disclosed herein for producing antigen-presenting T cells.

In any of the foregoing embodiments for producing antigen-presenting T cells, the manufactured T cells or population thereof can be inoculated in the culture medium at a starting concentration of about $1 \times 10^6$ T cells per mL to $50 \times 10^6$ cells per mL. By way of example but not limitation, said cell density may be about $1 \times 10^6$ cells per mL to $5 \times 10^6$ cells per mL, $1 \times 10^6$ cells per mL to $10 \times 10^6$ cells per mL, $1 \times 10^6$ cells per mL to $15 \times 10^6$ cells per mL, $15 \times 10^6$ cells per mL to $22.5 \times 10^6$ cells per mL, $10 \times 10^6$ cells per mL to $22.5 \times 10^6$ cells per mL, $10 \times 10^6$ cells per mL to $22.5 \times 10^6$ cells per mL, $5 \times 10^6$ cells per mL to $22.5 \times 10^6$ cells per mL, $1 \times 10^6$ cell per mL to $50 \times 10^6$ cells per mL, $10 \times 10^6$ cells per mL to $40 \times 10^6$ cells per mL, $20 \times 10^6$ cells per mL to $40 \times 10^6$ cells per mL, $1 \times 10^6$ cells per mL, $2.5 \times 10^6$ cells per mL, $5 \times 10^6$ cells per mL, $7.5 \times 10^6$ cells per mL, $10 \times 10^6$ cells per mL, $12.5 \times 10^6$ cells per mL, $15 \times 10^6$ cells per mL, $17.5 \times 10^6$ cells per mL, $20 \times 10^6$ cells per mL, $22.5 \times 10^6$ cells per mL, $25 \times 10^6$ T cells per mL, $30 \times 10^6$ cells per mL, $35 \times 10^6$ cells per mL, $40 \times 10^6$ cells per mL, $45 \times 10^6$ cells per mL, or $50 \times 10^6$ cells per mL.

In any of the foregoing embodiments for producing antigen-presenting T cells, the culture medium can further comprise X-Vivo 20 medium. In any of the foregoing embodiments, said culture medium can further comprise TexMACS (Miltenyi®) medium. Any suitable culture medium can be used for culturing T cells.

In any of the foregoing embodiments for producing antigen-presenting T cells, the IL-7 can be added to or present in the culture medium at from about 0.1 ng/mL to about 100 ng/mL. By way of example, but not limitation, the IL-7 can be added to or present in the culture medium at from about 0.1 ng/mL to about 100 ng/mL, about 0.1 ng/mL to about 50 ng/mL, about 0.1 ng/mL to about 10 ng/mL, about 0.1 ng/mL to about 5 ng/mL, about 0.1 ng/mL to about 1 ng/mL, about 1 ng/mL to about 10 ng/mL, about 1 ng/mL to about 20 ng/mL, about 1 ng/mL to about 25 ng/mL, about 1 ng/mL to about 30 ng/mL, about 1 ng/mL to about 40 ng/mL, about 1 ng/mL to about 50 ng/mL, about 1 ng/mL to about 75 ng/mL, about 5 ng/mL to about 10 ng/mL, about 5 ng/mL to about 20 ng/mL, about 5 ng/mL to about 25 ng/mL, about 5 ng/mL to about 30 ng/mL, about 5 ng/mL to about 40 ng/mL, about 5 ng/mL to about 50 ng/mL, about 5 ng/mL to about 75 ng/mL, about 5 ng/mL to about 100 ng/mL, about 10 ng/mL to about 20 ng/mL, about 10 ng/mL to about 25 ng/mL, about 10 ng/mL to about 30 ng/mL, about 10 ng/mL to about 40 ng/mL, about 10 ng/mL to about 50 ng/mL, about 10 ng/mL to about 75 ng/mL, about 10 ng/mL to about 100 ng/mL, about 20 ng/mL to about 30 ng/mL, about 20 ng/mL to about 40 ng/mL, about 20 ng/mL to about 50 ng/mL, about 20 ng/mL to about 75 ng/mL, about 20 ng/mL to about 100 ng/mL, about 25 ng/mL to about 40 ng/mL, about 25 ng/mL to about 50 ng/mL, about 25 ng/mL to about 75 ng/mL, about 25 ng/mL to about 100 ng/mL, about 30 ng/mL to about 40 ng/mL, about 30 ng/mL to about 50 ng/mL, about 30 ng/mL to about 75 ng/mL, about 30 ng/mL to about 100 ng/mL, about 40 ng/mL to about 50 ng/mL, about 40 ng/mL to about 75 ng/mL, about 40 ng/mL to about 100 ng/mL, about 50 ng/mL to about 75 ng/mL, about 50 ng/mL to about 100 ng/mL, about 75 ng/mL to about 100 ng/mL, about 1 ng/mL, about 2 ng/mL, about 3 ng/mL, about 4 ng/mL, about 5 ng/mL, about 6 ng/mL, about 7 ng/mL, about 8 ng/mL, about 9 ng/mL, about 10 ng/mL, about 12.5 ng/mL, about 15 ng/mL, about 20 ng/mL, about 25 ng/mL, about 30 ng/mL, about 40 ng/mL, about 50 ng/mL, about 75 ng/mL, or about 100 ng/mL. It should be understood that a sufficient amount of IL-7 can be present in or added to the culture medium in an amount sufficient to improve the antigen-presentation capacity of the manufactured T cells.

In any of the foregoing embodiments for producing antigen-presenting T cells, the IL-15 can be added to or present in the culture medium at from about 0.1 ng/mL to about 100 ng/mL. By way of example, but not limitation, the IL-15 can be added to or present in the culture medium at from about 0.1 ng/mL to about 100 ng/mL, about 0.1 ng/mL to about 50 ng/mL, about 0.1 ng/mL to about 10 ng/mL, about 0.1 ng/mL to about 5 ng/mL, about 0.1 ng/mL to about 1 ng/mL, about 1 ng/mL to about 10 ng/mL, about 1 ng/mL to about 20 ng/mL, about 1 ng/mL to about 25 ng/mL, about 1 ng/mL to about 30 ng/mL, about 1 ng/mL to about 40 ng/mL, about 1 ng/mL to about 50 ng/mL, about 1 ng/mL to about 75 ng/mL, about 5 ng/mL to about 10 ng/mL, about 5 ng/mL to about 20 ng/mL, about 5 ng/mL to about 25 ng/mL, about 5 ng/mL to about 30 ng/mL, about 5 ng/mL to about 40 ng/mL, about 5 ng/mL to about 50 ng/mL, about 5 ng/mL to about 75 ng/mL, about 5 ng/mL to about 100 ng/mL, about 10 ng/mL to about 20 ng/mL, about 10 ng/mL to about 25 ng/mL, about 10 ng/mL to about 30 ng/mL, about 10 ng/mL to about 40 ng/mL, about 10 ng/mL to about 50 ng/mL, about 10 ng/mL to about 75 ng/mL, about 10 ng/mL to about 100 ng/mL, about 20 ng/mL to about 30 ng/mL, about 20 ng/mL to about 40 ng/mL, about 20 ng/mL to about 50 ng/mL, about 20 ng/mL to about 75 ng/mL, about 20 ng/mL to about 100 ng/mL, about 25 ng/mL to about 40 ng/mL, about 25 ng/mL to about 50 ng/mL, about 25 ng/mL to about 75 ng/mL, about 25 ng/mL to about 100 ng/mL, about 30 ng/mL to about 40 ng/mL, about 30 ng/mL to about 50 ng/mL, about 30 ng/mL to about 75 ng/mL, about 30 ng/mL to about 100 ng/mL, about 40 ng/mL to about 50 ng/mL, about 40 ng/mL to about 75 ng/mL, about 40 ng/mL to about 100 ng/mL, about 50 ng/mL to about 75 ng/mL, about 50 ng/mL to about 100 ng/mL, about 75 ng/mL to about 100 ng/mL, about 1 ng/mL, about 2 ng/mL, about 3 ng/mL, about 4 ng/mL, about 5 ng/mL, about 6 ng/mL, about 7 ng/mL, about 8 ng/mL, about 9 ng/mL, about 10 ng/mL, about 12.5 ng/mL, about 15 ng/mL, about 20 ng/mL, about 25 ng/mL, about 30 ng/mL, about 40 ng/mL, about 50 ng/mL, about 75 ng/mL, or about 100 ng/mL. It should be understood that a sufficient amount of IL-15 can be present in or added to the culture medium in an amount sufficient to improve the antigen-presentation capacity of the manufactured T cells.

In any of the foregoing embodiments for producing antigen-presenting T cells, the culture medium can have GM-CSF added to or present in the culture medium at from about 10 ng/mL to about 1000 ng/mL. By way of example, but not limitation, the GM-CSF can be added to or present in the culture medium at from about 10 ng/mL to about 1000 ng/mL, about 10 ng/mL to about 500 ng/mL, about 10 ng/mL to about 100 ng/mL, about 10 ng/mL to about 50 ng/mL, about 100 ng/mL to about 1000 ng/mL, about 100 ng/mL to about 500 ng/mL, about 100 ng/mL to about 250 ng/mL, about 50 ng/mL to about 500 ng/mL, about 50 ng/mL to about 250 ng/mL, about 10 ng/mL, about 25 ng/mL, about 50 ng/mL, about 75 ng/mL, about 100 ng/mL, about 250 ng/mL, about 500 ng/mL, about 750 ng/mL, or about 1000 ng/mL. Alternatively, in some embodiments, the culture medium does not include GM-CSF and no GM-CSF is added to the culture medium.

In any of the foregoing embodiments for producing antigen-presenting T cells, the culture medium can have IL-4 added to or present in the culture medium at from about 100 IU/mL to about 10,000 IU/mL. By way of example, but not limitation, the IL-4 can be added to or present in the culture medium at from about 100 IU/mL to about 10,000 IU/mL, about 500 IU/mL to about 10,000 IU/mL, about 1000 IU/mL to about 10,000 IU/mL, about 2500 IU/mL to about 10,000 IU/mL, about 5000 IU/mL to about 10,000 IU/mL, about 500 IU/mL to about 5000 IU/mL, about 500 IU/mL to about 2500 IU/mL, about 500 IU/mL to about 2000 IU/mL, about 500 IU/mL to about 1500 IU/mL, about 2500 IU/mL to about 10,000 IU/mL, about 5000 IU/mL to about 10,000 IU/mL, about 100, 250, 500, 750, 1000, 1250, 1500, 1750, 2000, 2500, 3750, 5000, 6000, 7000, 8000, 9000, or 10,000 IU/mL. Alternatively, in some embodiments, the culture medium does not include IL-4 and no IL-4 is added to the culture medium.

In any of the foregoing embodiments for producing antigen-presenting T cells, the culture medium can have IL-2 added to or present in the culture medium at from about 20 IU/mL to about 1000 IU/mL. By way of example, but not limitation, the IL-2 can be added or present in the culture medium at from about 20 IU/mL to about 1000 IU/mL, about 50 IU/mL to about 1000 IU/mL, about 100 IU/mL to about 1000 IU/mL, about 250 IU/mL to about 1000 IU/mL, about 500 IU/mL to about 1000 IU/mL, about 20 IU/mL to about 500 IU/mL, about 50 IU/mL to about 500 IU/mL, about 100 IU/mL to about 500 IU/mL, about 20, 50, 100, 250, 500, 750 or 1000 IU/mL. Alternatively, in some embodiments, the culture medium does not include IL-2 and no IL-2 is added to the culture medium.

In any of the foregoing embodiments, the culture medium can not include dendritic cells.

In any of the foregoing embodiments for producing antigen-presenting T cells, the culture medium can further comprise 5% human serum, such as, by way of example, but not limitation, human AB serum. In some embodiments, said culture medium can further comprise 1%-20% human serum. By way of example but not limitation, said culture medium may comprise about 1%, 2%, 3%, 4%, 5%, 6%, 7%, 8%, 9%, 10%, 11%, 12%, 13%, 14%, 15%, 16%, 17%, 18%, 19% or 20% human serum. In some embodiments, said culture medium can comprise at least 1%, 2%, 3%, 4%, 5%, 6%, 7%, 8%, 9%, 10%, 11%, 12%, 13%, 14%, 15%, 16%, 17%, 18%, 19% or 20% human serum. In any of the foregoing embodiments for producing antigen-presenting T cells, no serum can be added to or present in the culture medium.

In any of the foregoing embodiments for producing antigen-presenting T cells, the anti-CD3/anti-CD28 co-stimulation can be performed by adding anti-CD3/anti-CD28-coated magnetic beads to the culture medium, where the bead:T cell ratio can be 1:3 to 3:1. By way of example but not limitation, ratios of 1:1, 1:1.5, 1:2, 1:2.5, 1:3, 1.5:1, 2:1, 2.5:1 and 3:1 can be used. It should be further understood that anti-CD3/anti-CD28 co-stimulation can be performed using anti-CD3/anti-CD28-coated magnetic beads or any equivalent monoclonal antibody or pharmacologic method, including but not limited to, using nanoparticles or microparticles or staphylococcal enterotoxin B (SEB) or lenalidomide. One of skill in the art can, through routine experimentation, determine the appropriate amount of these compounds to add to the culture to achieve the desired effect. By way of example, but not limitation, nanoparticles or microparticles can be used at the manufacturer's recommended concentration or within 3-10× more dilute or more concentrated. By way of further example, but not limitation, SEB can be used at about 1 μg/mL to about 100 μg/mL, such as at about 10 μg/mL or lenalidomide can be used at about 0.01 μmol/L to about 2.0 μmol/L. In some embodiments, co-stimulation of the culture input population of cells can be achieved using anti-CD3/anti-CD28 containing nanoparticles which can be used at a reduced concentration than recommended. By way of example, but not limitation, such nanoparticles can be used at about 0.01× to about 0.1×, about 0.025× to about 0.1×, about 0.05× to about 0.1×, about 0.075× to about 0.1×, about 0.01× to about 0.075×, about 0.01× to about 0.05×, about 0.01× to about 0.025×, about 0.025× to about 0.075×, about 0.025× to about 0.05×, about 0.05× to about 0.075×, or about 0.01×, about 0.025×, about 0.05×, about 0.075×, or about 0.01× the recommended dose. By way of example but not limitation, a reagent such as Miltenyi® T Cell TransAct™ could be used at a reduced dose compared to the recommended dose of 10 μL per $1 \times 10^6$ T cells such as, by way of example but not limitation, 1.1 μL (a nine-fold decrease) or about 0.11×. Alternatively, if anti-CD3/anti-CD28 co-stimulation is to be used for producing antigen-presenting T cells, the source of co-stimulation can be provided by dissolvable anti-CD3/anti-CD28 micropar- ticles. By way of example, but not limitation, the dissolvable anti-CD3/anti-CD28 microparticles can be used at 20% of the strength recommended by the manufacturer (e.g. Cloudz®; Bio-Techne). By way of further example, the dissolvable anti-CD3-anti-CD28 microparticles can be used at 5%, 10%, 15%, 20%, 25% or 30% of the manufacturer's recommended strength. The specific amount of anti-CD3/ anti-CD28 reagent to be added can be titrated based on the desired functional characteristics of the final antigen-pre- senting T cell product. Specifically, a sufficient amount of reagent can be added to maintain T cell viability in vitro in the presence of the inhibitory molecules described in the present disclosure. However, any specific anti-CD3/anti- CD28 reagent should not be added in excess, as defined by: inappropriately high level of T cell activation (increase in CD25 expression by flow cytometry relative to the T cell culture with the optimal, minimal amount of co-stimula- tion); inappropriately high level of T cell checkpoint inhibi- tor receptor expression by flow cytometry; and inappropri- ately altered expression of molecules associated with T cell effector memory cells by flow cytometry (such as reduction in levels of CD62L and CCR7; such as increase in levels of CD45RO and KLRG). In any of the foregoing embodiments for producing antigen-presenting T cells, the anti-CD3/anti- CD28 co-stimulation can be added at the time of inoculating the at least a portion of manufactured T cells or population thereof or at any time during the period time. By way of example, but not limitation, the co-stimulation can be added at about the start of incubation, at 24 hours post-inoculation, 36 hours post-inoculation, 42 hours post-inoculation, 48 hours post-inoculation, or 60 hours post-inoculation.

In any of the foregoing embodiments for producing antigen-presenting T cells, the period of time can be any suitable time to yield antigen-presenting T cells, such as from about 24 hours to about 72 hours. By way of example, but not limitation, the period of time can be about 12, about 18, about 24, about 30, about 36, about 42, about 48, about 54, about 60, about 66, about 72, from about 24 to about 72 hours, from about 24 to about 36 hours, from about 24 to about 48 hours, from about 24 to about 60 hours, from about 30 to about 72 hours, from about 30 to about 30 to about 48 hours, from about 30 to about 36 hours, from about 36 to about 72 hours, from about 36 to about 60 hours, from about 36 to about 48 hours, from about 48 hours to about 72 hours, from about 48 hours to about 60 hours, or from about 60 hours to about 72 hours.

In any of the foregoing embodiments for producing antigen-presenting T cells, the method can further include, prior to inoculating the manufactured T cells or population thereof, enriching the manufactured T cells or population thereof for CD4$^+$ T cells. By way of example, but not limitation, the manufactured T cells or population thereof, can be enriched to include about 50% to about 100% CD4$^+$ T cells, about 60% to about 100% CD4$^+$ T Cells, about 70% to about 100% CD4$^+$ T cells, about 80% to about 100% CD4$^+$ T cells, about 90% to about 100% CD4$^+$ T cells, about 95% to about 100% CD4$^+$ T cells, about 50% to about 60% CD4$^+$ T cells, about 60% to about 70% CD4$^+$ T cells, about 70% to about 80% CD4$^+$ T cells, about 80% to about 90% CD4$^+$ T cells, about 90% to about 95% CD4$^+$ T cells, about 60% to about 80% CD4$^+$ T cells, about 70% to about 90% CD4$^+$ T cells, greater than about 50%, 60%, 70%, 80%, 90%, 95%, 98%, or 99% CD4$^+$ T cells out of the total T cells in the manufactured T cells or population thereof. The enrichment can be performed by any suitable method known by one of skill in the art. By way of example, but not limitation, the method can be by antibody-based purification such as that offered by the Miltenyi cell selection system.

The present disclosure also provides an antigen-present- ing T cell as produced by any of the foregoing embodiments for producing antigen-presenting T cells. In some embodi- ments, an antigen-presenting T cell is provided. In any of the foregoing embodiments, the antigen-presenting T cell can express at least one of CD40, CD80, CD83, CD86, CD4, HLA Class II, or a combination thereof. By way of example, but not limitation, CD40, CD80, CD83, CD86, CD4, and HLA Class II expression can be measured by flow cytom- etry. In any of the foregoing embodiments, the antigen- presenting T cell or population thereof can exhibit at least one of the following properties: at least a two-fold increase in mRNA expression of LC3B relative to a control T cell population characteristic of the T cells from which the antigen-presenting T cell was produced, at least a two-fold decrease in mRNA expression of type II gransgluatminase (TGM2) relative to a control T cell population characteristic of the T cells from which the antigen-presenting T cell was produced, at least a 30% increase in expression of LC3B-II as measured by Western blot relative to a control T cell population characteristic of the T cells from which the antigen-presenting T cell was produced, or a decrease of at least 30% in mitochondrial mass relative to a control T cell population characteristic of the T cells from which the antigen-presenting T cell was produced as measured by flow cytometry. By way of example, mRNA expression can be measured by any standard method, such as Luminex-based oligonucleotide array, RNA sequence or reverse-transcrip- tion polymerase chain reaction (RT-PCR). It should be understood that the control T cell population characteristic of the T cells from which the antigen-present T cell was produced are not the manufactured T cells, but would be characteristic of the cells used to generate the manufactured T cells.

In any of the foregoing embodiments or of the present disclosure, the antigen-presenting T cell of the present disclosure can be capable of stimulating a responder T cell population to react to an antigen that is presented by the antigen-presenting T cell and/or is derived from a manufac- tured T cell of any of the embodiments of the present disclosure. Such stimulatory capacity can be measured by incubating the antigen-presenting T cell with an immuno- genic composition as described herein for producing a population of loaded, antigen-presenting T cells which can then be co-cultured with a population of manufactured T cells of the present disclosure at a ratio of 1:40 and a concentration of 1×10$^6$ cells/mL for about 10 days in stan- dard culture media, e.g. X-Vivo 20 media, where, after this sensitization step, the population of sensitized, manufac- tured T cells produced is harvested and re-inoculated into standard media at a ratio of 1:40 (loaded, antigen-presenting T cells (with the same immunogenic composition or anti- gen):sensitized, manufactured T cells) and a concentration of 1×10$^6$ cells/mL, e.g. in 200 μL, and grown for 24 hours upon which the supernatant can be harvested and tested for cytokine secretion, where the cytokine secretion is for IFN-γ, GM-CSF and TNF-α as measured by a Luminex assay, where cytokine secretion of greater than 10 pg/mL/ 1×10$^6$ cells/24 hours is indicative that the cells are sensitized to the antigen. As a negative control, loaded, antigen- presenting T cells can be prepared from an irrelevant immu- nogenic composition and co-incubated as described above with the sensitized, manufactured T cells. By way of example, but not limitation, the secretion can be at least 20 pg/mL/24 hours/1×10$^6$ cells, 50 pg/mL/24 hours/1×10$^6$ cells, 100 pg/mL/24 hours/1×10$^6$ cells, 1000 pg/mL/24 hours/1×10$^6$ cells or more. It should be understood that absent such re-stimulation, the sensitized, manufactured T cells would be expected to secrete a low, likely undetectable level of these cytokines. Alternatively, in some embodiments, instead of manufactured T cells, normal T cells can be used in this assay as the antigen-presenting function can still sensitize T cells; in such instances, rather than sensitized, manufactured T cells, sensitized T cells would be used for the re-stimulation. Thus, this assay provides a method to determine whether a T cell can be an antigen-presenting T cell or loaded, antigen-presenting T cell of the present disclosure, or whether a sensitized T cell is "sensitized" to the antigen presented by the antigen-presenting T cells (using the 24 hour culture and supernatant evaluation). It should be understood that other methods for assessing whether a sensitized, manufactured T cell is sensitized to an antigen can also include T cell repertoire analysis by next generation sequences (Sidhom J-H et al., *Nature Communications* 12:1605 (2021) and other methods such as functional assays (such as tumor-specific or peptide-specific reactivity), major histocompatibility multimer libraries, in silico peptide prediction, and mass cytometry of the HLA-ligandome (D'Ippolito, E. et al.; International Journal of Molecular Sciences 21:8324 (2020)).

The present disclosure also provides a composition comprising a manufactured T cell of the present disclosure or population thereof, IL-7 and IL-15. The present disclosure also provides a composition comprising a manufactured T cell of the present disclosure or population thereof and an antigen-presenting T cell or population thereof of the present disclosure. In any of the foregoing embodiments of this paragraph, the composition can further include a source of anti-CD3/anti-CD28 co-stimulation such as anti-CD3/anti-CD28-coated magnetic beads at a ratio of 1:3 to 3:1 as described herein. In the foregoing embodiments, where IL-7 and IL-15 are present, these can be present as described above at between about 0.1 ng/mL and 100 ng/mL. In any of the foregoing embodiments, the composition can not include IL-2, GM-CSF, or IL-4. In any of the foregoing embodiments, the composition can not include dendritic cells.

In some embodiments, a manufactured T cell of the present disclosure comprising an antigen according to the present disclosure is provided. In some aspects, the antigen is a viral, bacterial, fungal or cancer-associated antigen as described herein. By way of example, but not limitation, the antigen can be associated with any of the cancers, bacterial, fungal or viral infections disclosed herein.

In some embodiments, a manufactured T cell of the present disclosure having antigen-presenting capacity is provided. By way of example, but not limitation, such stimulatory capacity can be measured by incubating the antigen-presenting T cell with an immunogenic composition as described herein for producing a population of loaded, antigen-presenting T cells which can then be co-cultured with a population of manufactured T cells of the present disclosure at a ratio of 1:40 and a concentration of 1×10$^6$ cells/mL for about 10 days in standard culture media, e.g. X-Vivo 20 media, where, after this sensitization step, the population of sensitized, manufactured T cells produced is harvested and re-inoculated into standard media at a ratio of 1:40 (loaded, antigen-presenting T cells (with the same immunogenic composition or antigen):sensitized, manufactured T cells) and a concentration of 1×10$^6$ cells/mL e.g. in 200 μL, and grown for 24 hours upon which the supernatant can be harvested and tested for cytokine secretion, where the cytokine secretion is for IFN-γ, GM-CSF and TNF-α as measured by a Luminex assay, where cytokine secretion of greater than 10 pg/mL/1×10$^6$ cells/24 hours is indicative that the cells are sensitized to the antigen. As a negative control, loaded, antigen-presenting T cells can be prepared from an irrelevant immunogenic composition and co-incubated as described above with the sensitized, manufactured T cells. By way of example, but not limitation, the secretion can be at least 20 pg/mL/24 hours/1×10$^6$ cells, 50 pg/mL/24 hours/1×10$^6$ cells, 100 pg/mL/24 hours/1×10$^6$ cells, 1000 pg/mL/24 hours/1×10$^6$ cells or more. It should be understood that absent such re-stimulation, the sensitized, manufactured T cells would be expected to secrete a low, likely undetectable level of these cytokines. Alternatively, in some embodiments, instead of manufactured T cells, normal T cells can be used in this assay as the antigen-presenting function can still sensitize T cells; in such instances, rather than sensitized, manufactured T cells, sensitized T cells would be used for the re-stimulation. Thus, this assay provides a method to determine whether a T cell can be an antigen-presenting T cell or loaded, antigen-presenting T cell of the present disclosure, or whether a sensitized T cell is "sensitized" to the antigen presented by the antigen-presenting T cells (using the 24 hour culture and supernatant evaluation). It should be understood that other methods for assessing whether a sensitized, manufactured T cell is sensitized to an antigen can also include T cell repertoire analysis by next generation sequences (Sidhom J-H et al., *Nature Communications* 12:1605 (2021) and other methods such as functional assays (such as tumor-specific or peptide-specific reactivity), major histocompatibility multimer libraries, in silico peptide prediction, and mass cytometry of the HLA-ligandome.

Methods for Producing Loaded, Antigen-Presenting T Cells (and Sensitized, Manufactured T Cells)

In some embodiments, a method for producing loaded, antigen-presenting T cells is provided that include inoculating a manufactured T cell or population thereof of the present disclosure in a culture medium, adding an immunogenic composition comprising an antigen to the culture medium and incubating manufactured T cells or a population thereof for a period of time to yield a population of loaded, antigen-presenting T cells that include the antigen or a portion thereof, where the culture medium includes IL-7 and IL-15.

In some embodiments, a method is provided for producing loaded, antigen-presenting T cells that can include, adding an immunogenic composition comprising an antigen to the culture medium in any of the foregoing embodiments for producing antigen-presenting T cells or adding the immunogenic composition to the antigen-presenting T cells of the present disclosure. It should be understood that the immunogenic composition comprising an antigen can be added to the culture medium at the time of inoculating the at least a portion of manufactured T cells or population thereof, during the period of time, after the period of time, before co-stimulation, or after co-stimulation. Where the immunogenic composition is added after the period of time, the antigen-presenting T cells and immunogenic composition can be incubated for an additional period of time. That is, the immunogenic composition can be added at any time between day 0 and day 6 of the loaded, antigen-presenting T cell manufacturing. Where the immunogenic composition added after the period of time, the antigen-presenting T cells and immunogenic composition can be incubation for an additional period of time. The resulting loaded, antigen-presenting T cells can include the antigen or a portion thereof from the immunogenic composition.

In any of the foregoing embodiments for producing loaded, antigen-presenting T cells, anti-CD3/anti-CD28 co-stimulation as described herein can be added to the culture medium. In any of the foregoing embodiments for producing loaded, antigen-presenting T cells, the anti-CD3/anti-CD28 co-stimulation can be performed by adding anti-CD3/anti-CD28-coated magnetic beads to the culture medium, where the bead:T cell ratio can be 1:3 to 3:1. By way of example but not limitation, ratios of 1:1, 1:1.5, 1:2, 1:2.5, 1:3, 1.5:1, 2:1, 2.5:1 and 3:1 can be used. It should be further understood that anti-CD3/anti-CD28 co-stimulation can be performed using anti-CD3/anti-CD28-coated magnetic beads or any equivalent monoclonal antibody or pharmacologic method, including but not limited to, using nanoparticles or microparticles or staphylococcal enterotoxin B (SEB) or lenalidomide. One of skill in the art can, through routine experimentation, determine the appropriate amount of these compounds to add to the culture to achieve the desired effect. By way of example, but not limitation, nanoparticles or microparticles can be used at the manufacturer's recommended concentration or within 3-10× more dilute or more concentrated. By way of further example, but not limitation, SEB can be used at about 1 μg/mL to about 100 μg/mL, such as at about 10 μg/mL or lenalidomide can be used at about 0.01 μmol/L to about 2.0 μmol/L. In some embodiments, co-stimulation of the culture input population of cells can be achieved using anti-CD3/anti-CD28 containing nanoparticles which can be used at a reduced concentration than recommended. By way of example, but not limitation, such nanoparticles can be used at about 0.01× to about 0.1×, about 0.025× to about 0.1×, about 0.05× to about 0.1×, about 0.075× to about 0.1×, about 0.01× to about 0.075×, about 0.01× to about 0.05×, about 0.01× to about 0.025×, about 0.025× to about 0.075×, about 0.025× to about 0.05×, about 0.05× to about 0.075×, or about 0.01×, about 0.025×, about 0.05×, about 0.075×, or about 0.01× the recommended dose. By way of example but not limitation, a reagent such as Miltenyi® T Cell TransAct™ could be used at a reduced dose compared to the recommended dose of 10 μL per 1×10⁶ T cells such as, by way of example but not limitation, 1.1 μL (a nine-fold decrease) or about 0.11×. Alternatively, if anti-CD3/anti-CD28 co-stimulation is to be used for producing antigen-presenting T cells, the source of co-stimulation can be provided by dissolvable anti-CD3/anti-CD28 micropar-ticles. By way of example, but not limitation, the dissolvable anti-CD3/anti-CD28 microparticles can be used at 20% of the strength recommended by the manufacturer (e.g. Cloudz®; Bio-Techne). By way of further example, the dissolvable anti-CD3-anti-CD28 microparticles can be used at 5%, 10%, 15%, 20%, 25% or 30% of the manufacturer's recommended strength. The specific amount of anti-CD3/anti-CD28 reagent to be added can be titrated based on the desired functional characteristics of the final antigen-pre-senting T cell product. Specifically, a sufficient amount of reagent can be added to maintain T cell viability in vitro in the presence of the inhibitory molecules described in the present disclosure. However, any specific anti-CD3/anti-CD28 reagent should not be added in excess, as defined by: inappropriately high level of T cell activation (increase in CD25 expression by flow cytometry relative to the T cell culture with the optimal, minimal amount of co-stimulation); inappropriately high level of T cell checkpoint inhibitor receptor expression by flow cytometry; and inappropri-ately altered expression of molecules associated with T cell effector memory cells by flow cytometry (such as reduction in levels of CD62L and CCR7; such as increase in levels of CD45RO and KLRG). In any of the foregoing embodiments for producing antigen-presenting T cells, the anti-CD3/anti-CD28 co-stimulation can be added at the time of inoculating the at least a portion of manufactured T cells or population thereof or at any time during the period time. By way of example, but not limitation, the co-stimulation can be added at about the start of incubation, at 24 hours post-inoculation, 36 hours post-inoculation, 42 hours post-inoculation, 48 hours post-inoculation, or 60 hours post-inoculation.

In any of the foregoing embodiments for producing loaded, antigen-presenting T cells, the period of time can be any suitable time to yield loaded, antigen-presenting T cells, such as from about 24 hours to about 72 hours. By way of example, but not limitation, the period of time can be about 12, about 18, about 24, about 30, about 36, about 42, about 48, about 54, about 60, about 66, about 72, from about 24 to about 72 hours, from about 24 to about 36 hours, from about 24 to about 48 hours, from about 24 to about 60 hours, from about 30 to about 72 hours, from about 30 to about 30 to about 48 hours, from about 30 to about 36 hours, from about 36 to about 72 hours, from about 36 to about 60 hours, from about 36 to about 48 hours, from about 48 hours to about 72 hours, from about 48 hours to about 60 hours, or from about 60 hours to about 72 hours.

In any of the foregoing embodiments for producing loaded, antigen-producing T cells, a starting concentration of T cells in the culture can be at a starting concentration of about 1×10⁶ T cells per mL to 50×10⁶ cells per mL. By way of example but not limitation, said cell density may be about 1×10⁶ cells per mL to 5×10⁶ cells per mL, 1×10⁶ cells per mL to 10×10⁶ cells per mL, 1×10⁶ cells per mL to 15×10⁶ cells per mL, 15×10⁶ cells per mL to 22.5×10⁶ cells per mL, 10×10⁶ cells per mL to 22.5×10⁶ cells per mL, 10×10⁶ cells per mL to 22.5×10⁶ cells per mL, 5×10⁶ cells per mL to 22.5×10⁶ cells per mL, 1×10⁶ cell per mL to 50×10⁶ cells per mL, 10×10⁶ cells per mL to 40×10⁶ cells per mL, 20×10⁶ cells per mL to 40×10⁶ cells per mL, 1×10⁶ cells per mL, 2.5×10⁶ cells per mL, 5×10⁶ cells per mL, 7.5×10⁶ cells per mL, 10×10⁶ cells per mL, 12.5×10⁶ cells per mL, 15×10⁶ cells per mL, 17.5×10⁶ cells per mL, 20×10⁶ cells per mL, 22.5×10⁶ cells per mL, 25×10⁶ T cells per mL, 30×10⁶ cells per mL, 35×10⁶ cells per mL, 40×10⁶ cells per mL, 45×10⁶ cells per mL, or 50×10⁶ cells per mL In any of the foregoing embodiments for producing loaded, antigen-presenting T cells, the culture medium can be X-Vivo 20 or TexMACS media. However, any suitable medium can be used.

In any of the foregoing embodiments for producing loaded, antigen-presenting T cells, the culture medium can further include IL-7 and IL-15.

In any of the foregoing embodiments for producing loaded, antigen-presenting T cells, the IL-7 can be added to or present in the culture medium at from about 0.1 ng/mL to about 100 ng/mL. By way of example, but not limitation, the IL-7 can be added to or present in the culture medium at from about 0.1 ng/mL to about 100 ng/mL, about 0.1 ng/mL to about 50 ng/mL, about 0.1 ng/mL to about 10 ng/mL, about 0.1 ng/mL to about 5 ng/mL, about 0.1 ng/mL to about 1 ng/mL, about 1 ng/mL to about 10 ng/mL, about 1 ng/mL to about 20 ng/mL, about 1 ng/mL to about 25 ng/mL, about 1 ng/mL to about 30 ng/mL, about 1 ng/mL to about 40 ng/mL, about 1 ng/mL to about 50 ng/mL, about 1 ng/mL to about 75 ng/mL, about 5 ng/mL to about 10 ng/mL, about 5 ng/mL to about 20 ng/mL, about 5 ng/mL to about 25 ng/mL, about 5 ng/mL to about 30 ng/mL, about 5 ng/mL to about 40 ng/mL, about 5 ng/mL to about 50 ng/mL, about 5 ng/mL to about 75 ng/mL, about 5 ng/mL to about 100
ng/mL, about 10 ng/mL to about 20 ng/mL, about 10 ng/mL
to about 25 ng/mL, about 10 ng/mL to about 30 ng/mL,
about 10 ng/mL to about 40 ng/mL, about 10 ng/mL to about
50 ng/mL, about 10 ng/mL to about 75 ng/mL, about 10
ng/mL to about 100 ng/mL, about 20 ng/mL to about 30
ng/mL, about 20 ng/mL to about 40 ng/mL, about 20 ng/mL
to about 50 ng/mL, about 20 ng/mL to about 75 ng/mL,
about 20 ng/mL to about 100 ng/mL, about 25 ng/mL to
about 40 ng/mL, about 25 ng/mL to about 50 ng/mL, about
25 ng/mL to about 75 ng/mL, about 25 ng/mL to about 100
ng/mL, about 30 ng/mL to about 40 ng/mL, about 30 ng/mL
to about 50 ng/mL, about 30 ng/mL to about 75 ng/mL,
about 30 ng/mL to about 100 ng/mL, about 40 ng/mL to
about 50 ng/mL, about 40 ng/mL to about 75 ng/mL, about
40 ng/mL to about 100 ng/mL, about 50 ng/mL to about 75
ng/mL, about 50 ng/mL to about 100 ng/mL, about 75
ng/mL to about 100 ng/mL, about 1 ng/mL, about 2 ng/mL,
about 3 ng/mL, about 4 ng/mL, about 5 ng/mL, about 6
ng/mL, about 7 ng/mL, about 8 ng/mL, about 9 ng/mL,
about 10 ng/mL, about 12.5 ng/mL, about 15 ng/mL, about
20 ng/mL, about 25 ng/mL, about 30 ng/mL, about 40
ng/mL, about 50 ng/mL, about 75 ng/mL, or about 100
ng/mL. It should be understood that a sufficient amount of
IL-7 can be present in or added to the culture medium in an
amount sufficient to yield the loaded, antigen-presenting T
cells.

In any of the foregoing embodiments for producing
loaded, antigen-presenting T cells, the IL-15 can be added to
or present in the culture medium at from about 0.1 ng/mL to
about 100 ng/mL. By way of example, but not limitation, the
IL-15 can be added to or present in the culture medium at
from about 0.1 ng/mL to about 100 ng/mL, about 0.1 ng/mL
to about 50 ng/mL, about 0.1 ng/mL to about 10 ng/mL,
about 0.1 ng/mL to about 5 ng/mL, about 0.1 ng/mL to about
1 ng/mL, about 1 ng/mL to about 10 ng/mL, about 1 ng/mL
to about 20 ng/mL, about 1 ng/mL to about 25 ng/mL, about
1 ng/mL to about 30 ng/mL, about 1 ng/mL to about 40
ng/mL, about 1 ng/mL to about 50 ng/mL, about 1 ng/mL to
about 75 ng/mL, about 5 ng/mL to about 10 ng/mL, about 5
ng/mL to about 20 ng/mL, about 5 ng/mL to about 25
ng/mL, about 5 ng/mL to about 30 ng/mL, about 5 ng/mL to
about 40 ng/mL, about 5 ng/mL to about 50 ng/mL, about 5
ng/mL to about 75 ng/mL, about 5 ng/mL to about 100
ng/mL, about 10 ng/mL to about 20 ng/mL, about 10 ng/mL
to about 25 ng/mL, about 10 ng/mL to about 30 ng/mL,
about 10 ng/mL to about 40 ng/mL, about 10 ng/mL to about
50 ng/mL, about 10 ng/mL to about 75 ng/mL, about 10
ng/mL to about 100 ng/mL, about 20 ng/mL to about 30
ng/mL, about 20 ng/mL to about 40 ng/mL, about 20 ng/mL
to about 50 ng/mL, about 20 ng/mL to about 75 ng/mL,
about 20 ng/mL to about 100 ng/mL, about 25 ng/mL to
about 40 ng/mL, about 25 ng/mL to about 50 ng/mL, about
25 ng/mL to about 75 ng/mL, about 25 ng/mL to about 100
ng/mL, about 30 ng/mL to about 40 ng/mL, about 30 ng/mL
to about 50 ng/mL, about 30 ng/mL to about 75 ng/mL,
about 30 ng/mL to about 100 ng/mL, about 40 ng/mL to
about 50 ng/mL, about 40 ng/mL to about 75 ng/mL, about
40 ng/mL to about 100 ng/mL, about 50 ng/mL to about 75
ng/mL, about 50 ng/mL to about 100 ng/mL, about 75
ng/mL to about 100 ng/mL, about 1 ng/mL, about 2 ng/mL,
about 3 ng/mL, about 4 ng/mL, about 5 ng/mL, about 6
ng/mL, about 7 ng/mL, about 8 ng/mL, about 9 ng/mL,
about 10 ng/mL, about 12.5 ng/mL, about 15 ng/mL, about
20 ng/mL, about 25 ng/mL, about 30 ng/mL, about 40
ng/mL, about 50 ng/mL, about 75 ng/mL, or about 100
ng/mL. It should be understood that a sufficient amount of IL-15 can be present in or added to the culture medium in an
amount sufficient to yield the loaded, antigen-presenting T
cells.

In any of the foregoing embodiments for producing
loaded, antigen-presenting T cells, the culture medium can
further comprise 5% human serum, such as, by way of
example, but not limitation, human AB serum. In some
embodiments, said culture medium can further comprise
1%-20% human serum. By way of example but not limita-
tion, said culture medium may comprise about 1%, 2%, 3%,
4%, 5%, 6%, 7%, 8%, 9%, 10%, 11%, 12%, 13%, 14%,
15%, 16%, 17%, 18%, 19% or 20% human serum. In some
embodiments, said culture medium can comprise at least
1%, 2%, 3%, 4%, 5%, 6%, 7%, 8%, 9%, 10%, 11%, 12%,
13%, 14%, 15%, 16%, 17%, 18%, 19% or 20% human
serum. In any of the foregoing embodiments for producing
antigen-presenting T cells, no serum can be added to or
present in the culture medium.

In any of the foregoing embodiments for producing
loaded, antigen-presenting T cells, the culture medium can
have GM-CSF added to or present in the culture medium at
from about 10 ng/mL to about 1000 ng/mL. By way of
example, but not limitation, the GM-CSF can be added to or
present in the culture medium at from about 10 ng/mL to
about 1000 ng/mL, about 10 ng/mL to about 500 ng/mL,
about 10 ng/mL to about 100 ng/mL, about 10 ng/mL to
about 50 ng/mL, about 100 ng/mL to about 1000 ng/mL,
about 100 ng/mL to about 500 ng/mL, about 100 ng/mL to
about 250 ng/mL, about 50 ng/mL to about 500 ng/mL,
about 50 ng/mL to about 250 ng/mL, about 10 ng/mL, about
25 ng/mL, about 50 ng/mL, about 75 ng/mL, about 100
ng/mL, about 250 ng/mL, about 500 ng/mL, about 750
ng/mL, or about 1000 ng/mL. Alternatively, in some
embodiments, the culture medium does not include GM-
CSF and no GM-CSF is added to the culture medium.

In any of the foregoing embodiments for producing
loaded, antigen-presenting T cells, the culture medium can
have IL-4 added to or present in the culture medium at from
about 100 IU/mL to about 10,000 IU/mL, about 500 IU/mL
to about 10,000 IU/mL, about 1000 IU/mL to about 10,000
IU/mL, about 2500 IU/mL to about 10,000 IU/mL, about
5000 IU/mL to about 10,000 IU/mL, about 500 IU/mL to
about 5000 IU/mL, about 500 IU/mL to about 2500 IU/mL,
about 500 IU/mL to about 2000 IU/mL, about 500 IU/mL to
about 1500 IU/mL, about 2500 IU/mL to about 10,000
IU/mL, about 5000 IU/mL to about 10,000 IU/mL, about
100, 250, 500, 750, 1000, 1250, 1500, 1750, 2000, 2500,
3750, 5000, 6000, 7000, 8000, 9000, or 10,000 IU/mL.
Alternatively, in some embodiments, the culture medium
does not include IL-4 and no IL-4 is added to the culture
medium.

In any of the foregoing embodiments for producing
loaded, antigen-presenting T cells, the culture medium can
have IL-2 added to or present in the culture medium at from
about 20 IU/mL to about 1000 IU/mL. By way of example,
but not limitation, the IL-2 can be added or present in the
culture medium at from about 20 IU/mL to about 1000
IU/mL, about 50 IU/mL to about 1000 IU/mL, about 100
IU/mL to about 1000 IU/mL, about 250 IU/mL to about
1000 IU/mL, about 500 IU/mL to about 1000 IU/mL, about
20 IU/mL to about 500 IU/mL, about 50 IU/mL to about 500
IU/mL, about 100 IU/mL to about 500 IU/mL, about 20, 50,
100, 250, 500, 750 or 1000 IU/mL. Alternatively, in some
embodiments, the culture medium does not include IL-2 and
no IL-2 is added to the culture medium In any of the foregoing embodiments for producing loaded, antigen-presenting T cells, the culture medium can not include dendritic cells.

In any of the foregoing embodiments for producing loaded, antigen-producing T cells, where the culture is incubated for an additional period of time, the additional period of time can be from about 2 days to about 14 days. By way of example, but not limitation, the additional period of time can be from about 2 days to about 14 days, 2 days to about 10 days, about 5 to about 14 days, about 5 days to about 10 days, about 2, 3, 4, 5, 6, 7, 8, 9, 10, 11, 12, 13, or 14 days.

In any of the foregoing embodiments for producing loaded, antigen-presenting T cells, the immunogenic composition can be added before or after anti-CD3/anti-CD28 co-stimulation, if provided. By way of example, but not limitation, the immunogenic composition can be provided at the start of the incubation while the anti-CD3/anti-CD28 co-stimulation can be added at day 1 of the incubation or vice versa.

In any of the foregoing embodiments or embodiments of the present disclosure for producing loaded, antigen-presenting T cells, the antigen can be a bacterial, viral, fungal or cancer-associated antigen. By way of example, but not limitation, the immunogenic composition can be a tumor lysate from a cancer. By way of further example, but not limitation, the tumor lysate can be obtained by treating the tumor with etoposide in an amount effective to produce an immunogenic composition. (See Wang Y-J et al; Genes and Diseases 5:194-203 (2018)). It should be understood that any treatment that can yield an immunogenic composition can be used. By way of example, but not limitation, such methods can include, for cancers, treatment with bortezomib, doxorubicin, epirubicin, cyclophosphamide, oxaliplatin, 5-fluorouracil, gemcitabine, mitoxantrone, bleomycin, radiation, cryotherapy, dactinomycin, lurbinectedin, teniposide, or a combination thereof. By way of further example, for bacterial immunogenic compositions, bacteriostatic antibacterials that can be used include chloramphenicol, trimethoprim, erythromycin, penicillins, carbapenems such as imipenem, aztreonam, cefepime, aminoglycosides, such as gentamycin and amikacin, quinolones such as levofloxacin and ciprofloxacin, macrolides such as erythromycin and azithromycin, freezing or freeze-thaw, mechanical disruption, enzymatic disruption or any other suitable method to generate an immunogenic composition. (See Vanmermeek et al.; Oncoimmunology 9(1):1703449 (2020); Fucikoca et al; Cell Death and Disease 11:1013 (2020)). By way of still further example, for viral immunogenic compositions, anti-viral treatments that can be used to generate the immunogenic composition can include viral RNA polymerase inhibitors such as remdesivir, viral protein synthesis inhibitors such as ritonavir, lopinavir, inhibitors of viral entry such as hydroxycloroquine, acyclovir, valacyclovir, foscarnet, ribavirin, lamivudine, amantadine, oseltamivir, zanamivir, protease inhibitors such as amprenavir and atazanavir, reverse transcriptase inhibitors such as abacavir, stavudine, zidovudine, integrase inhibitors such as bictegravir and dolutegravir, NS3/4A protease inhibitors such as danoprevir and glecaprevir, NS5A phosphoprotein inhibitors such as daclatasvir and ledipasvir, neuraminidase inhibitors such as laninamivir and oseltamivir, mechanical disruption, enzymatic disruption, freezing or freeze-thaw or any other suitable method to generate an immunogenic composition. By still way of further example, for fungal immunogenic compositions, anti-fungal treatments that can be used to generate the immunogenic composition can include polyenes such as amphotericin, azoles such as ketoconazole and itraconazole, allylamines such as terbinafine, echinocandins such as caspofungin and micafungin, griseofulvin, mechanical disruption, enzymatic disruption, freezing or freeze-thaw or any other suitable method to generate an immunogenic composition. Immunogenic compositions can be also be derived from synthesized, e.g. recombinant antigens, such as recombinant cancer-associated antigens, or can be introduced by lentiviral transformation of the T cells in culture.

In any of the foregoing embodiments for producing loaded, antigen-presenting T cells, the method can further include, prior to inoculating the manufactured T cells or population thereof, enriching the manufactured T cells or population thereof for CD4$^+$ T cells. By way of example, but not limitation, the manufactured T cells or population thereof, can be enriched to include about 50% to about 100% CD4$^+$ T cells, about 60% to about 100% CD4$^+$ T Cells, about 70% to about 100% CD4$^+$ T cells, about 80% to about 100% CD4$^+$ T cells, about 90% to about 100% CD4$^+$ T cells, about 95% to about 100% CD4$^+$ T cells, about 50% to about 60% CD4$^+$ T cells, about 60% to about 70% CD4$^+$ T cells, about 70% to about 80% CD4$^+$ T cells, about 80% to about 90% CD4$^+$ T cells, about 90% to about 95% CD4$^+$ T cells, about 60% to about 80% CD4$^+$ T cells, about 70% to about 90% CD4$^+$ T cells, greater than about 50%, 60%, 70%, 80%, 90%, 95%, 98%, or 99% CD4$^+$ T cells out of the total T cells in the manufactured T cells or population thereof. The enrichment can be performed by any suitable method known by one of skill in the art. By way of example, but not limitation, the method can be by antibody-based purification such as that offered by the Miltenyi cell selection system It should be understood that the amount of immunogenic composition added can be an amount sufficient to yield the loaded, antigen-presenting T cells.

It should be further understood that the immunogenic composition includes an antigen and that at least a portion of the antigen can be on a surface of the loaded, antigen-presenting T cell.

It should be understood that the foregoing methods of producing loaded, antigen-presenting T cells can also produce sensitized, manufactured T cells if manufactured T cells are present in the culture. The sensitized, manufactured T cells can have any of the properties or characteristics of the manufactured T cells described herein, but are further sensitized to the antigen or a portion thereof which can be tested as described herein.

The present disclosure also provides a loaded, antigen-presenting T cell or population thereof produced by the methods of the present disclosure. Also provided is a loaded, antigen-presenting T cell. In any of the foregoing embodiments, the loaded, antigen-presenting T cell can express at least one of CD40, CD80, CD83, CD86, CD4, HLA Class II, or a combination thereof. By way of example, but not limitation, CD40, CD80, CD83, CD86, CD4, and HLA Class II expression can be measured by flow cytometry. In any of the foregoing embodiments, the loaded, antigen-presenting T cell or population thereof can exhibit at least one of the following properties: at least a two-fold increase in mRNA expression of LC3B relative to a control T cell population characteristic of the T cells from which the antigen-presenting T cell was produced, at least a two-fold decrease in mRNA expression of type II gransgluatminase (TGM2) relative to a control T cell population characteristic of the T cells from which the antigen-presenting T cell was produced, at least a 30% increase in expression of LC3B-II as measured by Western blot relative to a control T cell population characteristic of the T cells from which the antigen-presenting T cell was produced, or a decrease of at least 30% in mitochondrial mass relative to a control T cell population characteristic of the T cells from which the antigen-presenting T cell was produced as measured by flow cytometry (Monteiro et al., MethodsX 7:100938 (2020)). By way of example, mRNA expression can be measured by any standard method, such as Luminex-based oligonucleotide array, RNA sequence or reverse-transcription polymerase chain reaction (RT-PCR). It should be understood that the control T cell population characteristic of the T cells from which the loaded, antigen-present T cell was produced are not the manufactured T cells, but would be characteristic of the cells used to generate the manufactured T cells. In any of the foregoing embodiments, the loaded, antigen-presenting T cell can further include the antigen or a portion thereof that is not endogenous to the loaded, antigen-presenting T cell.

In any of the foregoing embodiments or of the present disclosure, the loaded, antigen-presenting T cell of the present disclosure can be capable of stimulating a responder T cell population to react to an antigen that is presented by the antigen-presenting T cell and/or is derived from a manufactured T cell of any of the embodiments of the present disclosure. Such stimulatory capacity can be measured by co-culturing the loaded, antigen-presenting T cells with a population of manufactured T cells of the present disclosure at a ratio of 1:40 and a concentration of $1 \times 10^6$ cells/mL for about 10 days in standard culture media, e.g. X-Vivo 20 media, where, after this sensitization step, the population of sensitized, manufactured T cells produced is harvested and re-inoculated into standard media at a ratio of 1:40 (loaded, antigen-presenting T cells (with the same, but fresh, loaded, antigen-presenting T cells loaded with the same immunogenic composition or antigen):sensitized, manufactured T cells) and a concentration of $1 \times 10^6$ cells/mL e.g. in 200 μL, and grown for 24 hours upon which the supernatant can be harvested and tested for cytokine secretion, where the cytokine secretion is for IFN-γ, GM-CSF and TNF-α as measured by a Luminex assay, where cytokine secretion of greater than 10 pg/mL/$1 \times 10^6$ cells/24 hours is indicative that the cells are sensitized to the antigen. As a negative control, loaded, antigen-presenting T cells can be prepared from an irrelevant immunogenic composition and co-incubated as described above with the sensitized, manufactured T cells. By way of example, but not limitation, the secretion can be at least 20 pg/mL/24 hours/$1 \times 10^6$ cells, 50 pg/mL/24 hours/$1 \times 10^6$ cells, 100 pg/mL/24 hours/$1 \times 10^6$ cells, 1000 pg/mL/24 hours/$1 \times 10^6$ cells or more. It should be understood that absent such re-stimulation, the sensitized, manufactured T cells would be expected to secrete a low, likely undetectable level of these cytokines. Alternatively, in some embodiments, instead of manufactured T cells, normal T cells can be used in this assay as the antigen-presenting function can still sensitize T cells; in such instances, rather than sensitized, manufactured T cells, sensitized T cells would be used for the re-stimulation. Thus, this assay provides a method to determine whether a T cell can be an antigen-presenting T cell or loaded, antigen-presenting T cell of the present disclosure, or whether a sensitized T cell is "sensitized" to the antigen presented by the antigen-presenting T cells (using the 24 hour culture and supernatant evaluation). It should be understood that other methods for assessing whether a sensitized, manufactured T cell is sensitized to an antigen can also include T cell repertoire analysis by next generation sequences (Sidhom J-H et al., *Nature Communications* 12:1605 (2021) and other methods such as functional assays (such as tumor-specific or peptide-specific reactivity), major histocompatibility multimer libraries, in silico peptide prediction, and mass cytometry of the HLA-ligandome.

In some embodiments, a composition can include a manufactured T cell or population thereof of the present disclosure and a loaded, antigen-presenting T cell of the present disclosure.

In some embodiments, a composition can include a manufactured T cell or population thereof of the present disclosure, IL-7 such as at about 0.1 ng/mL to about 100 ng/mL, IL-15 such as at about 0.1 ng/mL to about 100 ng/mL, and an immunogenic composition as described in the present disclosure.

In any of the foregoing embodiments, the composition can further include a source of anti-CD3/anti-CD28 co-stimulation. By way of example, but not limitation, the source of anti-CD3/anti-CD28 co-stimulation can be anti-CD3/anti-CD28-coated magnetic beads at a bead:T cell ratio of 1:3 to 3:1 as described herein.

In any of the foregoing compositions, the compositions can include GM-CSF, IL-4, IL-2 or a combination thereof in the amounts described herein. Alternatively, the compositions can not include GM-CSF, IL-4, IL-2 or a combination thereof. In any of the foregoing compositions, the composition can not include dendritic cells.

In any of the foregoing embodiments, the composition can include an immunogenic composition as described herein.

In some embodiments, a composition can include a loaded, antigen-presenting T cell or population thereof of the present disclosure and a sensitized, manufactured T cell or population thereof of the present disclosure. In such embodiments, the sensitized, manufactured T cell can have any of the properties or characteristics described in the present disclosure with respect to the manufactured T cells of the present disclosure, but is also further sensitized to an antigen as described herein.

It should be understood that the loaded, antigen-presenting T cells or antigen-presenting T cells of the present disclosure can have decreased p70S6 kinase or phosphory-lated p70S6 kinase relative to a control population of T cells characteristic of those from which the loaded, antigen-presenting T cells or antigen-presenting T cells were produced. It should be understood that this control population is not the manufactured T cells, but would be characteristic of the cells used to generate the manufactured T cells, e.g. normal T cells. By way of example, but not limitation, p70S6 kinase and phosphorylated p70S6 kinase levels can be measured by Western blot or intracellular flow cytometry.

It should be understood that the loaded, antigen-presenting T cells of the present disclosure can include an antigen or portion thereof on their surface. The antigen or portion thereof can be from an immunogenic composition including those described herein and those derived from cancers and infectious diseases, including those described herein.

Methods for Producing Sensitized, Manufactured T Cells

As described above, sensitized, manufactured T cells can be a by-product of producing loaded, antigen-presenting T cells.

In any of the foregoing embodiments for producing loaded, antigen-presenting T cells comprising an antigen, the method can further include incubating the loaded, antigen-presenting T cells with manufactured T cells at a ratio in a co-incubation culture medium for a co-incubation period of time to yield a population of sensitized manufactured T cells, wherein the manufactured T cells are sensitized to the antigen. In any of the foregoing embodiments for producing loaded, antigen-presenting T cells comprising an antigen, the method can further include incubating the loaded, antigen-presenting T cells with manufactured T cells at a ratio in a co-incubation culture medium for a co-incubation period of time to yield a population of sensitized manufactured T cells, wherein the manufactured T cells are sensitized to the antigen, where the co-incubation culture medium optionally comprises IL-7 and IL-15.

In any of the foregoing embodiments for producing antigen-presenting T cells, the method can further include co-incubating the population of antigen-presenting T cells with manufactured T cells at a ratio in a co-incubation culture medium for a co-incubation period of time, and adding an immunogenic composition comprising an antigen to the co-incubation culture medium to yield a population of sensitized, manufactured cells that are sensitized to the antigen or a portion thereof, where the co-incubation culture medium comprises IL-7 and IL-15.

In some embodiments, a method for producing a population of sensitized, manufactured T cells includes co-incubating a population of loaded, antigen-presenting T cells of the present disclosure which include an antigen with manufactured T cells or populations thereof of the present disclosure at a ratio in a co-incubation culture medium for a co-incubation period of time to yield a population of sensitized, manufactured T cells that are sensitized to the antigen or a portion thereof. In some embodiments, a method for producing a population of sensitized, manufactured T cells includes co-incubating a population of loaded, antigen-presenting T cells of the present disclosure which include an antigen with manufactured T cells or populations thereof of the present disclosure at a ratio in a co-incubation culture medium for a co-incubation period of time to yield a population of sensitized, manufactured T cells that are sensitized to the antigen or a portion thereof, where the co-incubation culture medium comprises IL-7 and IL-15.

In some embodiments, a method for producing a population of sensitized, manufactured T cells includes co-incubating a population of antigen-presenting T cells of the present disclosure and manufactured T cells of the present disclosure at a ratio in a co-incubation culture medium for a co-incubation period of time, and adding an immunogenic composition to the co-incubation culture medium, where the sensitized, manufactured T cells are sensitized to the antigen or a portion thereof, and where the co-incubation culture medium includes IL-7 and IL-15.

In any of the foregoing embodiments for producing a population of sensitized, manufactured T cells, the ratio can be from about 1 antigen-presenting T cell or loaded, antigen-presenting T cell to about 1 manufactured T cell (1:1) and about 1 antigen-presenting T cell or loaded, antigen-presenting T cell to about 100 manufactured T cells (1:100). By way of example, but not limitation, the ratio can be from about 1:10 to about 1:100, about 1:20 to about 1:100, about 1:40 to about 1:100, about 1:50 to about 1:100, about 1:10 to about 1:50, about 1:5, 1:10, 1:20, 1:30, 1:40, 1:50, 1:60, 1:70, 1:80, 1:90, or 1:100.

In any of the foregoing embodiments for producing a population of sensitized, manufactured T cells, a starting concentration of total T cells can be from about $1\times10^6$ to $50\times10^6$ cells per mL. By way of example but not limitation, said cell density may be about $1\times10^6$ cells per mL to $5\times10^6$ cells per mL, $1\times10^6$ cells per mL to $10\times10^6$ cells per mL, $1\times10^6$ cells per mL to $15\times10^6$ cells per mL, $15\times10^6$ cells per mL to $22.5\times10^6$ cells per mL, $10\times10^6$ cells per mL to $22.5\times10^6$ cells per mL, $10\times10^6$ cells per mL to $22.5\times10^6$ cells per mL, $5\times10^6$ cells per mL to $22.5\times10^6$ cells per mL, $1\times10^6$ cell per mL to $50\times10^6$ cells per mL, $10\times10^6$ cells per mL to $40\times10^6$ cells per mL, $20\times10^6$ cells per mL to $40\times10^6$ cells per mL, $1\times10^6$ cells per mL, $2.5\times10^6$ cells per mL, $5\times10^6$ cells per mL, $7.5\times10^6$ cells per mL, $10\times10^6$ cells per mL, $12.5\times10^6$ cells per mL, $15\times10^6$ cells per mL, $17.5\times10^6$ cells per mL, $20\times10^6$ cells per mL, $22.5\times10^6$ cells per mL, $25\times10^6$ T cells per mL, $30\times10^6$ cells per mL, $35\times10^6$ cells per mL, $40\times10^6$ cells per mL, $45\times10^6$ cells per mL, or $50\times10^6$ cells per mL.

In any of the foregoing embodiments for producing a population of sensitized, manufactured T cells, the co-incubation period of time can be from about 2 days to about 14 days. By way of example, but not limitation, the additional period of time can be from about 2 days to about 10 days, about 5 to about 14 days, about 5 days to about 10 days, about 2, 3, 4, 5, 6, 7, 8, 9, 10, 11, 12, 13, or 14 days.

In any of the foregoing embodiments for producing a population of sensitized, manufactured T cells, the co-incubation culture medium can be X-Vivo 20 or TexMACS media. However, any suitable culture medium can be used.

In any of the foregoing embodiments for producing a population of sensitized, manufactured T cells, the culture medium can further comprise 5% human serum, such as, by way of example, but not limitation, human AB serum. In some embodiments, said culture medium can further comprise 1%-20% human serum. By way of example but not limitation, said culture medium may comprise about 1%, 2%, 3%, 4%, 5%, 6%, 7%, 8%, 9%, 10%, 11%, 12%, 13%, 14%, 15%, 16%, 17%, 18%, 19% or 20% human serum. In some embodiments, said culture medium can comprise at least 1%, 2%, 3%, 4%, 5%, 6%, 7%, 8%, 9%, 10%, 11%, 12%, 13%, 14%, 15%, 16%, 17%, 18%, 19% or 20% human serum. In any of the foregoing embodiments for producing antigen-presenting T cells, no serum can be added to or present in the culture medium.

In any of the foregoing embodiments for producing a population of sensitized, manufactured T cells, the IL-7 can be added to or present in the culture medium at from about 0.1 ng/mL to about 100 ng/mL. By way of example, but not limitation, the IL-7 can be added to or present in the culture medium at from about 0.1 ng/mL to about 100 ng/mL, about 0.1 ng/mL to about 50 ng/mL, about 0.1 ng/mL to about 10 ng/mL, about 0.1 ng/mL to about 5 ng/mL, about 0.1 ng/mL to about 1 ng/mL, about 1 ng/mL to about 10 ng/mL, about 1 ng/mL to about 20 ng/mL, about 1 ng/mL to about 25 ng/mL, about 1 ng/mL to about 30 ng/mL, about 1 ng/mL to about 40 ng/mL, about 1 ng/mL to about 50 ng/mL, about 1 ng/mL to about 75 ng/mL, about 5 ng/mL to about 10 ng/mL, about 5 ng/mL to about 20 ng/mL, about 5 ng/mL to about 25 ng/mL, about 5 ng/mL to about 30 ng/mL, about 5 ng/mL to about 40 ng/mL, about 5 ng/mL to about 50 ng/mL, about 5 ng/mL to about 75 ng/mL, about 5 ng/mL to about 100 ng/mL, about 10 ng/mL to about 20 ng/mL, about 10 ng/mL to about 25 ng/mL, about 10 ng/mL to about 30 ng/mL, about 10 ng/mL to about 40 ng/mL, about 10 ng/mL to about 50 ng/mL, about 10 ng/mL to about 75 ng/mL, about 10 ng/mL to about 100 ng/mL, about 20 ng/mL to about 30 ng/mL, about 20 ng/mL to about 40 ng/mL, about 20 ng/mL to about 50 ng/mL, about 20 ng/mL to about 75 ng/mL, about 20 ng/mL to about 100 ng/mL, about 25 ng/mL to about 40 ng/mL, about 25 ng/mL to about 50 ng/mL, about 25 ng/mL to about 75 ng/mL, about 25 ng/mL to about 100 ng/mL, about 30 ng/mL to about 40 ng/mL, about 30 ng/mL to about 50 ng/mL, about 30 ng/mL to about 75 ng/mL, about 30 ng/mL to about 100 ng/mL, about 40 ng/mL to about 50 ng/mL, about 40 ng/mL to about 75 ng/mL, about 40 ng/mL to about 100 ng/mL, about 50 ng/mL to about 75 ng/mL, about 50 ng/mL to about 100 ng/mL, about 75 ng/mL to about 100 ng/mL, about 1 ng/mL, about 2 ng/mL, about 3 ng/mL, about 4 ng/mL, about 5 ng/mL, about 6 ng/mL, about 7 ng/mL, about 8 ng/mL, about 9 ng/mL, about 10 ng/mL, about 12.5 ng/mL, about 15 ng/mL, about 20 ng/mL, about 25 ng/mL, about 30 ng/mL, about 40 ng/mL, about 50 ng/mL, about 75 ng/mL, or about 100 ng/mL. It should be understood that a sufficient amount of IL-7 can be present in or added to the culture medium in an amount sufficient to yield the loaded, antigen-presenting T cells.

In any of the foregoing embodiments for producing a population of sensitized, manufactured T cells, the IL-15 can be added to or present in the culture medium at from about 0.1 ng/mL to about 100 ng/mL. By way of example, but not limitation, the IL-15 can be added to or present in the culture medium at from about 0.1 ng/mL to about 100 ng/mL, about 0.1 ng/mL to about 50 ng/mL, about 0.1 ng/mL to about 10 ng/mL, about 0.1 ng/mL to about 5 ng/mL, about 0.1 ng/mL to about 1 ng/mL, about 1 ng/mL to about 10 ng/mL, about 1 ng/mL to about 20 ng/mL, about 1 ng/mL to about 25 ng/mL, about 1 ng/mL to about 30 ng/mL, about 1 ng/mL to about 40 ng/mL, about 1 ng/mL to about 50 ng/mL, about 1 ng/mL to about 75 ng/mL, about 5 ng/mL to about 10 ng/mL, about 5 ng/mL to about 20 ng/mL, about 5 ng/mL to about 25 ng/mL, about 5 ng/mL to about 30 ng/mL, about 5 ng/mL to about 40 ng/mL, about 5 ng/mL to about 50 ng/mL, about 5 ng/mL to about 75 ng/mL, about 5 ng/mL to about 100 ng/mL, about 10 ng/mL to about 20 ng/mL, about 10 ng/mL to about 25 ng/mL, about 10 ng/mL to about 30 ng/mL, about 10 ng/mL to about 40 ng/mL, about 10 ng/mL to about 50 ng/mL, about 10 ng/mL to about 75 ng/mL, about 10 ng/mL to about 100 ng/mL, about 20 ng/mL to about 30 ng/mL, about 20 ng/mL to about 40 ng/mL, about 20 ng/mL to about 50 ng/mL, about 20 ng/mL to about 75 ng/mL, about 20 ng/mL to about 100 ng/mL, about 25 ng/mL to about 40 ng/mL, about 25 ng/mL to about 50 ng/mL, about 25 ng/mL to about 75 ng/mL, about 25 ng/mL to about 100 ng/mL, about 30 ng/mL to about 40 ng/mL, about 30 ng/mL to about 50 ng/mL, about 30 ng/mL to about 75 ng/mL, about 30 ng/mL to about 100 ng/mL, about 40 ng/mL to about 50 ng/mL, about 40 ng/mL to about 75 ng/mL, about 40 ng/mL to about 100 ng/mL, about 50 ng/mL to about 75 ng/mL, about 50 ng/mL to about 100 ng/mL, about 75 ng/mL to about 100 ng/mL, about 1 ng/mL, about 2 ng/mL, about 3 ng/mL, about 4 ng/mL, about 5 ng/mL, about 6 ng/mL, about 7 ng/mL, about 8 ng/mL, about 9 ng/mL, about 10 ng/mL, about 12.5 ng/mL, about 15 ng/mL, about 20 ng/mL, about 25 ng/mL, about 30 ng/mL, about 40 ng/mL, about 50 ng/mL, about 75 ng/mL, or about 100 ng/mL. It should be understood that a sufficient amount of IL-15 can be present in or added to the culture medium in an amount sufficient to yield the loaded, antigen-presenting T cells.

In any of the foregoing embodiments for producing a population of sensitized, manufactured T cells, the culture medium can have IL-2 added to or present in the culture medium at from about 20 IU/mL to about 1000 IU/mL. By way of example, but not limitation, the IL-2 can be added or present in the culture medium at from about 20 IU/mL to about 1000 IU/mL, about 50 IU/mL to about 1000 IU/mL, about 100 IU/mL to about 1000 IU/mL, about 250 IU/mL to about 1000 IU/mL, about 500 IU/mL to about 1000 IU/mL, about 20 IU/mL to about 500 IU/mL, about 50 IU/mL to about 500 IU/mL, about 100 IU/mL to about 500 IU/mL, about 20, 50, 100, 250, 500, 750 or 1000 IU/mL. Alternatively, in some embodiments, the culture medium does not include IL-2 and no IL-2 is added to the culture medium.

In any of the foregoing embodiments for producing a population of sensitized, manufactured T cells, the culture medium can have GM-CSF added to or present in the culture medium at from about 10 ng/mL to about 1000 ng/mL. By way of example, but not limitation, the GM-CSF can be added to or present in the culture medium at from about 10 ng/mL to about 1000 ng/mL, about 10 ng/mL to about 500 ng/mL, about 10 ng/mL to about 100 ng/mL, about 10 ng/mL to about 50 ng/mL, about 100 ng/mL to about 1000 ng/mL, about 100 ng/mL to about 500 ng/mL, about 100 ng/mL to about 250 ng/mL, about 50 ng/mL to about 500 ng/mL, about 50 ng/mL to about 250 ng/mL, about 10 ng/mL, about 25 ng/mL, about 50 ng/mL, about 75 ng/mL, about 100 ng/mL, about 250 ng/mL, about 500 ng/mL, about 750 ng/mL, or about 1000 ng/mL. Alternatively, in some embodiments, the culture medium does not include GM-CSF and no GM-CSF is added to the culture medium.

In any of the foregoing embodiments for producing a population of sensitized, manufactured T cells, the culture medium can have IL-4 added to or present in the culture medium at from about 100 IU/mL to about 10,000 IU/mL, about 500 IU/mL to about 10,000 IU/mL, about 1000 IU/mL to about 10,000 IU/mL, about 2500 IU/mL to about 10,000 IU/mL, about 5000 IU/mL to about 10,000 IU/mL, about 500 IU/mL to about 5000 IU/mL, about 500 IU/mL to about 2500 IU/mL, about 500 IU/mL to about 2000 IU/mL, about 500 IU/mL to about 1500 IU/mL, about 2500 IU/mL to about 10,000 IU/mL, about 5000 IU/mL to about 10,000 IU/mL, about 100, 250, 500, 750, 1000, 1250, 1500, 1750, 2000, 2500, 3750, 5000, 6000, 7000, 8000, 9000, or 10,000 IU/mL. Alternatively, in some embodiments, the culture medium does not include IL-4 and no IL-4 is added to the culture medium.

In any of the foregoing embodiments for producing a population of sensitized, manufactured T cells, the antigen-presenting T cells or loaded, antigen-presenting T cells can be enriched for CD4$^+$ T cells. By way of example, but not limitation, the manufactured T cells or population thereof, can be enriched to include about 50% to about 100% CD4$^+$ T cells, about 60% to about 100% CD4$^+$ T Cells, about 70% to about 100% CD4$^+$ T cells, about 80% to about 100% CD4$^+$ T cells, about 90% to about 100% CD4$^+$ T cells, about 95% to about 100% CD4$^+$ T cells, about 50% to about 60% CD4$^+$ T cells, about 60% to about 70% CD4$^+$ T cells, about 70% to about 80% CD4$^+$ T cells, about 80% to about 90% CD4$^+$ T cells, about 90% to about 95% CD4$^+$ T cells, about 60% to about 80% CD4$^+$ T cells, about 70% to about 90% CD4$^+$ T cells, greater than about 50%, 60%, 70%, 80%, 90% or 95% CD4$^+$ T cells out of the total T cells in the manufactured T cells or population thereof.

In any of the foregoing embodiments for producing a population of sensitized, manufactured T cells, where an immunogenic composition is added, the immunogenic composition can be added at about day 0 or day 1 of the incubation.

In any of the foregoing embodiments for producing a population of sensitized, manufactured T cells, where an immunogenic composition is added, the antigen can be a bacterial, viral, fungal or cancer-associated antigen.

In any of the foregoing embodiments for producing a population of sensitized, manufactured T cells, where an immunogenic composition is added, the immunogenic composition can be added in an amount sufficient to sensitize the sensitized, manufactured T cells to the antigen or a portion thereof.

In any of the foregoing embodiments for producing a population of sensitized, manufactured T cells, where an immunogenic composition is added, the immunogenic composition can be a tumor lysate. By way of example, but not limitation, the tumor lysate can be obtained by treating the tumor with an amount of etoposide sufficient to yield an immunogenic composition.

In any of the foregoing embodiments for producing a population of sensitized, manufactured T cells, additional antigen-presenting T cells or loaded, antigen-presenting T cells can be added during the co-incubation.

In some embodiments, a sensitized, manufactured T cell produced by the methods of the present disclosure is provided. In any of the foregoing embodiments, the sensitized, manufactured T cells can have any of the properties or characteristics of the manufactured T cells of the present disclosure. By way of example, but not limitation, the sensitized, manufactured T cell or population thereof can have an increase in CD45RA, CD62L, CCR7, or a combination thereof. By way of further example, but not limitation, the sensitized, manufactured T cell or population thereof can have reduced checkpoint molecules such as PD1, CTLA4, TIM3, LAG3, and combinations thereof. The increase and decrease can be relative to sensitized, control T cells prepared by the same method. By way of example, but not limitation, CD45RA, CD62L, CCR7, PD1, CTLA4, TIM3 and LAG3 can be measured by flow cytometry.

In some embodiments, a composition is provided comprising an antigen-presenting T cell of any of the embodiments of the present disclosure.

In some embodiments, a composition is provided comprising loaded, antigen-presenting T cells and manufactured T cells of any of the embodiments of the present disclosure.

In some embodiments, a composition is provided comprising loaded, antigen-presenting T cells and sensitized, manufactured T cells of any of the embodiments of the present disclosure.

In any of the foregoing embodiments or of the present disclosure, the "sensitized" T cells or sensitized, manufactured T cells can react to an antigen that is presented by loaded, antigen-presenting T cell and/or are derived from a manufactured T cell of any of the embodiments of the present disclosure. Such responsiveness can be measured by culturing the sensitized, manufactured T in standard media, e.g. X-Vivo 20, at a ratio of 1:40 (loaded, antigen-presenting T cells (loaded with the immunogenic composition/antigen to which the "sensitized" cells are sensitized to):sensitized, manufactured T cells) and a concentration of $1 \times 10^6$ cells/mL e.g. in 200 µL, and grown for 24 hours upon which the supernatant can be harvested and tested for cytokine secretion, where the cytokine secretion is for IFN-γ, GM-CSF and TNF-α as measured by a Luminex assay, where cytokine secretion of greater than 10 pg/mL/$1 \times 10^6$ cells/24 hours is indicative that the cells are sensitized to the antigen. As a negative control, loaded, antigen-presenting T cells can be prepared from an irrelevant immunogenic composition and co-incubated as described above with the sensitized, manufactured T cells. By way of example, but not limitation, the secretion can be at least 20 pg/mL/24 hours/$1 \times 10^6$ cells, 50 pg/mL/24 hours/$1 \times 10^6$ cells, 100 pg/mL/24 hours/$1 \times 10^6$ cells, 1000 pg/mL/24 hours/$1 \times 10^6$ cells or more. It should be understood that absent such re-stimulation, the sensitized, manufactured T cells would be expected to secrete a low, likely undetectable level of these cytokines. Alternatively, in some embodiments, instead of manufactured T cells, normal T cells can be used in this assay as the antigen-presenting function can still sensitize T cells; in such instances, rather than sensitized, manufactured T cells, sensitized T cells would be used for the re-stimulation. Thus, this assay provides a method to determine whether a sensitized T cell is "sensitized" to the antigen presented by the antigen-presenting T cells (using the 24 hour culture and supernatant evaluation). It should be understood that other methods for assessing whether a sensitized, manufactured T cell is sensitized to an antigen can also include T cell repertoire analysis by next generation sequences (Sidhom J-H et al., *Nature Communications* 12:1605 (2021) and other methods such as functional assays (such as tumor-specific or peptide-specific reactivity), major histocompatibility multimer libraries, in silico peptide prediction, and mass cytometry of the HLA-ligandome.

Methods for Sensitizing Normal T Cells

In any of the foregoing embodiments for producing sensitized, manufactured T cells, the use of manufactured T cells can be substituted by normal T cells that have not been modified by the manufacturing interventions of the present disclosure. It should be understood that such methods will yield sensitized, T cells which are expected to have measurable cytokine secretion in response to re-stimulation as described herein.

In some embodiments, a composition is provided that can include an antigen-presenting T cell of any of the embodiments of the present disclosure and a T cell. In some embodiments, a composition is provided that can include a loaded, antigen-presenting T cell of any of the embodiments of the present disclosure and a T cell.

It should be understood that for any of the foregoing manufacturing embodiments where sensitized, manufactured T cells are to be produced, the embodiments can be modified such that the culture medium or co-incubation medium does not include IL-7 or IL-15. By way of example, but not limitation, where loaded, antigen-presented T cells are co-incubated with the manufactured T cells or regular T cells, IL-7 and IL-15 can be omitted from the culture medium.

It should be understood that in any of the foregoing manufacturing embodiments for any type of cells, that the resulting cells can be further expanded in culture. It should be further understood that in any of the foregoing manufacturing embodiments for any type of cells, the culture medium can not include a checkpoint inhibitor, such as anti-PD1 antibody.

In any of the foregoing embodiments or of the present disclosure, the "sensitized" T cells can react to an antigen that is presented by loaded, antigen-presenting T cell and/or are derived from a manufactured T cell of any of the embodiments of the present disclosure. Such responsiveness can be measured by culturing the sensitized, manufactured T in standard media, e.g. X-Vivo media, at a ratio of 1:40 (loaded, antigen-presenting T cells (loaded with the immunogenic composition/antigen to which the "sensitized" cells are sensitized to):sensitized, manufactured T cells) and a concentration of $1 \times 10^6$ cells/mL e.g. in 200 µL, and grown for 24 hours upon which the supernatant can be harvested and tested for cytokine secretion, where the cytokine secretion is for IFN-γ, GM-CSF and TNF-α as measured by a Luminex assay, where cytokine secretion of greater than 10 pg/mL/$1 \times 10^6$ cells/24 hours is indicative that the cells are sensitized to the antigen. As a negative control, loaded, antigen-presenting T cells can be prepared from an irrelevant immunogenic composition and co-incubated as described above with the sensitized, manufactured T cells. By way of example, but not limitation, the secretion can be at least 20 pg/mL/24 hours/$1 \times 10^6$ cells, 50 pg/mL/24 hours/$1 \times 10^6$ cells, 100 pg/mL/24 hours/1×10$^6$ cells, 1000 pg/mL/24 hours/1×10$^6$ cells or more. It should be understood that absent such re-stimulation, the sensitized, manufactured T cells would be expected to secrete a low, likely undetectable level of these cytokines. Alternatively, in some embodiments, instead of manufactured T cells, normal T cells can be used in this assay as the antigen-presenting function can still sensitize T cells; in such instances, rather than sensitized, manufactured T cells, sensitized T cells would be used for the re-stimulation. Thus, this assay provides a method to determine whether a sensitized T cell is "sensitized" to the antigen presented by the antigen-presenting T cells (using the 24 hour culture and supernatant evaluation). It should be understood that other methods for assessing whether a sensitized, manufactured T cell is sensitized to an antigen can also include T cell repertoire analysis by next generation sequences (Sidhom J-H et al., *Nature Communications* 12:1605 (2021) and other methods such as functional assays (such as tumor-specific or peptide-specific reactivity), major histocompatibility multimer libraries, in silico peptide prediction, and mass cytometry of the HLA-ligandome.

It should be understood that the properties and characteristics described herein of manufactured T cells, sensitized, manufactured T cells, antigen-presenting T cells, loaded, antigen-presenting T cells and sensitized T cells can apply on the cellular level or on the population level as applicable.

Methods for Treating Cancer and Infectious Diseases Using Antigen-Presenting T Cells, Sensitized, Manufactured T Cells and/or Loaded, Antigen-Presenting T Cells Patients with relapsed multiple myeloma (MM) have limited survival and curative therapy has been elusive. As such, patients with relapsed MM are suitable for a novel T cell therapy.

The immune therapy can differ from existing approaches of immune therapy in several important categories. First, the manufactured T cell product is manufactured to be inhibited at the level of the mammalian target of rapamycin (mTOR) pathway, which translates into resistance to apoptosis and into enrichment for central memory differentiation. Second, the manufactured T cell product is manufactured in high-dose IFN-alpha, which promotes a CD4$^+$Th1 and CD8$^+$Tc1 differentiation. Third, the manufactured T cell product is minimally co-stimulated with monoclonal antibodies or not co-stimulated and expresses a diverse T cell receptor (TCR) repertoire; as such, anti-tumor effects mediated by manufactured T cells are anticipated to occur primarily through in vivo clonal expansion to tumor antigens. Such a mechanism may be favorable in multiple myeloma, where tumor antigens are either not known or are variable over time due to a high tumor mutational rate. Characterization of in vivo emergent T cell responses will be critical to improving an understanding of potential mechanisms of manufactured T cell therapy and will be evaluated as a secondary objective on this study. And fourth, we will evaluate the manufactured T cell therapy on a novel immune-depleting and immune-suppressing regimen that consists of pentostatin combined with low-dose, dose-adjusted cyclophosphamide (PC regimen). This PC regimen is relatively sparing of myeloid cells, thereby permitting repeat therapeutic cycles without substantial neutropenia; this regimen is advantageous in terms of cost (can be administered in the outpatient setting) and safety (reduced rate of infection due to myeloid cell preservation). Multiple myeloma is a disease that is critically promoted by inflammatory signaling; as such, the inflammatory inhibition mediated by the PC regimen will be one component contributing to the regimen efficacy. Each of these factors was considered during the design of the clinical trial, which focuses on multiple infusions of manufactured T cells after PC conditioning.

The manufactured T cells express greatly reduced levels of the checkpoint inhibitors, and thus offers a novel ex vivo method to release the immune system from checkpoint inhibition, which is currently achieved through monoclonal antibody therapy. Along this line, it is anticipated that the manufactured T cell therapy will meet with success in cancers that are susceptible to checkpoint inhibitor therapy, including but not limited to: melanoma, renal cell carcinoma, bladder cancer, lung cancer, lymphoma, multiple myeloma, and colon cancer. It should also be noted that checkpoint inhibitor monoclonal antibody therapy has been relatively toxic in multiple myeloma patients, thereby creating a need for an alternative approach to avoid immune checkpoints, such as the manufactured T cell therapy.

In addition, the ability of manufactured T cells to undergo extensive clonal expansion to a wide variety of tumor antigens predicts that tumor cells with an increased mutational rate and tumors with micro-satellite instability will be particularly sensitive to manufactured T cell therapy.

In some embodiments, the method for treating cancer comprises administering to said subject a manufactured T cells of the present disclosure at a therapeutically effective dose, and administering to the subject a chemotherapeutic agent sufficient and in an amount sufficient to induce immunogenic cancer cell death in the subject, an agent sufficient to and in an amount sufficient to induce increased IL-7 or IL-15 expression in the subject, exogenous IL-7 or IL-15, or a combination thereof.

In some embodiments, the method for treating cancer can include administering antigen-presenting T cells of the present disclosure at a therapeutically effective dose to the subject. In some embodiments, the method for treating cancer can include administer loaded, antigen-presenting T cells of the present disclosure at a therapeutically effective dose to the subject.

In some embodiments, the method for treating cancer can include administering antigen-presenting T cells of the present disclosure and manufactured T cells of the present disclosure in a therapeutically effective dose to the subject. In some embodiments, the method for treating cancer can include administer loaded, antigen-presenting T cells of the present disclosure and manufactured T cells of the present disclosure in a therapeutically effective dose to the subject.

In any of the foregoing methods for treating cancer, where loaded, antigen-presenting T cells are administered, the loaded, antigen-presenting T cells can include an antigen associated with said cancer.

In any of the foregoing methods for treating cancer, where sensitized, manufactured T cells are administered, the sensitized, manufactured T cells can be sensitized to an antigen or a portion thereof associated with said cancer.

In any of the foregoing embodiments methods for treating cancer, where manufactured T cells are administered with antigen-presenting T cells or loaded, antigen-presenting T cells, a ratio between the antigen-presenting T cells or loaded, antigen-presenting T cells and the manufactured T cells can be about 1:10 to about 1:50. By way of example, but not limitation, the ratio can be from about 1:10 to about 1:100, about 1:20 to about 1:100, about 1:40 to about 1:100, about 1:50 to about 1:100, about 1:10 to about 1:50, about 1:5, 1:10, 1:20, 1:30, 1:40, 1:50, 1:60, 1:70, 1:80, 1:90, or 1:100.

In any of the foregoing methods for treating cancer, unless otherwise added, the method can further comprise administering to the subject a chemotherapeutic agent sufficient and in an amount sufficient to induce immunogenic cancer cell death in the subject, an agent sufficient to and in an amount sufficient to induce increased IL-7 or IL-15 expression in the subject, exogenous IL-7 or IL-15, or a combination thereof.

In any of the foregoing methods for treating cancer, the sensitized, manufactured T cells can have been co-cultured with loaded, antigen-presenting T cells comprising the antigen, wherein the sensitized, manufactured T cells are sensitized to the antigen or a portion thereof. In such embodiments, the loaded, antigen-presenting T cells can have been exposed to an immunogenic composition comprising the antigen, such as a tumor lysate, such as a tumor lysate from an etoposide-treated tumor.

In any of the foregoing methods for treating cancer, the sensitized, manufactured T cells can be sensitized to an antigen from the subject's cancer. By way of example, but not limitation, the methods by which the loaded, antigen-presenting T cells or sensitized, manufactured T cells can have further included harvesting a sample of the cancer from the subject and using the same as the immunogenic composition such as, by way of example but not limitation, to generate a lysate as the immunogenic composition. In other words, the sensitized, manufactured T cells can be sensitized to a tumor lysate of the cancer.

In any of the foregoing embodiments for treating cancer, the chemotherapeutic agent sufficient to induce immunogenic cancer cell death can be selected from the group consisting of etoposide, bortezomib, doxorubicin, epirubicin, cyclophosphamide, oxaliplatin, 5-fluorouracil, gemcitabine, mitoxantrone, bleomycin, dactinomycin, lurbinectedin, teniposide, radiation, cryotherapy, and combinations thereof.

In any of the foregoing embodiments for treating cancer, the agent sufficient to induce IL-7 or IL-15 expression in the subject can be selected from the group consisting of cyclophosphamide, melphalan, pentostatin, fludabine, bendamustine, ifosamide, temoxolomide, carboplatin, cisplatin, oxaliplatin, methotrexate, pemetrexed, trimetrexate, cladribine, azacytidine, capecitabine, cytarabine, alemtuzumab, basiliximab, temsirolimus, axitinib, erlotinib, ibrutinib, cabazitaxel, docetaxel, paclitaxel, etoposide, irinotecan, teniposide, topotecan, vinblastine, vincristine, vinorelbine, and combinations thereof.

In any of the foregoing embodiments for treating cancer, a total amount of cells administered to the subject per administration can be about $0.1 \times 10^6$ cells/kg to about $5 \times 10^6$ cells/kg of subject body weight. By way of example, but not limitation, the total amount of cells administered to the subject per administration can be about $1 \times 10^5$ to $5 \times 10^6$, $1 \times 10^6$ to $2.5 \times 10^6$ cells/kg, $2.5 \times 10^6$ to $5 \times 10^6$ cells/kg, $1 \times 10^5$ to $2.5 \times 10^6$ cells/kg, $2.5 \times 10^5$ to $5 \times 10^6$ cells/kg, $1 \times 10^5$ to $2.5 \times 10^5$ cells/kg, $2.5 \times 10^5$ to $5 \times 10^5$ cells/kg, $1 \times 10^5$ cells/kg, $2 \times 10^5$ cells/kg, $3 \times 10^5$ cells/kg, $4 \times 10^5$ cells/kg, $5 \times 10^5$ cells/kg, $1 \times 10^6$ cells/kg, $2 \times 10^6$ cells/kg, $3 \times 10^6$ cells/kg, $4 \times 10^6$ cells/kg, or $5 \times 10^6$ cells/kg manufactured T cells per kg of the subject's body weight. In any of the foregoing embodiments, the cells can be administered to said subject by infusion.

In any of the foregoing embodiments for treating cancer, the cancer can be a solid tumor or hematologic cancer.

In any of the foregoing embodiments for treating cancer, the cancer can be selected from the group consisting of multiple myeloma, renal cell carcinoma, bladder cancer, lung cancer, small-cell lung cancer, non-small cell lung cancer, liver cancer, lymphoma, Hodgkin's lymphoma, non-Hodgkin's lymphoma, gastric cancer, colon cancer, sarcoma, pancreatic cancer, prostate cancer, ovarian cancer, breast cancer, rectal cancer, endometrial cancer, kidney cancer, acute myeloid leukemia, acute lymphoid leukemia, chronic myeloid leukemia, chronic lymphoid leukemia, leukemia, bile duct cancer, thyroid cancer, melanoma, non-melanoma skin cancer, esophageal cancer, cervical cancer, oral cavity cancer, pharyngeal cancer, stomach cancer, brain cancer, and colorectal cancer. In some embodiments, the cancer is multiple myeloma. In some embodiments, the multiple myeloma is relapsed multiple myeloma. By way of further example, but not limitation, the cancer can be sarcoma, pancreatic cancer, prostate cancer, ovarian cancer, breast cancer or colorectal cancer. In some embodiments, the cancer is a PDL1-negative cancer. In some embodiments, the cancer is susceptible to checkpoint inhibitor therapy. In some embodiments, the multiple myeloma is relapsed, refractory multiple myeloma. In some embodiments, the multiple myeloma is quad- or penta-refractory multiple myeloma. In some embodiments, the multiple myeloma is smoldering multiple myeloma. In some embodiments, said subject is suffering from multiple myeloma that has relapsed. In certain aspects, the subject is suffering from multiple myeloma that has relapsed, by way of example but not limitation, 1, 2, 3, 4, 5, 6, 7, 8, 9, 10 or more times. In some embodiments, said subject is suffering from smoldering multiple myeloma. In some embodiments, said subject is suffering from quad- or penta-refractory multiple myeloma. In some embodiments, said subject is suffering from multiple myeloma that is refractory to, by way of example but not limitation, 1, 2, 3, 4, 5 or more treatments.

In some embodiments, said subject has previously been treated and is now at the time of second or third relapse after having received different lines of treatment selected from the group consisting of administration of a proteasome inhibitor, administration of immune modulatory drugs, administration of alkylators, administration of CD38 monoclonal antibodies, and administration of glucocorticoids. This patient population is considered suitable for evaluation of a phase 3 randomized clinical trial, where randomization to a control cohort to receive standard chemotherapy for patients in second or third relapse is justifiable.

In a separate embodiment, said subject is highly-refractory to multiple standard drugs and therefore, a randomized clinical trial is not justified. Rather, such highly refractory patients can be treated with the Rapa-T therapy on a single-arm, clinical trial. Highly refractory status can be quantified by the nomenclature quad- or penta-refractory, whereby such a subject is refractory to either 4 or 5 of the top drugs used to treat multiple myeloma, namely: bortezomib, carfilzomib, lenalidomide, pomalidomide, and daratumumab.

In any of the foregoing embodiments for treating cancer, the T cells (antigen-presenting T cells, loaded, antigen-presenting T cells, sensitized, manufactured T cells, or manufactured T cells) administered to the subject can be autologous or allogenic. Thus, prior to administering the cells to the subject, autologous cells can be harvested from the subject. Preferably, this is done before any immune depletion regimen is administered to the subject.

In the case of the embodiment relating to the phase 3 clinical trial of treating MM at the time of second or third relapse, the primary study objective will relate to progression-free survival as the study endpoint, with progression-free status being defined as said subject has less than a 25% increase in M-protein/free light chain difference when monitored on a monthly basis.

In any of the foregoing embodiments for treating cancer, the method can further include subjecting the subject to an immune depletion regimen.

In any of the foregoing embodiments, the method further comprises subjecting said subject to an immune depletion regimen to reduce at least a portion of regulatory T cells and/or end-stage senescent effector T cells or to reduce at least a portion of the function of regulatory T cells and/or end-stage senescent effector T cells, prior to administering to said subject the composition comprising manufactured T cells at a therapeutically effective dose.

In some embodiments, said immune depletion regimen comprises administering to said subject a first composition comprising pentostatin; and administering to said subject a second composition comprising cyclophosphamide.

In some embodiments, the method comprises a first treatment cycle and one or more additional treatment cycles, said first treatment cycle comprising: subjecting said subject to a first immune depletion regimen to reduce at least a portion of regulatory T cells and/or end-stage senescent effector T cells or to reduce at least a portion of the function of regulatory T cells and/or end-stage senescent effector T cells; each of said one or more additional treatment cycles comprising: subjecting said subject to a second immune depletion regimen to reduce at least a portion of regulatory T cells and/or end-stage senescent effector T cells or to reduce at least a portion of the function of regulatory T cells and/or end-stage senescent effector T cells; and administering to said subject a composition comprising manufactured T cells at a therapeutically effective dose.

In any of the foregoing embodiments, the method can further comprise prior to administering one or more additional doses of pentostatin to said subject, measuring the creatine clearance (CrCl) of said subject and adjusting a dose of pentostatin to be administered to said subject based on the CrCl, wherein pentostatin is administered at 4 mg/m$^2$ when CrCl≥60 mL/min/1.73 m$^2$, wherein pentostatin is administered at 2 mg/m$^2$ when 60 mL/min/1.73 m$^2$>CrCl≥30 mL/min/1.73 m$^2$, and wherein pentostatin is not administered when CrCl<30 mL/min/1.73 m$^2$. In some embodiments, the dose of pentostatin can be adjusted based on CrCl such that a dose of pentostatin is reduced by 50% when 60 mL/min/1.73 m$^2$>CrCl≥30 mL/min/1.73 m$^2$, and wherein pentostatin is not administered when CrCl<30 mL/min/1.73 m$^2$.

In any of the foregoing embodiments, the method can further comprise prior to administering one or more additional doses of cyclophosphamide, measuring absolute lymphocyte count (ALC) and absolute neutrophil count (ANC) and adjusting a dose of cyclophosphamide to be administered to said subject based on the ALC and ANC, wherein cyclophosphamide is administered at a dose of 200 mg when ANC>1000 per microliter, wherein cyclophosphamide is administered at a dose of 100 mg when ANC is 500-999 per microliter and ALC≥50 per microliter, and wherein cyclophosphamide is not administered when ALC<50 per microliter or ANC<500 per microliter. In some embodiments the dose of cyclophosphamide can be adjusted based on ALC and ANC such that a dose of cyclophosphamide is reduced by 50% when ANC is 500-999 per microliter and ALC≥50 per microliter or is not administered when ALC<50 per microliter or ANC<500 per microliter.

In any of the foregoing embodiments, said immune depletion regimen can include administering to said subject at least one of pentostatin and cyclophosphamide. In some embodiments, pentostatin is administered to said subject, and wherein a dose of said pentostatin can be between 0.5-4 mg/m$^2$, 0.5-3 mg/m$^2$, 0.5-2 mg/m$^2$, 0.5-1 mg/m$^2$, 1-4 mg/m$^2$, 2-4 mg/m$^2$, or 3-4 mg/m$^2$. By way of non-limiting example, a dose of said pentostatin is about 0.5 mg/m$^2$, 1 mg/m$^2$, 1.5 mg/m$^2$, 2 mg/m$^2$, 2.5 mg/m$^2$, 3 mg/m$^2$, 3.5 mg/m$^2$, or 4 mg/m$^2$. In some embodiments, cyclophosphamide is administered to said subject, and wherein a dose of said cyclophosphamide can be between 50-400 mg, 50-300 mg, 50-200 mg, 50-100 mg, 100-400 mg, 200-400 mg, 300-400 mg, 200-300 mg, or 100-200 mg. By way of non-limiting example, a dose of said cyclophosphamide is about 50 mg, 100 mg, 150 mg, 200 mg, 250 mg, 300 mg, 350 mg, or 400 mg. In some embodiments, both pentostatin and cyclophosphamide are administered to said subject. In some embodiments, said pentostatin and cyclophosphamide are administered to said subject in a single composition. In some embodiments, said single composition is administered intravenously to said subject.

In any of the foregoing embodiments, said immune depletion regimen can include administering to said subject a first composition comprising pentostatin; and administering to said subject a second composition comprising cyclophosphamide. In some embodiments, said first composition is administered at a dose of 1-4 mg/m2 of pentostatin is between 0.5-4 mg/m$^2$, 0.5-3 mg/m$^2$, 0.5-2 mg/m$^2$, 0.5-1 mg/m$^2$, 1-4 mg/m$^2$, 1-3 mg/m$^2$, 1-2 mg/m$^2$, or 3-4 mg/m$^2$. By way of non-limiting example, a dose of said pentostatin is about 1 mg/m$^2$, 1.5 mg/m$^2$, 2 mg/m$^2$, 2.5 mg/m$^2$, 3 mg/m$^2$, 3.5 mg/m$^2$, or 4 mg/m$^2$. In some embodiments, said second composition comprises cyclophosphamide and is administered at a dose of said cyclophosphamide between 50-400 mg, 50-300 mg, 50-200 mg, 50-100 mg, 100-400 mg, 200-400 mg, 300-400 mg, 200-300 mg, or 100-200 mg. By way of non-limiting example, a dose of said cyclophosphamide is about 50 mg, 100 mg, 150 mg, 200 mg, 250 mg, 300 mg, 350 mg, or 400 mg.

In any of the foregoing embodiments, the first treatment cycle can be a minimum of 28 days in duration. In any of the foregoing embodiments, each of said one or more additional treatment cycles can be a minimum of 35 days in duration.

In some embodiments, said step of administering pentostatin to said subject is repeated during the first treatment cycle. In some embodiments, said step of administering pentostatin to said subject is performed on days 1, 4, 8, and/or 11 of said first treatment cycle. In some embodiments, said step of administering cyclophosphamide to said subject is repeated during the first treatment cycle. In some embodiments, said step of administering cyclophosphamide to said subject is performed on days 1, 2, 3, 4, 5, 8, 9, 10, 11 and/or 12 of the first treatment cycle.

In any of the above embodiments, each of said one or more additional treatment cycles are separated by 0 to 4 weeks. In any of the above embodiments, said first treatment cycle and a first of said one or more additional treatment cycles are separated by 0 to 4 weeks. In any of the above embodiments, said step of administering to said subject the T cells of any of the foregoing methods for treating cancer at a therapeutically effective dose can be performed on day 15, 16, 17 or 18 of each of said one or more additional treatment cycles.

In some embodiments, said subject is in the second or third relapse of MM after having received regimens consisting of administration of a proteasome inhibitor, administration of immune modulatory drugs, administration of alkylators, administration of CD38 monoclonal antibodies, and administration of glucocorticoids.

In some embodiments, said subject is in a late stage of MM relapse and quad- or penta-refractory whereby standard therapies do not exist.

In some embodiments relating to a phase 3 clinical trial, the primary study objective will relate to progression-free survival, with progression-free being defined as less than a 25% increase in M-protein/free light chain difference between treatments.

In some embodiments, the method comprises subjecting said subject to an immune depletion regimen to reduce at least a portion of regulatory T cells and/or end-stage senescent effector T cells or to reduce at least a portion of the function of regulatory T cells and/or end-stage senescent effector T cells; and administering to said subject T cells of any of the foregoing methods for treating cancer at a therapeutically effective dose after said immune depletion regimen.

In some embodiments, said immune depletion regimen comprises: administering pentostatin to said subject; and administering cyclophosphamide to said subject; administering one or more additional doses of pentostatin to said subject if said subject's creatine clearance is ≥30 mL/min/ 1.73 m$^2$; administering one or more additional doses of cyclophosphamide to said subject if said subject's absolute lymphocyte count is 50 per microliter or greater and said subject's absolute neutrophil count is 500 per microliter or greater.

In some embodiments, said step of measuring the CrCl of said subject and adjusting a dose of pentostatin to be administered is performed on days 1, 4, 8, and/or 11 of said immune depletion regimen.

In some embodiments, said step of measuring ALC and ANC and adjusting a dose of cyclophosphamide to be administered is performed on days 1, 2, 3, 4, 5, 8, 9, 10, 11 and/or 12 of the immune depletion regimen.

In some embodiments, said step of administering to said subject a composition T cells of any of the foregoing methods for treating cancer at a therapeutically effective dose after said immune depletion regimen is performed 15-18 days after the start of the immune depletion regimen.

In any of the foregoing embodiments, the steps subjecting said subject to an immune depletion regimen to reduce at least a portion of regulatory T cells and/or end-stage senescent effector T cells or to reduce at least a portion of the function of regulatory T cells and/or end-stage senescent effector T cells and administering to said subject a composition comprising manufactured T cells at a therapeutically effective dose after said immune depletion regimen are repeated at least twice. In any of the foregoing embodiments, the steps subjecting said subject to an immune depletion regimen to reduce at least a portion of regulatory T cells and/or end-stage senescent effector T cells or to reduce at least a portion of the function of regulatory T cells and/or end-stage senescent effector T cells and administering to said subject T cells of any of the foregoing methods for treating cancer at a therapeutically effective dose after said immune depletion regimen can be repeated up to 8 times or more. In any of the foregoing embodiments, each step of administering to said subject a composition comprising manufactured T cells at a therapeutically effective dose after said immune depletion regimen can be separated by 0 to 9 weeks.

It should also be understood that, in any embodiments of the present disclosure, where co-stimulation by anti-CD3/ anti-CD28 antibodies is performed, this co-stimulation can be provided in any form of anti-CD3/anti-CD28 antibodies. By way of example, but not limitation, where co-stimulation is indicated as being performed by using anti-CD3/anti-CD28 beads, anti-CD3/anti-CD28 nanoparticles or microparticles can be used. Alternative methods of providing T cell co-stimulation can be envisioned, including but not limited to alternative methods of delivering co-stimulation via novel hydrogel technology (Jesuraj N J et al; Blood, 2016; 128(22):3368: A Novel Phase-Change Hydrogel Substrate for T Cell Activation Promotes Increased Expansion of CD8+ Cells Expressing Central Memory and Naïve Phenotype Markers), alternative monoclonal antibodies (Han X et al; International Review in Cellular and Molecular Biology, 2019; 342: 1-25: Stimulating T cells against cancer with agonist immunostimulatory monoclonal antibodies) or pharmacologic agents that yield co-stimulatory signals such a staphylococcal enterotoxin B or lenalidomide ([1] Popugailo A et al; Frontiers in Immunology; 2019; 10:942: Staphylococcal and Streptococcal Superantigens Trigger B7/CD28 Costimulatory Receptor Engagement to Hyperinduce Inflammatory Cytokines; and [2] LeBlanc R et al; Blood, 2004; 103(5):1787-90: Immunomodulatory drug costimulates T cells via the B7-CD28 pathway). An amount of these other forms sufficient to cause the phenotypic effect desired can be added. Such an amount can be determined by one of skill in the art with routine experimentation.

In previous basic research and translational clinical trials, it was identified that the ex vivo manufacture of T cells in the mTOR inhibitor rapamycin resulted in rapamycin-resistant T cells that were of limited differentiation status, had an anti-apoptotic propensity, and had an increased ability to mediate transplantation responses after adoptive T cell transfer.

Specifically, ex vivo T cell manufacturing can include the use of culture methods comprised of the following: culture devoid of anti-CD3/anti-CD28 co-stimulation; culture of T cells at a relatively high density (about $9 \times 10^6$ cells/mL); use of culture media devoid of IL-2 and supplemented with an anti-IL-2 receptor blocking monoclonal antibody; supplementation of culture media with a high concentration (about 4.5 μM) of the mTOR inhibitory molecule temsirolimus and a high concentration of the type I polarizing cytokine IFN-α (about 10,000 IU/ml).

The resultant ex vivo manufactured T cells have a specific T cell phenotype that would predictably be beneficial for the mediation of anti-tumor effects, including: reduced STAT-5 signaling; increased T central memory composition, as defined by cell surface expression of CD62L and CCR7; increased T cell quiescence, as indicated by reduced CD25 expression; preserved secretion of IL-2 with reduced secretion of effector memory cytokines such as IFN-γ and TNF-α[8]; reduced expression of checkpoint inhibitor receptors[9], including LAIR1, 2B4, TIGIT, CTLA4, TIM3, LAG3, and PD1; and increased responsiveness to the key T cell homeostatic cytokines, IL-7 and IL-15.

We have also described the following key elements for cancer therapy using manufactured T cells: preparation of the patient with an immune depletion regimen comprised of the combination of pentostatin plus cyclophosphamide; and treatment of patients with multiple myeloma, including the earliest stages (smoldering) and the latest stages of disease (relapsed, refractory). We expect, without being bound to theory, that the T cells manufactured according to the present disclosure, which possess reduction in multiple key checkpoint inhibitory receptors, would theoretically represent a suitable T cell population for the adoptive T cell therapy of solid tumors. Towards this end, FIG. 36 details the schema of the clinical trial in development to address the manufactured T cells in patients with various solid tumors, including but not limited to: tumors with a high mutational rate (most notably, renal cell carcinoma, hepatocellular carcinoma, gastric cancer, lung cancer, and bladder cancer) and tumors with a relatively low mutational rate (most notably, pancreatic cancer, sarcoma, prostate cancer, ovarian cancer, breast cancer, and colorectal cancer).

We provide herein ex vivo manufacturing modifications to the methods detailed in the present disclosure. These manufacturing modifications allow one to sensitize such T cells to tumor lysates via T cell co-culture with a subset of T cells that are incubated with lysate or antigen. That is, one can use the T cells as APC for lysate or antigen presentation rather than direct inoculation of lysate or antigen into the T cell culture. These observations are important from various perspectives, including: (a) demonstration of the APC capacity of the manufactured T cells; and (b) identification of a new manufacturing method of T cell-to-T cell co-culture that can be optimized for the ex vivo or in vivo sensitization of T cells to solid tumors.

Methods for Treating Infectious Disease

In some embodiments, the method for treating an infectious disease caused by an infectious agent in a subject comprises administering to said subject a manufactured T cells of the present disclosure at a therapeutically effective dose, and administering to the subject an anti-infectious agent sufficient and in an amount sufficient to induce production of immunogenic antigen from the infectious agent in the subject, an agent sufficient to and in an amount sufficient to induce increased IL-7 or IL-15 expression in the subject, exogenous IL-7 or IL-15, or a combination thereof.

In some embodiments, the method for treating an infectious disease can include administering antigen-presenting T cells of the present disclosure at a therapeutically effective dose to the subject. In some embodiments, the method for treating an infectious disease can include administer loaded, antigen-presenting T cells of the present disclosure at a therapeutically effective dose to the subject.

In some embodiments, the method for treating an infectious disease can include administering antigen-presenting T cells of the present disclosure and manufactured T cells of the present disclosure in a therapeutically effective dose to the subject. In some embodiments, the method for treating an infectious disease can include administer loaded, antigen-presenting T cells of the present disclosure and manufactured T cells of the present disclosure in a therapeutically effective dose to the subject.

In any of the foregoing methods for treating an infectious disease, the infectious agent can be bacterial, viral or fungal.

In any of the foregoing methods for treating an infectious disease, where loaded, antigen-presenting T cells are administered, the loaded, antigen-presenting T cells can include an antigen associated with said infectious agent.

In any of the foregoing methods for treating an infectious disease, where sensitized, manufactured T cells are administered, the sensitized, manufactured T cells can be sensitized to an antigen or a portion thereof associated with said infectious agent.

In any of the foregoing embodiments methods for treating an infectious disease, where manufactured T cells are administered with antigen-presenting T cells or loaded, antigen-presenting T cells, a ratio between the antigen-presenting T cells or loaded, antigen-presenting T cells and the manufactured T cells can be about 1:10 to about 1:50. By way of example, but not limitation, the ratio can be from about 1:10 to about 1:100, about 1:20 to about 1:100, about 1:40 to about 1:100, about 1:50 to about 1:100, about 1:10 to about 1:50, about 1:5, 1:10, 1:20, 1:30, 1:40, 1:50, 1:60, 1:70, 1:80, 1:90, or 1:100.

In any of the foregoing methods for treating an infectious disease, unless otherwise added, the method can further comprise administering to the subject an anti-infectious agent sufficient to induce production of an immunogenic composition of the infectious agent in the subject, an agent sufficient to and in an amount sufficient to induce increased IL-7 or IL-15 expression in the subject, exogenous IL-7 or IL-15, or a combination thereof.

In any of the foregoing methods for treating an infectious disease, the sensitized, manufactured T cells can have been co-cultured with loaded, antigen-presenting T cells comprising the antigen, wherein the sensitized, manufactured T cells are sensitized to the antigen or a portion thereof. In such embodiments, the loaded, antigen-presenting T cells can have been exposed to an immunogenic composition comprising the antigen, such as a lysate.

In any of the foregoing methods for treating an infectious disease, the sensitized, manufactured T cells can be sensitized to an antigen from the infectious agent. By way of example, but not limitation, the methods by which the loaded, antigen-presenting T cells or sensitized, manufactured T cells can have further included harvesting a sample of the infectious agent from the subject and using the same as the immunogenic composition such as, by way of example but not limitation, to generate a lysate as the immunogenic composition. In other words, the sensitized, manufactured T cells can be sensitized to a lysate of the infectious agent.

In any of the foregoing embodiments for treating an infectious disease, the anti-infectious agent can be an anti-bacterial, anti-viral or anti-fungal agent. By way of further example, for bacterial immunogenic compositions, bacteriostatic antibacterials that can be used include chloramphenicol, trimethoprim, erythromycin, penicillins, carbapenems such as imipenem, aztreonam, cefepime, aminoglycosides, such as gentamycin and amikacin, quinolones such as levofloxacin and ciprofloxacin, macrolides such as erythromycin and azithromycin, and combinations thereof. By way of still further example, for viral immunogenic compositions, antiviral treatments that can be used to generate the immunogenic composition can include viral RNA polymerase inhibitors such as remdesivir, viral protein synthesis inhibitors such as ritonavir, lopinavir, inhibitors of viral entry such as hydroxycloroquine, acyclovir, valacyclovir, foscarnet, ribavirin, lamivudine, amantadine, oseltamivir, zanamivir, protease inhibitors such as amprenavir and atazanavir, reverse transcriptase inhibitors such as abacavir, stavudine, zidovudine, integrase inhibitors such as bictegravir and dolutegravir, NS3/4A protease inhibitors such as danoprevir and glecaprevir, NSSA phosphoprotein inhibitors such as daclatasvir and ledipasvir, neuraminidase inhibitors such as laninamivir and oseltamivir, and combinations thereof. By still way of further example, for fungal immunogenic compositions, anti-fungal treatments that can be used to generate the immunogenic composition can include polyenes such as amphotericin, azoles such as ketoconazole and itraconazole, allylamines such as terbinafine, echinocandins such as caspofungin and micafungin, griseofulvin, and combinations thereof. Immunogenic compositions can be also be derived from synthesized, e.g. recombinant antigens, such as recombinant cancer-associated antigens, or can be introduced by lentiviral transformation of the T cells in culture. In the context of in vivo administration, these antigens can be administered to the subject.

In any of the foregoing embodiments for treating an infectious disease, the agent sufficient to induce IL-7 or IL-15 expression in the subject can be selected from the group consisting of cyclophosphamide, melphalan, pentostatin, fludabine, bendamustine, ifosamide, temoxolomide, carboplatin, cisplatin, oxaliplatin, methotrexate, pemetrexed, trimetrexate, cladribine, azacytidine, capecitabine, cytarabine, alemtuzumab, basiliximab, temsirolimus, axitinib, erlotinib, ibrutinib, cabazitaxel, docetaxel, paclitaxel, etoposide, irinotecan, teniposide, topotecan, vinblastine, vincristine, vinorelbine, and combinations thereof.

In any of the foregoing embodiments for treating an infectious disease, a total amount of cells administered to the subject per administration can be about $0.1\times10^6$ cells/kg to about $5\times10^6$ cells/kg of subject body weight. By way of example, but not limitation, the total amount of cells administered to the subject per administration can be about $1\times10^5$ to $5\times10^6$, $1\times10^6$ to $2.5\times10^6$ cells/kg, $2.5\times10^6$ to $5\times10^6$ cells/kg, $1\times10^5$ to $2.5\times10^6$ cells/kg, $2.5\times10^5$ to $5\times10^6$ cells/kg, $1\times10^5$ to $2.5\times10^5$ cells/kg, $2.5\times10^5$ to $5\times10^5$ cells/kg, $1\times10^5$ cells/kg, $2\times10^5$ cells/kg, $3\times10^5$ cells/kg, $4\times10^5$ cells/kg, $5\times10^5$ cells/kg, $1\times10^6$ cells/kg, $2\times10^6$ cells/kg, $3\times10^6$ cells/kg, $4\times10^6$ cells/kg, or $5\times10^6$ cells/kg manufactured T cells per kg of the subject's body weight. In any of the foregoing embodiments, the cells can be administered to said subject by infusion.

In any of the foregoing embodiments for treating an infectious disease, the infectious disease can be bacterial, viral or fungal. By way of example, but not limitation, the infectious disease can be chickenpox, diphtheria, *Escherichia coli* infection, giardiasis, HIV/AIDS, infectious mononucleosis, influenza, COVID-19, Lyme disease, malaria, bacterial pneumonia, *Salmonella* infections, herpes zoster, tuberculosis, viral hepatitis, West Nile Virus, Ebola virus, Candidiasis, *Clostridium difficile* infection, human papillomavirus disease, leprosy, meningitis, vancomycin-resistant Enterococci, Zika virus, tuberculosis, bacterial infection, invasive fungal infection (such as *Candida* or *Aspergillus*), and viral infection, including the agent causing COVID-19 disease, novel coronavirus diseases, such as Middle East Respiratory Syndrome (MERS); Lassa; Crimean Congo Haemorrhagic Fever (CCHF), Nipah virus Rift Valley Fever; Chikungunya; Dengue; Hantavirus; Plague; Marburg; and Q fever.

In any of the foregoing embodiments for treating an infectious disease, the T cells (antigen-presenting T cells, loaded, antigen-presenting T cells, sensitized, manufactured T cells, or manufactured T cells) administered to the subject can be autologous or allogenic. Thus, prior to administering the cells to the subject, autologous cells can be harvested from the subject. Preferably, this is done before any immune depletion regimen is administered to the subject.

In any of the foregoing embodiments for treating an infectious disease, the method can further include subjecting the subject to an immune depletion regimen.

In another embodiment, the method further comprises subjecting said subject to an immune depletion regimen to reduce at least a portion of regulatory T cells and/or end-stage senescent effector T cells or to reduce at least a portion of the function of regulatory T cells and/or end-stage senescent effector T cells, prior to administering to said subject the composition comprising manufactured T cells at a therapeutically effective dose.

In some embodiments, said immune depletion regimen comprises administering to said subject a first composition comprising pentostatin; and administering to said subject a second composition comprising cyclophosphamide.

In some embodiments, the method comprises a first treatment cycle and one or more additional treatment cycles, said first treatment cycle comprising: subjecting said subject to a first immune depletion regimen to reduce at least a portion of regulatory T cells and/or end-stage senescent effector T cells or to reduce at least a portion of the function of regulatory T cells and/or end-stage senescent effector T cells; each of said one or more additional treatment cycles comprising: subjecting said subject to a second immune depletion regimen to reduce at least a portion of regulatory T cells and/or end-stage senescent effector T cells or to reduce at least a portion of the function of regulatory T cells and/or end-stage senescent effector T cells; and administering to said subject a composition comprising manufactured T cells at a therapeutically effective dose.

In any of the foregoing embodiments, the method can further comprise prior to administering one or more additional doses of pentostatin to said subject, measuring the creatine clearance (CrCl) of said subject and adjusting a dose of pentostatin to be administered to said subject based on the CrCl, wherein pentostatin is administered at 4 mg/m$^2$ when CrCl≥60 mL/min/1.73 m$^2$, wherein pentostatin is administered at 2 mg/m$^2$ when 60 mL/min/1.73 m$^2$>CrCl≥30 mL/min/1.73 m$^2$, and wherein pentostatin is not administered when CrCl<30 mL/min/1.73 m$^2$. In some embodiments, the dose of pentostatin can be adjusted based on CrCl such that a dose of pentostatin is reduced by 50% when 60 mL/min/1.73 m$^2$>CrCl≥30 mL/min/1.73 m$^2$, and wherein pentostatin is not administered when CrCl<30 mL/min/1.73 m$^2$.

In any of the foregoing embodiments, the method can further comprise prior to administering one or more additional doses of cyclophosphamide, measuring absolute lymphocyte count (ALC) and absolute neutrophil count (ANC) and adjusting a dose of cyclophosphamide to be administered to said subject based on the ALC and ANC, wherein cyclophosphamide is administered at a dose of 200 mg when ANC>1000 per microliter, wherein cyclophosphamide is administered at a dose of 100 mg when ANC is 500-999 per microliter and ALC≥50 per microliter, and wherein cyclophosphamide is not administered when ALC<50 per microliter or ANC<500 per microliter. In some embodiments the dose of cyclophosphamide can be adjusted based on ALC and ANC such that a dose of cyclophosphamide is reduced by 50% when ANC is 500-999 per microliter and ALC≥50 per microliter or is not administered when ALC<50 per microliter or ANC<500 per microliter.

In any of the foregoing embodiments, said immune depletion regimen can include administering to said subject at least one of pentostatin and cyclophosphamide. In some embodiments, pentostatin is administered to said subject, and wherein a dose of said pentostatin can be between 0.5-4 mg/m$^2$, 0.5-3 mg/m$^2$, 0.5-2 mg/m$^2$, 0.5-1 mg/m$^2$, 1-4 mg/m$^2$, 2-4 mg/m$^2$, or 3-4 mg/m$^2$. By way of non-limiting example, a dose of said pentostatin is about 0.5 mg/m$^2$, 1 mg/m$^2$, 1.5 mg/m$^2$, 2 mg/m$^2$, 2.5 mg/m$^2$, 3 mg/m$^2$, 3.5 mg/m$^2$, or 4 mg/m$^2$. In some embodiments, cyclophosphamide is administered to said subject, and wherein a dose of said cyclophosphamide can be between 50-400 mg, 50-300 mg, 50-200 mg, 50-100 mg, 100-400 mg, 200-400 mg, 300-400 mg, 200-300 mg, or 100-200 mg. By way of non-limiting example, a dose of said cyclophosphamide is about 50 mg, 100 mg, 150 mg, 200 mg, 250 mg, 300 mg, 350 mg, or 400 mg. In some embodiments, both pentostatin and cyclophosphamide are administered to said subject. In some embodiments, said pentostatin and cyclophosphamide are administered to said subject in a single composition. In some embodiments, said single composition is administered intravenously to said subject.

In any of the foregoing embodiments, said immune depletion regimen can include administering to said subject a first composition comprising pentostatin; and administering to said subject a second composition comprising cyclophosphamide. In some embodiments, said first composition is administered at a dose of 1-4 mg/m2 of pentostatin is between 0.5-4 mg/m$^2$, 0.5-3 mg/m$^2$, 0.5-2 mg/m$^2$, 0.5-1 mg/m$^2$, 1-4 mg/m$^2$, 1-3 mg/m$^2$, 1-2 mg/m$^2$, or 3-4 mg/m$^2$. By way of non-limiting example, a dose of said pentostatin is about 1 mg/m$^2$, 1.5 mg/m$^2$, 2 mg/m$^2$, 2.5 mg/m$^2$, 3 mg/m$^2$, 3.5 mg/m$^2$, or 4 mg/m$^2$. In some embodiments, said second composition comprises cyclophosphamide and is administered at a dose of said cyclophosphamide between 50-400 mg, 50-300 mg, 50-200 mg, 50-100 mg, 100-400 mg, 200-400 mg, 300-400 mg, 200-300 mg, or 100-200 mg. By way of non-limiting example, a dose of said cyclophosphamide is about 50 mg, 100 mg, 150 mg, 200 mg, 250 mg, 300 mg, 350 mg, or 400 mg.

In any of the foregoing embodiments, the first treatment cycle can be a minimum of 28 days in duration. In any of the foregoing embodiments, each of said one or more additional treatment cycles can be a minimum of 35 days in duration.

In some embodiments, said step of administering pentostatin to said subject is repeated during the first treatment cycle. In some embodiments, said step of administering pentostatin to said subject is performed on days 1, 4, 8, and/or 11 of said first treatment cycle. In some embodiments, said step of administering cyclophosphamide to said subject is repeated during the first treatment cycle. In some embodiments, said step of administering cyclophosphamide to said subject is performed on days 1, 2, 3, 4, 5, 8, 9, 10, 11 and/or 12 of the first treatment cycle.

In any of the above embodiments, each of said one or more additional treatment cycles are separated by 0 to 4 weeks. In any of the above embodiments, said first treatment cycle and a first of said one or more additional treatment cycles are separated by 0 to 4 weeks. In any of the above embodiments, said step of administering to said subject the T cells of any of the foregoing methods for treating an infectious disease at a therapeutically effective dose is performed on day 15, 16, 17 or 18 of each of said one or more additional treatment cycles.

In some embodiments, said subject is in the second or third relapse of MM after having received regimens consisting of administration of a proteasome inhibitor, administration of immune modulatory drugs, administration of alkylators, administration of CD38 monoclonal antibodies, and administration of glucocorticoids.

In some embodiments, said subject is in a late stage of MM relapse and quad- or penta-refractory whereby standard therapies do not exist.

In some embodiments relating to a phase 3 clinical trial, the primary study objective will relate to progression-free survival, with progression-free being defined as less than a 25% increase in M-protein/free light chain difference between treatments.

In some embodiments, the method comprises subjecting said subject to an immune depletion regimen to reduce at least a portion of regulatory T cells and/or end-stage senescent effector T cells or to reduce at least a portion of the function of regulatory T cells and/or end-stage senescent effector T cells; and administering to said subject T cells of any of the foregoing methods for treating an infectious disease at a therapeutically effective dose after said immune depletion regimen.

In some embodiments, said immune depletion regimen comprises: administering pentostatin to said subject; and administering cyclophosphamide to said subject; administering one or more additional doses of pentostatin to said subject if said subject's creatine clearance is ≥30 mL/min/ 1.73 m$^2$; administering one or more additional doses of cyclophosphamide to said subject if said subject's absolute lymphocyte count is 50 per microliter or greater and said subject's absolute neutrophil count is 500 per microliter or greater.

In some embodiments, said step of measuring the CrCl of said subject and adjusting a dose of pentostatin to be administered is performed on days 1, 4, 8, and/or 11 of said immune depletion regimen.

In some embodiments, said step of measuring ALC and ANC and adjusting a dose of cyclophosphamide to be administered is performed on days 1, 2, 3, 4, 5, 8, 9, 10, 11 and/or 12 of the immune depletion regimen.

In some embodiments, said step of administering to said subject a composition T cells of any of the foregoing methods for treating an infectious disease at a therapeutically effective dose after said immune depletion regimen is performed 15-18 days after the start of the immune depletion regimen.

In any of the foregoing embodiments, the steps subjecting said subject to an immune depletion regimen to reduce at least a portion of regulatory T cells and/or end-stage senescent effector T cells or to reduce at least a portion of the function of regulatory T cells and/or end-stage senescent effector T cells and administering to said subject a composition comprising manufactured T cells at a therapeutically effective dose after said immune depletion regimen are repeated at least twice. In any of the foregoing embodiments, the steps subjecting said subject to an immune depletion regimen to reduce at least a portion of regulatory T cells and/or end-stage senescent effector T cells or to reduce at least a portion of the function of regulatory T cells and/or end-stage senescent effector T cells and administering to said subject T cells of any of the foregoing methods for treating an infectious disease at a therapeutically effective dose after said immune depletion regimen can be repeated up to 8 times or more. In any of the foregoing embodiments, each step of administering to said subject a composition comprising manufactured T cells at a therapeutically effective dose after said immune depletion regimen can be separated by 0 to 9 weeks In any of the foregoing embodiments, it should be understood that, where loaded, antigen-presenting T cells are administered, they can be loaded with an antigen associated with the cancer or infectious disease. Similarly, in any of the foregoing embodiments, it should be understood that, where sensitized, manufactured T cells are administered that sensitized T cells can be used instead. It should also be understood that, where sensitized, manufactured T cells or sensitized T cells are administered, they can be sensitized to an antigen associated with the cancer or infectious disease. It should likewise be understood that compositions of combinations of the manufactured T cells, antigen-presenting T cells, loaded, antigen-presenting T cells and sensitized manufactured T cells can be used to treat cancer or infectious disease In any of the foregoing embodiments for treating cancer or infectious disease, it should be understood that an immune depletion regimen as disclosed in any of the embodiments herein can be incorporated prior to administering T cells.

First, the current application demonstrates that these methods can enhance T cell reactivity to tumors that are considered classically immunogenic (such as lung cancer) or relatively non-immunogenic (pancreatic cancer). Therefore, this T cell APC method may be applicable to all solid tumor and should also be applicable to the wide variety of hematologic malignancy, which is often considered immunogenic. It should be understood that the methods described and claimed herein can be applied to the exemplary cancers discussed herein, but should not be limited thereto.

Second, although some focus of this application is placed upon solid tumor and other cancer therapy, the methods described herein can be utilized as an alternative to standard vaccine strategies to treat other conditions, particularly infectious diseases including but not limited to: tuberculosis, bacterial infection, invasive fungal infection (such as *Candida* or *Aspergillus*), and viral infection, including the agent causing COVID-19 disease. A recent report detailed pathogens of epidemic potential that may be treated by the methods detailed herein, including: novel coronavirus diseases, including Middle East Respiratory Syndrome (MERS); Lassa; Crimean Congo Haemorrhagic Fever (CCHF); Nipah; Zika; Ebola; Rift Valley Fever; Chikungunya; Dengue; Hantavirus; Plague; Marburg; and Q fever. The methods provided herein for treating cancer using the antigen-presenting T cells, sensitized, manufactured T cells, a combination of both or manufactured T cells with a therapy to produce immunogenic cell death, increase IL-7 and IL-15 expression or to administer IL-7 and IL-15, whether ex vivo or in vivo, can also be applied to other diseases or conditions because the therapeutic effect is believed, without being bound to theory, to be derived from the antigen-presenting properties of the manufactured T cells as modified in the present disclosure and their ability to sensitize manufactured T cells (or other T cells) to the antigen to improve therapeutic effect. For example, bacterial or viral pathogens include antigens that can be targeted by T cells and thus are a candidate pathology that can be treated. It should be understood that in such instances, the disease or condition to be treated will be matched to at least one antigen in the immunogenic composition used to pulse the manufactured T cells to create antigen-presenting T cells. For example, one could use a bacterial lysate or recombinantly expressed protein antigens. It should be understood that, to the extent the disclosure discusses tumor treatment using the APC properties of the manufactured T cells, this can be applied to other diseases and conditions.

Third, it is envisioned that the methods described herein may have implications for therapeutic use of manufactured T cells of the present disclosure either without or with any of the modification described in terms of APC. That is, there is potential for APC function in the manufactured T cells. Therefore, upon adoptive T cell transfer, such T cells can acquire a heightened level of APC function in vivo due to: ancillary in vivo administration of chemotherapeutics agents (including etoposide) or irradiation that induce immunogenic tumor death; administration of agents that increase the level of homeostatic cytokines IL-7 and IL-15; or exogenous cytokine administration. As noted above, it should be understood that such treatment can be used, as applicable, in the treatment of other diseases or conditions. For example, administration of agents that increase the level of homeostatic cytokines IL-7 and IL-15 or exogenous cytokine administration of at least IL-7 and IL-15 can be performed with a treatment comprising administering manufactured T cells to the patient. Similarly, by way of example, but not limitation, treatments that produce immunogenic compositions in the patient of the pathogen or agent of the disease or condition can also be administered, such as antibiotics that induce bacterial death.

Fourth, as a variation, T cell manufacturing according to the present disclosure can be modified to enhance APC function without ex vivo use of tumor lysate or any immunogenic composition. In this scenario, the tumor or antigen sensitization will occur in vivo either de novo or after induction of immunogenic tumor cell death (for example, in vivo infusion of etoposide). In this scenario, the T cell adoptive transfer strategy will be comprised of two components, namely: (1) the T cell product (responder T cells) generated according to the present disclosure; and (2) the APC-enriched T cell product (antigen-presenting T cells) manufactured according to the methods described in this disclosure. In a clinical translation step, patients with refractory solid tumors would be treated with various ratios of responder T cells and antigen-presenting T cells. In one scenario, successive cohorts could be treated with the following ratios of the T cell components: (1) 100% responder T cells; (2) 2.5% T cell APC plus 97.5% responder T cells (1:40 ratio); and (3) 10% T cell APC plus 90% responder T cells (1:10 ratio).

Fifth, it is envisioned that the therapeutic approach will incorporate both the ex vivo APC generation and the ex vivo T cell sensitization to tumor lysate. In this scenario, the tumor lysate can exist in different formats. In one format, the patient with refractory solid tumor will undergo tumor excision and a patient-specific lysate will be generated. In an alternative format, an off-the-shelf tumor lysate may be utilized for solid tumors that are characterized by tumor associated antigens, including but not limited to: cancer-testis-antigens; differentiation antigens such as prostate-specific antigen (PSA); over-expressed antigens such as HER-2/neu, and mutation-derived neoantigens.

Sixth, as a variation, this ex vivo T cell APC generation combined with ex vivo T cell sensitization to tumor lysate may be performed either without any further ex vivo T cell expansion or with an additional interval of T cell expansion. In this latter case, T cell expansion may be facilitated by additional culture interventions, including but not limited to cytokine addition (such as IL-7, IL-15, IL-2) and/or anti-CD3, anti-CD28 co-stimulation.

Seventh, it is also envisioned that the therapeutic approach of ex vivo APC generation combined with ex vivo T cell sensitization may incorporate other antigen delivery methods as an alternative to tumor lysate utilization. For example, potential tumor antigens or infectious disease antigens can be delivered by lentiviral vectors encoding the tumor or infectious disease antigen; alternatively, antigen delivery to the manufactured T cell APC can be performed by use of overlapping peptide pools.

In the examples below, T cells manufactured according to the methods of the present disclosure responded to tumor cell lysates isolated from human pancreatic cancer and lung cancer cell lines. Such tumor lysates were harvested after tumor cell exposure to etoposide, which is known to induce immunogenic cell death. However, T cells do not respond to tumor lysate in isolation; rather, such tumor-derived material is processed and presented by antigen-presenting-cells (APC) that are HLA-matched with the responding T cells, most notably dendritic cells, and then the T cell can respond to the tumor-derived material. We performed additional experiments to better define the ability of the manufactured T cells to present immunogenic lysates from solid tumor cells.

It should be understood that the methods disclosed herein for the treatment of cancer, including the use of immune depletion regimens can be incorporated into the foregoing treatment modalities. It should likewise be understood that the treatment modalities disclosed herein can be applied to the treatment of infectious disease, including that the loaded, antigen-presenting T cells can be loaded with an antigen associated with the infectious disease and sensitized, manufactured T cells can be sensitized to an antigen associated with the infectious disease. It should be understood that in such cases, the antigen used will be associated with the disease or condition of the patient, such as cancer or infectious disease. It should also be understood that the foregoing interventions can include multiple infusions of the T cells.

EXAMPLES

The following examples are provided to better illustrate the methods of the present disclosure and the resultant manufactured T cells. These examples are not intended to be limiting or to otherwise alter the scope of the methods, cells and compositions disclosed in the present disclosure.

Example 1

Use of Anti-IL-2 Receptor Blockade and mTOR Blockade for Th1 Enrichment. For adoptive T cell therapy, it is important to manufacture T cells that preferentially express a Th1 phenotype, with minimal contamination from cells with a regulatory T ($T_{REG}$) cell phenotype. Th1-type cells can be characterized in part by their expression of the cell fate transcription factor TBET, whereas $T_{REG}$ cells express the FoxP3 transcription factor.

Methods for promoting TBET while limiting FoxP3 were evaluated. We evaluated the mTOR inhibitor temsirolimus, which is an FDA-approved medication administered intra-venously for therapy of refractory renal cell carcinoma. The use of an mTOR inhibitor to manufacture T cells enriched for a Th1 phenotype may seem paradoxical, as inhibition of mTOR has, in general, been associated with the promotion of T cells of a $T_{REG}$ phenotype. The current experiments differ from the prior research because temsirolimus is an intra-venous formulation, which thereby is advantageous relative to rapamycin, which is less feasible for cell culture due to limited solubility in media.

The current experiments also differ from the past research because we evaluated the combination of temsirolimus and the anti-IL-2 receptor monoclonal antibody, daclizumab. Daclizumab and basiliximab are both FDA-approved monoclonal antibodies that have a common mechanism of action and therefore can be used inter-changeably in the system we have developed.

T cells were cultured ex vivo, as indicated, using various ratios of anti-CD3, anti-CD28 beads to T cells (1:1 or 1:12); the mTOR inhibitor temsirolimus (1 μM); without or with the anti-IL-2 receptor monoclonal antibody daclizumab (5 or 50 μg/ml); and either Th1 polarization cytokines (IFN-alpha; 10,000 IU/ml) or control regulatory T cell polarization (IL-2 plus TGF-β). At day 6 of culture, the T cells were evaluated for intra-cellular expression of the regulatory T cell transcription factor FoxP3 and the Th1 transcription factor TBET. (FIGS. 1A-1B).

It was found that addition of temsirolimus (1.0 μM concentration) in the setting of the type I polarizing cytokine IFN-α reduced the resultant T cell expression of FoxP3 relative to the day 0 input T cell population (see FIG. 1A). Furthermore, we found that blockade of the IL-2 receptor further reduced FoxP3 expression; use of the antibody at 50 μg/ml was more effective than use of the antibody at 5 μg/ml, thereby indicated a dose-response relationship. Temsirolimus was not effective at reducing FoxP3 expression if exogenous IL-2 was added in combination with IFN-α (FIG. 1A); furthermore, temsirolimus and daclizumab were not effective at limiting FoxP3 expression if the culture conditions were permissive for $T_{REG}$ cell differentiation, namely: reduction in the bead ratio to 1:12; elimination of IFN-α from culture; and addition of exogenous IL-2 plus TGF-β (FIG. 1A).

Figure 1B:
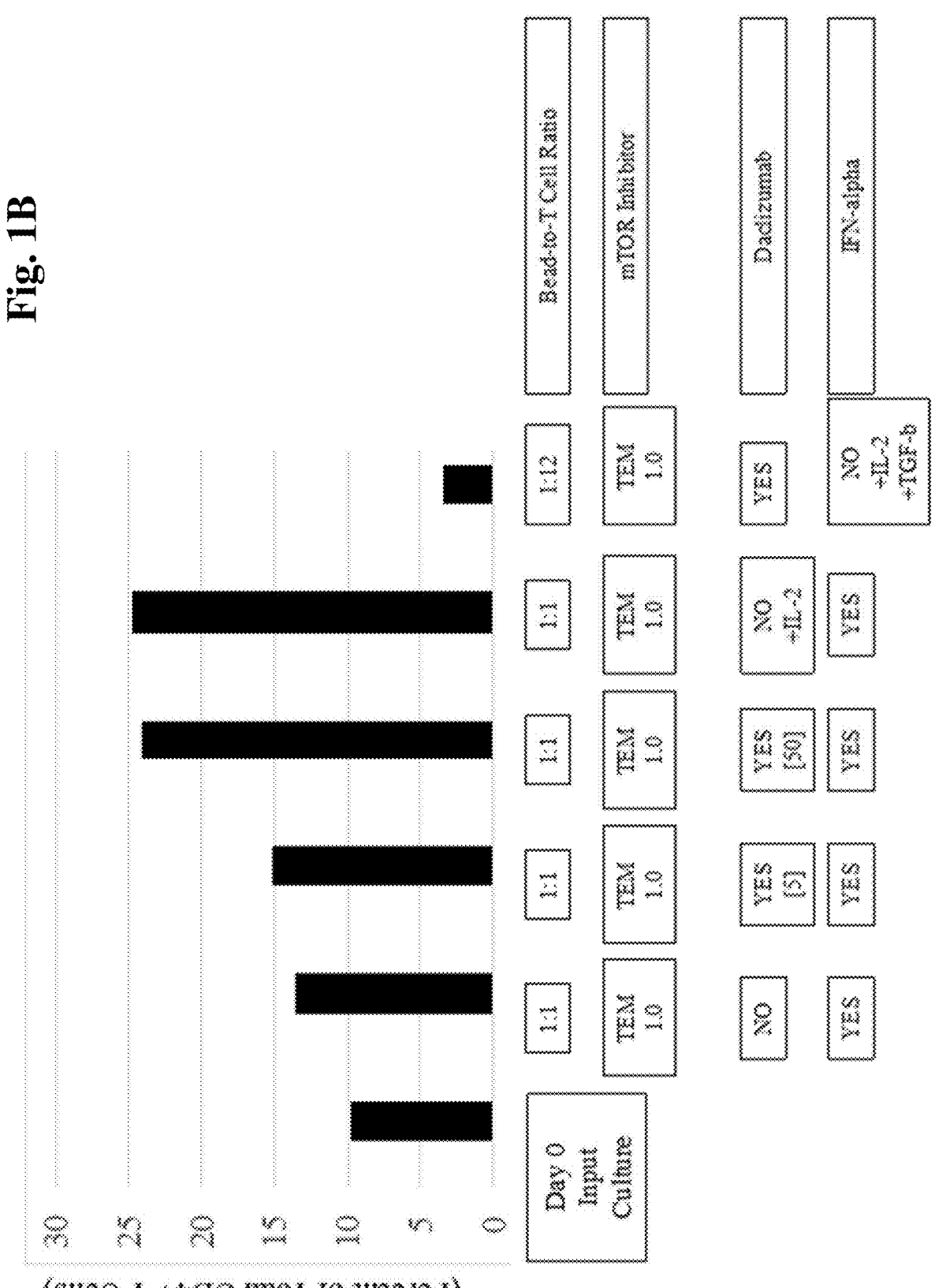
FIG. 1B depicts the percentage of CD4$^+$ T cells expressing TBET at day 0 and after various culture conditions.

In addition to limiting FoxP3 expression, the combination of temsirolimus and an anti-IL-2 receptor monoclonal antibody was effective at promoting the Th1 phenotype, as indicated by increased expression of TBET (FIG. 1B). Again, there was a dose response relationship, with 50 μg/ml daclizumab promoting TBET expression to a higher degree than 5 μg/ml (FIG. 1B). Although addition of IL-2 to the IFN-α polarization increased TBET, this was also associated with an increase in FoxP3, thereby indicated a lack of Th1-purity through exogenous IL-2 addition. Of note, the $T_{REG}$ control condition—IL-2 and TGF-β—as expected, had reduced expression of TBET (FIG. 1B).

As such, the combination of mTOR inhibition and IL-2 receptor blockade represents a new method for Th1 cell generation.

Development of a Combination of Interventions to Inhibit T Cells During Ex Vivo Manufacturing: mTOR Inhibition; IL-2 Receptor Blockade; Reduced T Cell Co-stimulation; and Inhibition of T Cells Prior to Co-stimulation (Overnight Pre-Incubation). Given these results demonstrating that the combination of mTOR inhibition and IL-2 receptor blockade can improve the manufacturing of Th1-type cells (improvement in the TBET-to-FoxP3 ratio; limitation of $T_{REG}$ cell contamination), we considered that additional interventions might also improve Th1 cell manufacturing.

One benefit to the use of mTOR inhibition for adoptive T cell therapy efforts is that this intervention can promote the manufacture of T cells with a more primitive differentiation status, such as the T central memory subset ($T_{CM}$) or the T stem cell memory subset ($T_{SCM}$). In prior research using ex vivo rapamycin, it was found that ex vivo rapamycin was effective for the manufacture of T cells of $T_{CM}$ phenotype; this result is consistent with the known role of mTOR in the control of T cell memory status. It is important to promote the $T_{CM}$ and/or $T_{SCM}$ status during manufacturing because such T cells of more primitive differentiation status have increased long-term engraftment after adoptive transfer and mediate increased in vivo effects in experimental models. Several other methodologies have been described to promote the manufacture of T cells of limited differentiation status, including: use of a GSK3 inhibitor for promotion of WNT signaling; inhibition of AKT signaling; and inhibition of PI3 kinase signaling.

We developed a method whereby the T cells were plated and incubated in X-Vivo 20 media supplemented with 5% human AB serum which was devoid of exogenous cytokines and contained the mTOR inhibitor temsirolimus and the IL-2 receptor blockade via monoclonal antibody addition. This method incorporated an approximate 16-hour "pre-incubation" prior to co-stimulation with anti-CD3, anti- CD28 coated magnetic beads. To our knowledge, this method has not been previously reported.

Figure 2A:
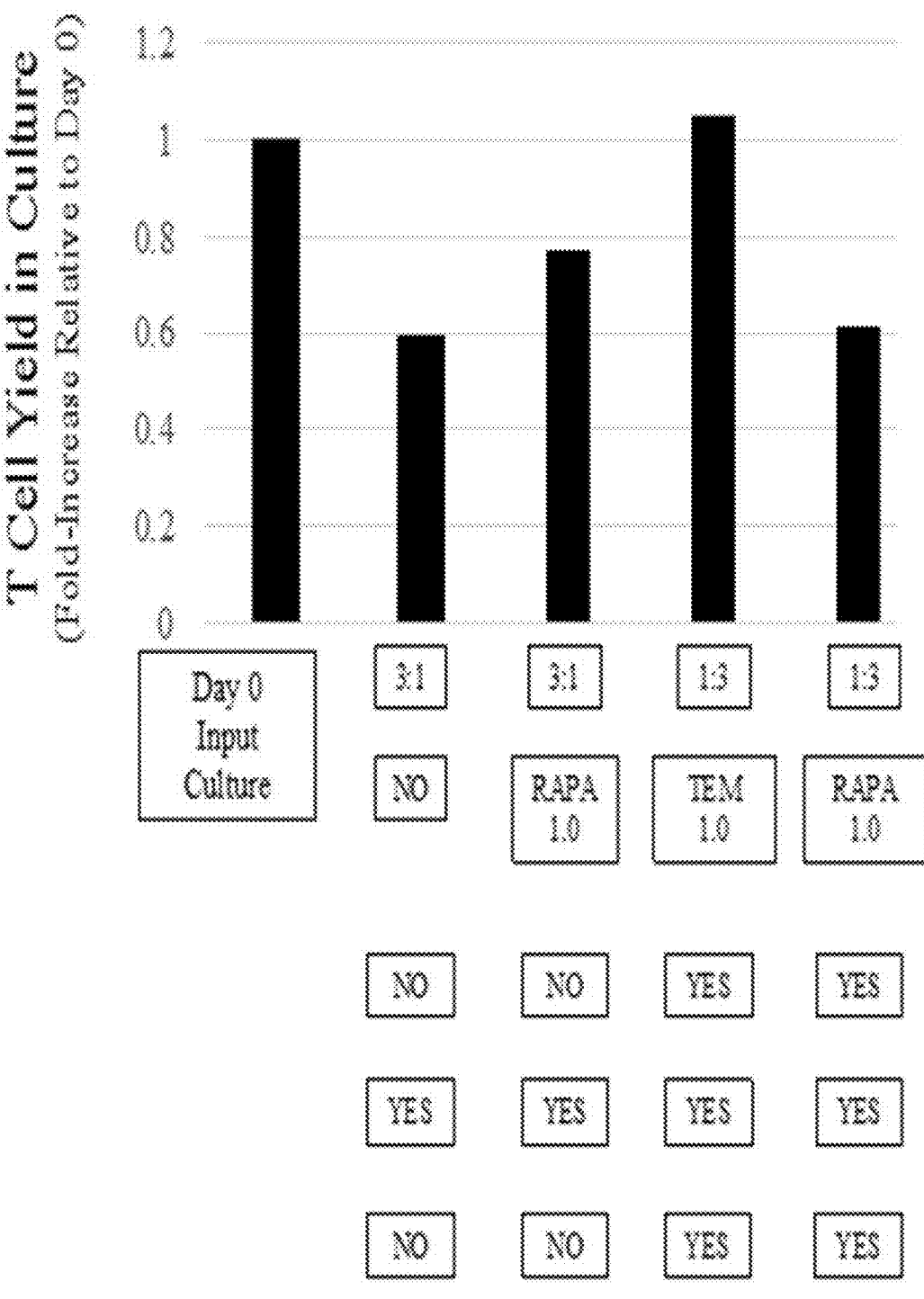
FIG. 2A depicts T cell yield after culturing CD4$^+$ and CD8$^+$ T cells under various conditions.
Figure 2A:
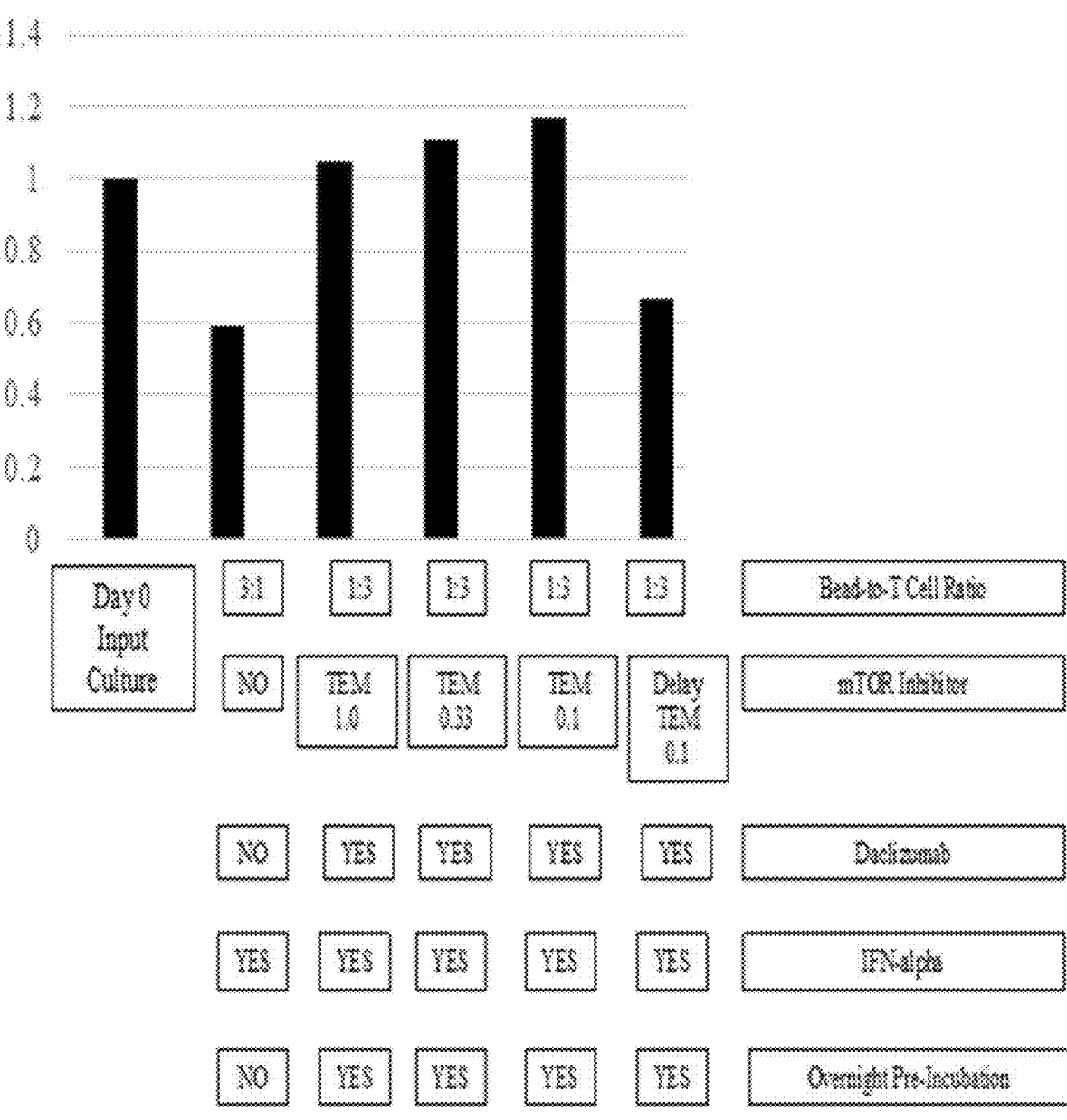
Figure 2B:
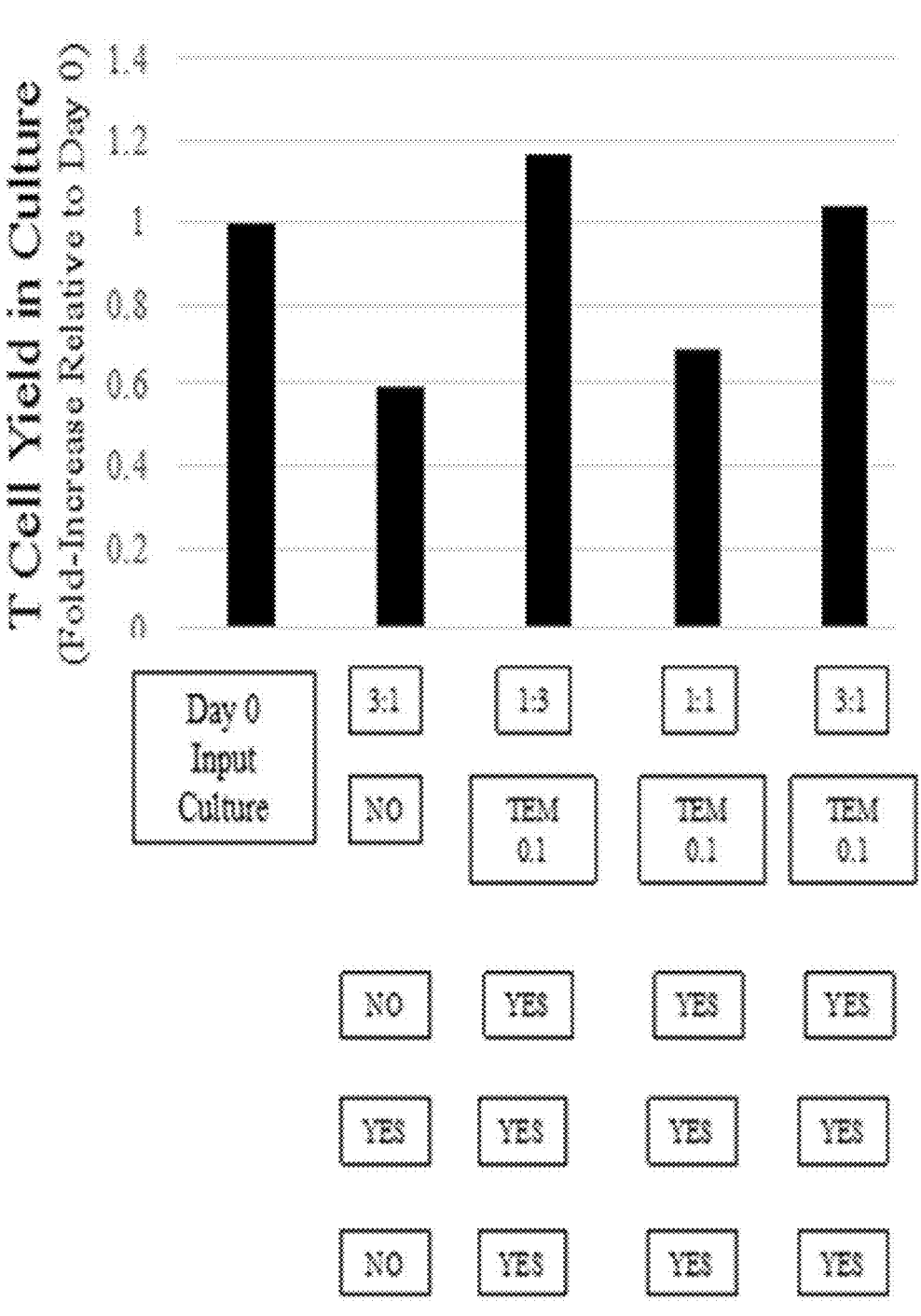
FIG. 2B depicts T cell yield after culturing CD4$^+$ and CD8$^+$ T cells under various conditions.
Figure 2B:
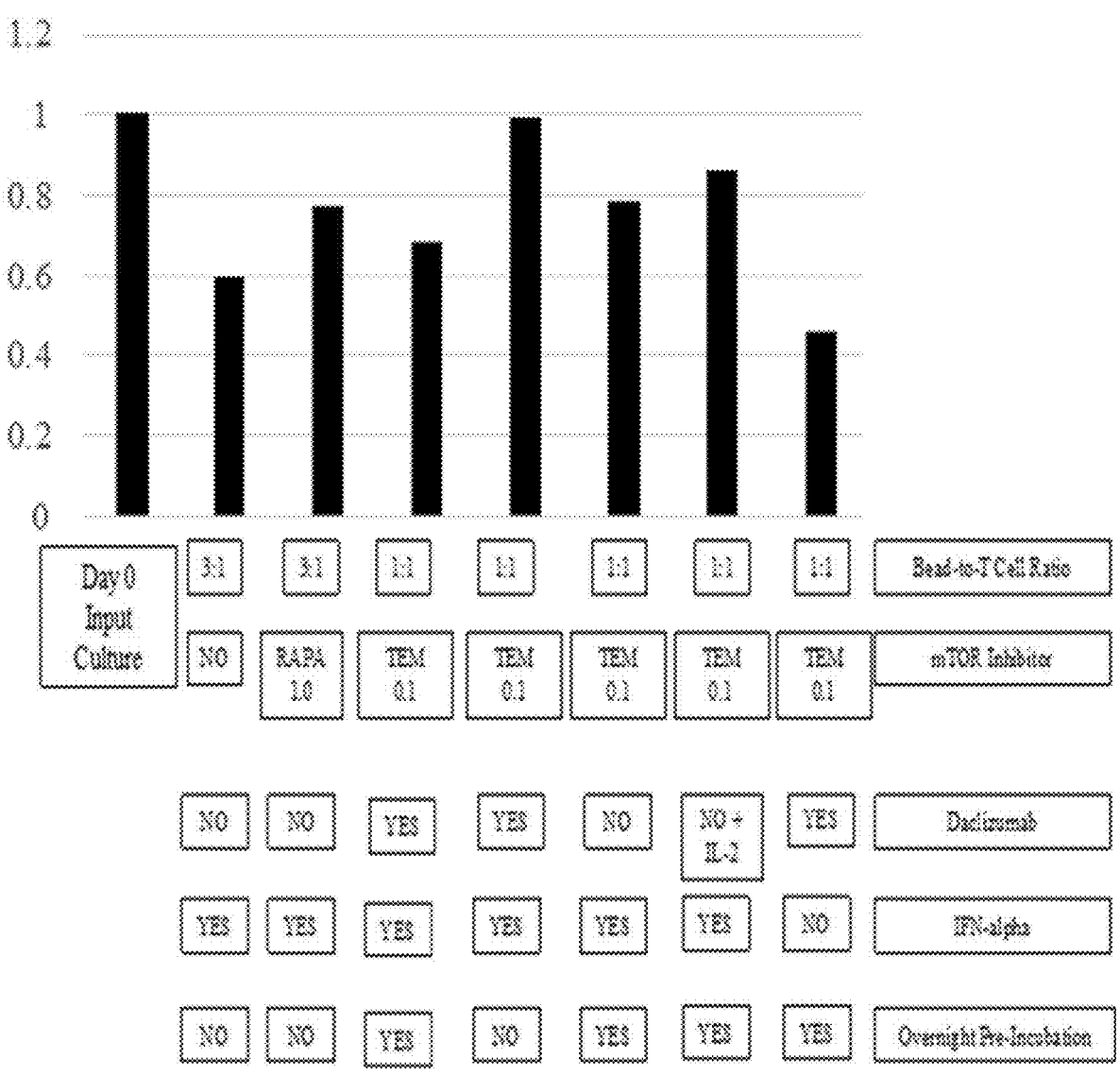

As a first step towards evaluating these increasingly stringent culture conditions, we evaluated whether the culture of CD4$^+$ and CD8$^+$ T cells under the various conditions would be feasible, as defined by the presence of viable cells at the end of the culture interval (for Th1 manufacturing, a 6-day culture interval). In FIGS. 2A-2B, CD4$^+$ and CD8$^+$ T cells were placed into culture under the various conditions, as indicated. The ratio of 3/28 beads to T cells was either 3:1, 1:1, or 1:3. The T cells were either co-stimulated at the same time as addition to culture ("No overnight pre-incubation") or after an overnight, 16-hour pre-incubation. In some conditions, the anti-IL-2 receptor monoclonal antibody daclizumab was added at a concentration of 50 μg/ml). For mTOR inhibition, temsirolimus was added either at 1.0 or 0.1 μM; alternatively, the control mTOR inhibitor rapamycin was added at a concentration of 1.0 μM. Most cultures also were supplemented with the type I cytokine promoting agent, IFN-α (10,000 IU/ml). As indicated, most of the culture conditions did not include the addition of exogenous IL-2. The T cell yield was calculated after 6-days in culture and compared to culture initiation ("Day 0 Input Culture").

As FIGS. 2A-2B illustrate, modification of the culture conditions to include not only mTOR inhibition (use of temsirolimus at either 1.0 μM or 0.1 μM; control use of rapamycin at 1.0 μM) and IL-2 receptor blockade (daclizumab) but also reduced co-stimulation (reduction from 3:1 beads-to-T cells to ratios of 1:1 and 1:3) and overnight pre-incubation resulted in similar numbers of viable T cells relative to control T cell cultures.

Importance of Pre-Incubation and High-dose Temsirolimus in Th1/Tc1 Manufacturing. At the time of cryopreservation of the Th1/Tc1 cell product (end of culture), it is important that the T cells have a relatively quiescent phenotype in addition to the T$_{CM}$ phenotype. That is, we previously found that rapamycin-generated T cells secreted very small amounts of cytokines at the time of adoptive transfer but resulted in large amounts of cytokines in vivo; of note, others have identified a similar inverse correlation between cell product effector function (minimal) and in vivo effector function (maximal). T cell quiescence at the time of adoptive transfer can improve T cell survival post-transfer and may also be important for reducing the risk of cytokine release syndrome, which is a cause of morbidity and mortality after other forms of adoptive T cell therapy, particularly gene-modified chimeric-antigen-receptor (CAR) T cell therapy.

Figure 3A:
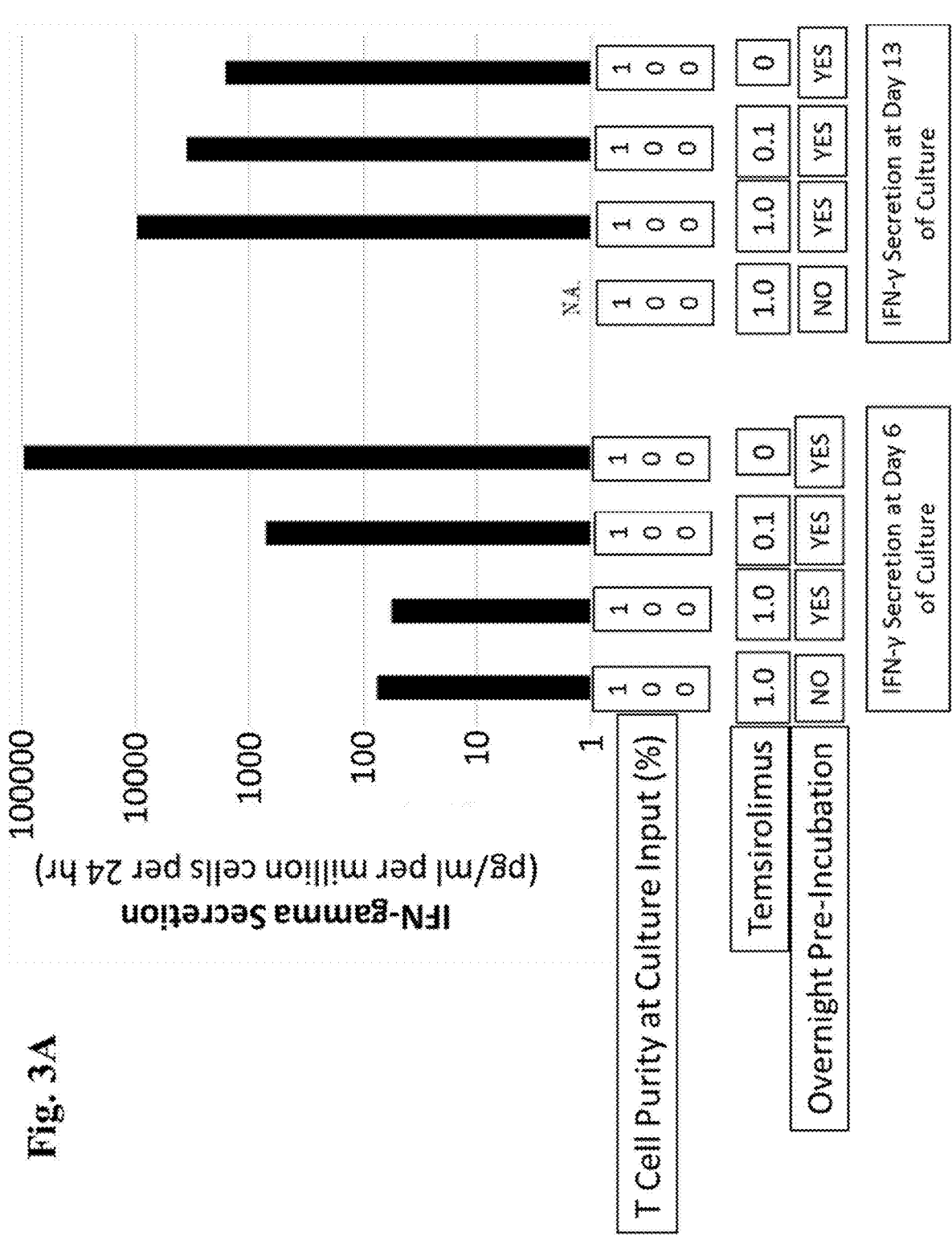
FIG. 3A depicts IFN-gamma secretion after culturing CD4$^+$ and CD8$^+$ T cells under various conditions.
Figure 3B:
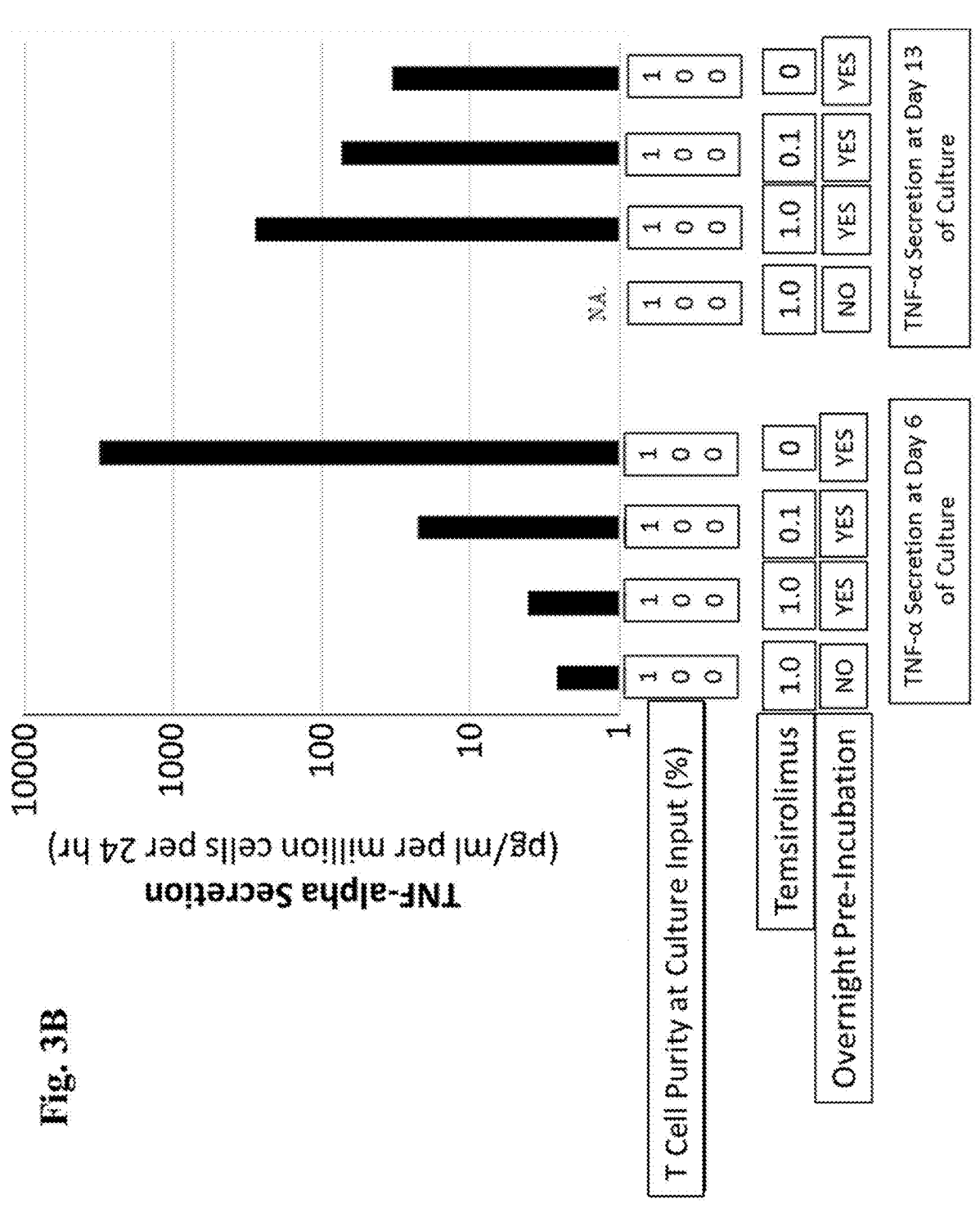
FIG. 3B depicts TNF-alpha secretion after culturing CD4$^+$ and CD8$^+$ T cells under various conditions.

To evaluate this, we tested cytokine secretion potential of the manufactured T cells at the end of cell culture (day 6) and then again one week after ex vivo expansion after maximal co-stimulation (3/28 bead-to-T cell ratio, 3:1) and propagation in media devoid of any inhibitors. In FIGS. 3A-3B, CD4$^+$ and CD8$^+$ T cells were purified and cultured for 6-days either with or without a 16-hr interval of pre-incubation prior to co-stimulation (1:1 ratio of 3/28 beads-to-T cells). As indicated, temsirolimus was added at concentrations of either 1.0 or 0.1 μM; all cultures were supplemented with IFN-α (10,000 IU/ml) and daclizumab (50 μg/ml). On day 6 of culture, the resultant T cells were co-stimulated for 24 hr using a 3:1 ratio of 3/28 beads; the supernatant was tested for cytokine content by Luminex assay (results are described as pg per ml of cytokine secreted per million cells per 24 hr). In addition, the resultant T cells were co-stimulated with a 3:1 ratio of 3/28 beads and maintained for one week in culture using media that did not contain any exogenous cytokines or inhibitors; after this T cell culture, at day 13 of culture, the T cells were harvested, re-stimulated with 3/28 beads (3:1 ratio), and the 24 hr supernatant was evaluated as above for cytokine content. N.A, abbreviation indicates not applicable (insufficient T cell yield to perform assay).

The results are shown in FIGS. 3A-3B, with IFN-γ secretion illustrated in FIG. 3A and TNF-α secretion in FIG. 3B. In each case, the day 6 T cell cytokine potential is shown in the left panels whereas the day 13 T cell cytokine potential is shown in the right panels.

These data indicate that high-dose temsirolimus (1.0 μM) resulted in the desired, very low levels of day 6 T cell IFN-γ and TNF-α secretion after 24 hr. of maximal co-stimulation in both the overnight pre-incubation condition and the condition without pre-incubation. Of note, use of temsirolimus at the concentration of 0.1 μM only partially reduced the day 6 T cell cytokine secretion potential. As such, temsirolimus in our method should be used at the higher concentration, that is, at least 1 μM. These data also indicate that the overnight pre-incubation intervention, when used alone, is not sufficient to yield the quiescent T cell phenotype. As such, the overnight pre-incubation step must be used in combination with high-dose temsirolimus to achieve the complete desired result.

In addition, this method results in the desired inverse relationship between initial T cell quiescence and resultant increased effector function after subsequent re-stimulation. That is, for both day 13 T cell values of IFN-γ and TNF-α secretion, the condition with the lowest level of day 6 cytokine potential (combination of pre-incubation plus high-dose temsirolimus) yielded the highest day 13 cytokine secretion values. Of note, the condition that consisted of high-dose temsirolimus without the overnight pre-incubation did not result in sufficient yield at day 13 of culture to evaluate cytokine secretion potential; as such, this result further confirms the value of the high-dose temsirolimus plus pre-incubation step for Th1/Tc1 cell generation.

New Combinatorial Method Results in Enhanced mTOR Inhibition and Abrogation of STAT5 Phosphorylation. The ability of the new combinatorial method (mTOR inhibition; IL-2 receptor blockade; pre-incubation for delay of co-stimulation; and use of a lower intensity of co-stimulation) to manufacture T cells of the desired phenotype resides in part upon its increased ability to control the molecular and cellular events that have been previously associated with the rapamycin-resistant T cell phenotype.

One component of this phenotype is the control of mTOR-dependent signaling events, such as that which occurs at the level of 4EBP1, which helps controls protein translation. To address this, we manufactured Th1/Tc1 cells using the T-Rapa method, which incorporated simultaneous T cell addition to culture with addition of high level co-stimulation (3/28 bead-to-T cell ratio, 3:1), high-dose rapamycin (1.0 μM), and cytokine addition (IL-2 plus IFN-α). In a side-by-side comparison, we manufactured T cells using a new combinatorial method of the present disclosure (16 hr pre-incubation step; co-stimulation at a reduced level (1:1 ratio); use of both temsirolimus (1.0 μM) and daclizumab (50 μg/ml); and addition of only IFN-α without IL-2.

Figure 4:
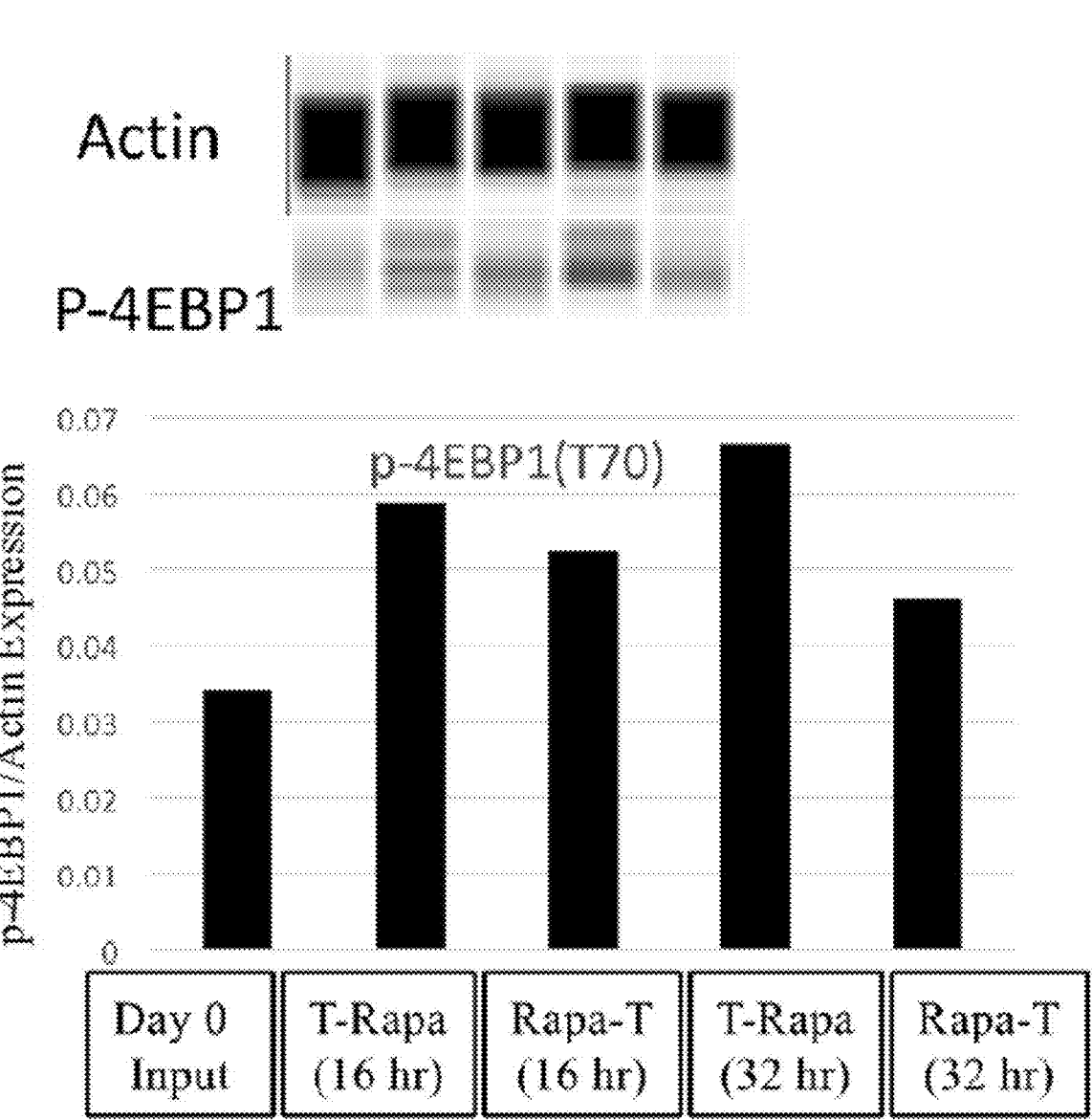
FIG. 4 depicts a Western blot of p-4EBP1 and actin proteins from CD4$^+$ and CD8$^+$ T cells cultured using T-Rapa methodology and a method of the present disclosure (Rapa-T) (top panel). The p-4EBP1 level was normalized by actin expression in in CD4$^+$ and CD8$^+$ T cells cultured using T-Rapa methodology and a method of the present disclosure (Rapa-T) (bottom panel).

In FIG. 4, CD4+ and CD8+ T cells were cultured using our previous methodology ["T-Rapa": simultaneous T cell addition to culture with addition of high level co-stimulation (3/28 bead-to-T cell ratio, 3:1), high-dose rapamycin (1.0 μM), and cytokine addition (IL-2 plus IFN-α)] or the new combinatorial methodology for manufactured T cells ["Rapa-T": 16 hr pre-incubation step; co-stimulation at a reduced level (1:1 ratio); use of both temsirolimus (1.0 μM)

and daclizumab (50 μg/ml); and addition of only IFN-α without IL-2]. At 16-hr and 32-hr of T cell culture, a fraction of the T cells was harvested, protein was isolated, and western blot analysis of the housekeeping gene β-Actin and the mTOR pathway molecule phosphor-4EBP1 were quantified. Results were compared relative to protein obtained from the day 0 input T cells prior to any T cell activation.

As FIG. 4 illustrates, the new combinatorial method for generating manufactured T cells ("Rapa-T" in FIG. 4) resulted in reduced activation of the mTOR pathway (as measured by phosphorylation of 4EBP1) relative to T cells manufactured using our previously described method ("T-Rapa") at both 16-hr and 32-hour culture time points.

Figure 5:
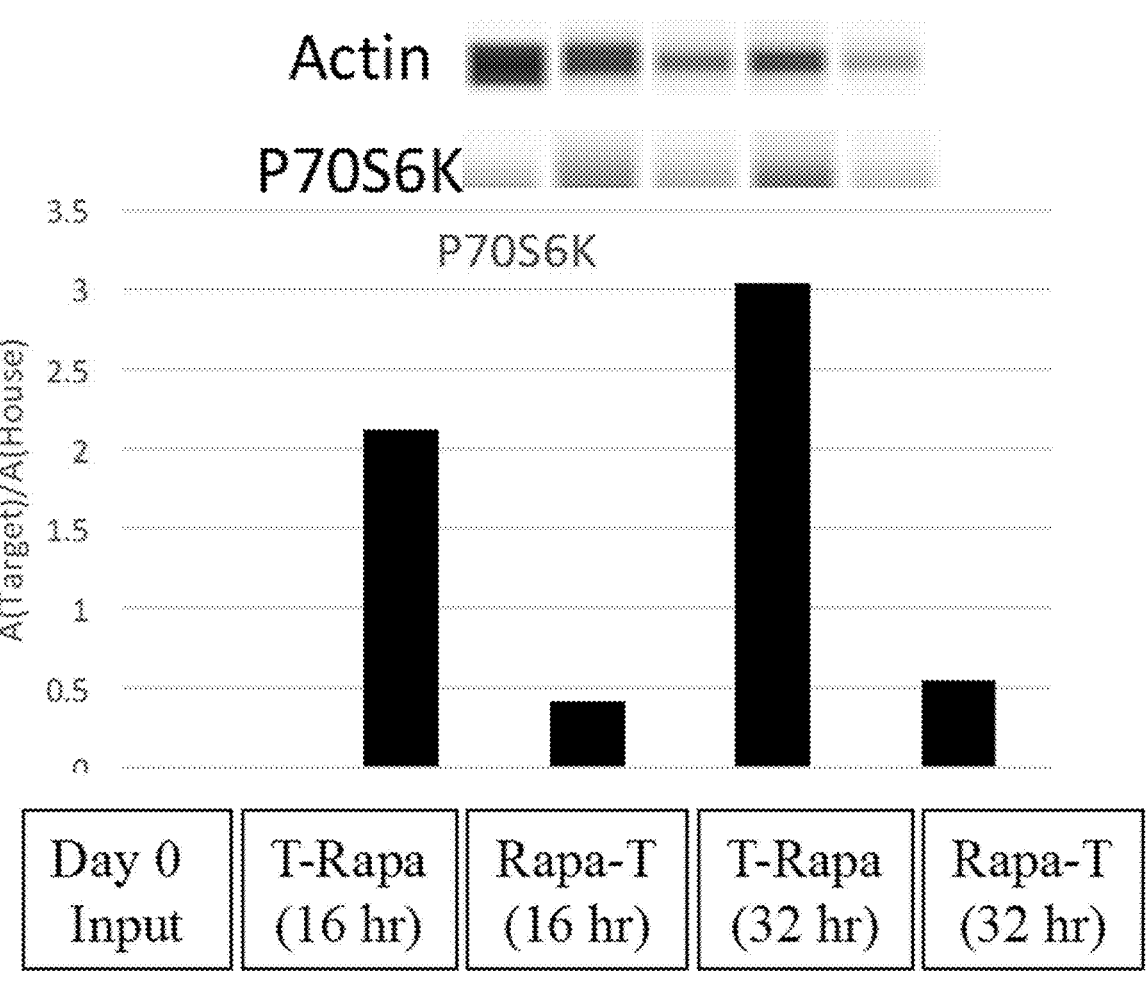
FIG. 5 depicts a Western blot of P70S6K and actin proteins from CD4$^+$ and CD8$^+$ T cells cultured using T-Rapa methodology and a method of the present disclosure (Rapa-T) (top panel) and P70S6K level normalized by actin expression in CD4$^+$ and CD8$^+$ T cells cultured using T-Rapa methodology and a method of the present disclosure (bottom panel).
Figure 6:
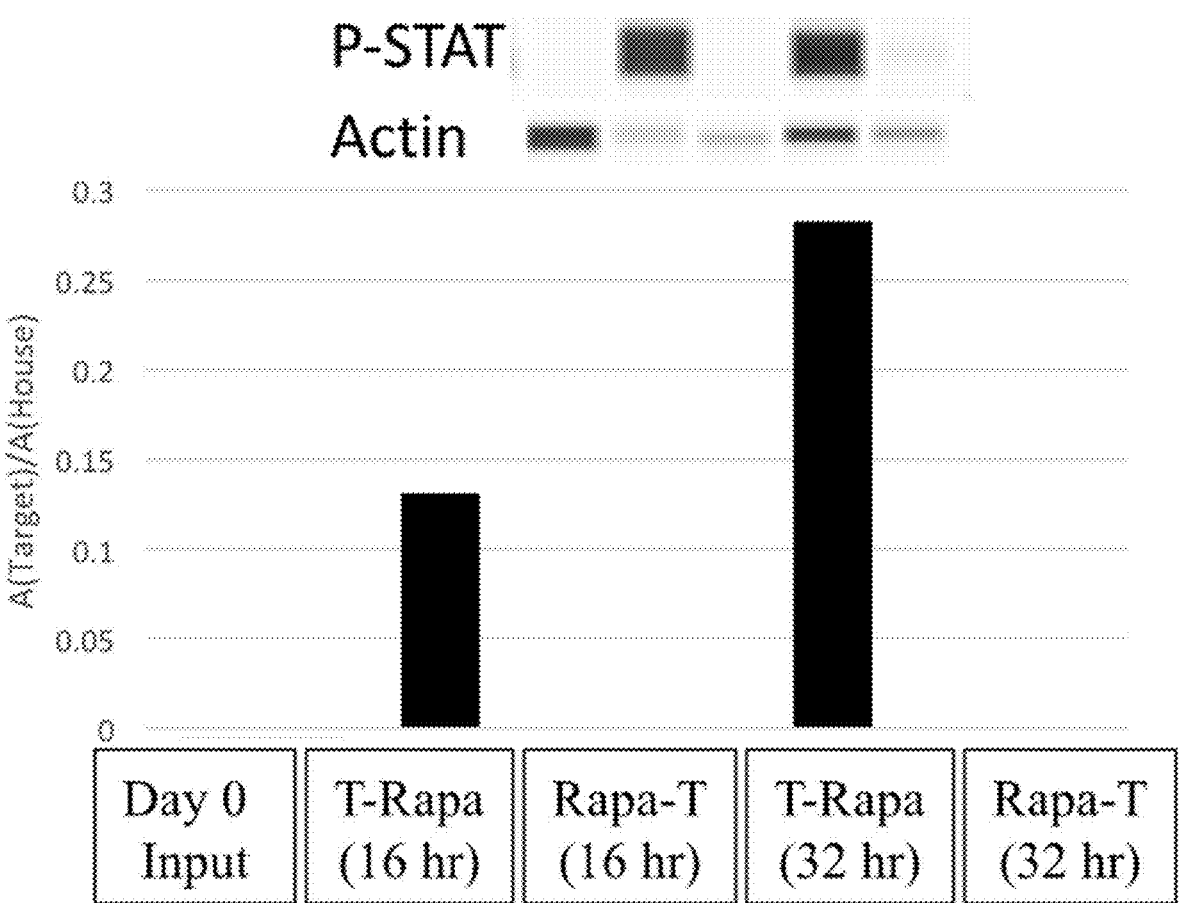
FIG. 6 depicts a Western blot of P-STAT5 and actin proteins from CD4$^+$ and CD8$^+$ T cells cultured using T-Rapa methodology and a method of the present disclosure (Rapa-T) (top panel) and P-STAT5 level normalized by actin expression in CD4$^+$ and CD8$^+$ T cells cultured using T-Rapa methodology and a method of the present disclosure (bottom panel).

P70S6 kinase is an additional critical molecule in the mTOR pathway. In FIGS. 5 and 6, CD4$^+$ and CD8$^+$ T cells were cultured using our previous methodology ["T-Rapa": simultaneous T cell addition to culture with addition of high level co-stimulation (3/28 bead-to-T cell ratio, 3:1), high-dose rapamycin (1.0 μM), and cytokine addition (IL-2 plus IFN-α)] or the new combinatorial methodology for generating manufactured T cells ["Rapa-T": 16 hr pre-incubation step; co-stimulation at a reduced level (1:1 ratio); use of both temsirolimus (1.0 μM) and daclizumab (50 μg/ml); and addition of only IFN-α without IL-2]. At 16-hr and 32-hr of T cell culture, a fraction of the T cells was harvested, protein was isolated, and western blot analysis of the housekeeping gene β-Actin and the mTOR pathway molecule P70S6K (FIG. 5) or phosphorylated STAT5 (FIG. 6) were quantified. Results were compared relative to protein obtained from the day 0 input T cells prior to any T cell activation.

In marked contrast, manufacturing using the new combinatorial method for generating manufactured T cells resulted in greatly blunted levels of P70S6K (FIG. 6, Rapa-T conditions). These data provide further evidence that the combinatorial method of Th1/Tc1 manufacturing provides improved control over mTOR activation. Using our previous methodology of manufacturing rapamycin-resistant T cells, we found substantial up-regulation of P70S6K at both 16-hr and 32-hr of T cell culture (FIG. 5, T-Rapa conditions).

The combinatorial method was associated with improvement in the purity of Th1-type cells (reduction in contamination with FoxP3-expressing cells. The previous manufacturing method results in substantial STAT5 phosphorylation (FIG. 6, T-Rapa results at 16-hr and 32-hr of culture); in marked contrast, the combinatorial approach abrogates STAT5 phosphorylation (FIG. 6; Rapa-T results at 16-hr and 32-hr of culture).

As such, the new combinatorial method is also advantageous with respect to increased control of mTOR signaling during T cell manufacturing and abrogation of signaling events that promote contamination with T$_{REG}$ cells (control of STAT5 phosphorylation).

Further Delineation of Individual Components of the Combinatorial Method of Th1/Tc1 Cell Generation. Further cultures were established to gain additional information regarding the individual contribution of culture interventions to the resultant Th1/Tc1 phenotype. For FIGS. 7-10, CD4$^+$ and CD8$^+$ T cells were cultured, as indicated in FIGS. 7-10, using various 3/28 bead ratios, various methods of mTOR inhibition, variable addition of anti-IL-2 receptor blockade, variable addition of the type I polarizing cytokine IFN-α, and variable use of an initial overnight pre-incubation step. Supernatants generated by repeat co-stimulation (3:1 bead ratio) were collected at day 6 and day 13 of culture and tested for IFN-γ (FIGS. 7A-7B), TNF-α (FIGS. 8A-8B), GM-CSF (FIGS. 9A-9B), or IL-2 (FIGS. 10A-10B) content by Luminex assay (results expressed as pg per ml per million cells per 24 hr).

Figure 7A:
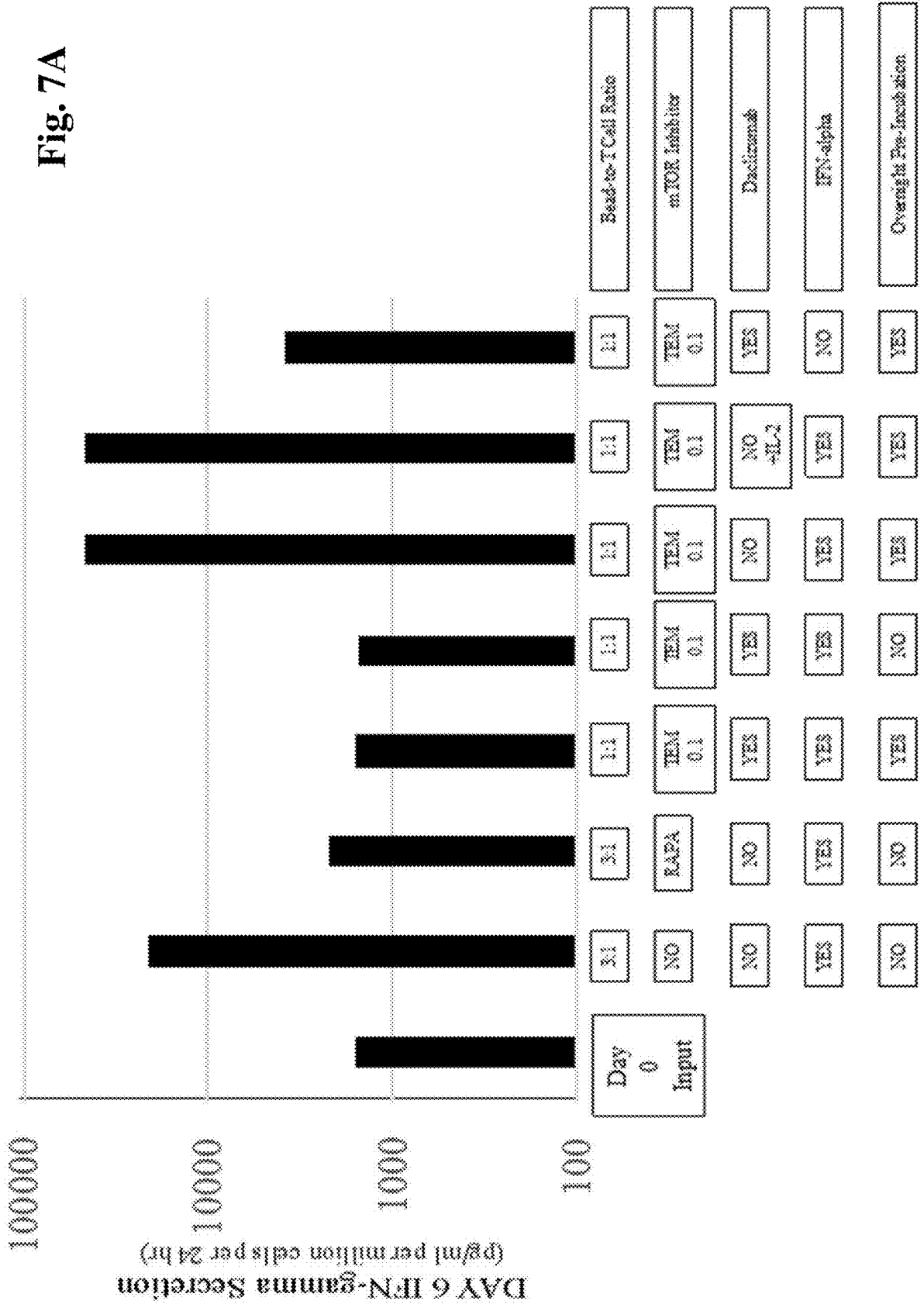
FIG. 7A depicts day 6 IFN-gamma secretion after culturing CD4$^+$ and CD8$^+$ T cells under various conditions.
Figure 7B:
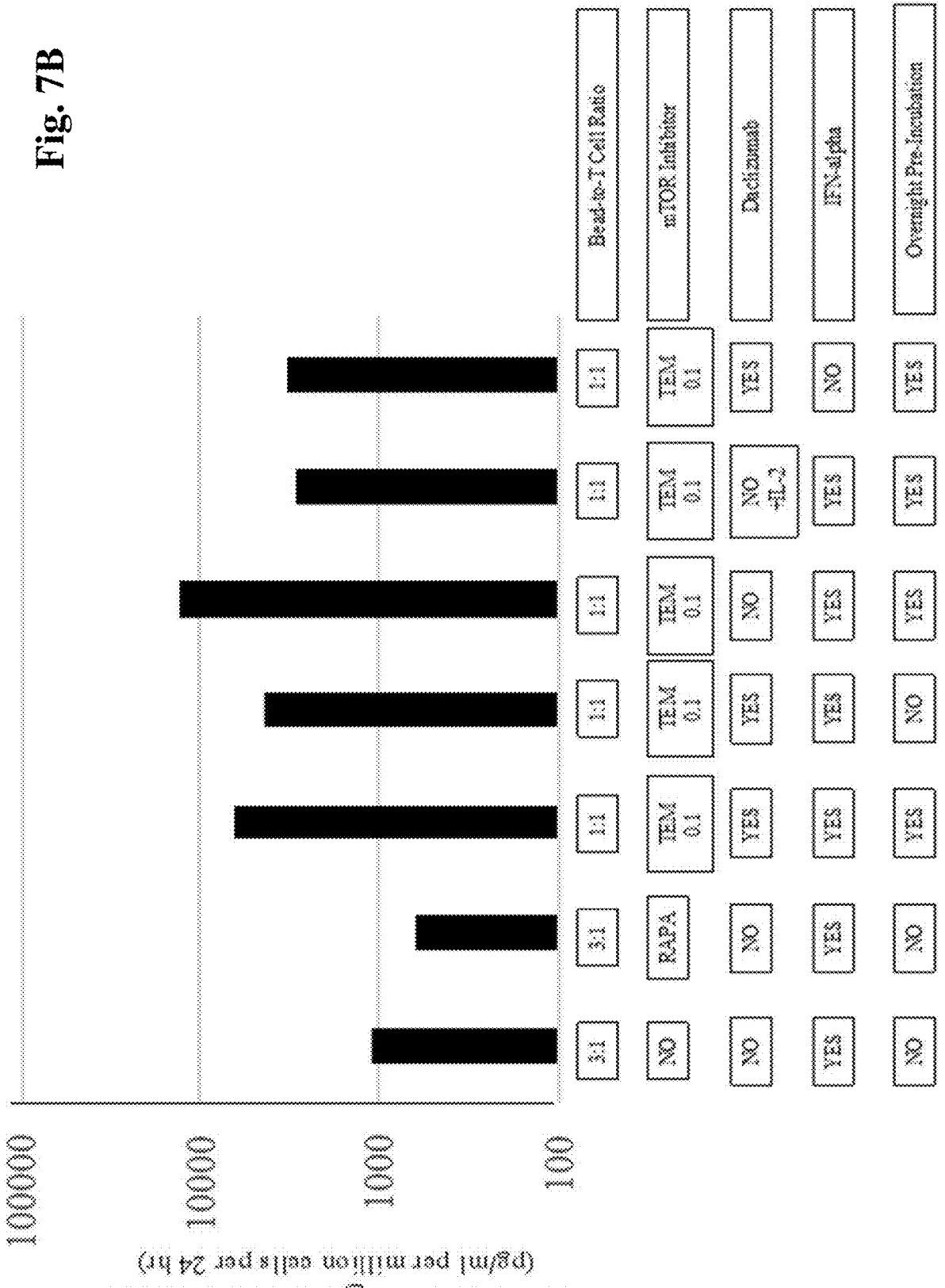
FIG. 7B depicts day 13 IFN-gamma secretion after culturing CD4$^+$ and CD8$^+$ T cells under various conditions.

FIGS. 7A-7B show the IFN-γ secretion results at the end of culture (day 6) and one week after further culture in the absence of inhibitors (day 13). The desired phenotype is comprised of relatively low cytokine secretion values at day 6 with concomitant relatively high cytokine values at day 13. FIGS. 7A-7B demonstrate that the culture condition that includes each of the combined elements (low level of co-stimulation [1:1 ratio]; delayed co-stimulation after overnight pre-incubation; addition of the polarizing cytokine IFN-α; addition of the mTOR inhibitor [in this experiment, use of the sub-optimal concentration of 0.1 μM]; and inclusion of the anti-IL-2 receptor antibody daclizumab) had a desirable phenotype in that this condition was reduced in IFN-γ secretion at day 6 yet high in IFN-γ secretion at day 13. T cell culture conditions that omitted one or more of these elements tended to have higher cytokine values at day 6 and/or lower values at day 13. In addition, our previous method for manufacturing rapamycin-resistant T cells (T-Rapa; FIGS. 7A-7B) expressed a less favorable pattern of cytokine secretion (higher values at day 6; lower values at day 13).

Figure 8A:
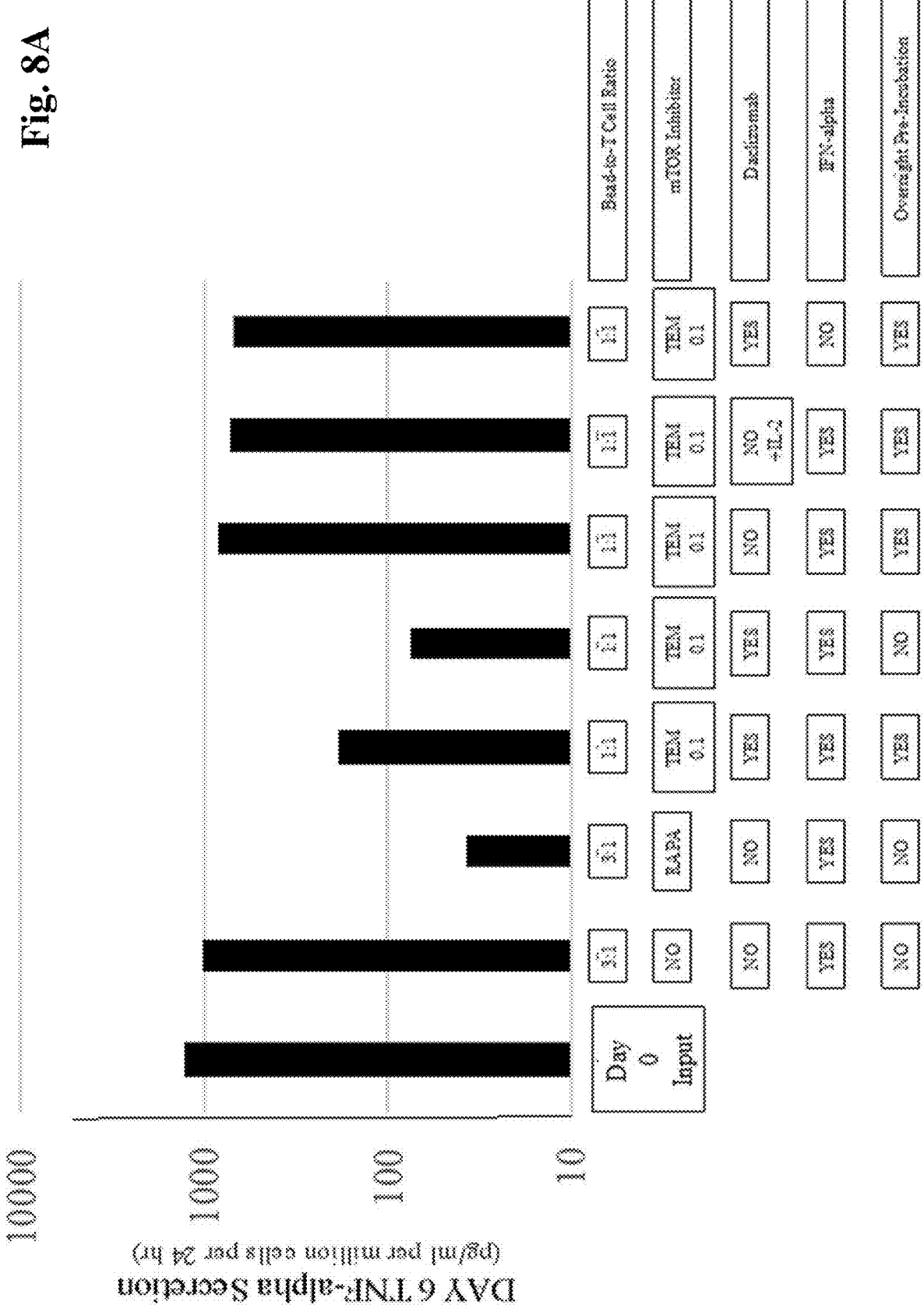
FIG. 8A depicts day 6 TNF-alpha secretion after culturing CD4$^+$ and CD8$^+$ T cells under various conditions.
Figure 9A:
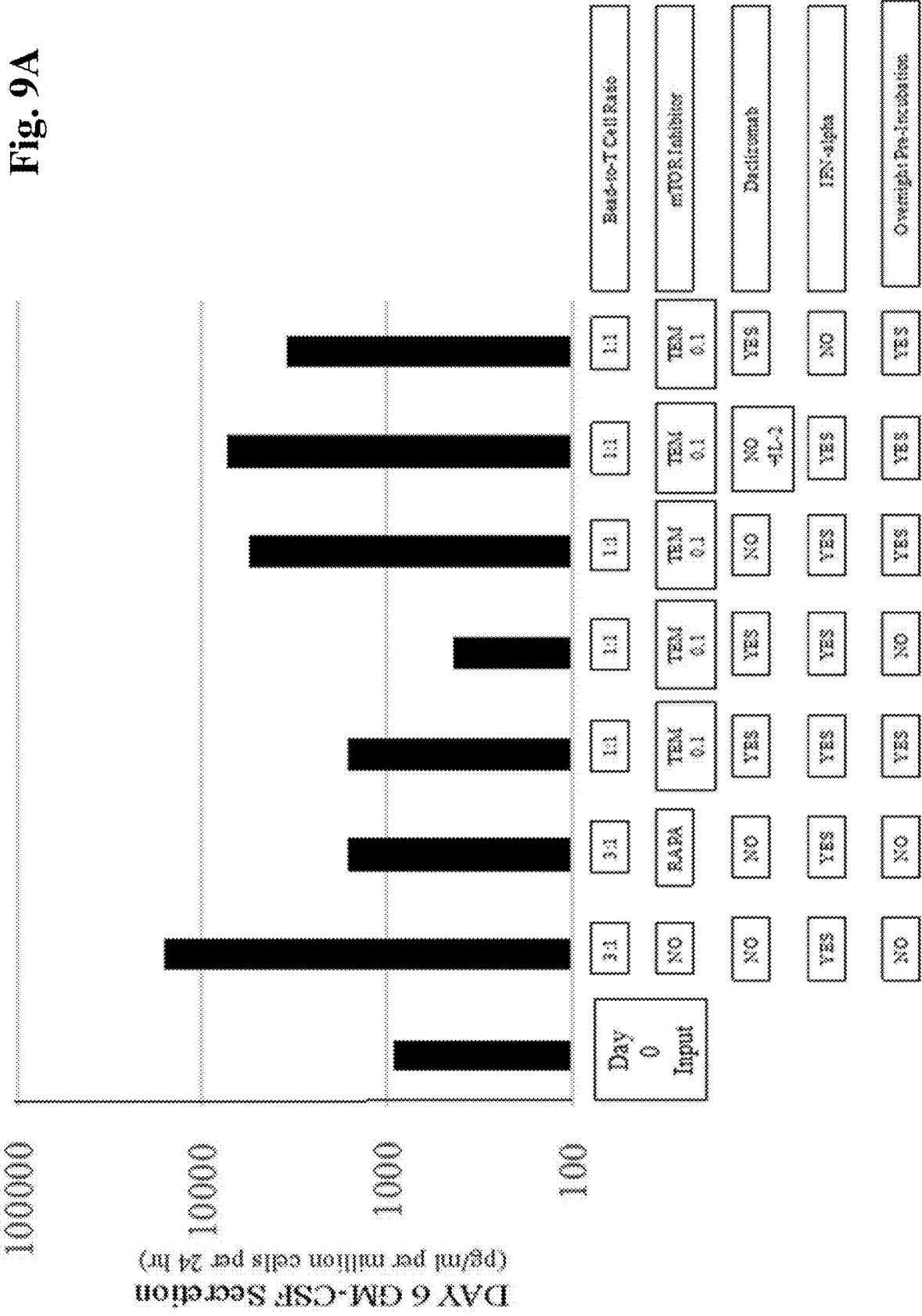
FIG. 9A depicts day 6 GM-CSF secretion after culturing CD4$^+$ and CD8$^+$ T cells under various conditions.
Figure 9B:
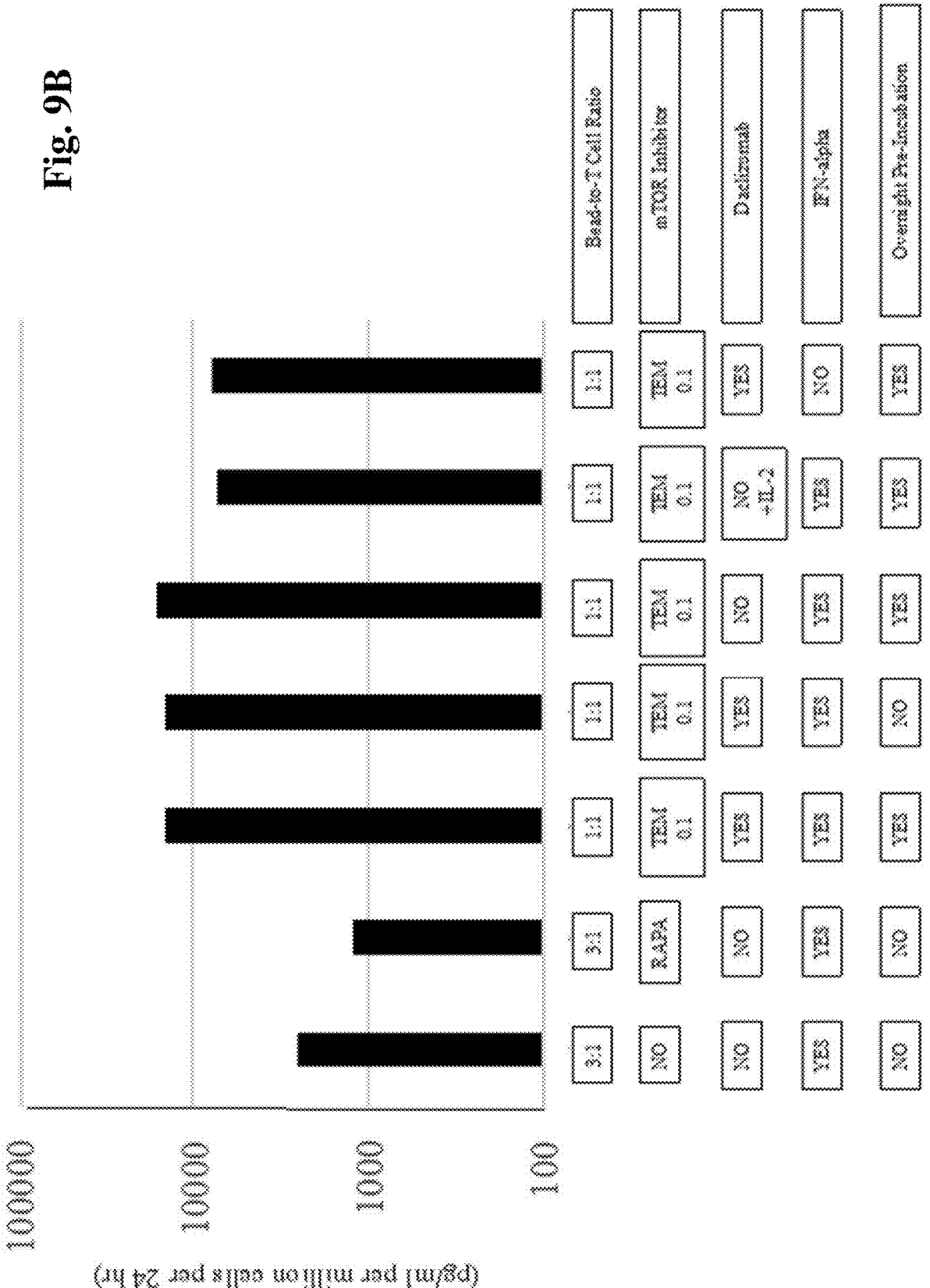
FIG. 9B depicts day 13 GM-CSF secretion after culturing CD4$^+$ and CD8$^+$ T cells under various conditions.
Figure 10A:
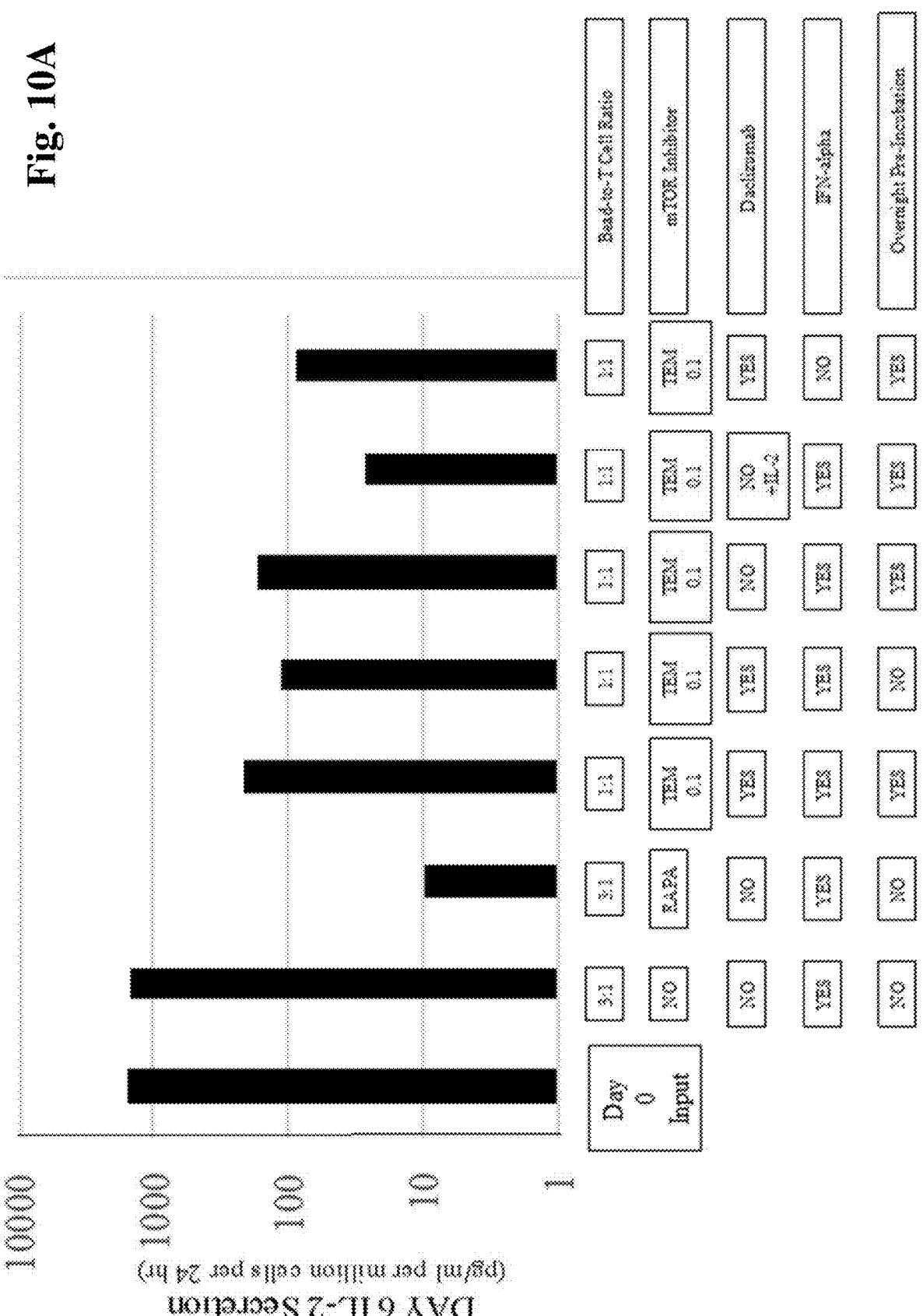
FIG. 10A depicts day 6 IL-2 secretion after culturing CD4$^+$ and CD8$^+$ T cells under various conditions.
Figure 10B:
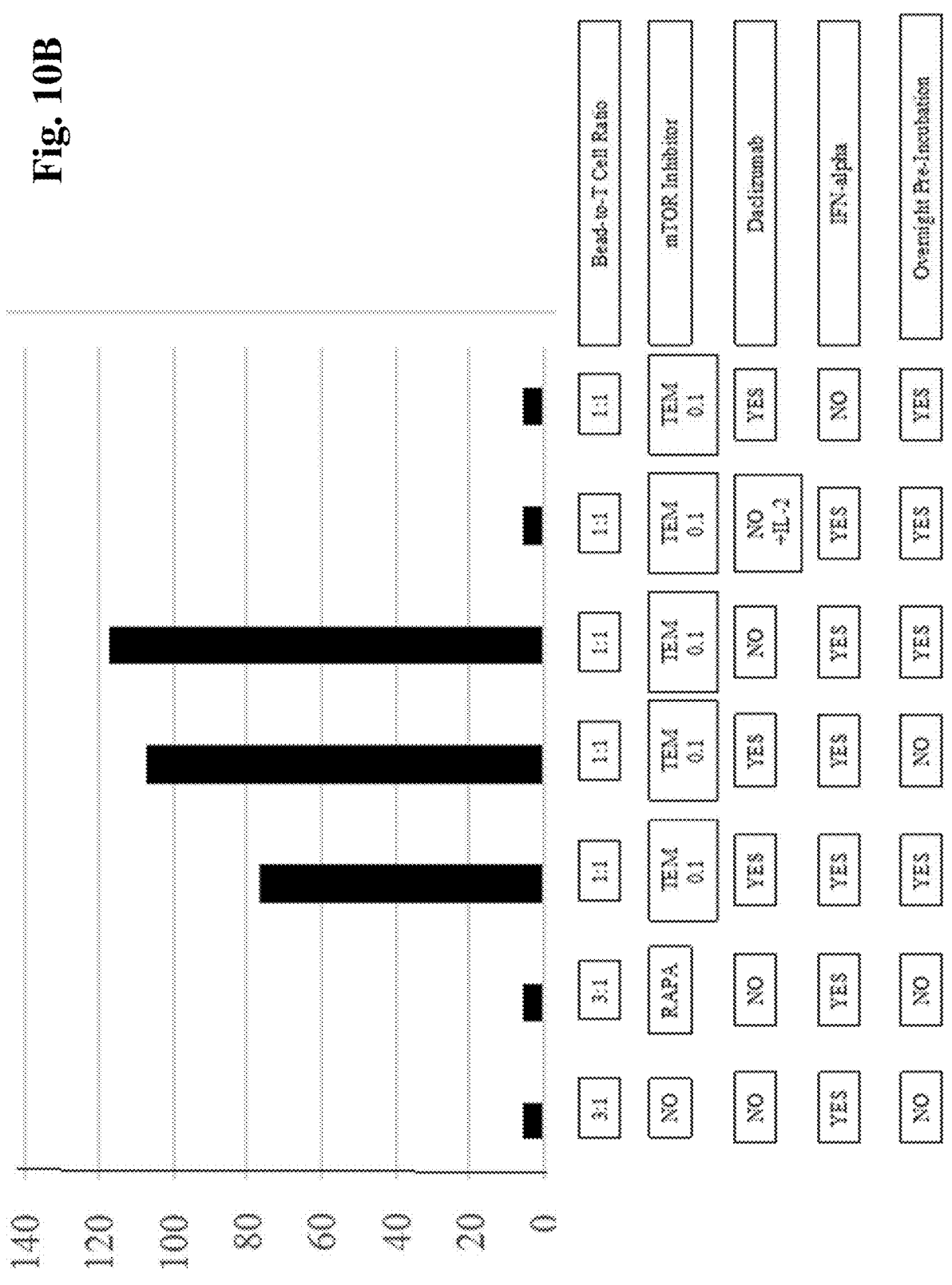
FIG. 10B depicts day 13 IL-2 secretion after culturing CD4$^+$ and CD8$^+$ T cells under various conditions.

The combinatorial method of Th1/Tc1 manufacturing also yielded a favorable cytokine phenotype (reduced values at day 6 combined with increased values at day 13) when the following cytokines were evaluated: TNF-α (FIGS. 8A-8B); GM-CSF (FIGS. 9A-9B); and IL-2 (FIGS. 10A-10B).

Taken together, these results provide further evidence that the new method of manufactured T cell manufacturing has important advantages relative to the prior T-Rapa method.

Molecular Changes Associated with Th1/Tc1 Cell Manufacturing Using the Combinatorial Methodology. We performed additional experiments to characterize molecules that are altered during Th1/Tc1 cell manufacturing using the combinatorial methodology. Such information is valuable not only because it can lead to an improved understanding of the T cell phenotype but also because such information can be utilized during manufacturing as a quality control element. In addition, such information can be used during the screening of additional combinatorial steps that might be used in future manufacturing efforts.

In previous efforts, we found that rapamycin-resistant T cells underwent autophagy during T cell manufacturing. It has long been known that autophagy is a direct result of mTOR inhibition: when mTOR is activated, T cells maintain a growth and proliferation state (autophagy signals are turned off); in contrast, when mTOR is inhibited, autophagy is promoted, thereby resulting in a reduction in T cell volume, including a reduction in mitochondrial volume (mitophagy). Indeed, autophagy is a necessary homeostatic process in T cell biology and is associated with T cell health, as energy requirements can be reduced and intra-cellular organelles and other cellular debris can be eliminated.

Figure 11:
FIG. 11 depicts a Western blot of P62 and actin proteins from CD4$^+$ and CD8$^+$ T cells cultured under various conditions (top panel) and P62 protein expression normalized by actin expression in CD4$^+$ and CD8$^+$ T cells under various conditions (bottom panel).
Figure 12:
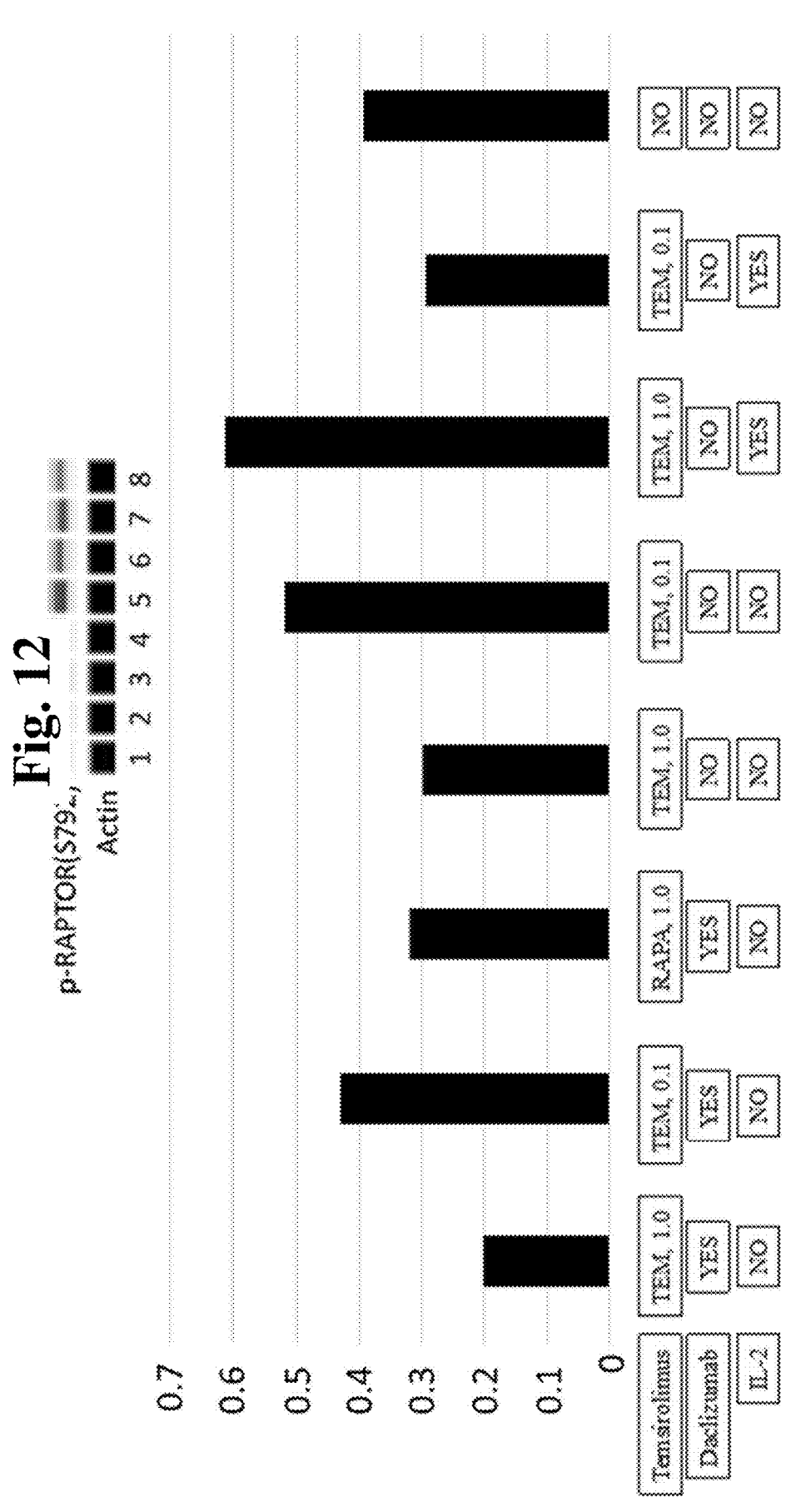
FIG. 12 depicts a Western blot of p-RAPTOR and actin proteins from CD4$^+$ and CD8$^+$ T cells cultured under various conditions (top panel) and p-RAPTOR level normalized by actin expression in CD4$^+$ and CD8$^+$ T cells cultured under various conditions (bottom panel).
Figure 13:
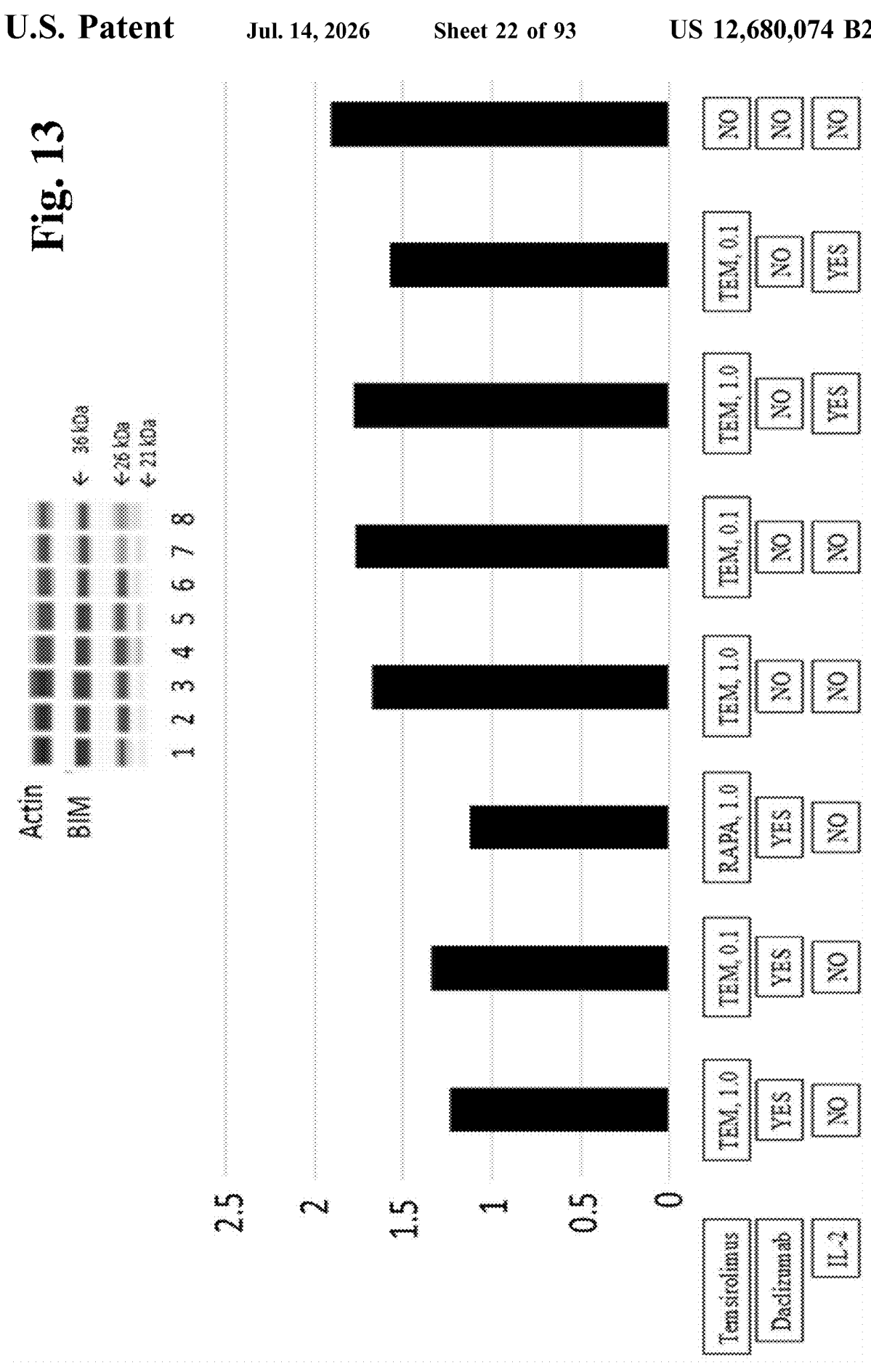
FIG. 13 depicts a Western blot of BIM and actin proteins from CD4$^+$ and CD8$^+$ T cells cultured under various conditions (top panel) and BIM protein expression normalized by actin expression in CD4$^+$ and CD8$^+$ T cells cultured under various conditions (bottom panel).

For FIGS. 11-13, human CD4$^+$ and CD8$^+$ T cells were cultured using a 16-hr pre-incubation interval prior to the addition of 3/28 beads at the reduced ratio of 1:3 beads-to-T cells. As indicated in FIGS. 11-13, the various T cell cultures received different methods of mTOR inhibition (rapamycin at 1.0 μM; temsirolimus at 1.0 or 0.1 μM), different conditions of exogenous IL-2 addition, and different conditions relative to addition of the anti-IL-2 receptor monoclonal antibody, daclizumab. After the 16-hr pre-incubation interval, cells were harvested from the T cell cultures, protein was isolated, and p62 (FIG. 11), phospho-RAPTOR (FIG.

12), or BIM (FIG. 13) and the housekeeper gene β-actin were quantified by western blot.

We evaluated the ability of the combinatorial method to promote autophagy, as measured by T cell expression of the autophagy marker, p62. As FIG. 11 indicates, the combinatorial method that included a pre-incubation step, a low level of co-stimulation (1:3 ratio of 3/28 beads to T cells), daclizumab blockade of the IL-2 receptor, and an mTOR inhibitor up-regulated the autophagy marker p62. If each of these factors was present, autophagy could be realized by mTOR inhibition with rapamycin (1 μM) or temsirolimus (1.0 or 0.1 μM). Elimination of IL-2 receptor blockade from the regimen substantially blunted the induction of autophagy.

In addition, the combinatorial method also resulted in improved inhibition of the mTOR pathway, as indicated by reduced expression of the phosphorylated form of RAPTOR (FIG. 12). Of note, the combinatorial method that incorporated high-dose temsirolimus yielded lower levels of phospho-RAPTOR compared to use of low-dose temsirolimus or high-dose rapamycin.

We also evaluated manufactured T cell expression of a pro-apoptotic member of the bcl-2 gene family, BIM. The bcl-2 family members operate primarily at the level of the mitochondria, and as such, mitochondrial autophagy (mitophagy) can influence the balance of bcl-2 family member genes, which help determine apoptosis threshold. Mitophagy has been shown to be beneficial in terms of reducing the apoptosis threshold, potentially be selectively eliminating mitochondria with unfavorable balances of the bcl-2 family of molecules. We found that the combinatorial method of manufacturing resulted in reduced expression of BIM (FIG. 13).

In sum, these experiments indicate that enhanced autophagy, reduced mTOR signaling, and reduced pro-apoptotic molecule expression are associated with the combinatorial method of Th1/Tc1 cell manufacturing. These changes likely contribute to the increased in vivo function of the manufactured T cells, and as such, can be used as quality control steps or to screen future, next-generation methods of T cell manufacturing.

The Combinatorial Method Promotes T Cell Quiescence, T Cell De-differentiation. We performed additional experiments to characterize the surface phenotype of Th1/Tc1 cells manufactured by the combinatorial method, as defined by the incorporation of a pre-incubation step, a low level of co-stimulation (1:3 ratio of 3/28 beads to T cells), daclizumab blockade of the IL-2 receptor, and an mTOR inhibitor. First, we evaluated the effect of culture variables on T cell expression of the CD45 isoform RA, which is a marker of T cell naivety, including T cells of the stem cell memory subset. As such, development of a T cell manufacturing method that preserves or increases expression of CD45RA is desirable.

For FIGS. 14A-15D, CD4+ and CD8+ T cells were cultured, as now indicated in FIGS. 14A-15D, using various 3/28 bead ratios, various methods of mTOR inhibition, variable addition of anti-IL-2 receptor blockade, variable addition of the type I polarizing cytokine IFN-α, and variable use of an initial overnight pre-incubation step. At day 6 of culture, T cells were harvested and evaluated for flow cytometric expression of CD45RA (FIGS. 14A-14D) or CD62L, CCR7, and CD127 (FIG. 15A-15D) on the CD4 cell subset, with comparison of results to the expression level at day 0 of culture ("Day 0 Input Culture").

Figure 14A:
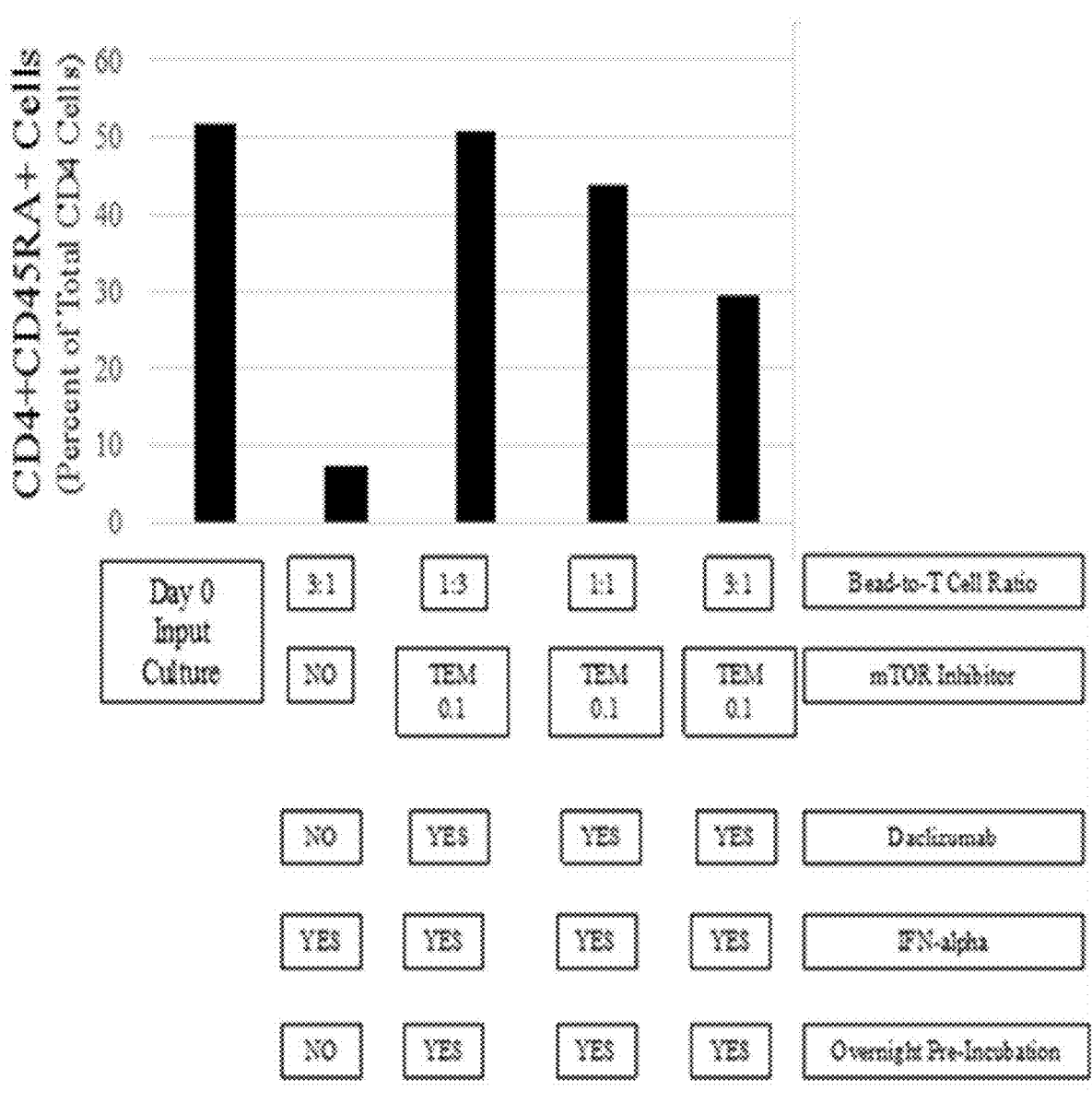
FIG. 14A depicts flow cytometry expression analysis of CD45RA on the CD4+ cell subset after culturing the T cells under various conditions.
Figure 14B:
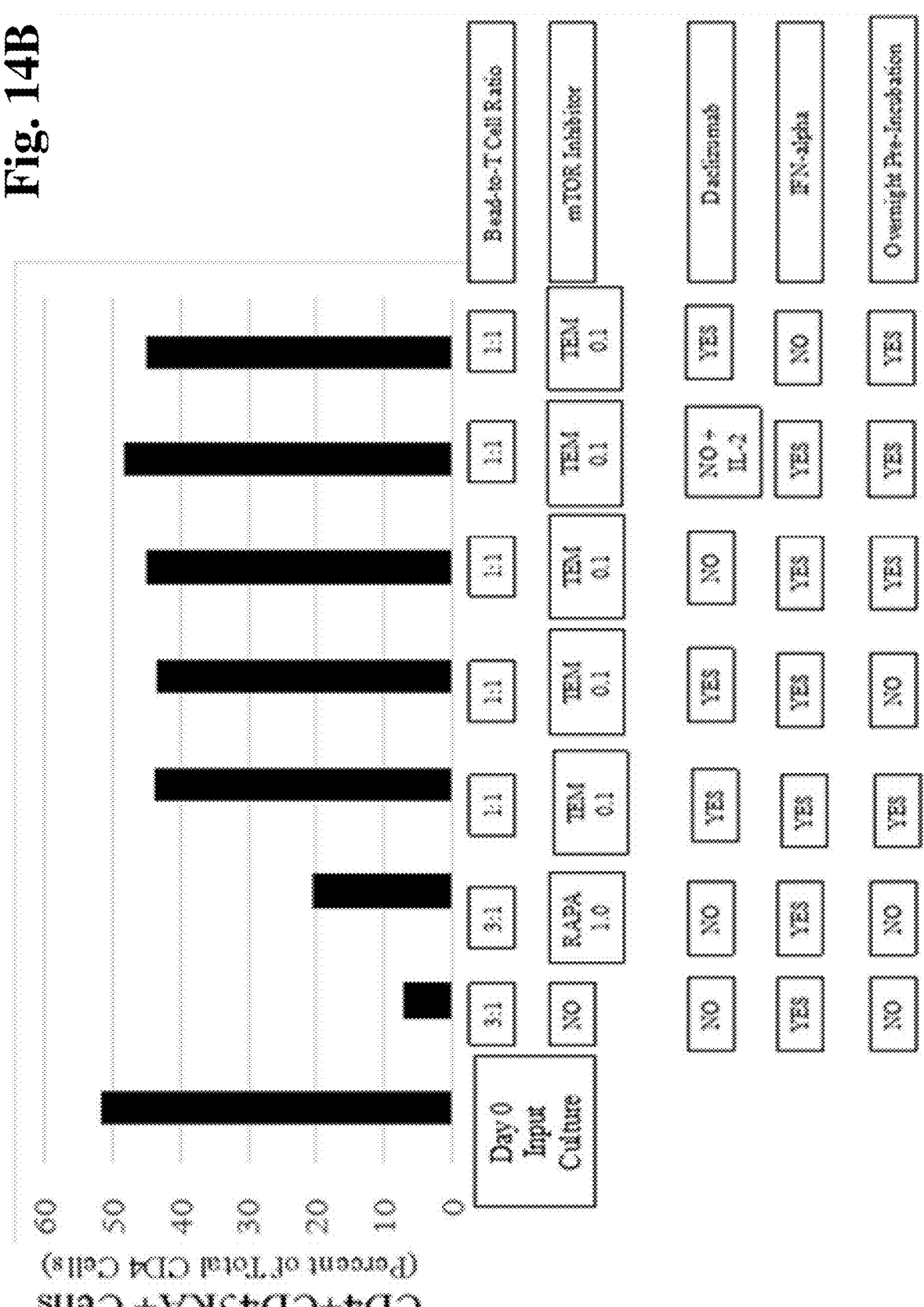
FIG. 14B depicts flow cytometry expression analysis of CD45RA on the CD4+ cell subset after culturing the T cells under various conditions.
Figure 14C:
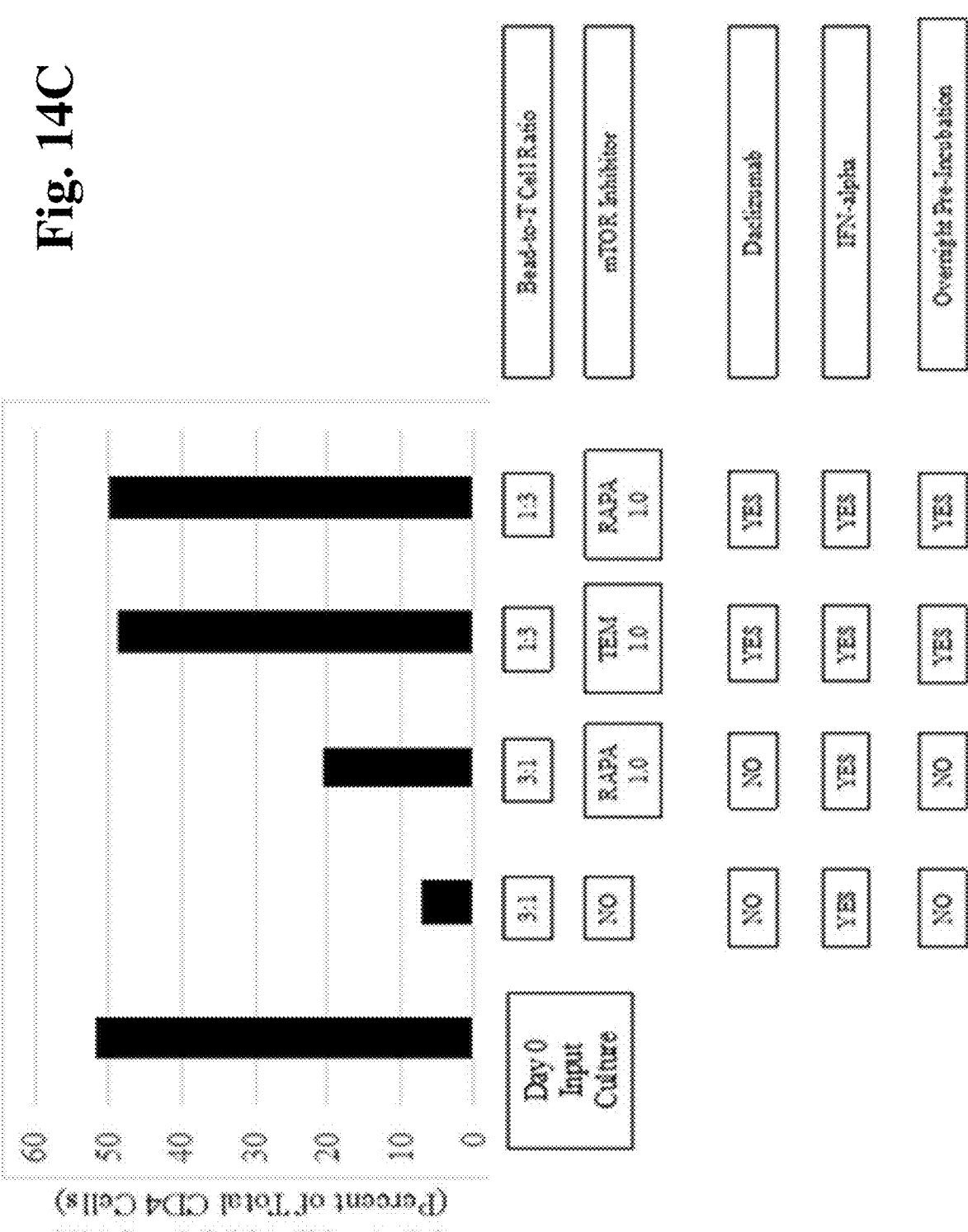
FIG. 14C depicts flow cytometry expression analysis of CD45RA on the CD4+ cell subset after culturing the T cells under various conditions.
Figure 14D:
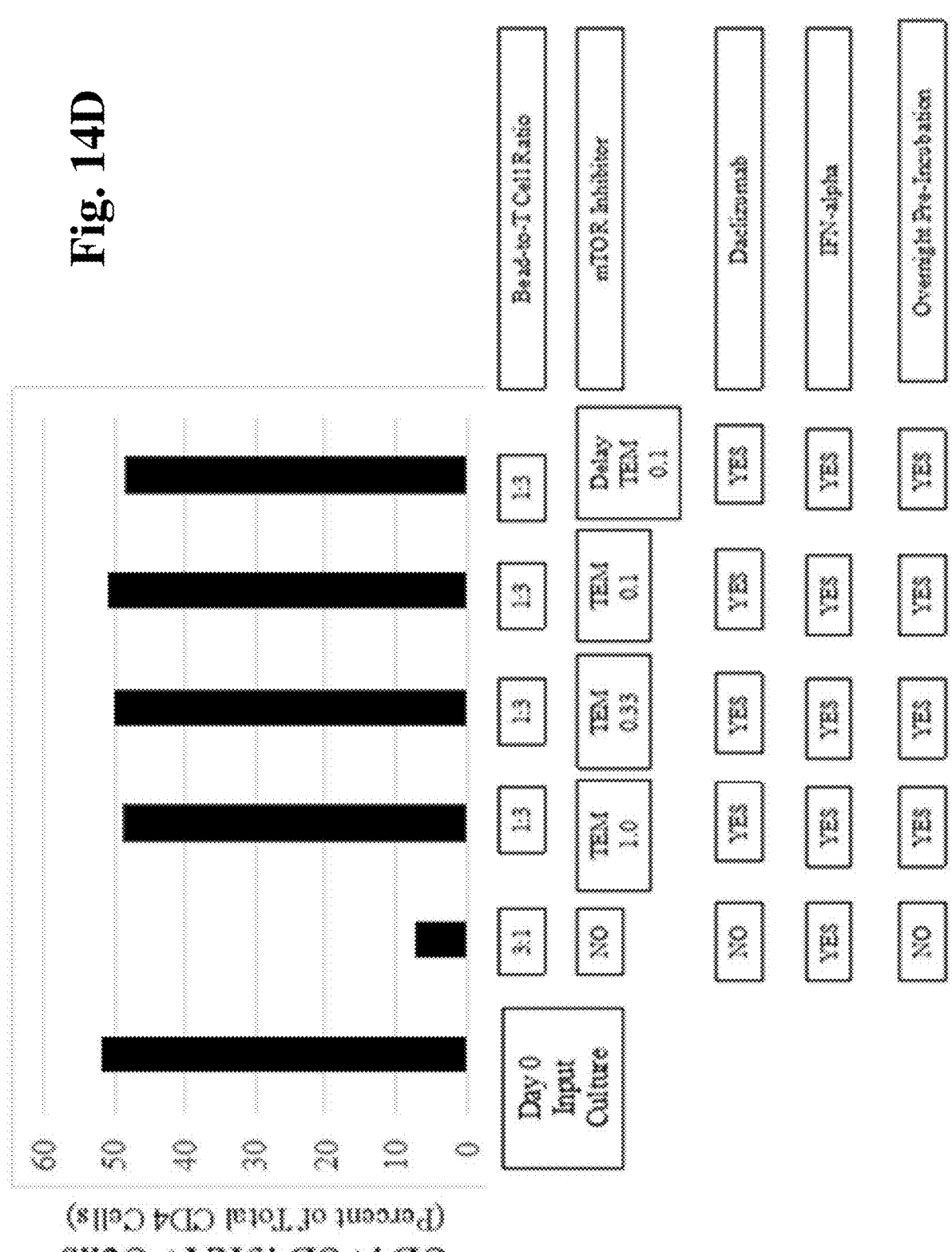
FIG. 14D depicts flow cytometry expression analysis of CD45RA on the CD4$^+$ cell subset after culturing the T cells under various conditions.

As FIGS. 14A-14D illustrate, T cell manufacturing without critical elements of the combinatorial method (use of high co-stimulation at a 3:1 bead-to-T cell ratio; no usage of daclizumab; no usage of an mTOR inhibitor) results in rapid deterioration of CD45RA expression (see column #2). In marked contrast, use of all of these components resulted in complete preservation of CD45RA expression (see column #4). Of note, T cells propagated using the prior manufacturing method that we identified did not have optimally preserved expression of CD45RA (T-Rapa cells; FIG. 14B, column #3).

Figure 15A:
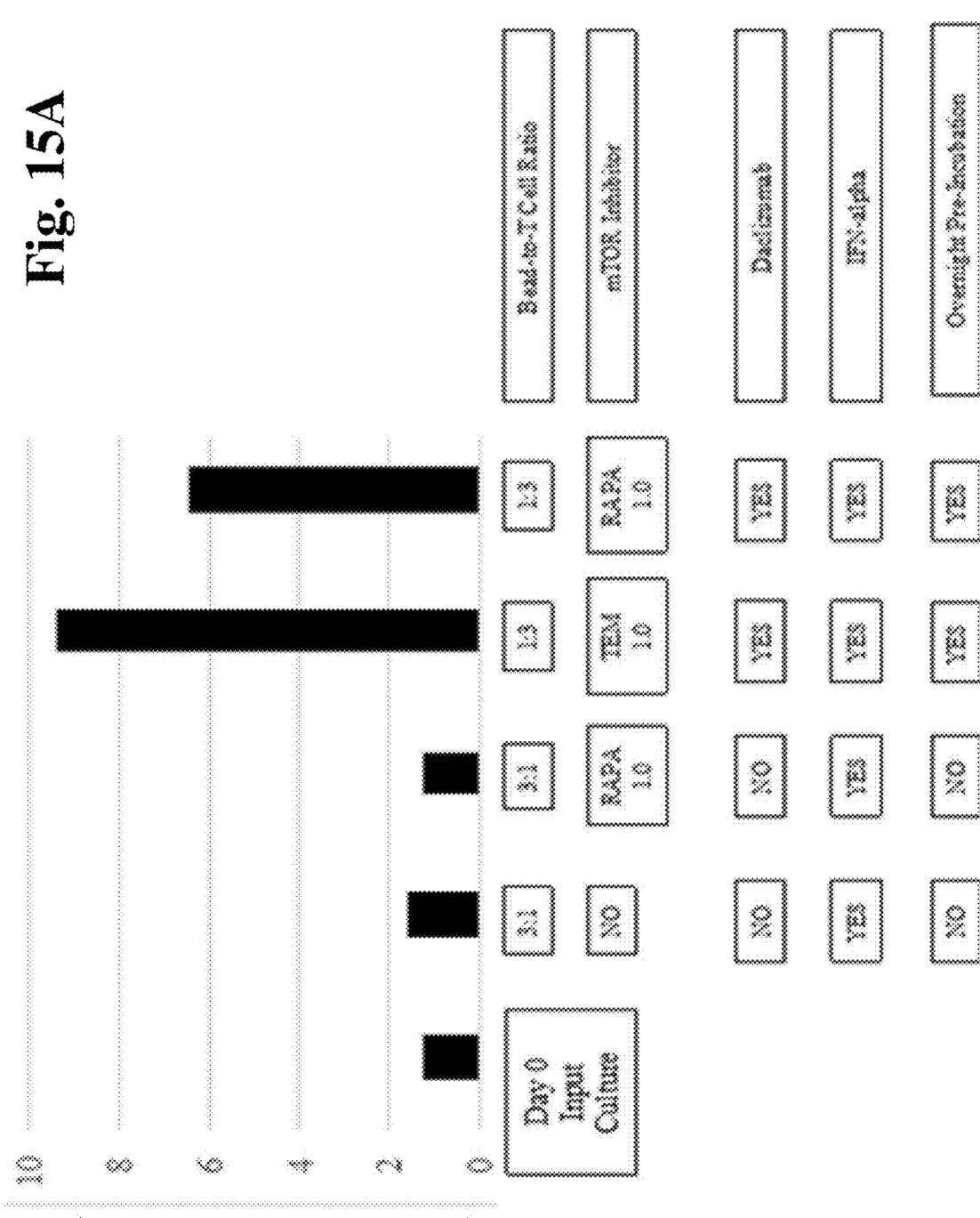
FIG. 15A depicts flow cytometry expression analysis of CD62L, CCR7, and CD127 on the CD4+ cell subset after culturing the T cells under various conditions.
Figure 15B:
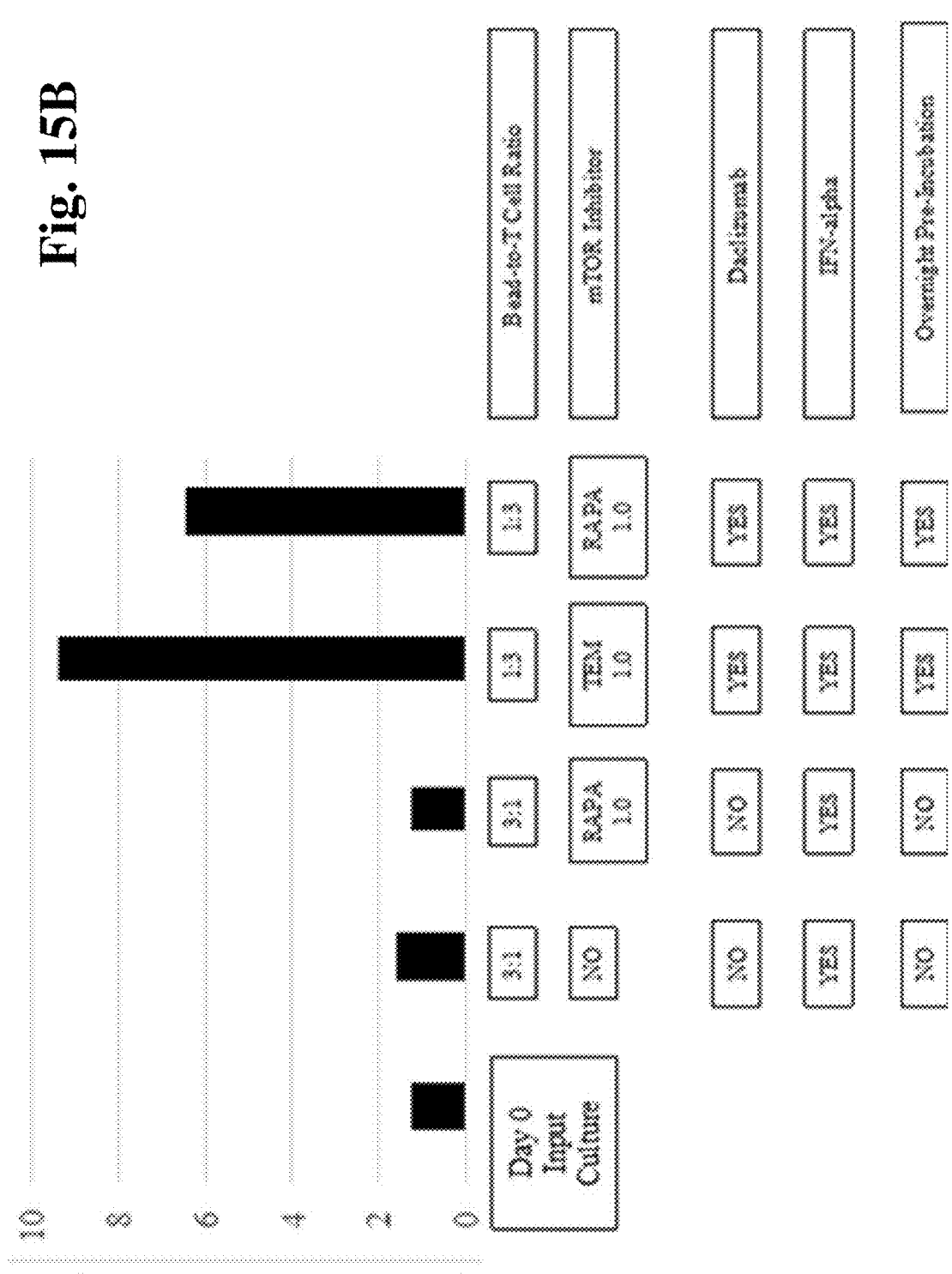
FIG. 15B depicts flow cytometry expression analysis of CD62L, CCR7, and CD127 on the CD4+ cell subset after culturing the T cells under various conditions
Figure 15C:
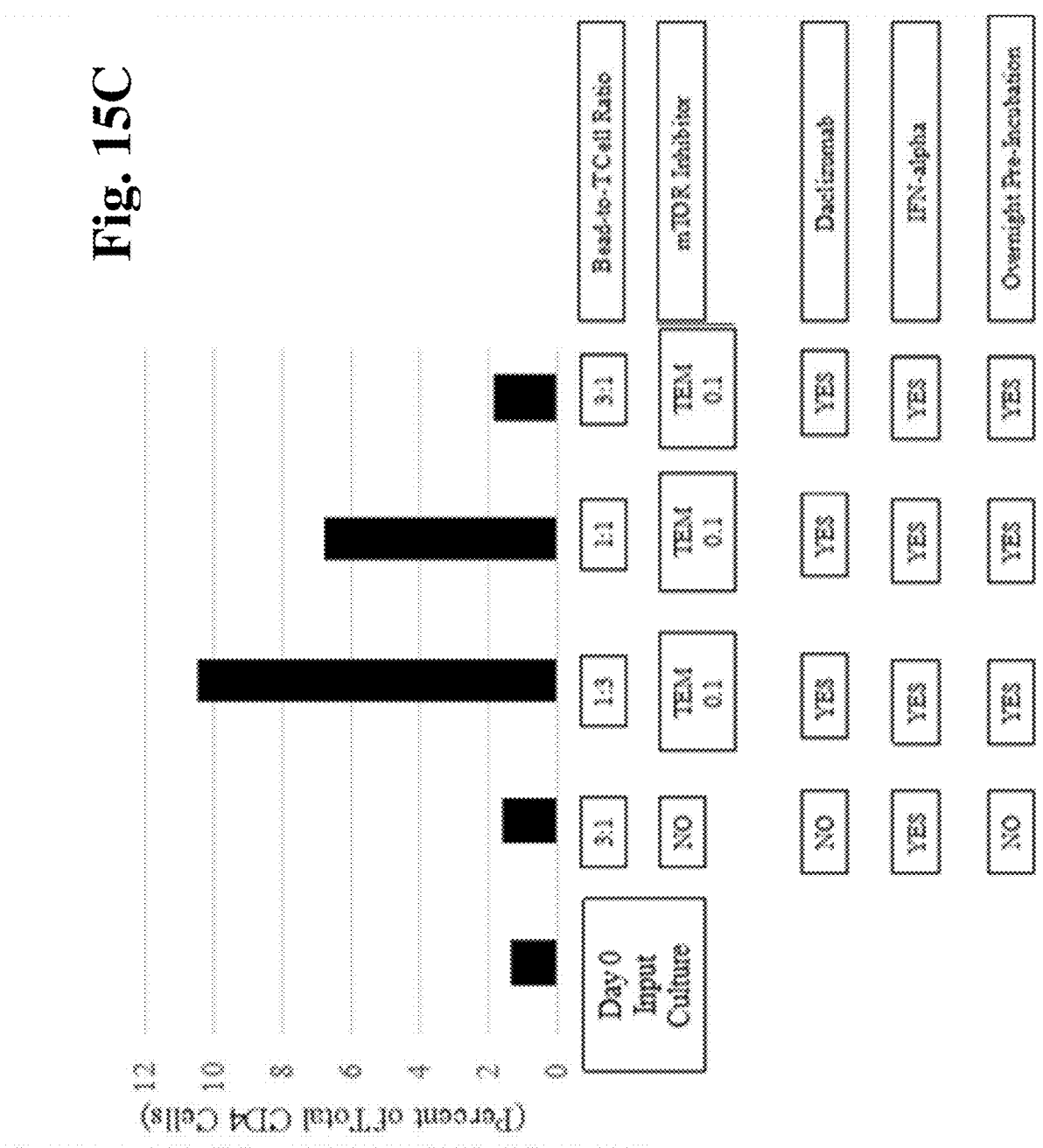
FIG. 15C depicts flow cytometry expression analysis of CD62L, CCR7, and CD127 on the CD4+ cell subset after culturing the T cells under various conditions
Figure 15D:
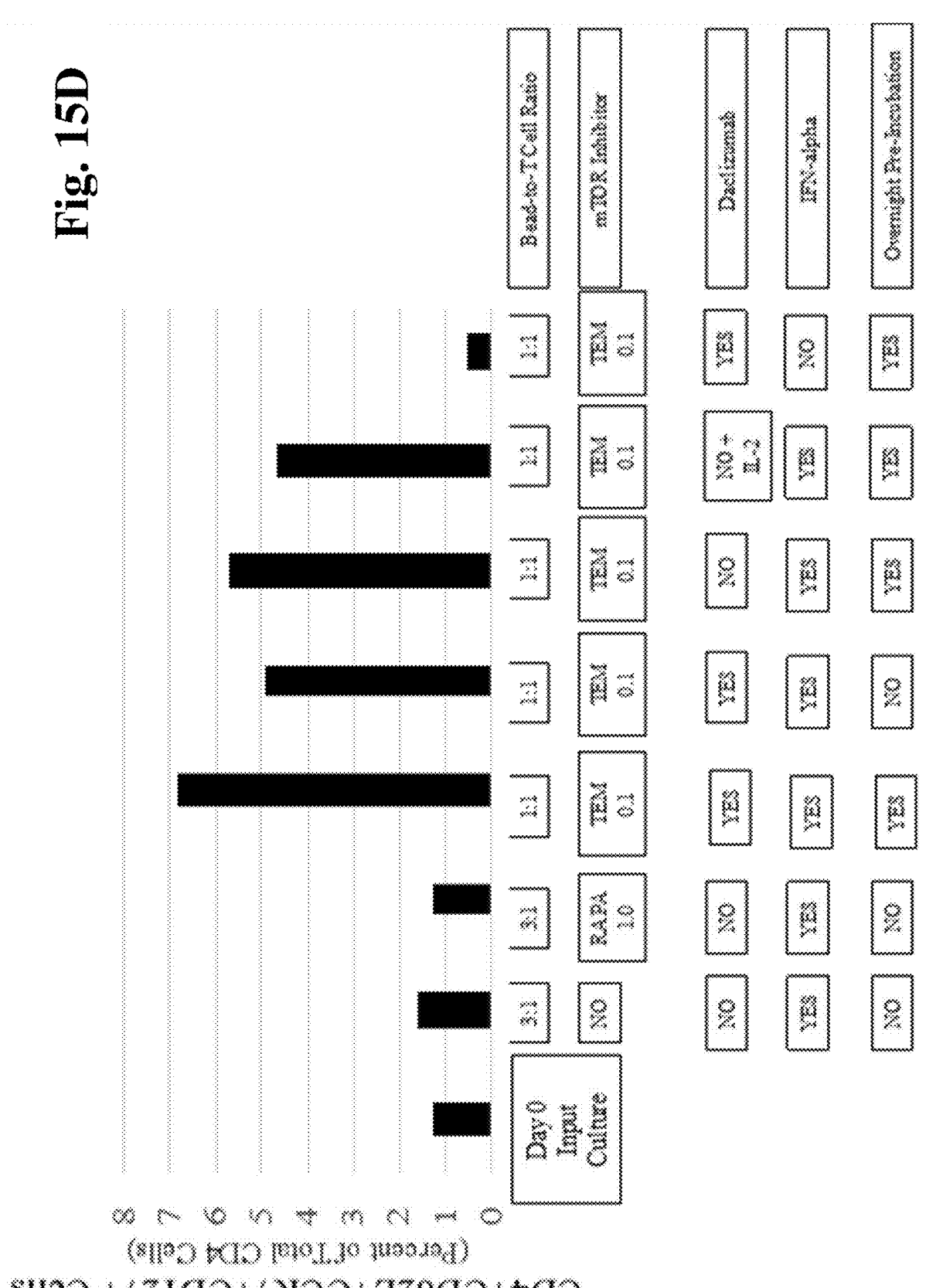
FIG. 15D depicts flow cytometry expression analysis of CD62L, CCR7, and CD127 on the CD4+ cell subset after culturing the T cells under various conditions

In addition, we evaluated whether the combinatorial method resulted in other markers of reduced T cell differentiation, including CD62L, CCR7, and CD127. FIG. 15A (column #4) indicates that T cells manufactured using the pre-incubation step, low level co-stimulation, antibody blockade of the IL-2 receptor, and an mTOR inhibitor had increased co-expression of these T cell markers. Of note, T cells propagated using the prior manufacturing method that we identified did not have optimally increased expression of these three memory markers (T-Rapa cells; FIG. 15A, column #3).

As such, the combinatorial method of Th1/Tc1 cell manufacturing is advantageous in terms of manufacturing T cells of limited differentiation status, which have been clearly and reproducibly shown to mediate increased in vivo effects.

The Combinatorial Method is Optimized by Reducing T Cell Purity at Culture Initiation. For T cell manufacturing, it is important to determine whether the culture input population must be purified to a high degree for T cell content or whether accessory cell populations such as monocytes might be tolerated. From a financial cost and labor standpoint, it is generally desirable to initiate cultures with populations that are not highly purified. However, contaminating populations of cells at culture initiation may be detrimental to T cell expansion or to generation of the desired T cell phenotype. To evaluate this parameter, we initiated cultures using the combinatorial method using input populations that were either 100%, 66%, 33%, or 10% pure for T cell content; the remaining populations of cells were primarily monocytes.

Figure 19:
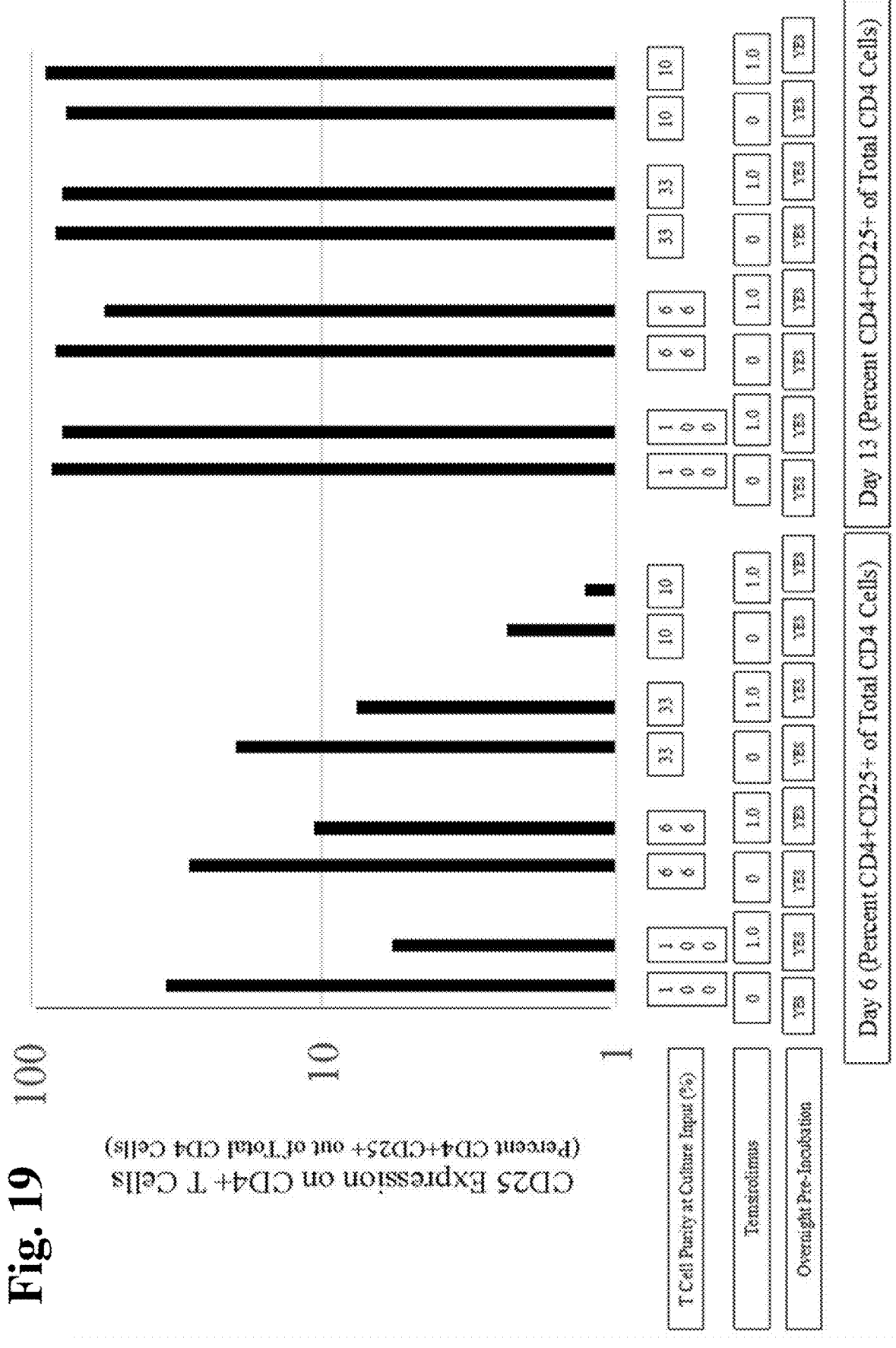
FIG. 19 depicts flow cytometry expression analysis of CD25 on the CD4$^+$ T cell subset on day 6 and day 13 after culturing T cells under various conditions.
Figure 20:
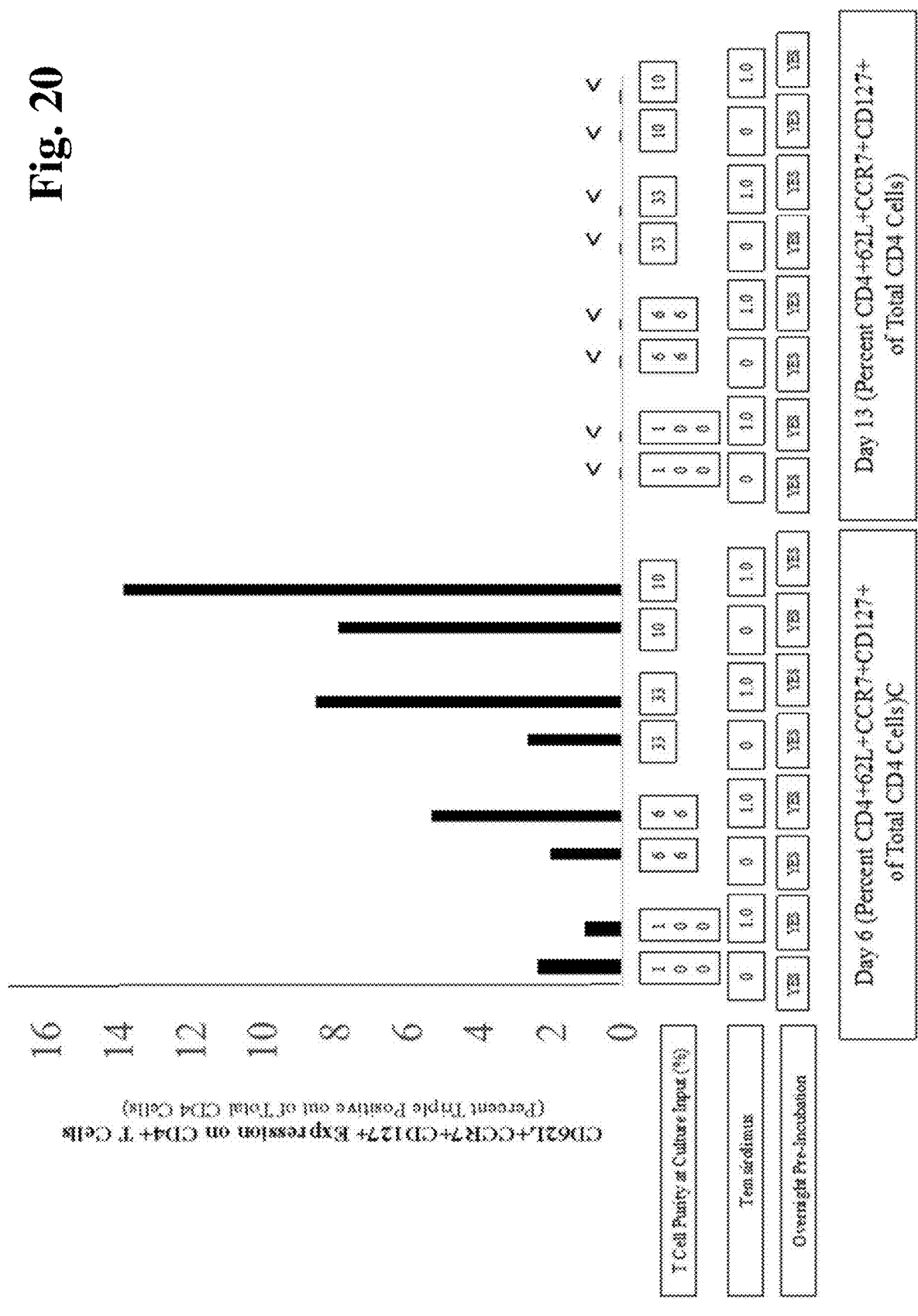
FIG. 20 depicts flow cytometry expression analysis of CD62L, CCR7, and CD127 on the CD4$^+$ T cell subset on day 6 and day 13 after culturing T cells under various conditions.

For FIGS. 16-20, prior to culture initiation, the input cell population was adjusted such that the purity of T cells was either 100%, 66%, 33%, or 10%; the remaining cell populations were comprised of the non-T cell populations contained in peripheral blood mononuclear cells (primarily monocytes). As indicated, T cells were expanded in media that variably contained or did not contain temsirolimus (concentration of either 1.0 or 0.1 μM); in addition, cultures variably included a 16-hr pre-incubation or no pre-incubation prior to anti-CD3, anti-CD28 bead co-stimulation (1:3 ratio). Each culture shown was propagated in media containing the anti-IL-2 receptor monoclonal antibody daclizumab (50 μg/ml) and IFN-α (10,000 IU/ml). At the end of the 6-day manufacturing interval, the T cells received a high-level of co-stimulation (3:1 bead-to-T cell ratio). For FIG. 16, after high level of co-stimulation the T cells were then expanded for one week in media that did not contain inhibitors. At the end of this expansion interval, the T cells were enumerated and graphed relative to day 0 input number. For FIGS. 17-18, after high level of co-stimulation the T cells were expanded until day 13 of culture. At both day 6 and day 13, the T cells were co-stimulated and the 24-hr supernatant was evaluated for IFN-γ (FIGS. 17A-17B) or TNF-α (FIGS. 18A-18B) content (result shown in pg per ml per million cells per 24 hrs). For FIGS. 19-20, after high level of co-stimulation the T cells were expanded until day 13 of culture. At both day 6 and day 13, the T cells were evaluated by flow cytometry for CD25 expression (results shown are percent of CD4+ T cells that co-express CD25) (FIG. 19) or for expression of CD62L, CCR7, and CD127 (FIG. 20).

Figure 16:
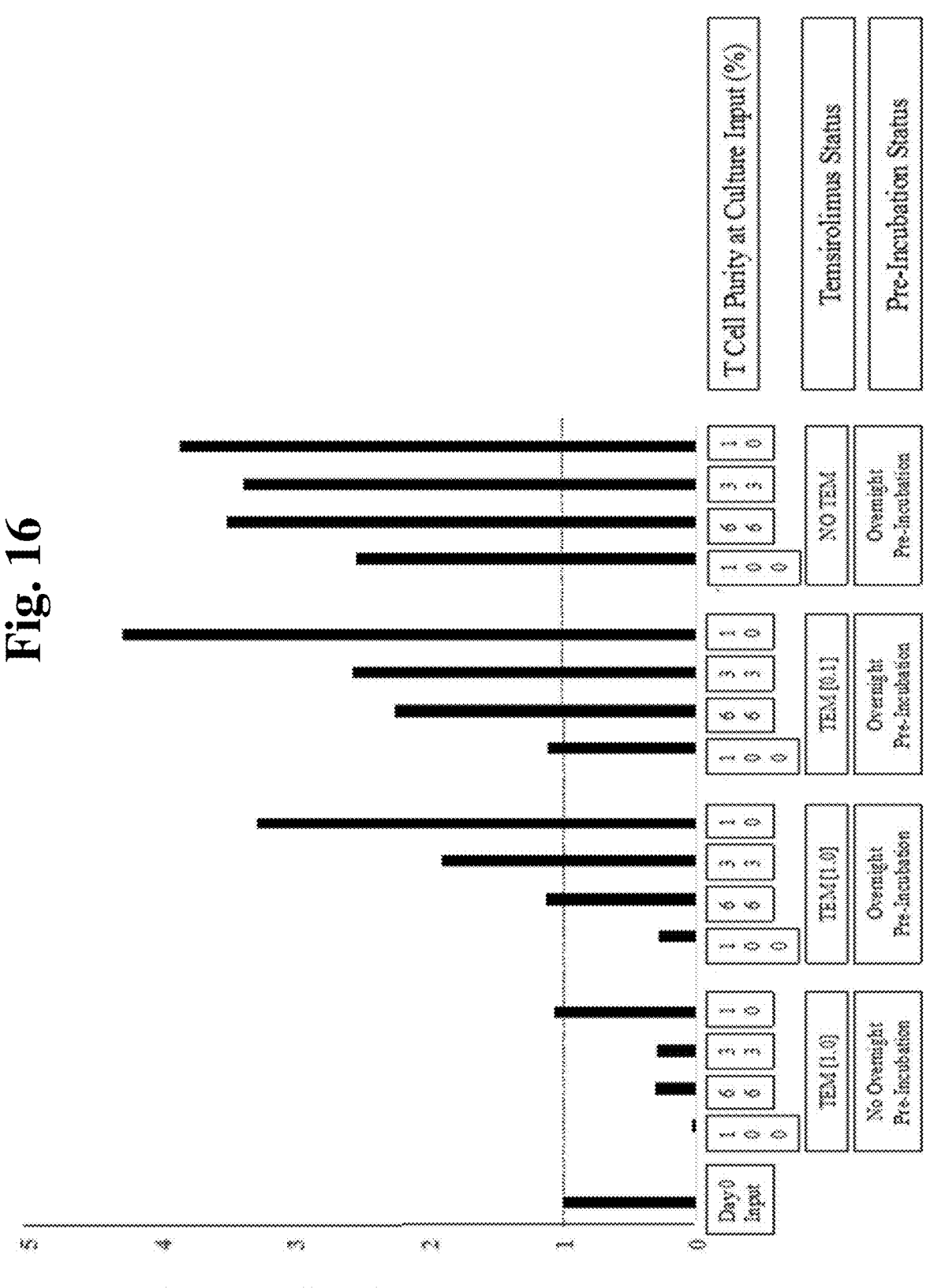
FIG. 16 depicts fold increase in culture yield of T cells cultured under various conditions.
Figure 17A:
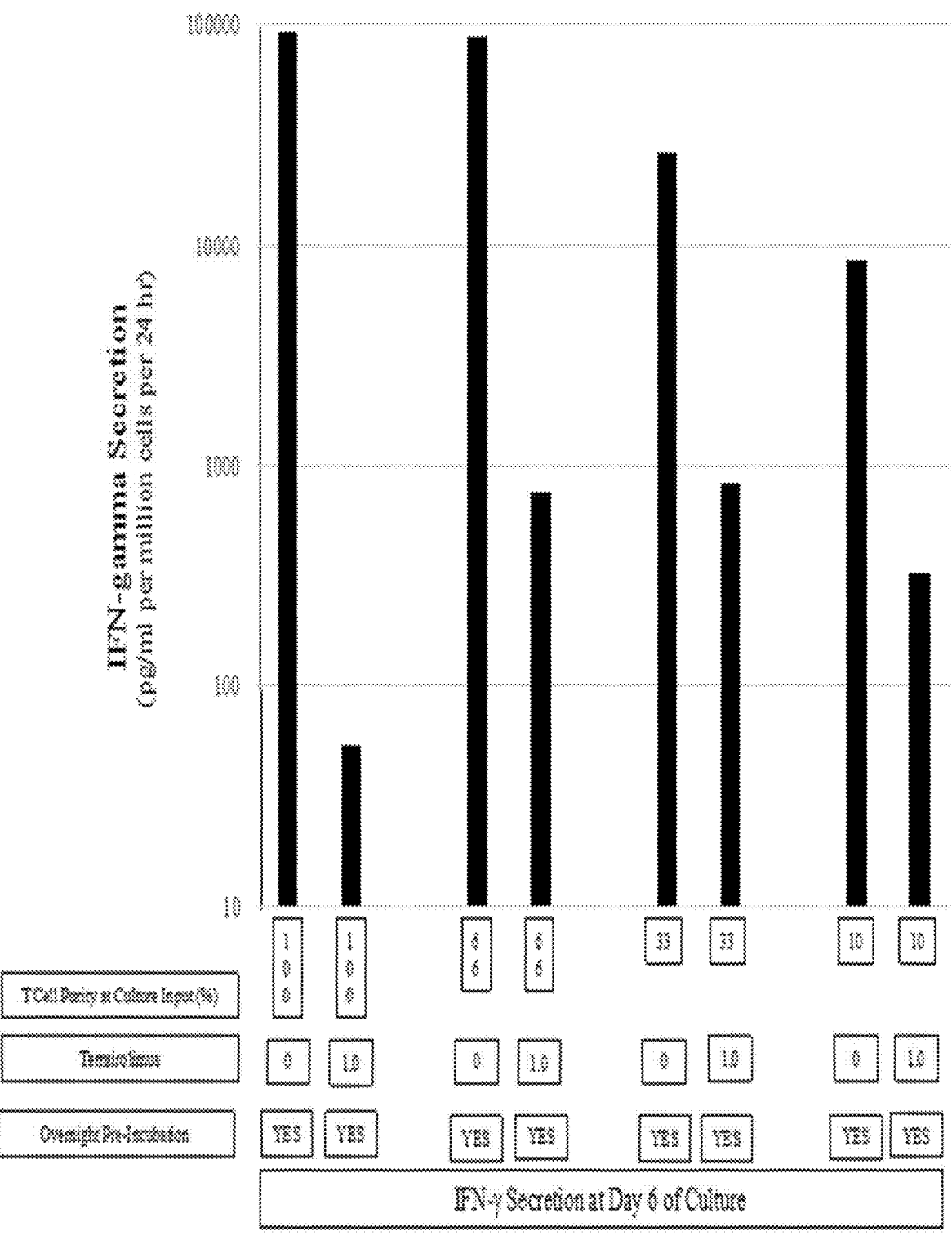
FIG. 17A depicts IFN-gamma secretion on day 6 after culturing T cells under various conditions.
Figure 17B:
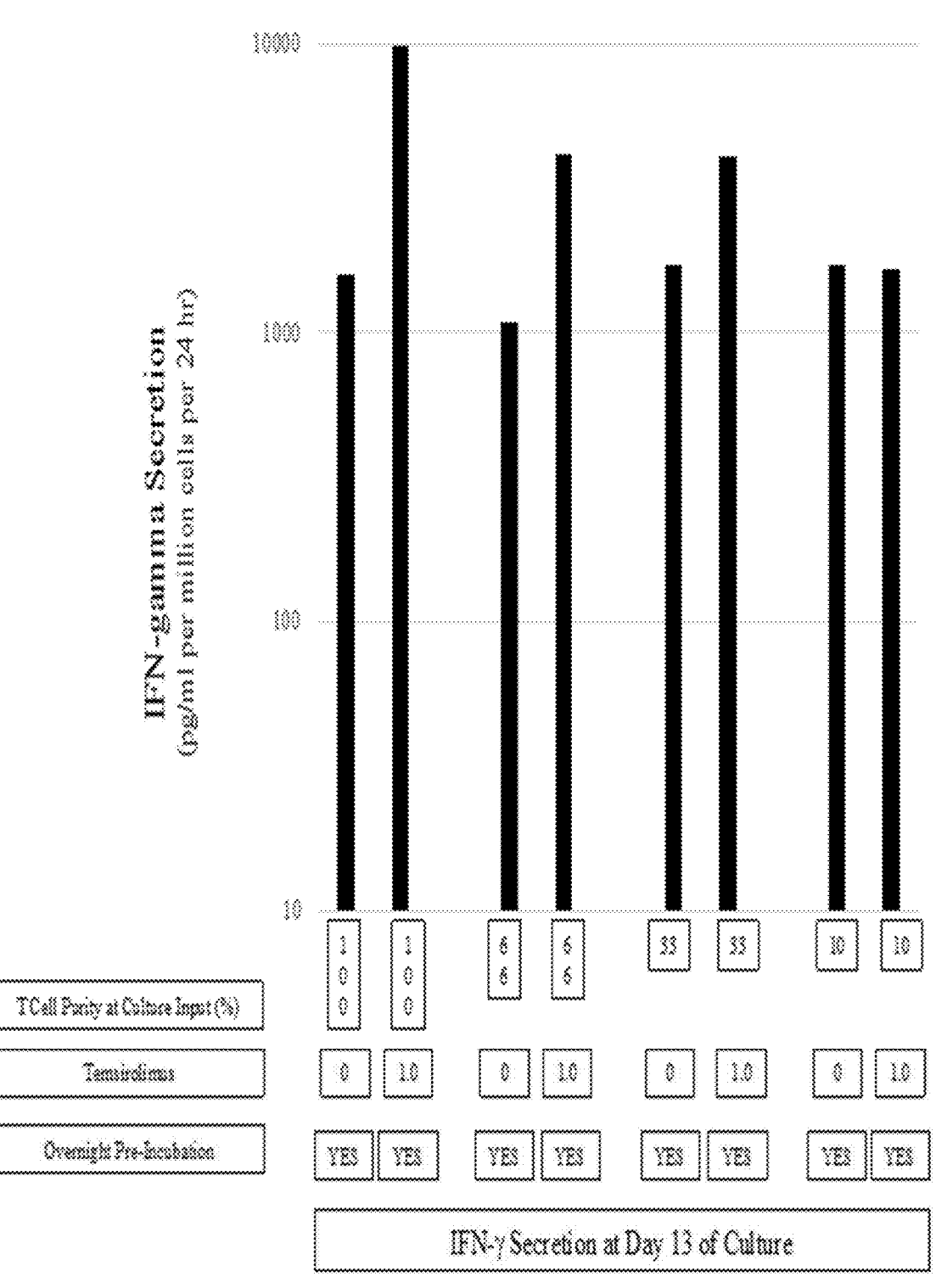
FIG. 17B depicts IFN-gamma secretion on day 13 after culturing T cells under various conditions.
Figure 18A:
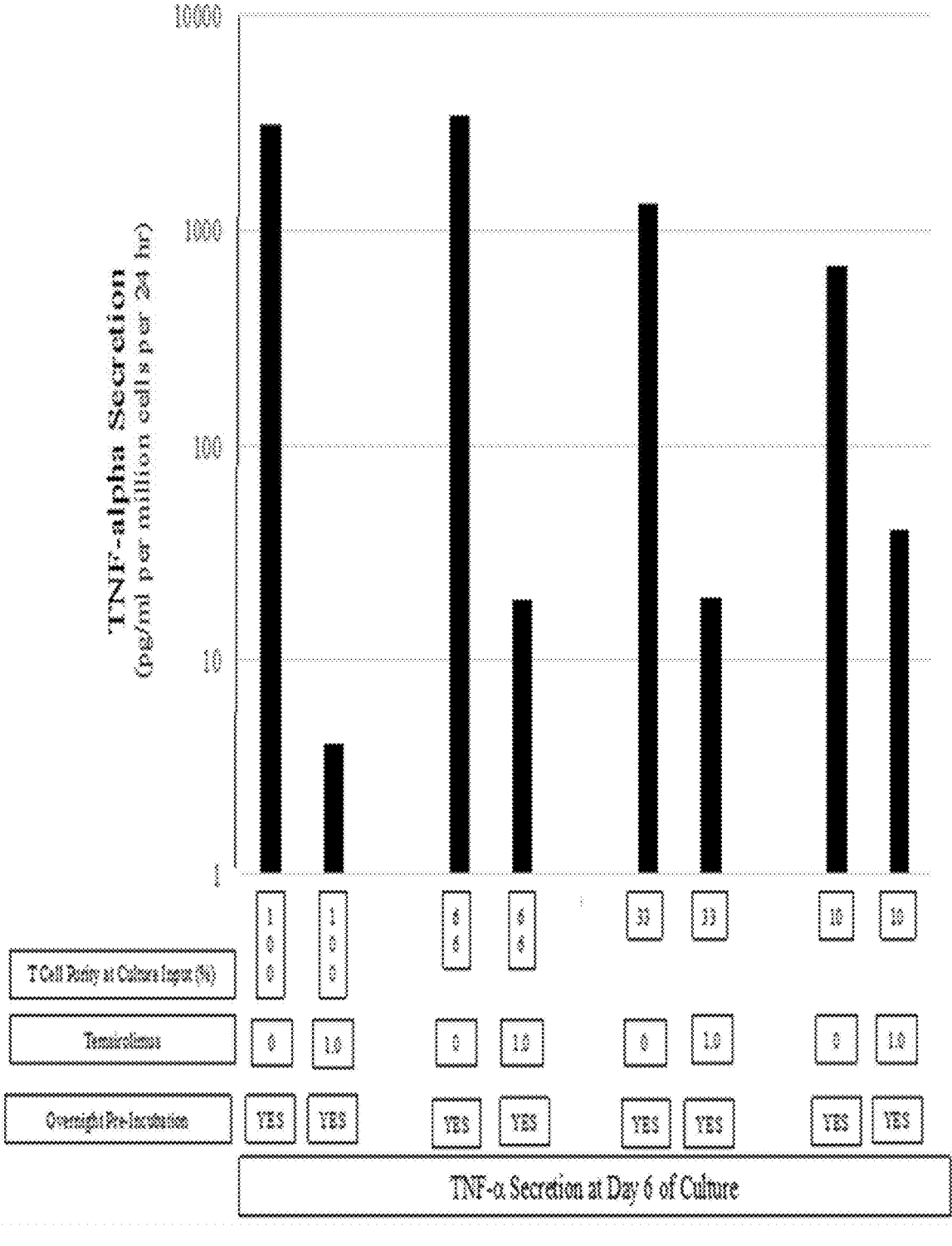
FIG. 18A depicts TNF-alpha secretion on day 6 after culturing T cells under various conditions.
Figure 18B:
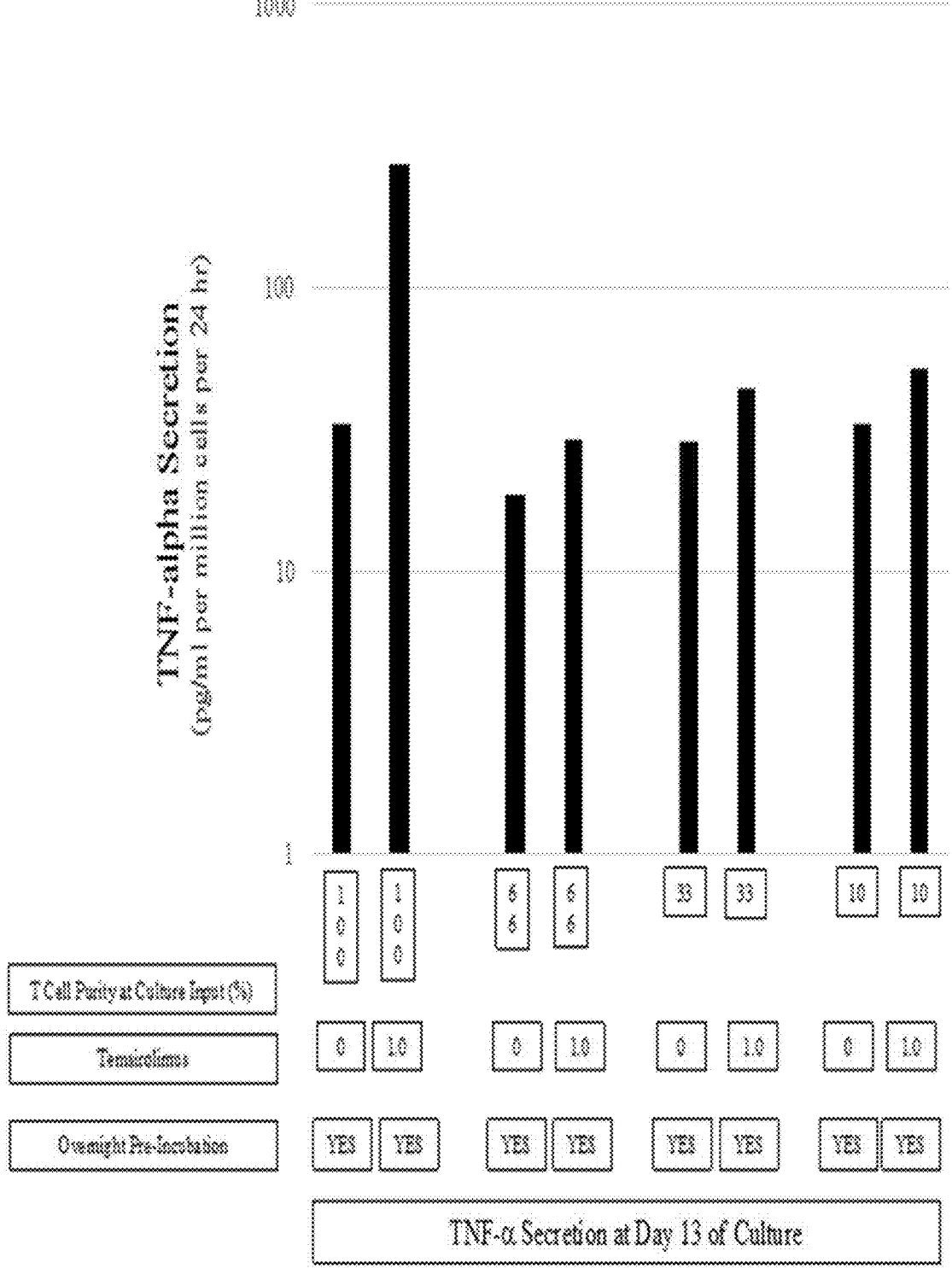
FIG. 18B depicts TNF-alpha secretion on day 13 after culturing T cells under various conditions.

As detailed in FIG. 16, cultures that were initiated with reduced T cell purity at culture input resulted in greater capacity for T cell expansion, with this relationship occurring in a dose-dependent manner. Of note, T cells that were propagated using the overnight pre-incubation step had a greater expansion relative to T cells that were co-stimulated at the time of culture initiation. These data provide further support to the combinatorial method and indicate that cell populations at culture initiation that may otherwise be considered contaminants appear to actually facilitate T cell expansion potential. As such, optimized use of the combinatorial method should also include the use of T cells that are not highly enriched at culture initiation; for quality assurance, it may be important to control the level of purity, by way of non-limiting example, initiating each culture with an inoculum that is either 66% or 33% pure for T cell content. As detailed in FIGS. 17A-17B and 18A-18B, T cells manufactured using the combinatorial method and input T cells that were not highly purified resulted in the desired cytokine secretion pattern, namely: (FIGS. 17A-17B) reduced IFN-γ secretion at the end of manufacturing (day 6) and increased IFN-γ secretion after one week expansion in media not containing inhibitors (day 13); and (FIGS. 18A-18B) reduced TNF-α secretion at the end of manufacturing (day 6) and increased TNF-α secretion after one week expansion in media not containing inhibitors (day 13).

In addition, we evaluated cell surface marker expression in T cells manufactured with the combinatorial method using input populations of reduced T cell purity. As shown in FIG. 19, such T cells had reduced CD25 expression at the end of manufacturing (day 6), consistent with a quiescent phenotype; after one week of culture without inhibitors, the T cells greatly up-regulated CD25. As shown in FIG. 20, such T cells also had increased co-expression of memory markers CD62L, CCR7, and CD127; these markers were then reduced after one week T cell expansion.

In sum, these data indicate that manufacture of Th1/Tc1 cells using the combinatorial method is possible using input T cells having substantial contamination with non-T cell populations. Indeed, purposeful inclusion of such non-T cell populations can be utilized to improve T cell yield and improve the resultant T cell memory profile.

Manufacturing from cryopreserved cell substrates. In the case of previously collected PBSC products, such cryopreserved cells will be stored in the vapor phase of liquid nitrogen until thawing of cells and manufacture of Rapa-T cells. In the case of freshly isolated cells by apheresis or in the future by simple blood collection, the cells will undergo immediate processing, and then may either be placed directly into culture or may be cryopreserved by controlled rate freezing technology and stored in the vapor phase of liquid nitrogen for subsequent use later.

T cell culture from cryopreserved cell substrates for from freshly isolated cell populations requires some type of T cell enrichment, for example, by use of monoclonal antibody and column technology (positive or negative selection). Enrichment of the raw cellular material used in Rapa-T manufacturing does not require such antibody-based methodologies because T cells are efficiently enriched during the culture interval; as such, our method is consistent with recommendations for effective cell therapy on a global level. The initial processing steps for manufacture of Rapa-T cells focuses on removal of di-methyl sulfoxide (DMSO) used in the cryopreservation steps (when applicable), lysis of red blood cells (RBCs), and centrifugal removal of contaminating granulocytes and to some extent, monocytes. These steps are performed in a relatively automated method using primarily closed-system technology; this procedure is advantageous as it reduces human error, provides detailed manufacturing data for batch records, improves consistency across manufacturing runs, and reduces the risk for infectious agent contamination of the final product. Processing for the Rapa-T products incorporates the following steps: (1) thaw of cryopreserved products (when applicable) using solid-state, non-water based methods to reduce infectious agent contamination; (2) automated washing of the cellular product using the LOVO permeable membrane device; (3) integration of lysis of RBCs using ammonium-chloride-potassium (ACK) buffer during the LOVO washing steps; (4) volume reduction of cellular content using the LOVO method with subsequent plating of cells into the closed-system, counter-flow, centrifugal elutriation (CCE) device (Elutra; Terumo); and (5) pre-programmed operation of the Elutra device for efficient removal of granulocytes and monocytes by CCE.

After this lymphocyte enrichment and media purification, the cells are plated into specialized chambers that possess an enriched capacity for oxygen exchange (G-Rex vessels; Wilson-Wolf). In addition to having enhanced gas permeability characteristics, the G-Rex vessels are closed system units and have the additional advantage of automated, closed system media volume reduction (GatheRex Liquid Handling Pump). The lymphocyte-enriched cells are maintained in the G-Rex vessels for 6-days.

Several specific culture conditions can be utilized to promote the manufacture of a mixture of CD4+ and CD8+ T cells in the G-Rex vessels with functional attributes of a manufactured T cell. These specific conditions include: (1) use of enriched media (including but not limited to X-Vivo 20; Lonza) that is further supplemented with 5% human serum; (2) incorporation of a 16-hour rest interval of cell plating into the G-Rex prior to co-stimulation (cells are plated at a relatively high density of 1.5×106 cells per ml); (3) during this initial rest interval, cells are optimally rested by addition of the monoclonal antibody basiliximab (which blocks the IL-2 receptor and thereby prevents autonomous T cell activation by endogenously produced IL-2) and temsirolimus (which is a pharmacologic inhibitor of mTORC1); (4) after this 16-hour rest interval, cells are either not co-stimulated or are co-stimulated with anti-CD3/anti-CD28 coated magnetic beads (3/28 beads) under sub-optimal conditions, as defined by a bead-to-T cell ratio of 1:3 (typically, most T cell expansion conditions utilize a 9-fold higher level of co-stimulation, a 3:1 bead-to-T cell ratio); (5) importantly, it is essential that the T cells are not washed after the initial rest interval; (6) after the rest interval, in addition to addition of 3/28 beads, it is essential to add the polarizing cytokine IFN-α at a high dose (10,000 IU/ml) to promote differentiation to CD4+ Th1 and CD8+ Tc1 phenotypes; (7) importantly, it is critical to avoid the addition of IL-2, which is a common additive to T cell cultures; and (8) after addition of the beads and IFN-α, it is important to leave the cells undisturbed until harvesting at day 6 of culture (no cell washing, no further culture additives).

Cryopreservation of Manufactured T Cells. 1) After the 6-day cell culture in the G-Rex vessels, the volume of the culture can be reduced in a closed system manner by the GatheRex instrument. Subsequently, the cells can be harvested, 3/28 beads can be removed by hand-held magnet, and cells can be placed into the LOVO device for serial washing of the cells to remove >99% of culture additives (Temsirolimus, Basiliximab, IFN-α).

Washed cells can be reconstituted into cryopreservation media, which contains 5% DMSO and 5% pentastarch. The cryopreservation is performed in multiple single use aliquots in 50 ml freezer bags. Rapa-T cells are cryopreserved by GMP-compliant controlled rate freezing methodology and shipped in the vapor phase of liquid nitrogen by certified cryo-shipper after the Rapa-T cells have passed the specified release criteria testing.

Release criteria testing of the Rapa-T cells includes standard tests such as content of CD3+, CD4+ and CD8+ T cell purity (final product can be >70% CD3+ T cell content by flow cytometry; CD4+ and CD8+ subsets can each be present at the 5% level). Cells can be >70% viable, as determined by flow cytometry annexin and 7-AAD assays. Furthermore, cells should be free of bacterial and fungal contamination upon a minimum of a 3-day culture interval (ideally, a 14-day culture interval); furthermore, the cell product should be below detection limit for bacterial LPS endotoxin.

In addition to these standard tests, specialized functional tests will constitute release criteria for the Rapa-T cell products. Prior to release of product and cell therapy, a Rapa-T cell can possess the following attributes relative to culture input T cells: (1) an enhanced T central memory phenotype, as defined by increased flow cytometric co-expression of CD62 ligand and CCR7; (2) low level expression of checkpoint inhibitory molecules, such as programmed death-1 (PD1); (3) a resting state, as defined by reduced levels of Th1/Tc1-type cytokine secretion upon maximal co-stimulation; (4) an autophagy signature, as evidenced by reduced mitochondrial mass by flow cytometry MitoTracker assay; (5) a resistant phenotype, as evidenced by at least 50% inhibition of mTORC1 and mTORC2 downstream targets; and (6) a multi-faceted differential gene expression profile of n=80 key transcription factor and differentiation molecules.

Figure 21:
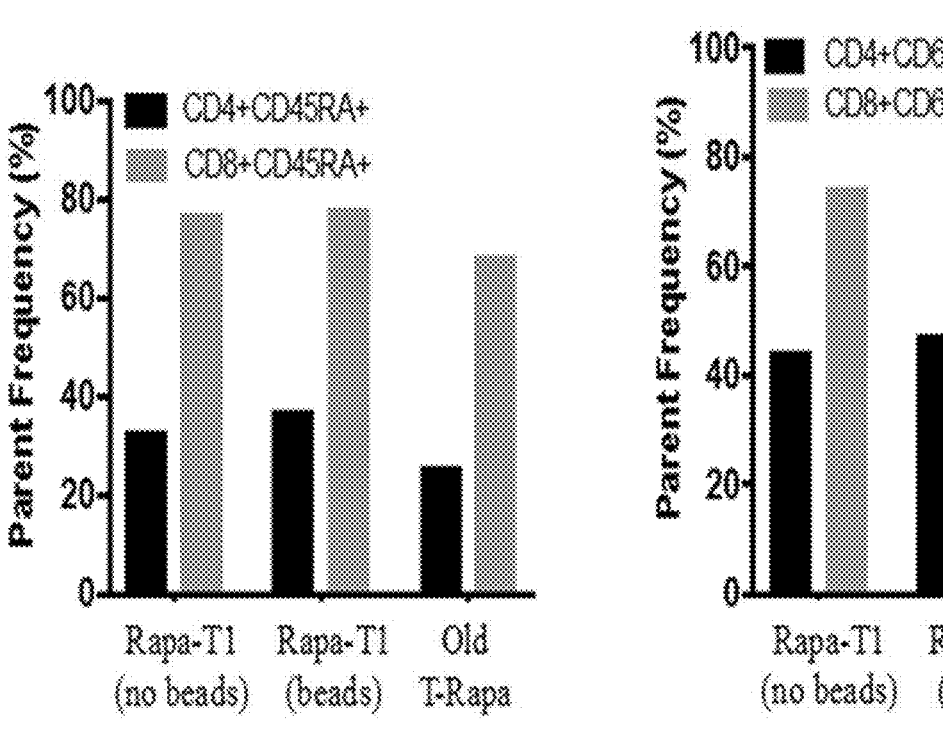
FIG. 21 depicts flow cytometry expression analysis comparing the new Rapa-T method that incorporates no bead co-stimulation, the new Rapa-T method that incorporates bead co-stimulation (bead-to-T cell ratio, 1:3), and the old T-Rapa method (bead-to-T cell ratio, 3:1) for the naïve and T central memory panels: CD45RA expression; co-expression of CD62L and CCR7; and co-expression of CD62L, CCR7, and CD127.
Figure 21:
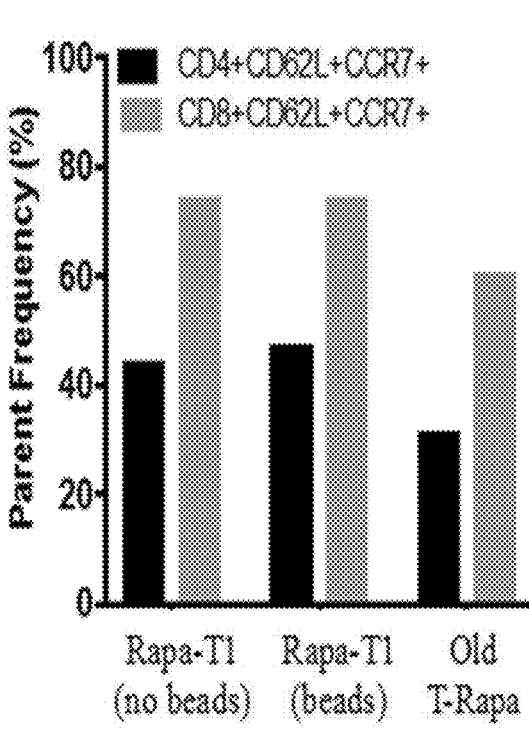
Figure 21:
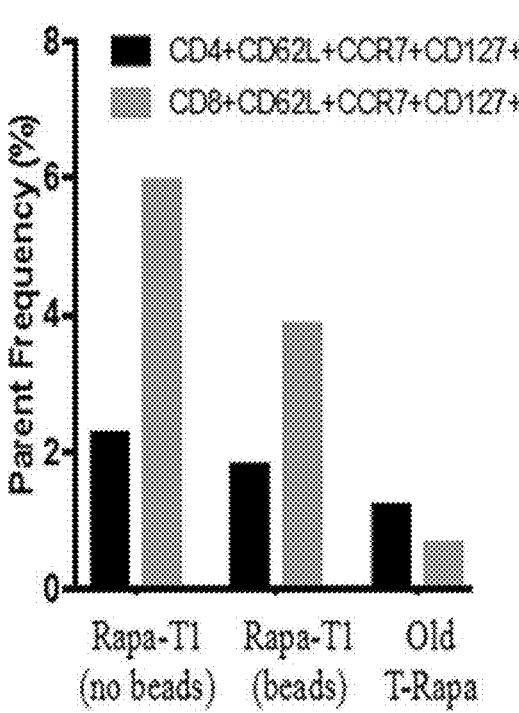

FIG. 21 illustrates that the new Rapa-T method generates T cells with increased expression of the naïve or T central-memory markers relative to T-Rapa cells, independent of whether the new Rapa-T method uses no bead co-stimulation or a low level of bead co-stimulation (1:3 ratio of beads-to-T cells). In FIG. 21, Rapa-T1 cells were generated by culture in IFN-α, temsirolimus, and basiliximab, as previously described, either without bead co-stimulation (first two columns in each panel) or with 1:3 bead-to-T cell co-stimulation (third and fourth column in each panel); the results were compared to culture using the previous T-Rapa method (use of rapamycin and 3:1 bead-to-T cells; fifth and sixth column in each panel). Flow cytometry was performed at the end of culture, with results detailed for both the CD4+ T cell subset (black columns) and the CD8+ T cell subset (gray columns). Results shown are for the naïve T cell subset, as defined by CD45RA+ expression (left panel); for the T central memory subset, as defined by co-expression of CD62L and CCR7); and for the more primitive T cell subset that co-expresses CD62L, CCR7, and CD127.

As detailed in FIG. 21, the CD4+ and CD8+ T cells manufactured according to the methods described in this disclosure have increased levels of expression of naïve and T central memory markers by flow cytometry relative to T-Rapa cells, including in conditions where the methods involve no bead co-stimulation or co-stimulation at a reduced level compared to the T-Rapa method.

Figure 22:
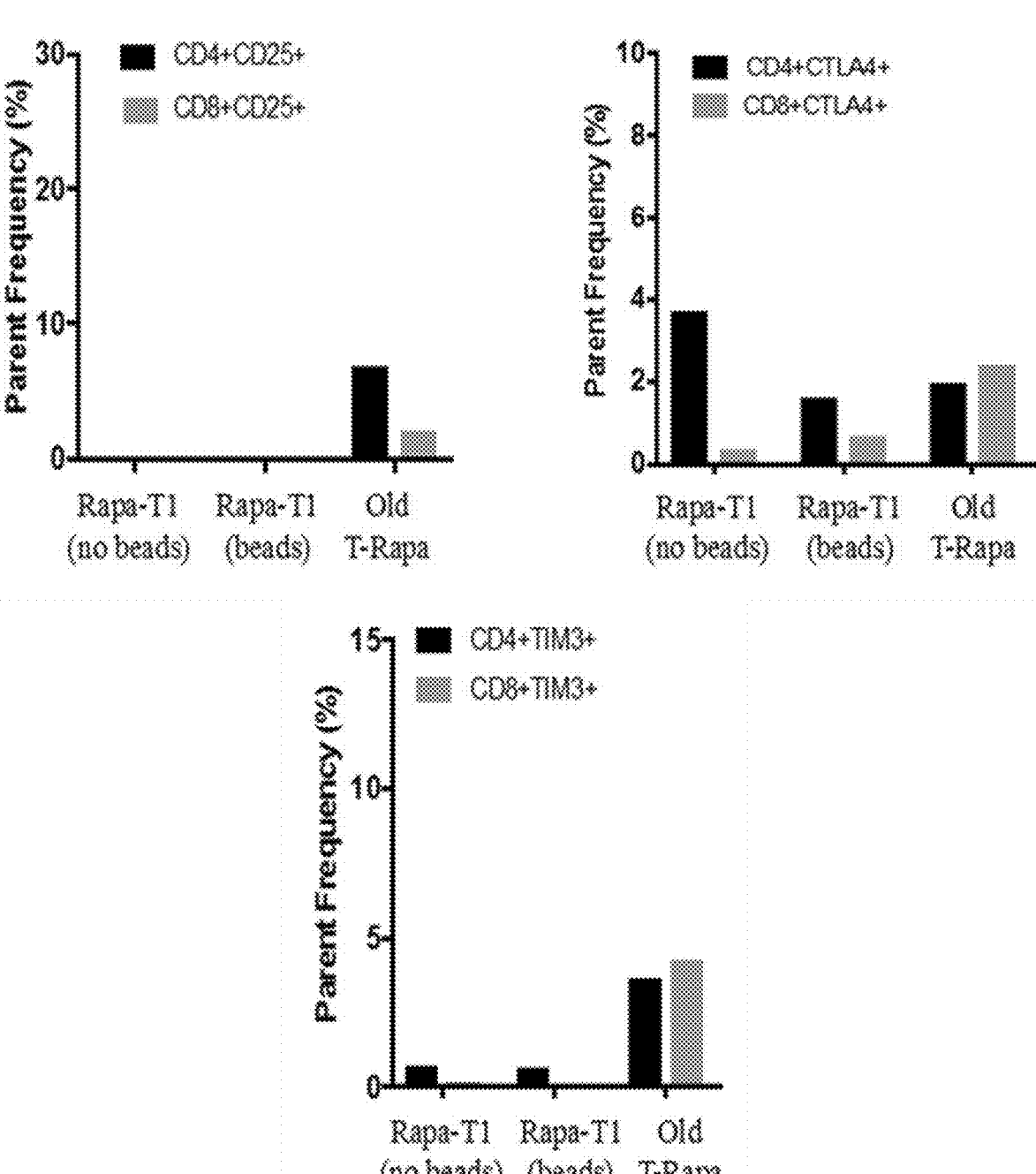
FIG. 22 depicts flow cytometry expression analysis comparing the new Rapa-T method that incorporates no bead co-stimulation, the new Rapa-T method that incorporates bead co-stimulation (bead-to-T cell ratio, 1:3), and the old T-Rapa method (bead-to-T cell ratio, 3:1) for: expression of the IL-2 receptor, CD25; and for expression of the immune suppressive molecules CTLA4 and TIM3.

FIG. 22 illustrates that the new Rapa-T method generates T cells with reduced expression of CD25, CTLA4, and TIM3 relative to T-Rapa cells, independent of whether the new Rapa-T method uses no bead co-stimulation or a low level of bead co-stimulation (1:3 ratio of beads-to-T cells). In FIG. 22, Rapa-T1 cells were generated by culture in IFN-α, temsirolimus, and basiliximab, as previously described, either without bead co-stimulation (first two columns in each panel) or with 1:3 bead-to-T cell co-stimulation (third and fourth column in each panel); the results were compared to culture using the previous T-Rapa method (use of rapamycin and 3:1 bead-to-T cells; fifth and sixth column in each panel). Flow cytometry was performed at the end of culture, with results detailed for both the CD4+ T cell subset (black columns) and the CD8+ T cell subset (gray columns). Results shown are for expression of the IL-2 receptor CD25 (left panel); for the immune suppressive and $T_{REG}$-associated molecule CTLA4; and for the immune checkpoint molecule TIM3.

As detailed in FIG. 22, the CD4+ and CD8+ T cells manufactured according to the methods described in this disclosure have reduced levels of expression of the IL-2 receptor CD25[2], which is associated with T cell activation and $T_{REG}$ cell function, and reduced levels of the immune suppressive molecule CTLA4[3] and the immune checkpoint inhibitory molecule TIM3[4] by flow cytometry relative to T-Rapa cells, including in conditions where the methods involve no bead co-stimulation or co-stimulation at a reduced level compared to the T-Rapa method.

Figure 23:
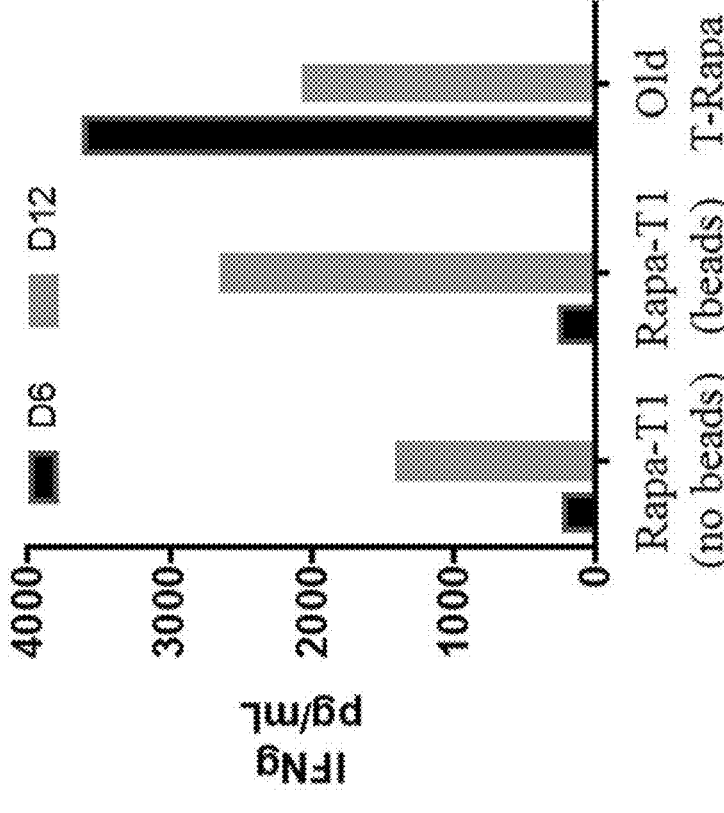
FIG. 23 depicts cytokine secretion results at the end of manufacturing and after an additional 6 days in culture without use of inhibitors comparing the new Rapa-T method that incorporates no bead co-stimulation, the new Rapa-T method that incorporates bead co-stimulation (bead-to-T cell ratio, 1:3), and the old T-Rapa method (bead-to-T cell ratio, 3:1) for: secretion of the type II cytokine IL-4; and secretion of the type I cytokine IFN-γ.
Figure 23:
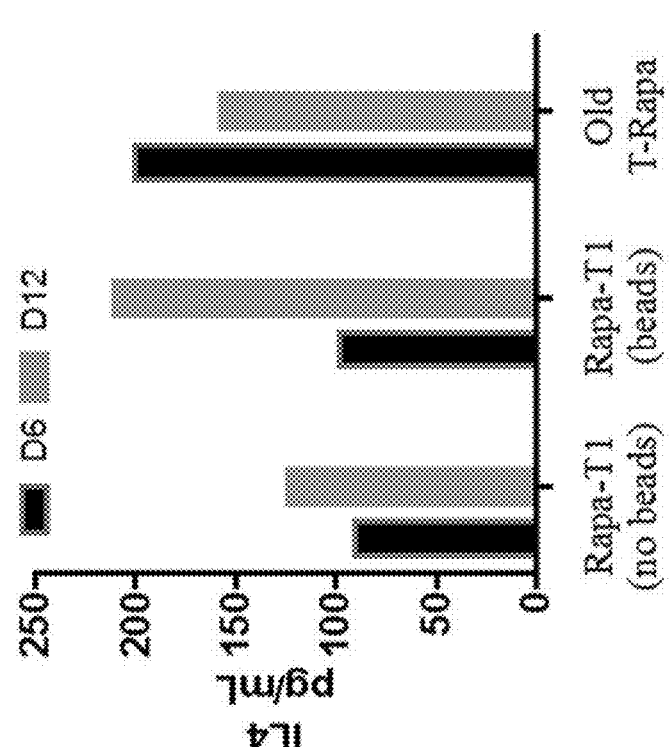

FIG. 23 illustrates that the new Rapa-T method generates T cells with a similar pattern of Th2 vs. Th1 polarization but increased quiescence relative to T-Rapa cells, independent of whether the new Rapa-T method uses no bead co-stimulation or a low level of bead co-stimulation (1:3 ratio of beads-to-T cells). In FIG. 23, Rapa-T1 cells were generated by culture in IFN-α, temsirolimus, and basiliximab, as previously described, either without bead co-stimulation (first two columns in each panel) or with 1:3 bead-to-T cell co-stimulation (third and fourth column in each panel); the results were compared to culture using the previous T-Rapa method (use of rapamycin and 3:1 bead-to-T cells; fifth and sixth column in each panel). Cytokine secretion analysis (IL-4 and IFN-g measurement) was performed at the end of culture, with results detailed at the end of T cell manufacturing (day 6) and after an additional 6 days in culture without inhibitors (day 12). In both instances, the cells were co-stimulated with anti-CD3/anti-CD28-coated magnetic beads at a 3:1 ratio on day 6.

As detailed in FIG. 23, the CD4+ and CD8+ T cells manufactured according to the methods described in this disclosure have a comparable degree of Th2 vs. Th1 cytokine polarization relative to T-Rapa cells, including in conditions where the methods involve no bead co-stimulation or co-stimulation at a reduced level, compared to the T-Rapa method. Specifically, there is a low level of secretion of the Th2-type cytokine IL-4 (with values at the end of manufacturing [day 6] and after an additional period of culture without inhibitors [day 12] in the range of 100 to 200 pg/ml at both day 6 and day 12) and a high level of secretion of the Th1-type cytokine IFN-γ at day 12 of culture (values between 1000 and 3000 pg/ml). The IFN-γ secretion in the new Rapa-T conditions at the end of manufacturing (day 6) was greatly reduced relative to the old T-Rapa condition, thereby indicating the favorable characteristic of T cell quiescence in the new Rapa-T manufacturing method, independent of whether the method utilized no bead co-stimulation or a low-level of bead co-stimulation (1:3 ratio of beads-to-T cells).

Figure 24:
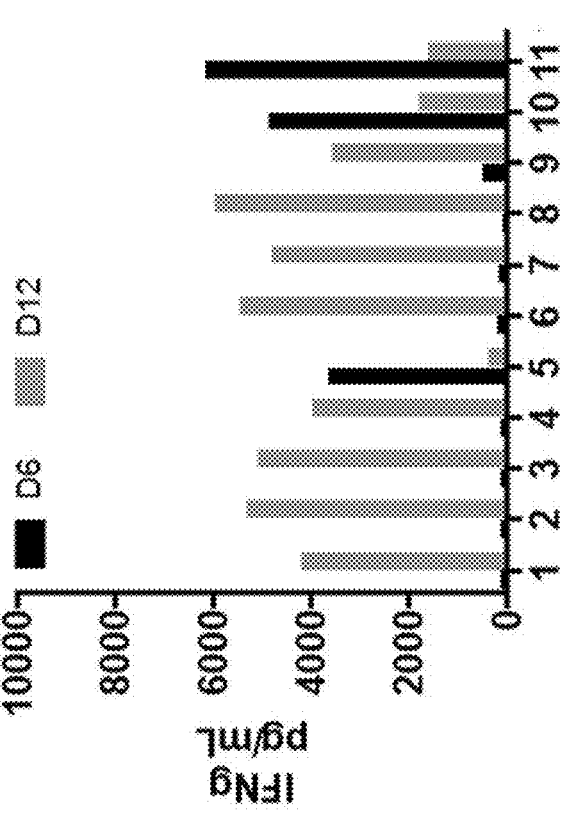
FIG. 24 depicts type I cytokine secretion (IL-2 and IFN-γ) results at the end of manufacturing and after an additional 6 days in culture without inhibitors in n=11 various culture conditions to further identify the role of no bead co-stimulation in the manufacture of the new Rapa-T cell population.
Figure 24:
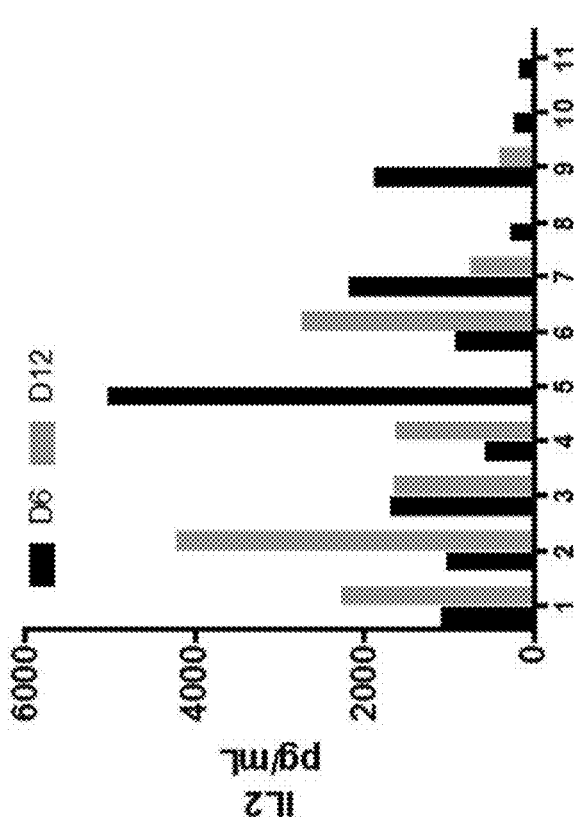

As detailed in FIG. 24, the CD4+ and CD8+ T cells manufactured according to the methods described in this disclosure have a pattern of Th1 cytokine polarization relative to T-Rapa cells, including in conditions where the methods involve no bead co-stimulation or co-stimulation at a reduced level, compared to the T-Rapa method.

FIG. 24 illustrates that the new Rapa-T method generates T cells with a favorable pattern of Th1 polarization relative to T-Rapa cells, independent of whether the new Rapa-T method uses no bead co-stimulation or a low level of bead co-stimulation (1:3 ratio of beads-to-T cells). In FIG. 24, Rapa-T1 cells were generated by culture in IFN-α, temsirolimus, and basiliximab, as previously described, either without bead co-stimulation or with 1:3 bead-to-T cell co-stimulation; various control cultures were also evaluated, including the previous T-Rapa method (use of rapamycin and 3:1 bead-to-T cells). All cultures were at $9 \times 10^6$ cells/ml concentration, did not have bead co-stimulation, did not have IL-2 addition, had a delay in addition of IFN-α, included temsirolimus at a concentration of 1 μM and basiliximab at a concentration of 10 μM, and used X-Vivo 20 media supplemented with 5% AB serum, unless otherwise specified. Specific culture conditions as per the legend in the figure are as follows: condition 1, Rapa-T method, as above; condition 2, Rapa-T method without serum; condition 3, Rapa-T method without basiliximab; condition 4, Rapa-T method without basiliximab and with reduced temsirolimus (0.1 μM); condition 5, Rapa-T method without temsirolimus or basiliximab; condition 6, Rapa-T method using input T cells contaminated with a high frequency of monocytes (79% of input cells were monocytes, increased from all other cultures, which had ~10% monocyte contamination); condition 7, Rapa-T method using no monocyte contamination (<1%); condition 8, Rapa-T method using simultaneous addition of IFN-α (no overnight delay); condition 9, Rapa-T method with 1:3 bead co-stimulation; condition 10, control T cell condition (no inhibitors; 3:1 beads); and condition 11, old T-Rapa condition, rapamycin (1 μM), IL-2 addition at 20 IU/ml, 3:1 beads, no overnight pre-incubation. Cytokine secretion analysis (IL-2 and IFN-γ measurement) was performed at the end of culture, with results detailed at the end of T cell manufacturing (day 6) and after an additional 6 days in culture without inhibitors (day 12).

As detailed in FIG. 24, the CD4$^+$ and CD8$^+$ T cells manufactured according to the methods described in this disclosure have a pattern of Th1 cytokine polarization relative to T-Rapa cells, including in conditions where the methods involve no bead co-stimulation or co-stimulation at a reduced level, compared to the T-Rapa method.

As depicted in FIG. 24, Condition #1, the Rapa-T condition manufactured without beads, had a favorably high level of IL-2 secretion capacity, particularly at day 12 after T cell expansion in the absence of inhibitors. A similar pattern was observed in condition #2, which was performed in media that was not supplemented with serum, thereby indicating the ability to manufacture the Rapa-T cells with or without serum supplementation. The increased IL-2 secretion capacity, particularly in comparison to culture #11 (the old T-Rapa condition), indicates that the new Rapa-T manufacturing method generates T cells of a reduced differentiation precursor profile that can function in vivo in a helper-independent manner. Condition #1 was also advantageous in this regard relative to culture #9, which is the new Rapa-T condition manufactured with a 1:3 bead-to-T cell ratio of co-stimulation.

As depicted in FIG. 24, Condition #1, the Rapa-T condition manufactured without beads, was also preferable in terms of IFN-γ secretion at day 6 end of manufacturing, as the levels were near the lower limit of detection, thereby indicating that the Rapa-T cell product was in a state of quiescence. By comparison, condition #5, which did not contain inhibitors, had nearly 4000 pg/ml secretion of IFN-γ at day 6; similarly, the old T-Rapa condition had a high level of IFN-γ secretion at day 6, approximately 6000 pg/ml. Of note, the new Rapa-T condition that utilized a 1:3 bead-to-T cell co-stimulation was less quiescent than condition #1 without beads, as there was approximately 200 pg/ml of IFN-γ secretion at the end of manufacturing, day 6. Finally, the new Rapa-T manufacturing method (either condition #1 without beads or condition #9 with beads) had a favorable increase in IFN-γ secretion capacity at day 12 of culture after a 6-day culture interval in the absence of inhibitors.

In summation, the new Rapa-T method can result in the manufacture of T cells with the following phenotypic characteristics: (a) relative to input normal T cells, a reduction in expression of regulatory T cells markers such as the transcription factor, FOXP3; and an increase in the Th1-type transcription factor, TBET; (b) relative to the old T-Rapa method, an increased state of quiescence, as indicated in part by reduced expression of the IL-2 receptor CD25 and by reduced secretion of the inflammatory cytokines IFN-γ and TNF-α at the end of manufacturing; (c) relative to the old T-Rapa method, a reduction in the expression of p-STAT5 and reduced levels of the mTOR pathway molecules p-RAPTOR, p-4EBP1 and p70S6K; (d) relative to input normal T cells, an increase in markers of autophagy, including but not limited to changes in expression of the molecule p62; (e) relative to input normal T cells, an increase in flow cytometry markers of naïve or T central memory populations, including CD45RA, co-expression of CD62L/CCR7, concomitant expression of CD62L/CCR7/CD127; (f) relative to the old T-Rapa method, reduced expression of co-inhibitory molecules including but not limited to CTLA4; (g) relative to the old T-Rapa method, reduced expression of checkpoint inhibitory receptor expression, including but not limited to TIM3; and (h) relative to input normal T cells, an altered RNA expression pattern, including but not limited to an increase in markers of de-differentiation (including but not limited to Nanog, KLF4, and KLF10) and a reduction in markers of differentiation (including but not limited to perforin, granzyme B, IFN-γ).

The majority of the phenotype characterization of the T cell product manufactured according to the Rapa-T method detailed in this disclosure can be ascertained at the end of culture. However, it is important to note that the T cell product can be cryopreserved, and as such, phenotypic characterization of T cells in the post-thaw state reflect the actual product to be adoptively transferred to the subject. The Rapa-T cells in the post-thaw state can be characterized by the following: (a) maintenance of a state of quiescence, as indicated by low level expression of the IL-2 receptor CD25 that is comparable between day 6 end of manufacturing sample and the post-thaw sample; (b) relative to the day 6 end of manufacturing sample, the post-thaw sample will continue to have low level secretion of the inflammatory cytokines IFN-γ and TNF-α (not increased relative to the sample collected at the end of manufacturing); (c) relative to input normal T cells, the post-thaw sample will maintain an increase in flow cytometry markers of naïve or T central memory populations, including CD45RA, co-expression of CD62L/CCR7, concomitant expression of CD62L/CCR7/CD127; (f) the post-thaw sample will continue to have reduced expression of co-inhibitory molecules including but not limited to CTLA4 (no increase in the post-thaw sample relative to the sample collected at the end of manufacturing); (g) the post-thaw sample will continue to have reduced expression of checkpoint inhibitory receptor expression, including but not limited to TIM3 (no increase in the post-thaw sample relative to the sample collected at the end of manufacturing); and (h) relative to input normal T cells, an altered RNA expression pattern, including but not limited to an increase in markers of de-differentiation (including but not limited to Nanog, KLF4, and KLF10) and a reduction in markers of differentiation (including but not limited to perforin, granzyme B, IFN-γ).

Manufacturing from cryopreserved cell substrates. In the case of previously collected PBSC products, such cryopreserved cells will be stored in the vapor phase of liquid nitrogen until thawing of cells and manufacture of Rapa-T cells. In the case of freshly isolated cells by apheresis or in the future by simple blood collection, the cells will undergo immediate processing, and then may either be placed directly into culture or may be cryopreserved by controlled rate freezing technology and stored in the vapor phase of liquid nitrogen for subsequent use later.

T cell culture from cryopreserved cell substrates for from freshly isolated cell populations requires some type of T cell enrichment, for example, by use of monoclonal antibody and column technology (positive or negative selection). Enrichment of the raw cellular material used in Rapa-T manufacturing does not require such antibody-based methodologies because T cells are efficiently enriched during the culture interval; as such, our method is consistent with recommendations for effective cell therapy on a global level. The initial processing steps for manufacture of Rapa-T cells focuses on removal of di-methyl sulfoxide (DMSO) used in the cryo-preservation steps (when applicable), lysis of red blood cells (RBCs), and centrifugal removal of contaminating granulocytes and to some extent, monocytes. These steps are performed in a relatively automated method using primarily closed-system technology; this procedure is advantageous as it reduces human error, provides detailed manufacturing data for batch records, improves consistency across manufacturing runs, and reduces the risk for infectious agent contamination of the final product. Processing for the Rapa-T products can include the following steps: (1) thaw of cryo-preserved products (when applicable) using solid-state, non-water based methods to reduce infectious agent contamination; (2) automated washing of the cellular product using the LOVO permeable membrane device; (3) integration of lysis of RBCs using ammonium-chloride-potassium (ACK) buffer during the LOVO washing steps; (4) volume reduction of cellular content using the LOVO method with subsequent plating of cells into the closed-system, counter-flow, centrifugal elutriation (CCE) device (Elutra; Terumo); and (5) pre-programmed operation of the Elutra device for efficient removal of granulocytes and monocytes by CCE.

After this lymphocyte enrichment and media purification, the cells can be plated into specialized chambers that possess an enriched capacity for oxygen exchange (G-Rex vessels; Wilson-Wolf). In addition to having enhanced gas permeability characteristics, the G-Rex vessels are closed system units and have the additional advantage of automated, closed system media volume reduction (GatheRex Liquid Handling Pump). The lymphocyte-enriched cells can be maintained in the G-Rex vessels for 6-days.

Several specific culture conditions can be utilized to promote the manufacture of a mixture of CD4$^+$ and CD8$^+$ T cells in the G-Rex vessels with functional attributes of a manufactured T cell. These specific conditions include: (1) use of enriched media (including but not limited to X-Vivo 20; Lonza) that is further supplemented with 5% human serum, or in some embodiments, no addition of serum; (2)

incorporation of a 16-hour rest interval of cell plating into the G-Rex prior to co-stimulation (cells are plated at a relatively high density of $1.5 \times 10^6$ T cells per ml); (3) during this initial rest interval, cells are optimally rested by addition of the monoclonal antibody basiliximab (which blocks the IL-2 receptor and thereby prevents autonomous T cell activation by endogenously produced IL-2) and temsirolimus (which is a pharmacologic inhibitor of mTORC1); (4) after this 16-hour rest interval, cells are co-stimulated with anti-CD3/anti-CD28 coated magnetic beads (3/28 beads) under sub-optimal conditions, as defined by a bead-to-T cell ratio of 1:3 (typically, most T cell expansion conditions utilize a 9-fold higher level of co-stimulation, a 3:1 bead-to-T cell ratio; in some cases, it is beneficial to avoid adding any co-stimulation reagent); (5) importantly, it is essential that the T cells are not washed after the initial rest interval; (6) after the rest interval, in addition to addition of 3/28 beads, it is essential to add the polarizing cytokine IFN-α at a high dose (10,000 IU/ml) to promote differentiation to CD4$^+$ Th1 and CD8$^+$ Tc1 phenotypes; (7) importantly, it is critical to avoid the addition of IL-2, which is a common additive to T cell cultures; and (8) after addition of the beads and IFN-α, it is important to leave the cells undisturbed until harvesting at day 6 of culture (no cell washing, no further culture additives).

Cryopreservation of Manufactured T Cells. 1) After the 6-day cell culture in the G-Rex vessels, the volume of the culture can be reduced in a closed system manner by the GatheRex instrument. Subsequently, the cells can be harvested, 3/28 beads can be removed by hand-held magnet, and cells can be placed into the LOVO device for serial washing of the cells to remove >99% of culture additives (Temsirolimus, Basiliximab, IFN-α).

Washed cells can be reconstituted into cryopreservation media, which contains 5% DMSO and 5% pentastarch. The cryopreservation is performed in multiple single use aliquots in 50 ml freezer bags. Rapa-T cells are cryopreserved by GMP-compliant controlled rate freezing methodology and shipped in the vapor phase of liquid nitrogen by certified cryo-shipper after the Rapa-T cells have passed the specified release criteria testing.

Release criteria testing of the Rapa-T cells includes standard tests such as content of CD3$^+$, CD4$^+$ and CD8$^+$ T cell purity (final product can be >70% CD3$^+$ T cell content by flow cytometry; CD4$^+$ and CD8$^+$ subsets can each be present at the 5% level). Cells can be >70% viable, as determined by flow cytometry annexin and 7-AAD assays. Furthermore, cells should be free of bacterial and fungal contamination upon a minimum of a 7-day culture interval (ideally, a 14-day culture interval); furthermore, the cell product should be below detection limit for bacterial LPS endotoxin and *Mycoplasma*.

In addition to these standard tests, specialized functional tests can constitute release criteria for the Rapa-T cell products. Prior to release of product and cell therapy, a Rapa-T cell can possess the following attributes relative to culture input T cells: (1) an enhanced T central memory phenotype, as defined by increased flow cytometric co-expression of CD62 ligand and CCR7; (2) low level expression of checkpoint inhibitory molecules, such as programmed death-1 (PD1); (3) a resting state, as defined by reduced levels of Th1/Tc1-type cytokine secretion upon maximal co-stimulation; (4) an autophagy signature, as evidenced by reduced mitochondrial mass by flow cytometry MitoTracker assay; (5) a resistant phenotype, as evidenced by at least 50% inhibition of mTORC1 and mTORC2 downstream targets; and (6) a multi-faceted differential gene expression profile of n=80 key transcription factor and differentiation molecules.

Example 2

Figures 25A, 25B:
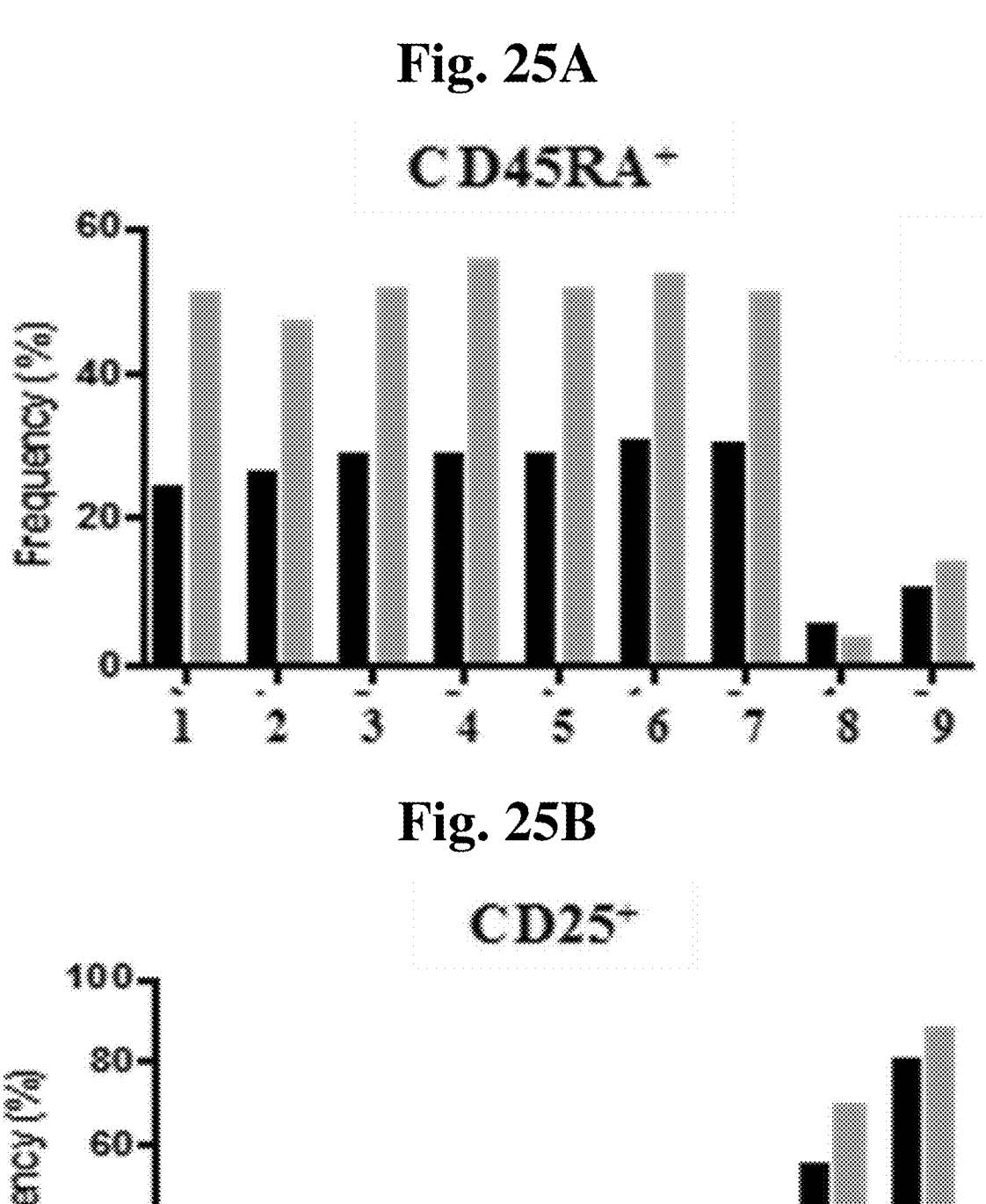
FIG. 25A depicts flow cytometry data measurements for CD45RA+ for T cells under various culture conditions.
FIG. 25B depicts flow cytometry data measurements for CD25+ for T cells under various culture conditions.
Figure 25C:
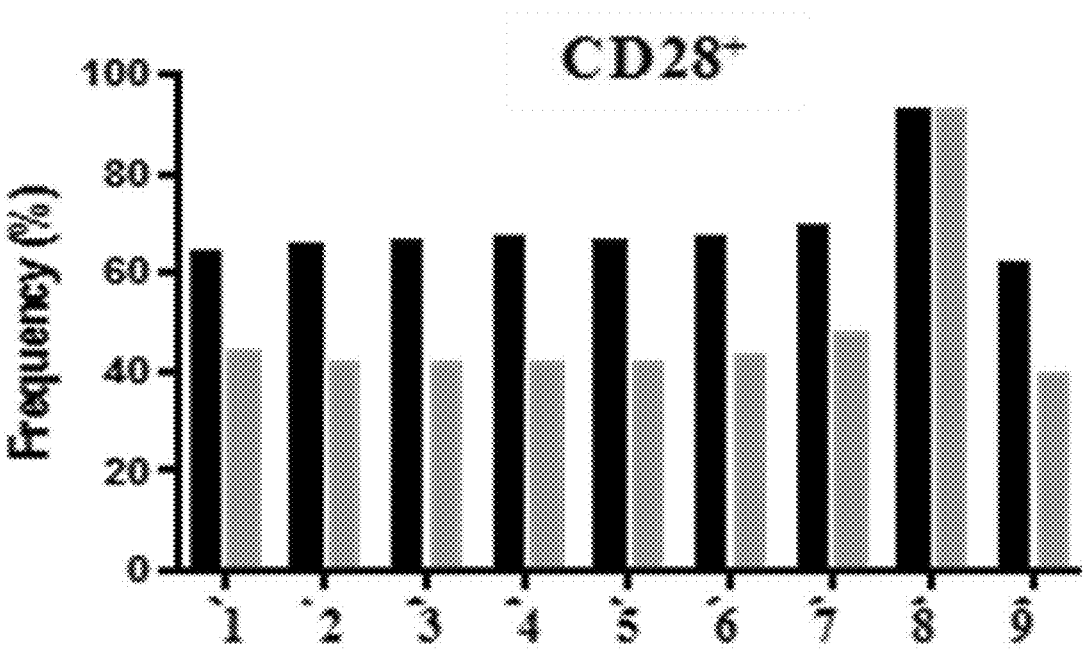
FIG. 25C depicts flow cytometry data measurements for CD28+ for T cells under various culture conditions.
Figure 25D:
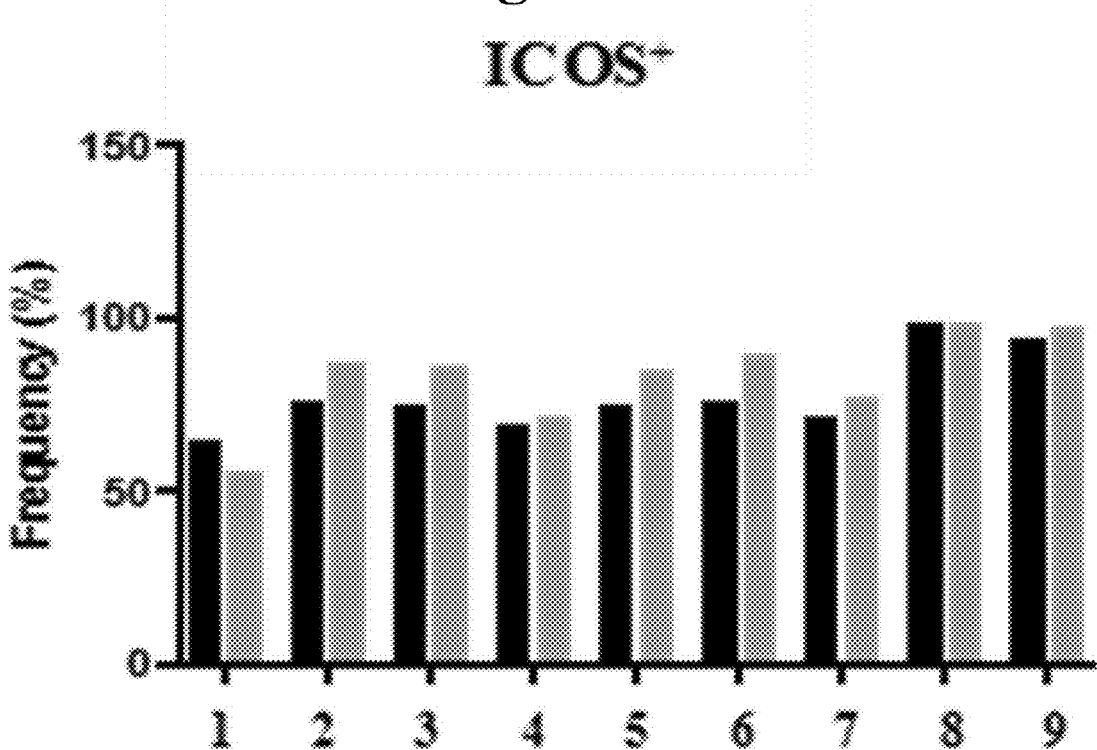
FIG. 25D depicts flow cytometry data measurements for ICOS+ for T cells under various culture conditions.
Figure 25E:
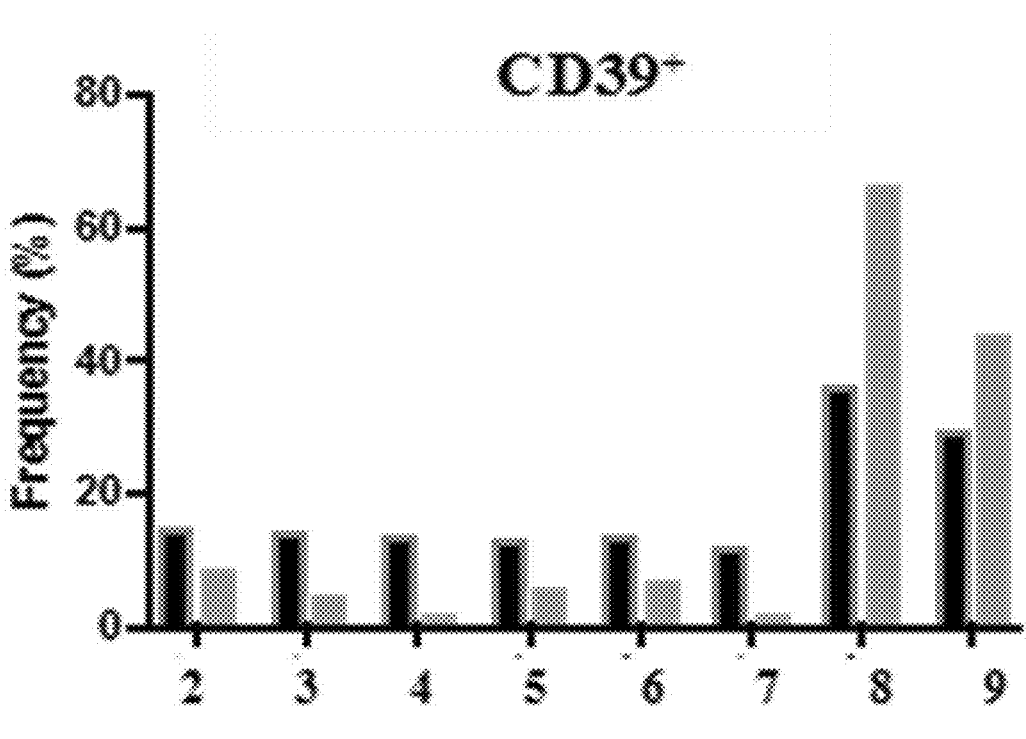
FIG. 25E depicts flow cytometry data measurements for CD39+ for T cells under various culture conditions.
Figure 25F:
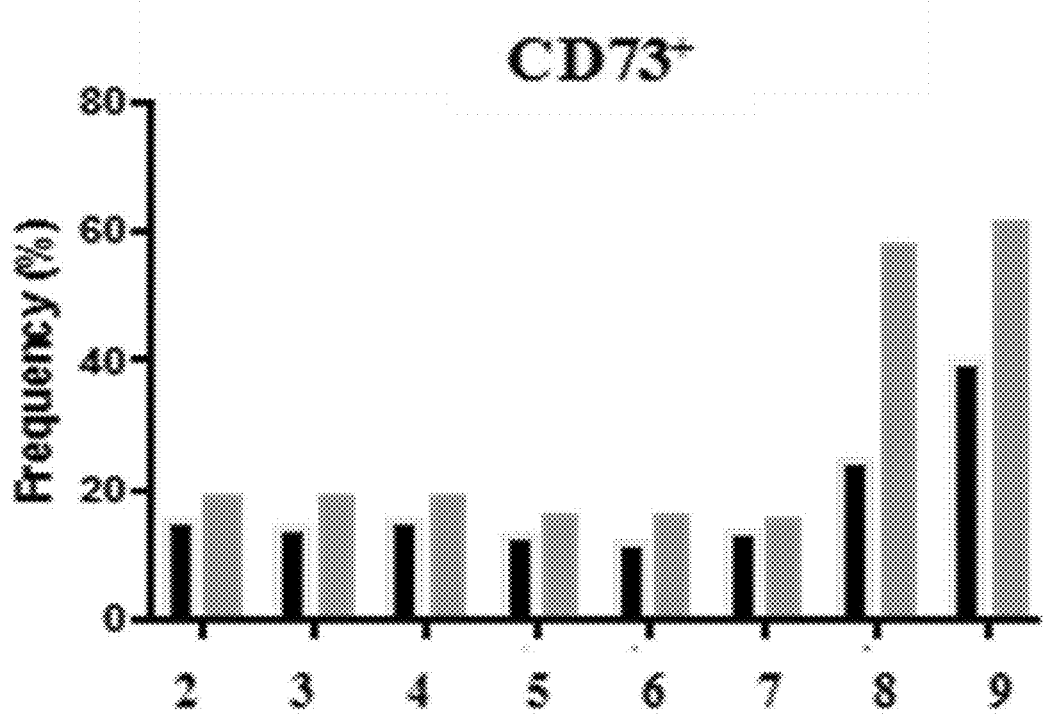
FIG. 25F depicts flow cytometry data measurements for CD73+ for T cells under various culture conditions.
Figure 25K:
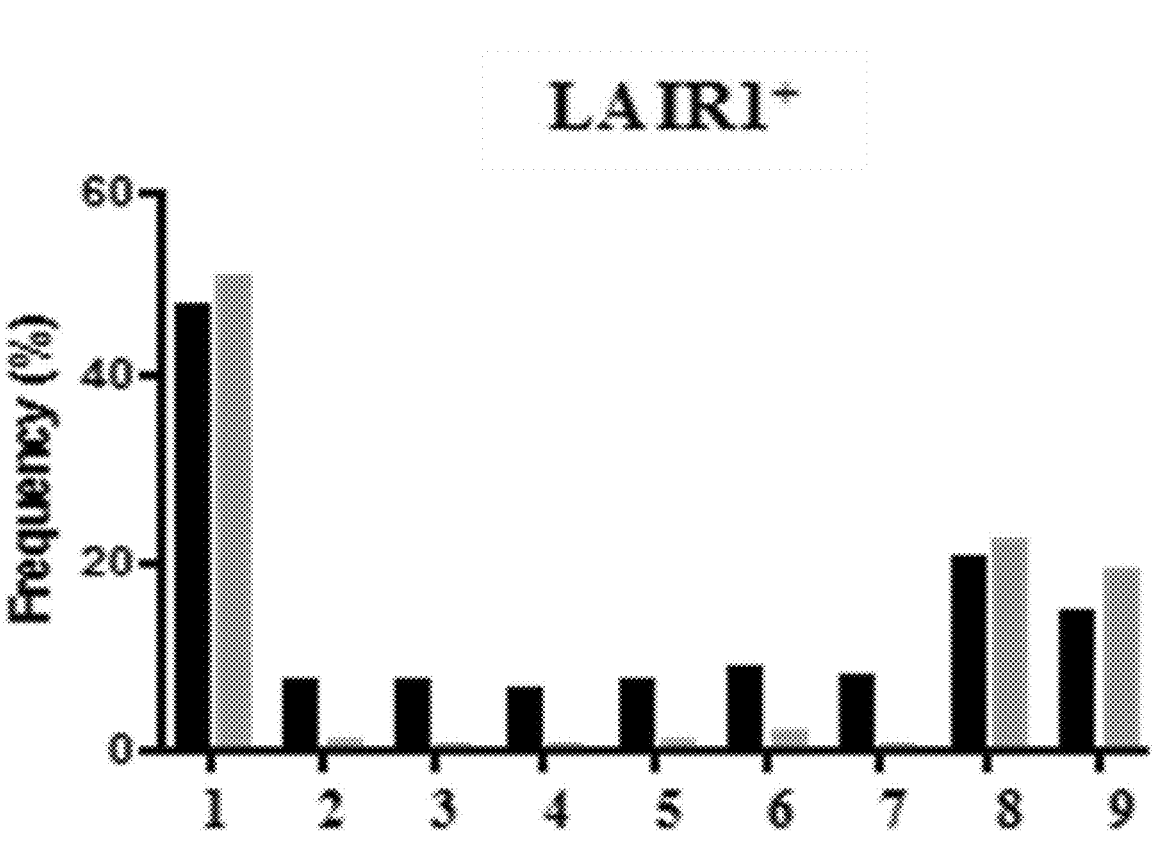
FIG. 25K depicts flow cytometry data measurements for LAIR1+ for T cells under various culture conditions.
Figure 25L:
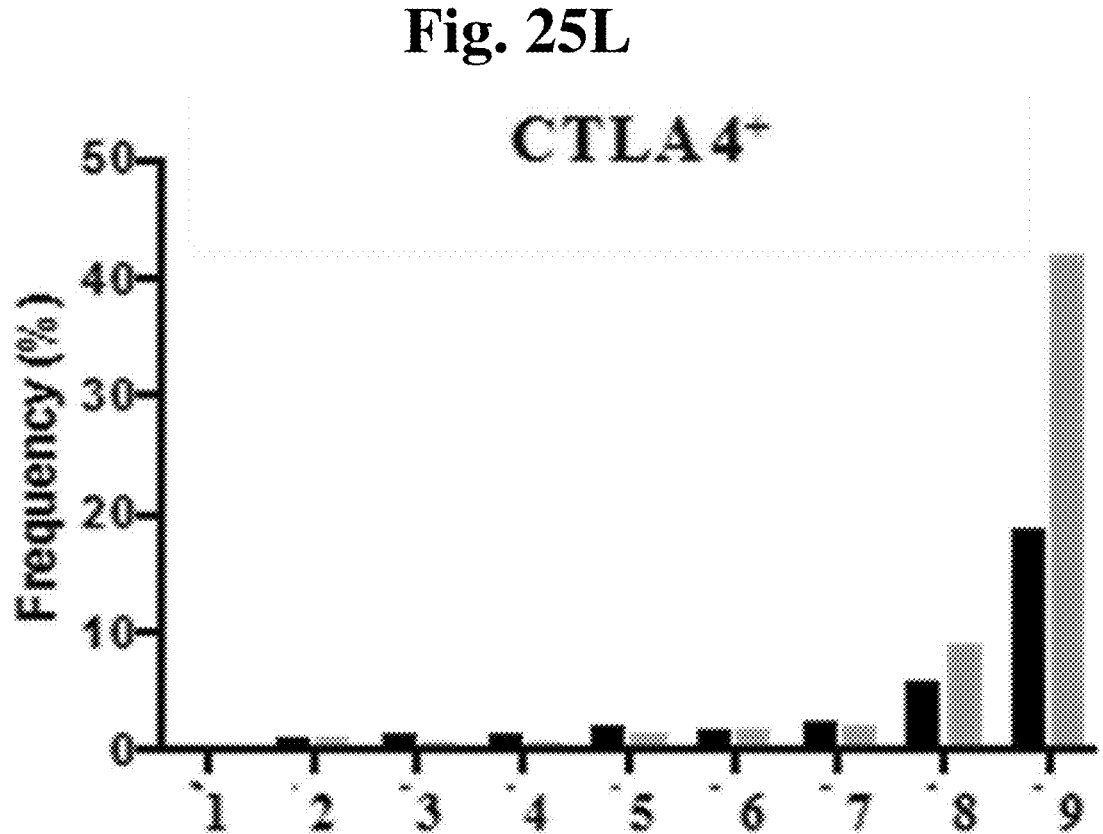
FIG. 25L depicts flow cytometry data measurements for CTLA4+ for T cells under various culture conditions.
Figure 25M:
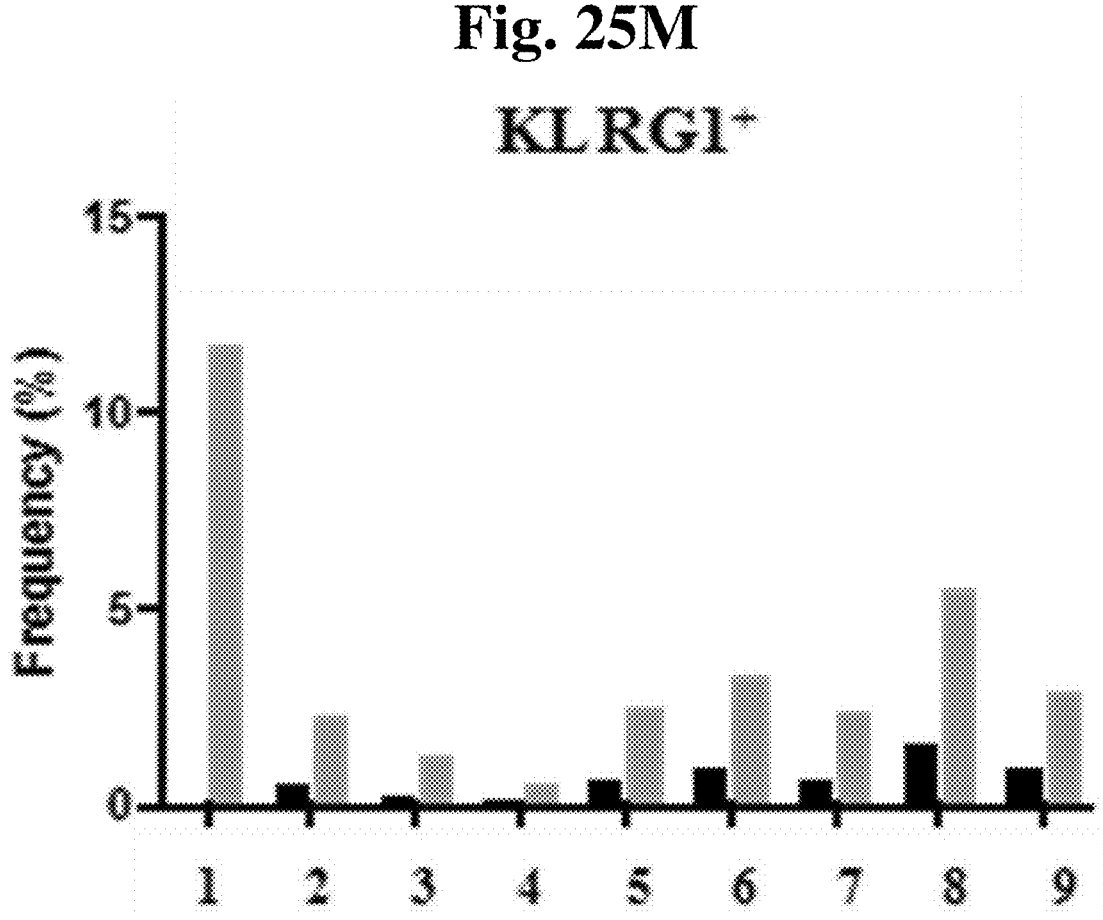
FIG. 25M depicts flow cytometry data measurements for KLRG1+ for T cells under various culture conditions.
Figure 25N:
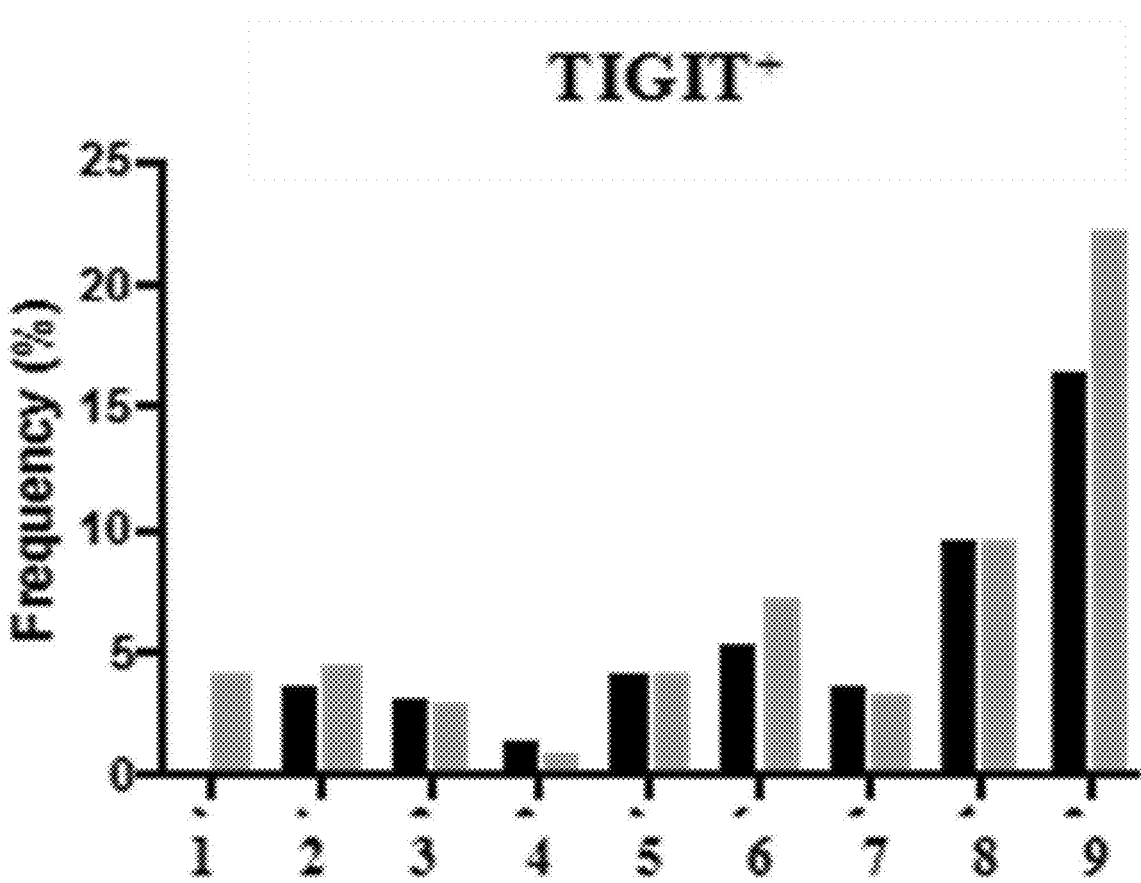
FIG. 25N depicts flow cytometry data measurements for TIGIT+ for T cells under various culture conditions.
Figure 25O:
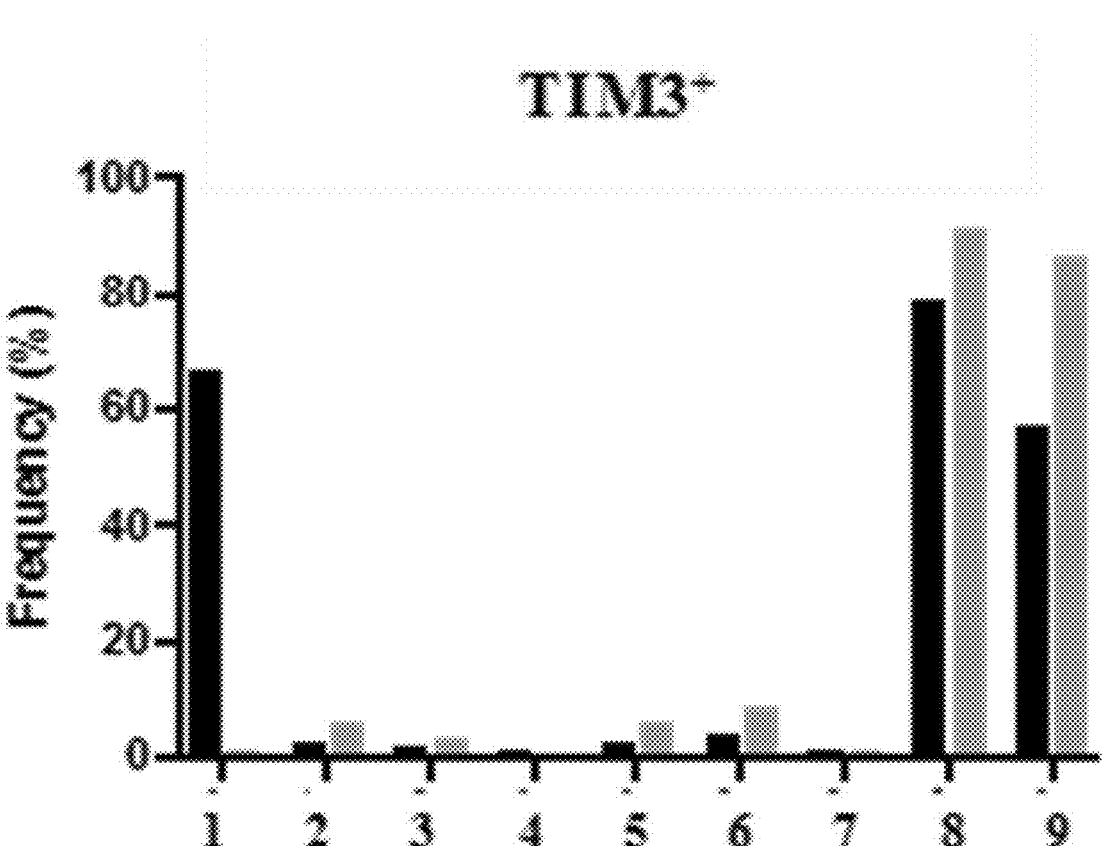
FIG. 25O depicts flow cytometry data measurements for TIM3+ for T cells under various culture conditions.

Steady-state apheresis was performed to obtain patient samples containing PBMCs. Lymphocytes in the samples were enriched by using an automated Ficoll procedure on a Sepax® instrument by GE by >95% elimination of the undesirable contaminating neutrophil population. The lymphocyte-enriched cell populations were then plated in G-REX culture vessels at the initial cell densities in the culture media and serum supplementation conditions indicated in Table 1 below and incubated in culture for 6 days. Condition 1 represents the pre-culture control (enriched lymphocytes after Sepax® automated Ficoll). Cultures were also initiated with variable inhibitor conditions by addition of temsirolimus, sirolimus and/or the anti-IL2 receptor monoclonal antibody basiliximab at the doses indicated in Table 1. Basiliximab was added at 10 µg/mL for Conditions 2-5 and 20 µg/mL for Conditions 6-8. Some culture conditions received anti-CD3, anti-CD28 co-stimulation using Dynal® 3/28 beads at bead:T cell ratios of 0.88:1 (Conditions 2-3 and 5-6) or 3:1 (Conditions 8-9). Cytokines were added at the indicated times, which consisted of either IFN-α alone (10,000 IU/mL) or IFN-α (10,000 IU/mL) in combination with IL-2 (20 IU/mL). Cytokine addition was either at culture initiation (Conditions 8-9) or at one day after culture initiation (Conditions 2-7). Cultures 3-4 and 6-7 received additional media two days after culture initiation to dilute them to the final cell densities indicated.

ecule expression within the CD4+(indicated in black columns) and CD8+(indicated in gray columns) T cell subsets as shown in FIGS. 25A-25O.

FIG. 25A (CD45RA+) demonstrates the importance of the RAPA-T culture conditions with regard to maintaining the naïve T cell marker expression on both CD4+ and CD8+ T cells relative to culture input cells; in marked contrast, the previous T-RAPA condition resulted in a marked reduction in CD45RA+ cells.

FIG. 25B (CD25+) demonstrates the importance of the RAPA-T culture conditions with respect to maintaining T cell quiescence in both CD4+ and CD8+ T cells relative to culture input cells; in marked contrast, the previous T-RAPA condition resulted in a markedly activated T cell state, as indicated by increased CD25 expression.

FIG. 25C (CD28+) and FIG. 25D (ICOS+) show that the RAPA-T and T-RAPA cell products had similar CD4+ and CD8+ T cell expression of these activating co-stimulatory molecules.

FIGS. 25E-25F (CD39+ and CD73+, respectively) show that the RAPA-T culture condition resulted in reduced expression of these ecto-nucleotidase molecules relative to the T-RAPA condition. These molecules exert an immune suppressive effect via metabolizing ATP into adenosine. Thus, the RAPA-T cell product is expected to be advantageous relative to the T-RAPA cell product in terms of therapeutic use.

The remaining data in FIGS. 25G-25O indicate that the new RAPA-T method results in greatly reduced expression of molecules associated with immune senescence (KLRG1),

TABLE 1

| | | | Culture Conditions | | | | | |
|---|---|---|---|---|---|---|---|---|
| Condition # | Media | Serum (AB) | Initial Cell Density (M/mL) | TEM (µM) | Anti-IL2R | Co-stim. | Cytokine Addition | Final Cell Density (M/mL) |
| 1 | N/A | N/A | N/A | N/A | N/A | N/A | N/A | N/A |
| 2 | TM | No | 4.5 | 3 | Yes | Yes | IFN-α | 4.5 |
| 3 | TM | No | 15 | 3 | Yes | Yes | IFN-α | 4.5 |
| 4 | TM | No | 15 | 3 | Yes | No | IFN-α | 4.5 |
| 5 | TM | No | 9 | 4.5 | Yes | Yes | IFN-α | 9 |
| 6 | TM | No | 30 | 4.5 | Yes | Yes | IFN-α | 9 |
| 7 | TM | No | 30 | 4.5 | Yes | No | IFN-α | 9 |
| 8 | XV | 5% AB | 1.5 | None | No | Yes | IL-2 + IFN-α | 1.5 |
| 9 | XV | 5% AB | 1.5 | RAPA | No | Yes | IL-2 + IFN-α | 1.5 |

M/mL = millions of cells per milliliter;
TEM = temsirolimus;
RAPA = sirolimus oral solution at 1 µM;
TM = TexMACS ® (Miltenyi ®);
XV = X-Vivo 20 ® (Lonza ®).
TexMACS is a proprietary media formulation.

Condition 9 represents the T-Rapa product. It was found that Condition 7 provided the optimal RAPA-T condition of those tested in Table 1. This condition had several key attributes: (1) serum-free media; (2) very high initial cell density (30 M/mL); (3) very high temsirolimus concentration (4.5 µM); (4) presence of anti-IL2 receptor monoclonal antibody; (5) absence of co-stimulation; (6) cytokine support with only IFN-α (no IL-2) added one day after culture initiation; and (7) cell dilution on day 2 of culture.

After 6 days in culture, the resultant T cells were harvested and evaluated by flow cytometry for specific mol-associated with an immune suppressive regulatory T cell phenotype (GITR), or associated with checkpoint inhibitory function (LAG3, PD1, 2B4, LAIR1, CTLA4, TIGIT, and TIM3). Each of the variable culture conditions linked to the RAPA-T cell product were greatly reduced in each of these molecules relative to the T-RAPA cell products. Condition 7 demonstrated the most profound and consistent reduction in these molecules of the conditions tested.

Example 3

T cells were prepared as in Example 2 with Culture Conditions 1-8 corresponding to Culture Conditions 2-9 of Example 2. At day 2 of the culture interval, the resultant T cells were harvested and evaluated by Western Blot Analysis (methods as per manufacturer's instruction; BioTechne Mr. Wes instrumentation) for molecules relevant to mTORC1, mTORC2, and STAT pathways.

Figure 26:
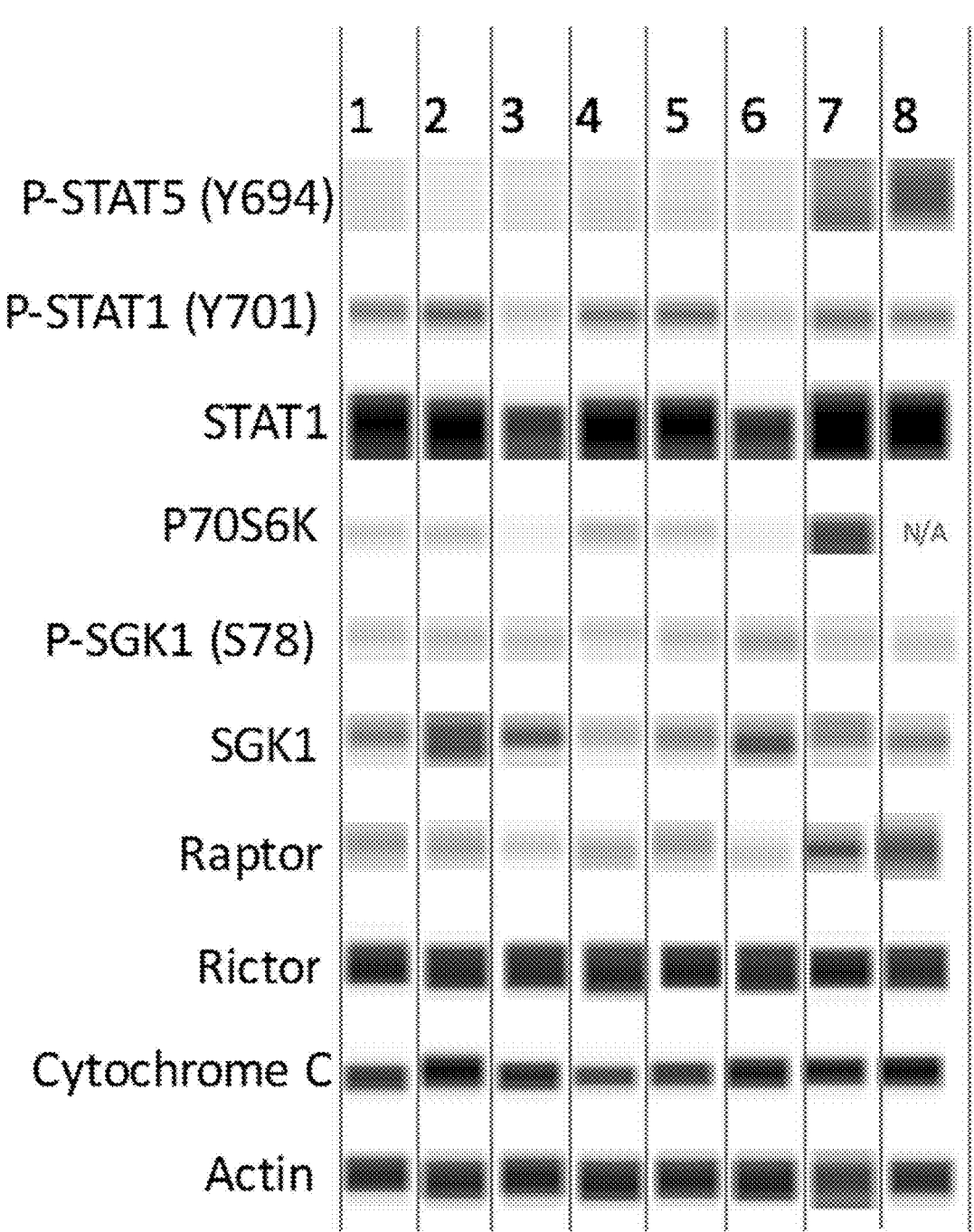
FIG. 26 depicts Western Blot results for p-STAT5, p-STAT1, STAT1, p70S6K, p-SGK1, SGK1, Raptor, Rictor, Cytochrome C and actin for cells under various culture conditions.

For optimal Th1/Tc1-type manufacturing, it is important to limit activation (phosphorylation) of STAT5, which can drive the regulatory T cell phenotype. As shown in FIG. 26, each of the Rapa-T cell culture conditions (Conditions 1-6) were relatively devoid of phosphorylated STAT5; in marked contrast, the T-Rapa conditions showed a significant presence of phosphorylated STAT5 (Conditions 7-8). The reduction of STAT5 phosphorylation of the Rapa-T cells relative to the T-Rapa cells can be more than 75%.

For optimal Th1/Tc1-type manufacturing, it is important to have active signaling through specific STAT molecules that drive type I differentiation, including STAT1. As shown in FIG. 26, each of the Rapa-T culture conditions showed a detectable level of STAT1 phosphorylation, albeit the level was somewhat reduced in Condition 6 (Example 2, Condition 7). However, the level of total STAT1 was also reduced in Condition 6.

The optimal phenotype of Rapa-T cells can also be characterized by a reduction in molecules associated with the mTORC1 pathway. Rapa-T Condition 6 (corresponding to Example 2, Condition 7) was essentially devoid in expression of the mTORC1-associated molecule, p70S6K. Provision of co-stimulation in other Rapa-T culture conditions (Conditions 1, 2, 4 and 5) increased p70S6K expression. Thus, during the Rapa-T manufacturing process, it may be beneficial to avoid co-stimulation.

The optimal phenotype of the Th1/Tc1-type RAPA-T cell manufacturing can also be contingent on the preservation of the mTORC2 signaling pathway. In this regard, it is beneficial that the optimal RAPA-T cell condition (Condition 6, corresponding to Example 2, Condition 7) has preservation of expression of mTORC2-associated molecules total SGK1 and phosphorylated SGK1. This characteristic of the optimal RAPA-T cell product regarding marked reduction in mTORC1 with relative preservation of mTORC2 is further exemplified by Condition 6, namely, marked reduction in the mTORC1-associated subunit molecule Raptor and relative preservation of the mTORC2-associated subunit molecule Rictor.

Example 4

Steady-state apheresis was performed to obtain patient samples containing PBMCs. Lymphocytes in the samples were enriched by using an automated Ficoll procedure on a Sepax® instrument by GE. The lymphocyte-enriched cell populations were then plated in G-REX culture vessels under two conditions, one corresponding to Condition 7 in Table 1 and one corresponding to Condition 9 in Table 1 (T-RAPA) and incubated in culture for 6 days as in Example 2. After 6 days of culture, the T cells were harvested and re-plated at a concentration of 1×106 cells/mL for generation of a 24-hour supernatant. At the time of re-plating, the T cells were co-stimulated with anti-CD3/anti-CD28 coated magnetic beads at bead:T cell ratios of 3:1, 1:1, 1:3 or 1:9. At each of these ratios, the 24-hour supernatant generation was performed with no cytokine addition (indicated by "−" symbol), addition of rhuIL-2 (100 IU/mL, indicated by "+IL-2"), addition of rhuIL-7 (10 ng/mL, indicated by "+IL-7"), addition of rhuIL-15 (10 ng/mL, indicated by "+IL-15"), or addition of both rhuIL-7 (10 ng/mL) and rhuIL-15 (10 ng/mL) (indicated by "+IL-7+IL-15"). IL-2 and TNF-α secretion was measured in the cells by known methods according to the manufacturer's instructions (Luminex). Results are shown in FIGS. 27A-27B.

CD4+ and CD8+ T cells at early states of differentiation, such as the naïve, central-memory, or stem central memory subsets may be beneficial for adoptive transfer. Such early differentiation T cells have been functionally characterized in part by their differential response to the key homeostatic cytokines, namely IL-7 and IL-15. As such, the ability of a given T cell product to respond to IL-7 and IL-15 is a desirable characteristic.

Figure 27A:
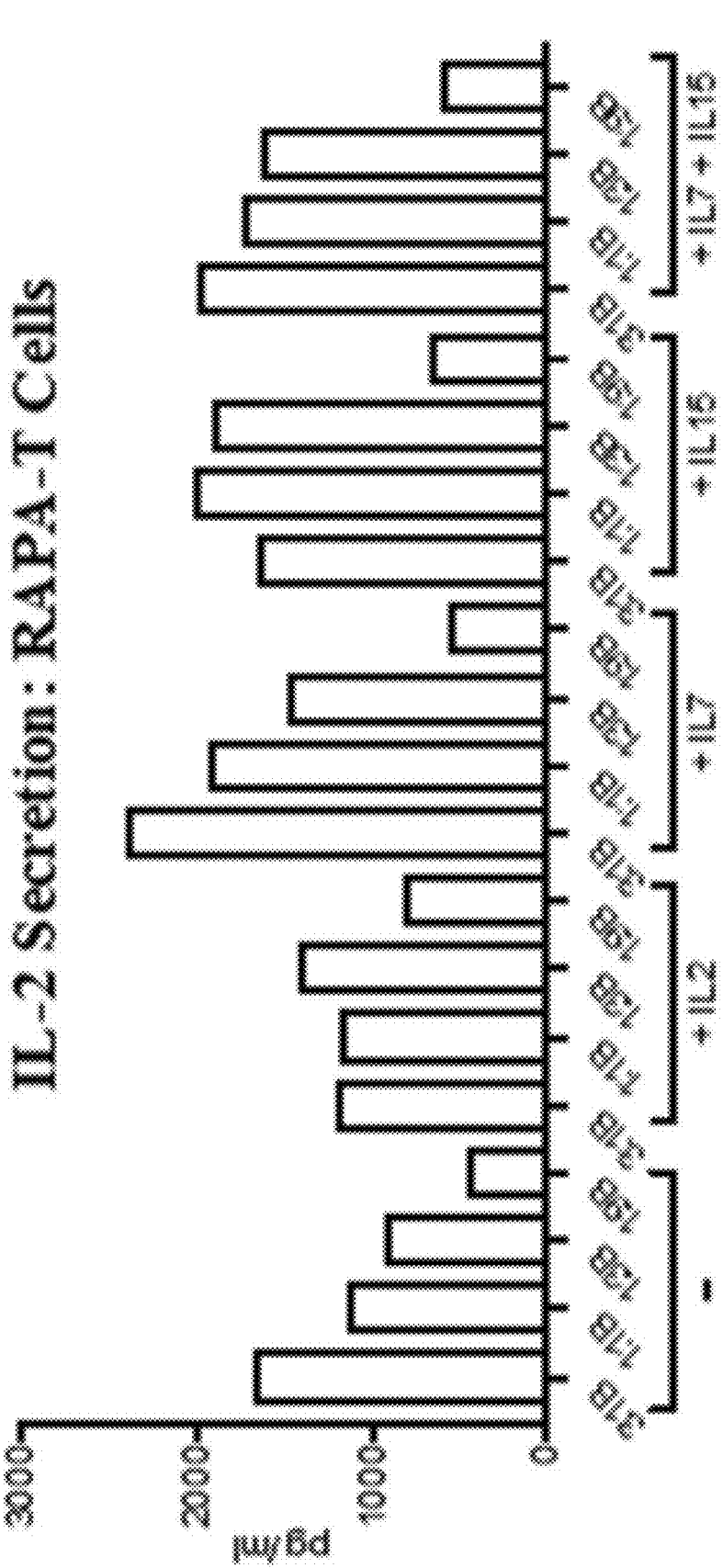
FIG. 27A depicts IL-2 secretion measurements for RAPA-T cells and T-RAPA cells from 24 hour supernatants after co-stimulation with anti-CD3/anti-CD28 coated magnetic beads and exposure to different cytokines.

FIG. 27A shows the IL-2 secretion profile of the optimal RAPA-T cell product whereas the lower panel shows the IL-2 secretion profile of the T-RAPA cell product. At maximal co-stimulation challenge and without exogenous cytokine support, the RAPA-T cell product secreted approximately a 5-fold higher amount of IL-2 relative to the T-RAPA cell product. Remarkably, even at very low levels of co-stimulation (1:9 bead:T cell ratio), the RAPA-T cell product secrets substantial IL-2; in marked contrast, this stimulation condition in the T-RAPA condition yielded undetectable levels of IL-2. IL-2 secretion capacity has been associated with the beneficial helper-independent T cell phenotype, which is a cytokine secretion characteristic observed in T cells at early states of differentiation. Finally, in the RAPA-T condition but not in the T-RAPA condition, addition of either IL-7 or IL-15 further augmented IL-2 secretion capacity. As such, the RAPA-T cells are uniquely responsive to the homeostatic cytokines IL-7 and IL-15.

Figure 27B:
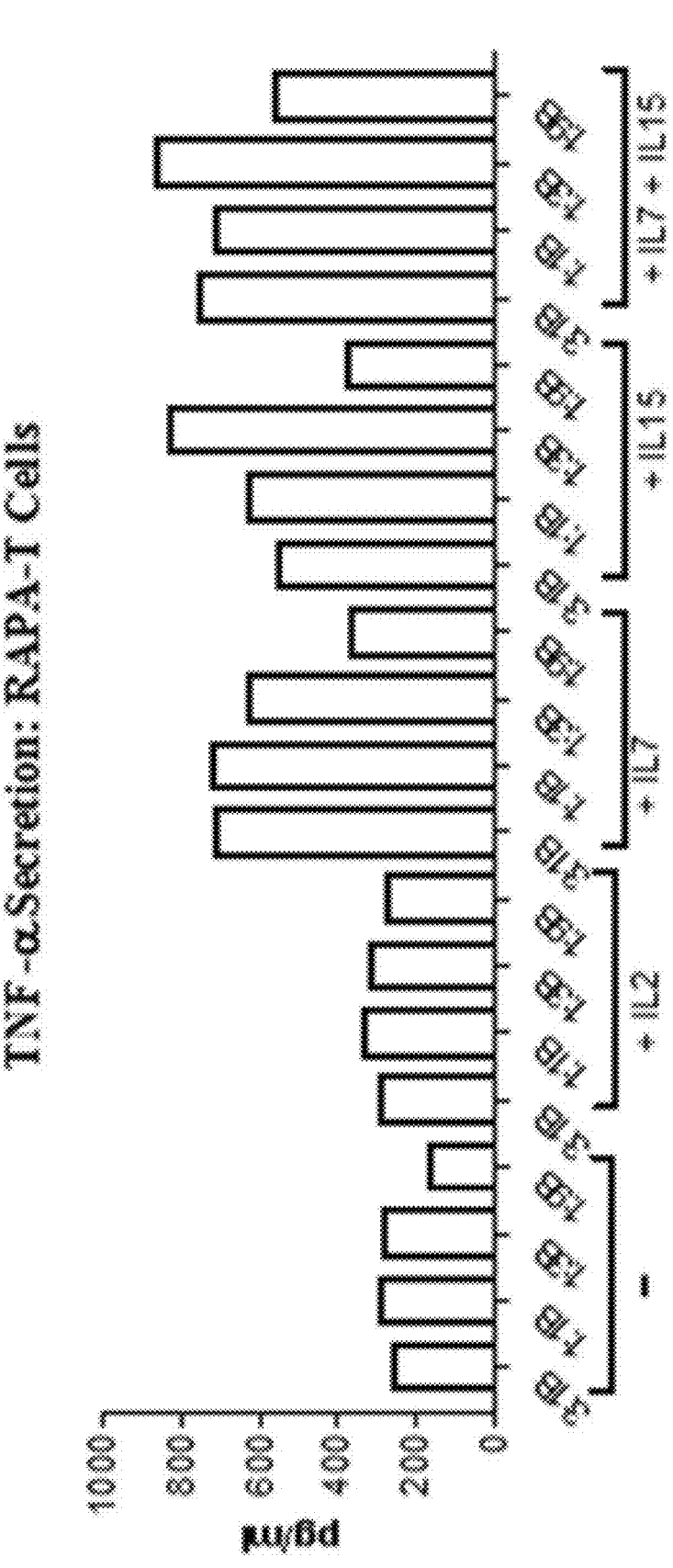
FIG. 27B depicts TNF-α secretion measurements for RAPA-T cells and T-RAPA cells from 24 hour supernatants after co-stimulation with anti-CD3/anti-CD28 coated magnetic beads and exposure to different cytokines.
Figure 27B:
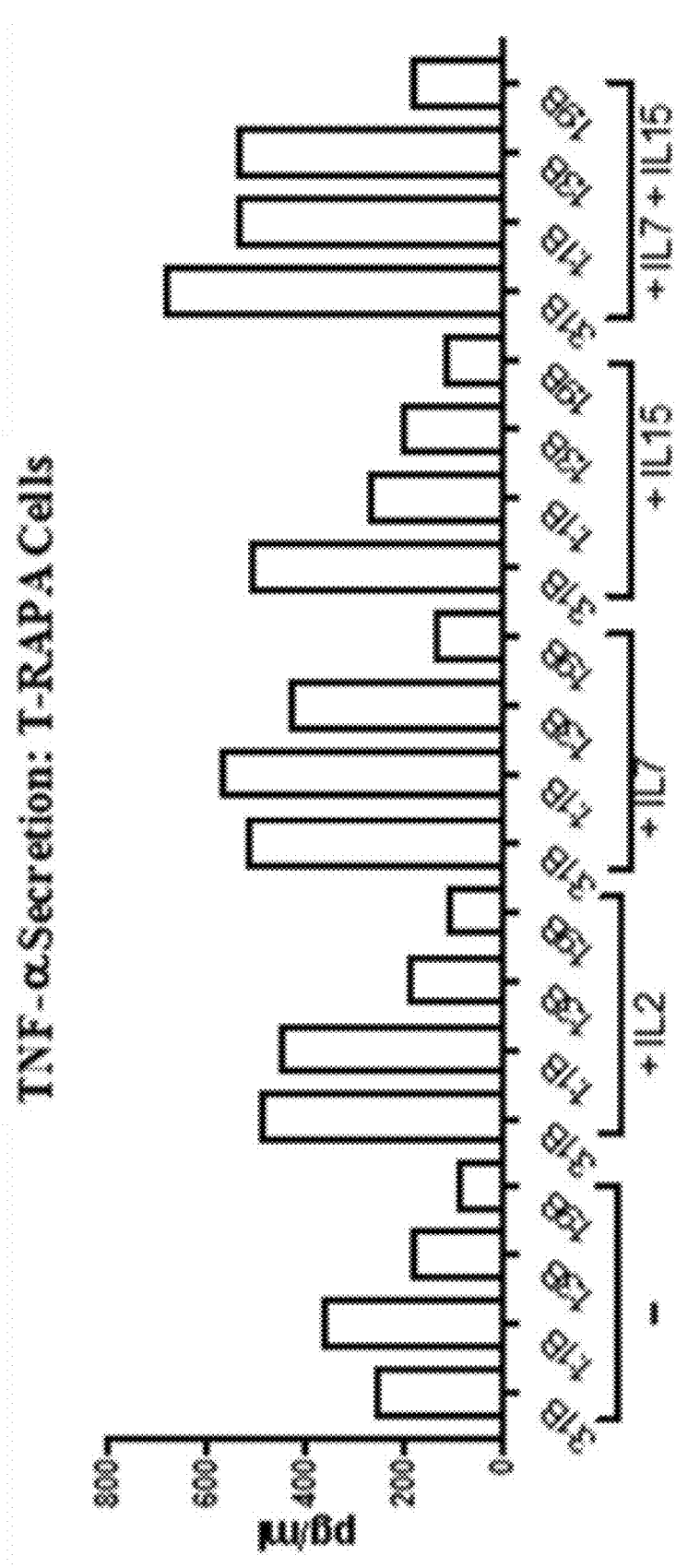

FIG. 27B shows the TNF-α secretion profile of the optimal RAPA-T cell product whereas the lower panel shows the TNF-α secretion profile of the previous T-RAPA cell product. At maximal co-stimulation challenge and without exogenous cytokine support, the RAPA-T cell product secreted approximately equivalent TNF-α relative to the T-RAPA cell product. However, addition of IL-7 or IL-15 to the co-stimulation resulted in a higher capacity to secrete TNF-α in the RAPA-T condition relative to the T-RAPA condition. As such, the RAPA-T cells are uniquely responsive to the homeostatic cytokines IL-7 and IL-15 in terms of inducing secretion of the Th1/Tc1 effector cytokine TNF-α.

Example 5

Human T cells were co-stimulated without any inhibitors ("Conventional"; addition of anti-CD23/anti-CD28 beads; 3:1 bead:T cell ratio). Alternatively, T cells were co-stimulated according to the RAPA-T cell conditions ("Rapamycin-Treated"), with the co-stimulation provided either by anti-CD3/anti-CD28 beads ("Dynabeads"; 1:3 bead:T cell ratio) or by Cloudz® dissolvable co-stimulation microparticles (Biot-Techne; use of Cloudz® at 20% of manufacturer's recommended dose; 50 μL of Cloudz® stock per 1×10⁶ cells). After a 6-day culture, the T cells were harvested, adjusted to 1×10⁶ cells/mL, and co-stimulated using anti-CD3/anti-CD28 beads (3:1 bead:T cells ratio). The 24-hour supernatants were then collected and tested for the content of IL-2, TNF-α, and IL-13 by Luminex assay (results shown as pg/mL per 1×10⁶ cells per 24 hours). Using the same protocol, the cells after 6-day culture were harvested and evaluated for flow cytometry for expression of cell surface markers, including CD4, CD8, CD25 and CTLA4.

Figure 28:
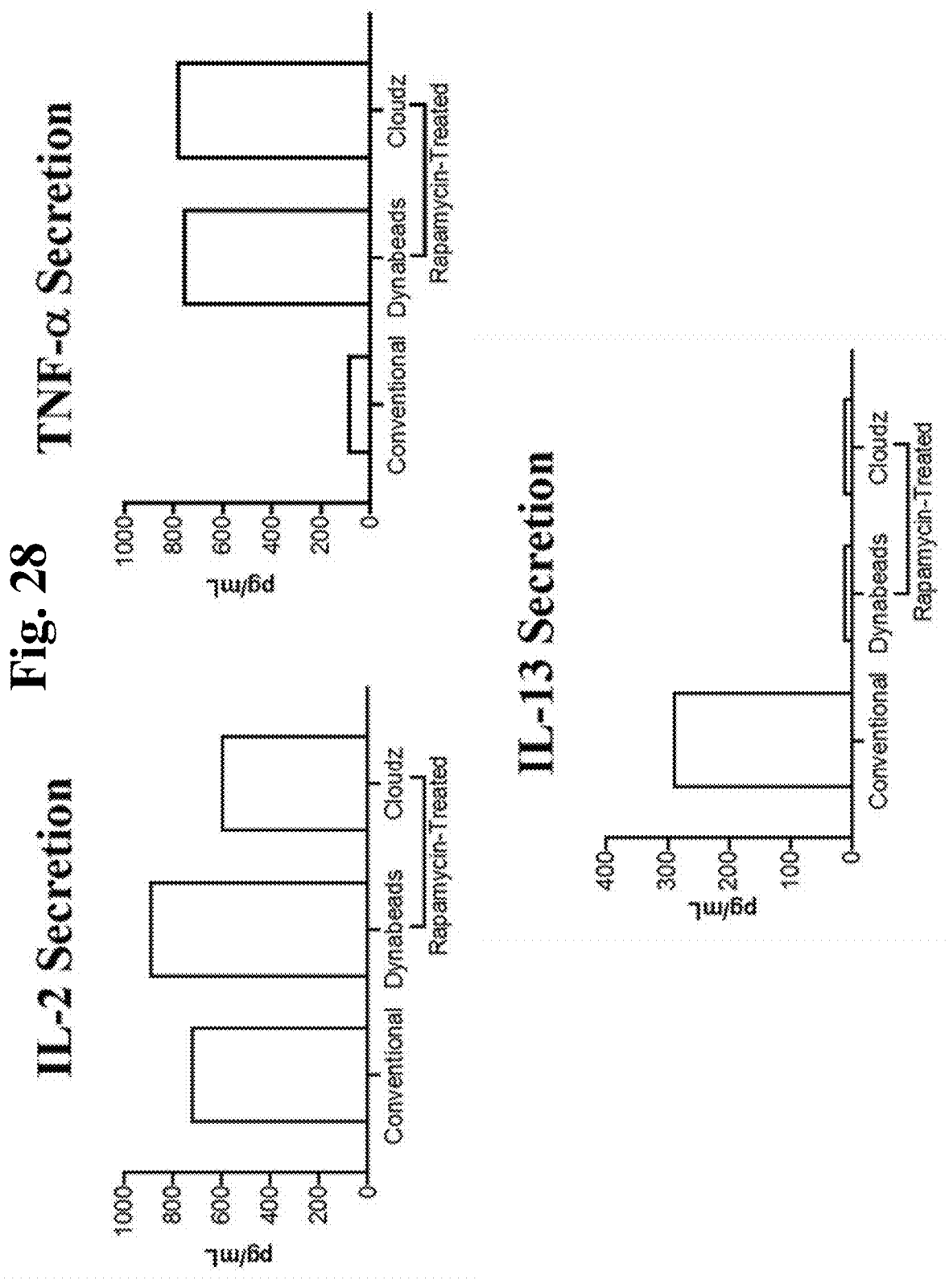
FIG. 28 depicts IL-2, TNF-α and IL-13 secretion measurements for RAPA-T cells after co-stimulation with anti-CD3/anti-CD28 coated beads or dissolvable anti-CD3/anti-CD28 microparticles.

FIG. 28 shows the IL-2, TNF-α and IL-13 secretion data. As shown in FIG. 28, the results between RAPA-T cells co-stimulated by anti-CD3/anti-CD28 nanoparticles ("Dynabeads") and dissolvable anti-CD3/anti-CD28 microparticles (Cloudz® reagent; Bio-Techne) are similar. These cells, as previously described, possess a Th1-type cytokine profile, as evidence by substantial secretion of IL-2 and TNF-α with minimal secretion of the Th2-type cytokine IL-13.

Figure 29:
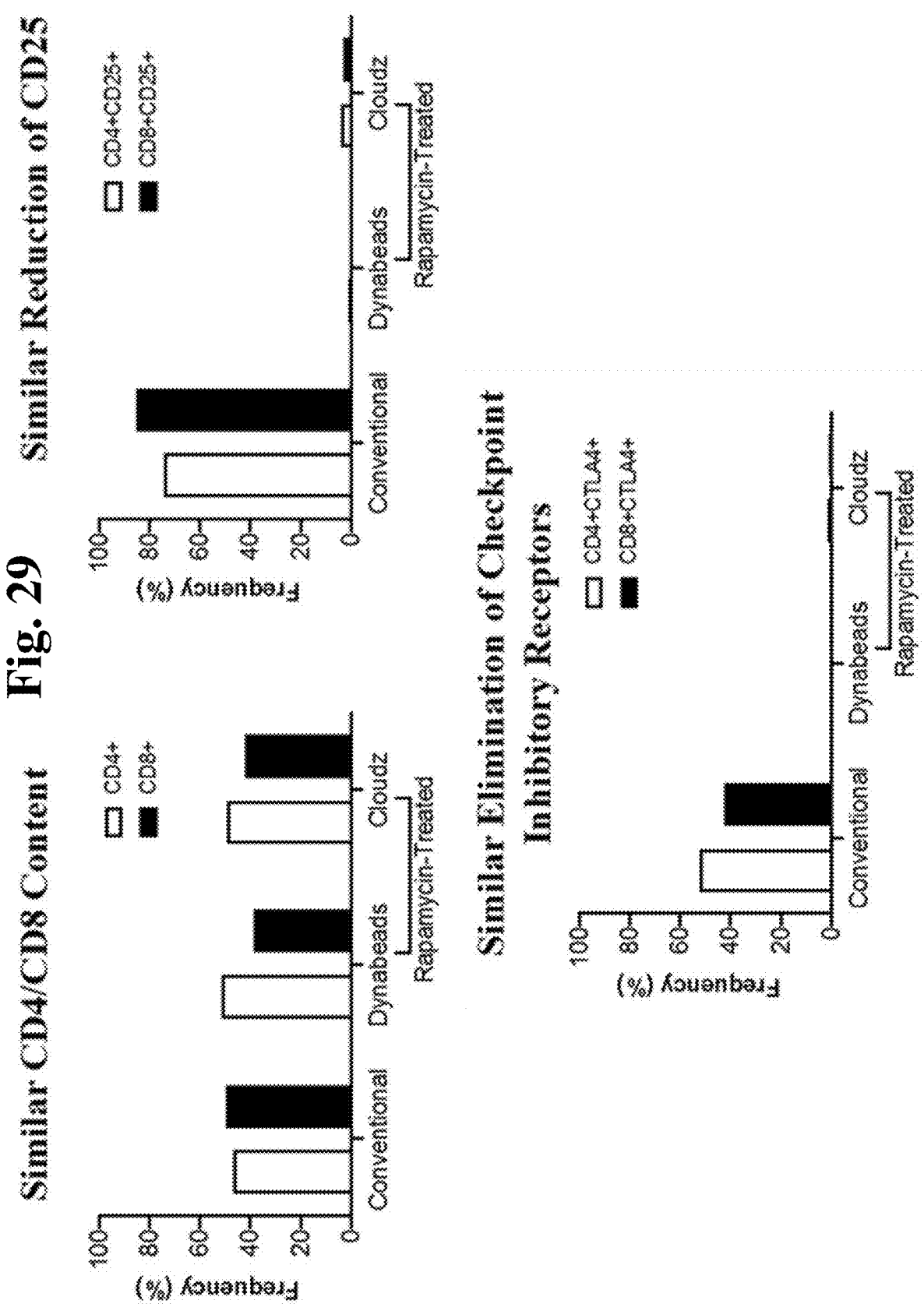
FIG. 29 depicts CD4, CD8, CD25 and CTLA4 expression as measured by flow cytometry for RAPA-T cells after co-stimulation with anti-CD3/anti-CD28 coated beads or dissolvable anti-CD3/anti-CD28 microparticles.

FIG. 29 shows the frequency of cells expressing the cell surface markers, CD4, CD8, CD25 and CTLA4 as measured by flow cytometry. As shown in FIG. 29, the results between RAPA-T cells co-stimulated by anti-CD3/anti-CD28 nanoparticles ("Dynabeads") and dissolvable anti-CD3/anti-CD28 microparticles (Cloudz® reagent; Bio-Techne) are similar. These cells, as previously described, are quiescent (as indicated by reduced expression of CD25) and have reduced expression of checkpoint inhibitory receptors (as indicated by reduced expression of CTLA4)

Figure 30:
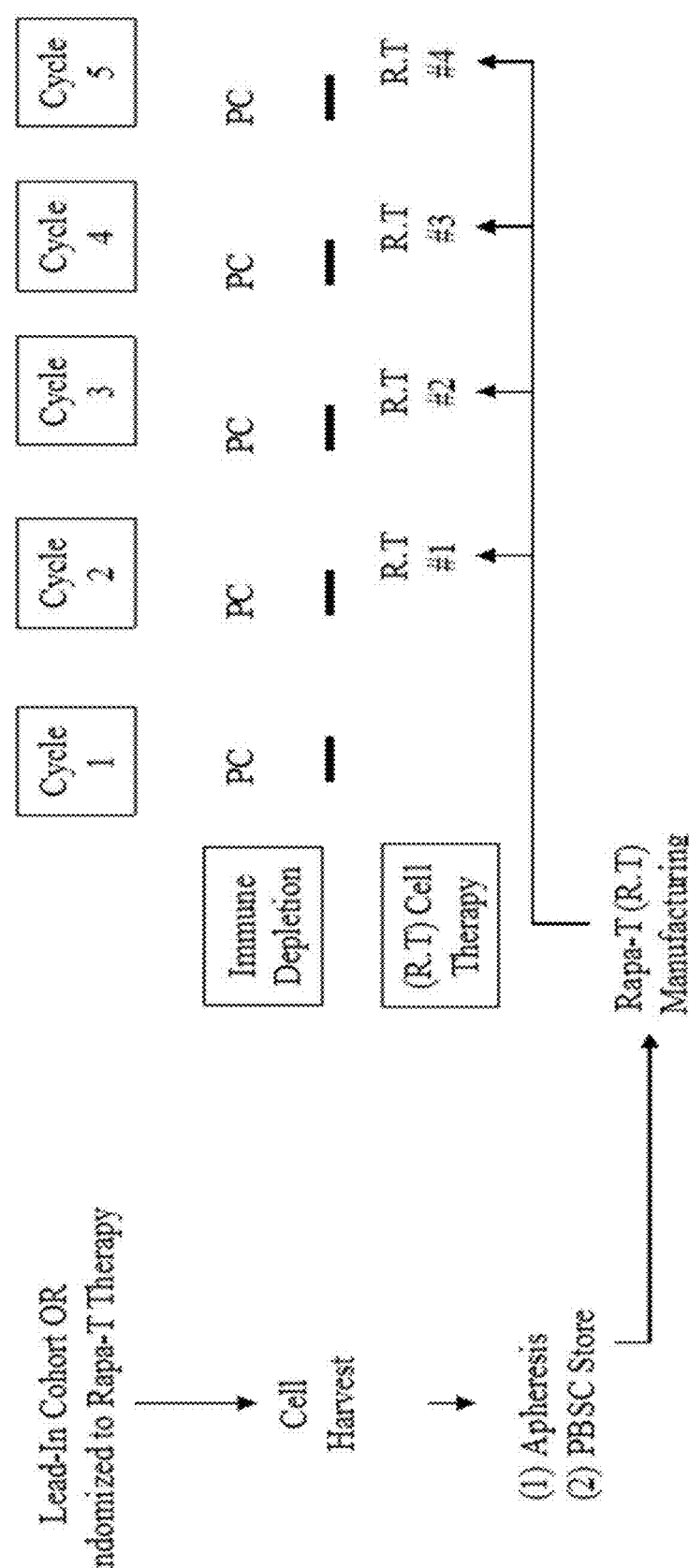
FIG. 30 depicts a manufactured T cell therapy schema.
Figure 30:
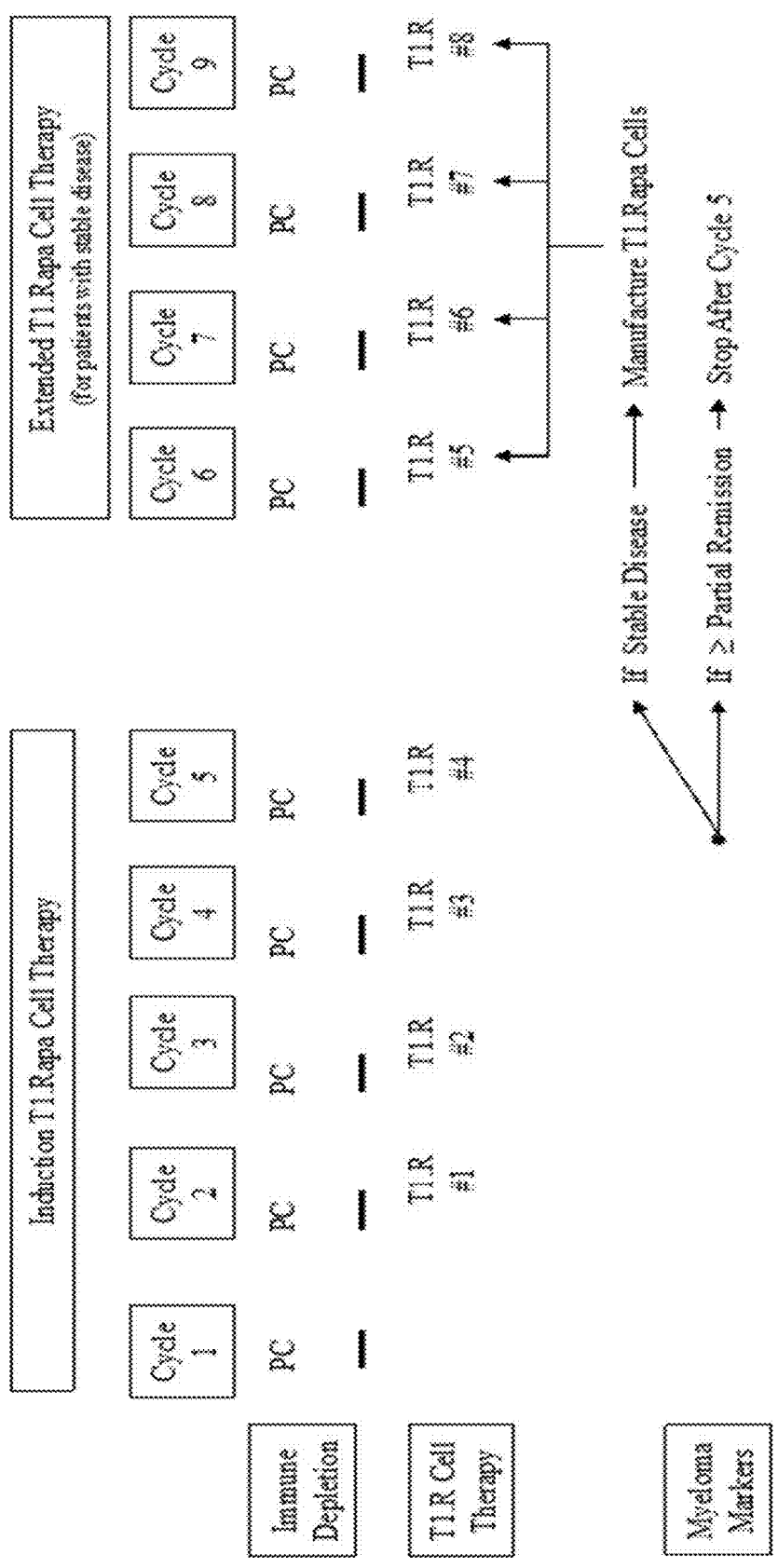

Example 6: Phase III Randomized Clinical Trial of Rapa-T Cell Therapy FIG. 30 depicts the Randomized Phase 3 Protocol Schema. In the upper panel of FIG. 30, for patients randomized to the Rapa-T therapy, autologous cells for Rapa-T cell manufacturing will be derived from a steady-state apheresis collected after randomization. The immune depleting regimen will be comprised of pentostatin and low-dose, dose-adjusted cyclophosphamide (PC regimen). The first PC cycle will be administered alone (without T cell therapy) at study entry during the interval of T1.Rapa manufacturing and will be 28 days in duration; PC cycles two, three, four, and five will be administered prior to each of the four T1.Rapa cell infusions and will be 35 days in duration. The lower panel of FIG. 30 depicts extended T1.Rapa cell therapy for stable disease. For T1.Rapa cell recipients who have stable disease after cycle 4, an additional lot of T1.Rapa cells will be manufactured to allow up to four additional cycles of T1.Rapa cell therapy (cycles 6 through 9).

FIG. 30 details manufactured T cell therapy, which will be administered to all patients randomized to the manufactured T cell Cohort. This therapy will involve: (1) collection of immune cells to be used as substrate for the manufactured T cell manufacturing, which will be obtained from either a previously harvested peripheral blood stem cell transplantation procedure or a fresh, steady-state apheresis procedure; (2) enrichment for mononuclear cell populations and subsequent incubation of mononuclear cells under the manufactured T cell culture conditions; (3) cryopreservation of single-use manufactured T cell therapeutic products, which undergo a verification step for identity and function; (4) patient treatment with a pentostatin plus cyclophosphamide drug regimen (PC regimen) will be initially in isolation and subsequently in combination with manufactured T cell therapy to both prepare the patient for manufactured T cell therapy and directly promote anti-tumor effects; and (5) specialized immune monitoring during and after therapy.

The immune depleting regimen will be comprised of pentostatin and low-dose, dose-adjusted cyclophosphamide (PC regimen). The first PC cycle will be administered alone (without T cell therapy) at study entry during the interval of manufactured T cell manufacturing and will be a minimum of 28 days in duration to allow blood count recovery; PC cycles two, three, four, and five will be administered prior to each of the four manufactured T cell infusions and will be a minimum of 35 days in duration to allow blood count recovery. There will be no maintenance therapy after completion of cycle 5 of manufactured T cell therapy. Treatment cycles can be longer than the indicated interval, extending to an indefinite interval, depending on the clinical situation. By way of example but not limitation, if a patient is in remission, cycles can be delayed until evidence of disease relapse. Moreover, additional maintenance cycles of the PC regimen plus adoptive manufactured T cell therapy is envisioned to maintain patients in a remission state, perhaps by administering 1 to 4 therapy cycles per year, or to treat disease relapse if it were to occur.

As indicated in FIG. 30, for patients who have stable disease after 4 cycles of therapy, an additional manufacturing of Rapa-T cells can be performed, thereby facilitating potential therapy with additional cycles, up to 9 total Rapa-T cell therapy cycles.

FIG. 31 details the specifics of the PC chemotherapy regimen. Each cycle of PC therapy will consist of a 14-day course just prior to the T1.Rapa cell infusion on day 15 of the cycle (T1.Rapa dose: between 0.1 and $5\times10^6$ cells/kg). For cycle 1, pentostatin (P) will be administered (i.v.) at a dose of 4 mg/m$^2$ on days 1, 4, 8, and 11; cyclophosphamide (Cy) will be administered at a dose of 200 mg per day on days 1 through 5 and days 8 through 12. For subsequent cycles, pentostatin will be reduced to a dose of 2 mg/m$^2$.

Figure 32A:
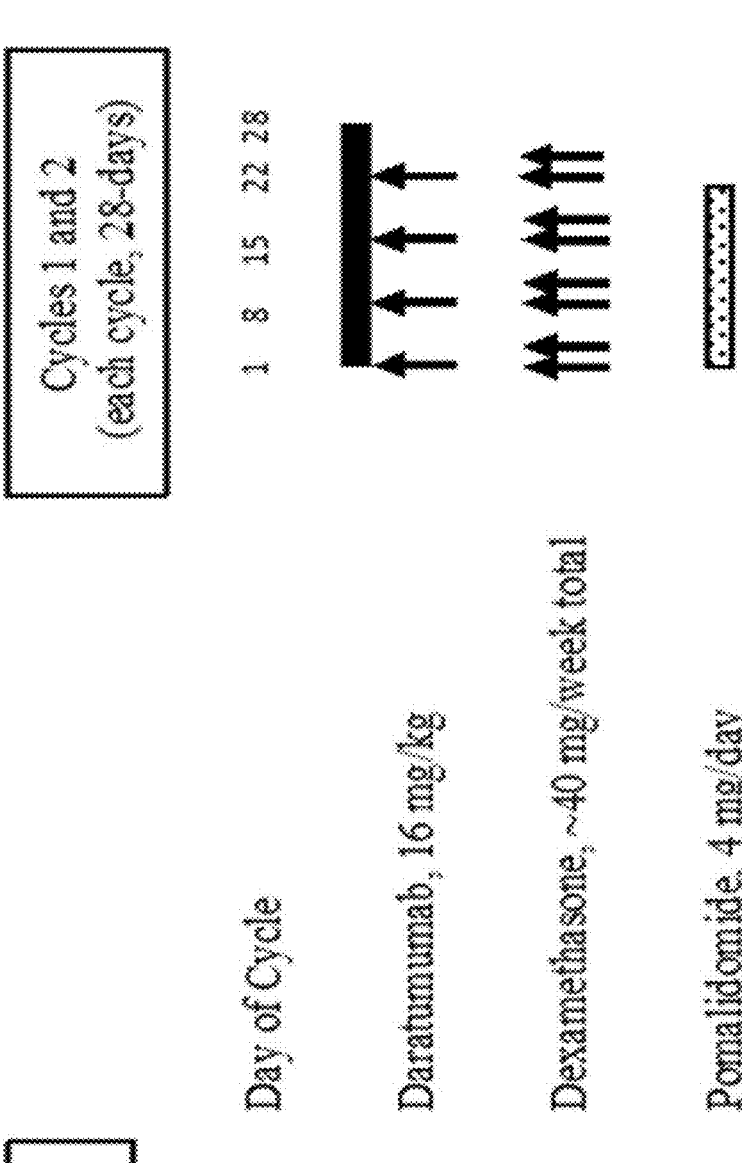
FIGS. 32A-32C details the nature of the control arm, that is, subjects that are not randomized to the Rapa-T cell therapy will receive one of three FDA-approved triplet regimens suitable for subjects with MM in the second or third relapse, namely: the DPd regimen (A); the DRd regimen (B); or the KRd regimen (C).
Figure 32A:
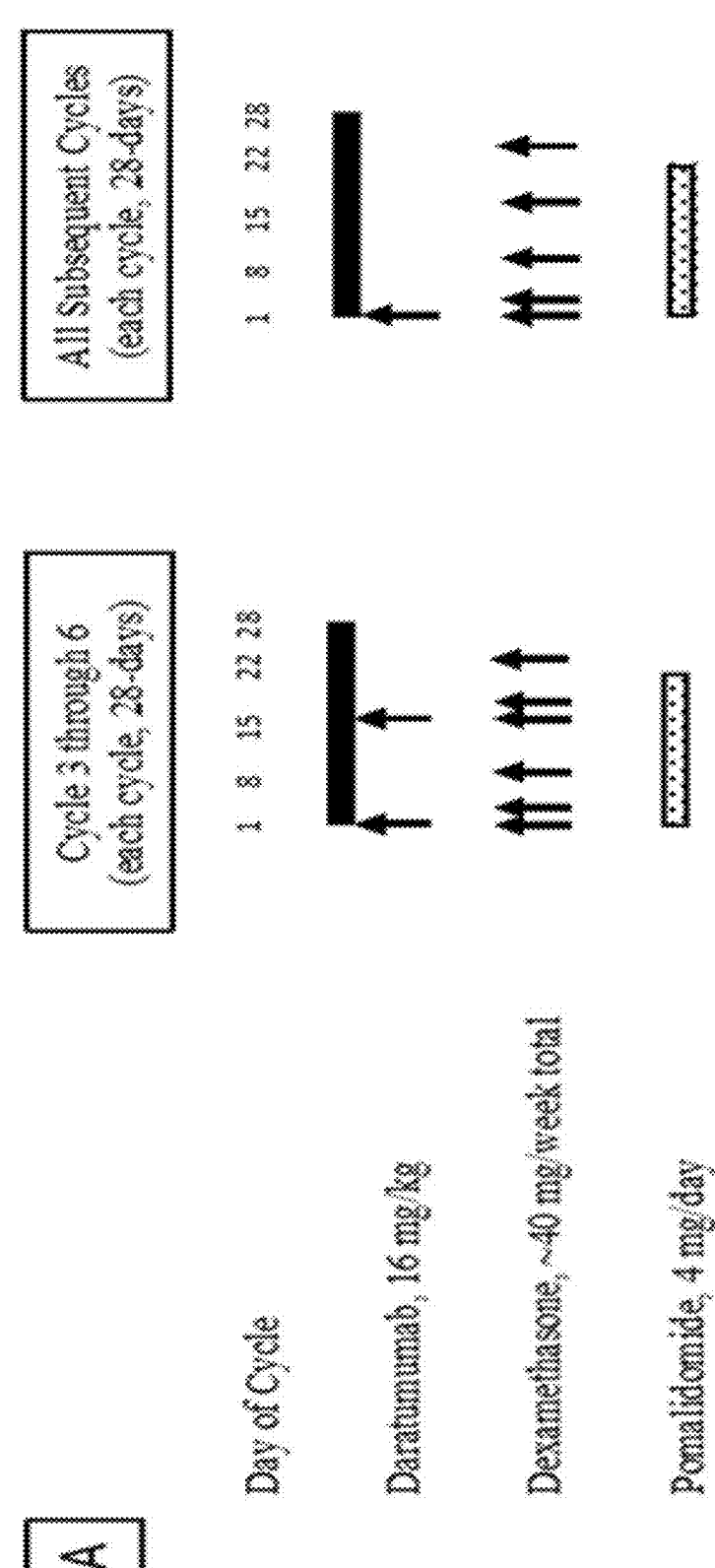
Figure 32B:
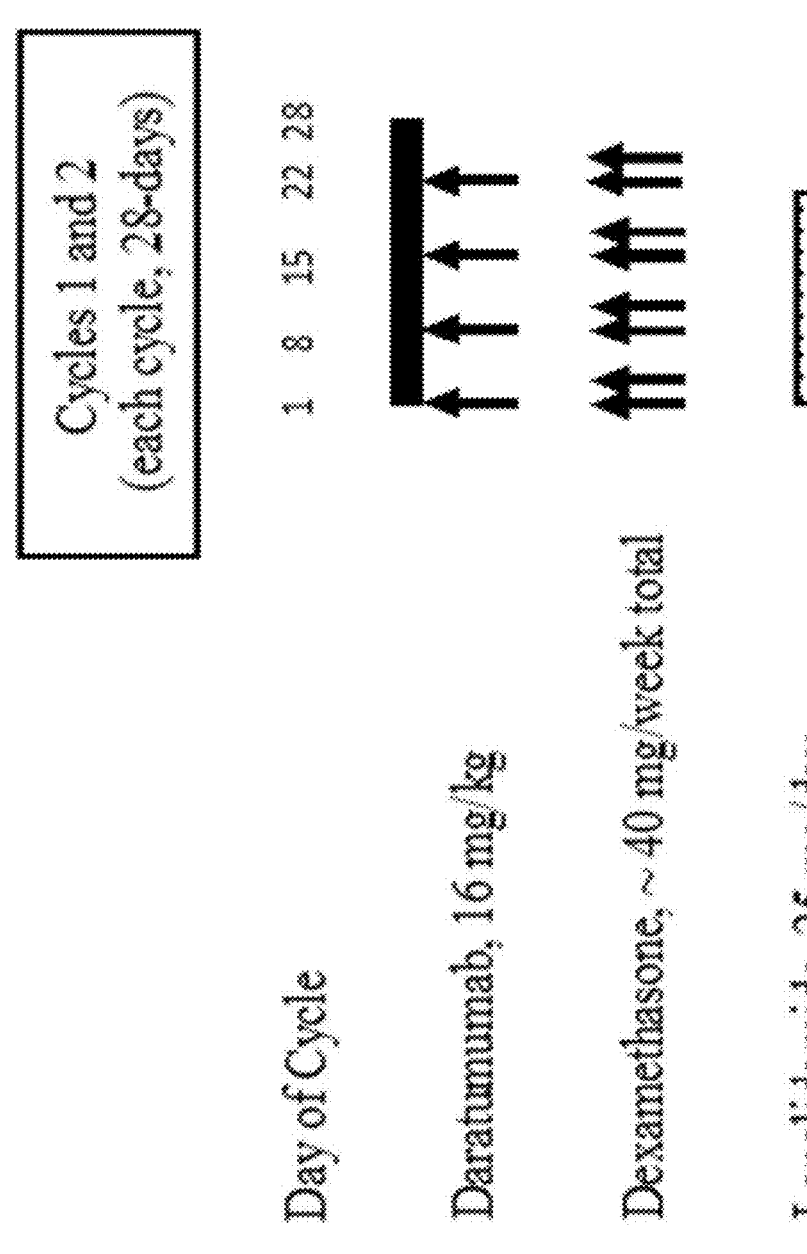
Figure 32B:
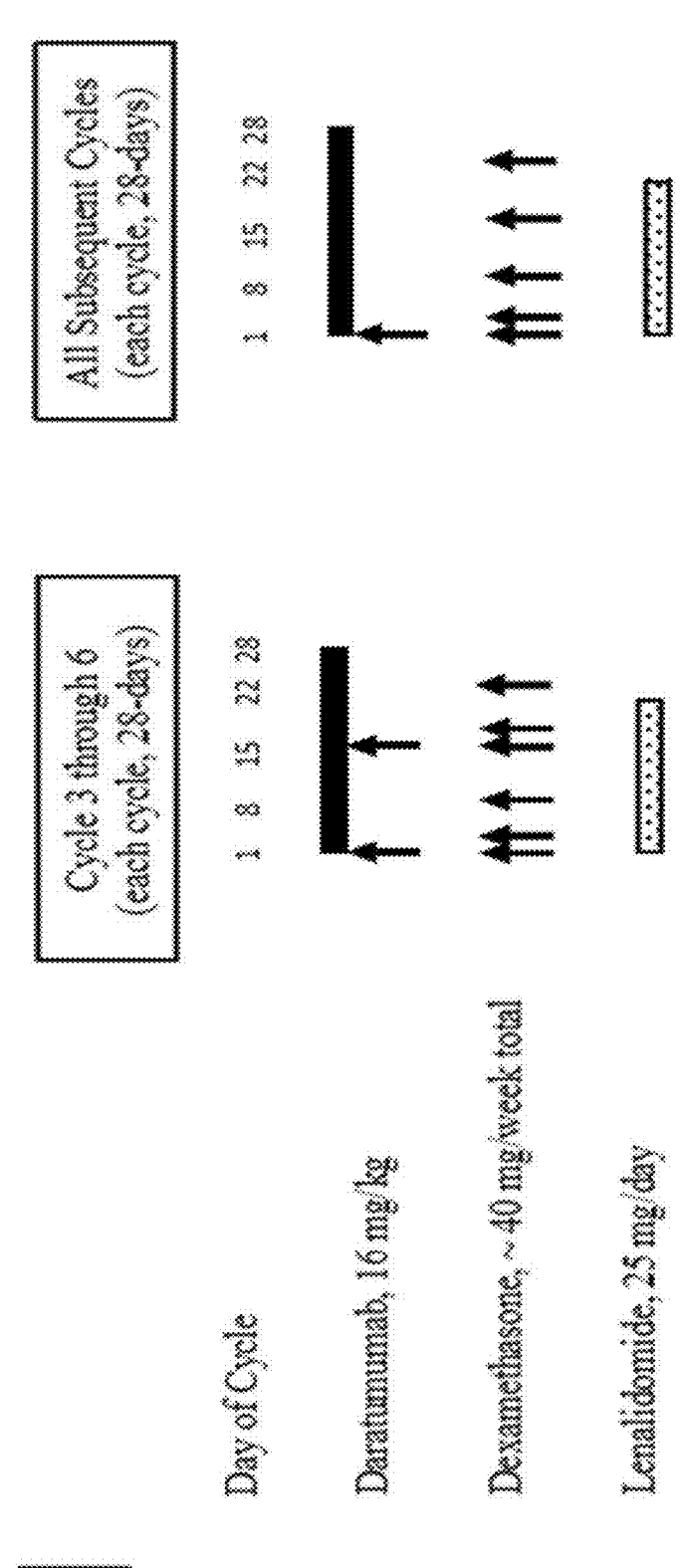
Figure 32C:
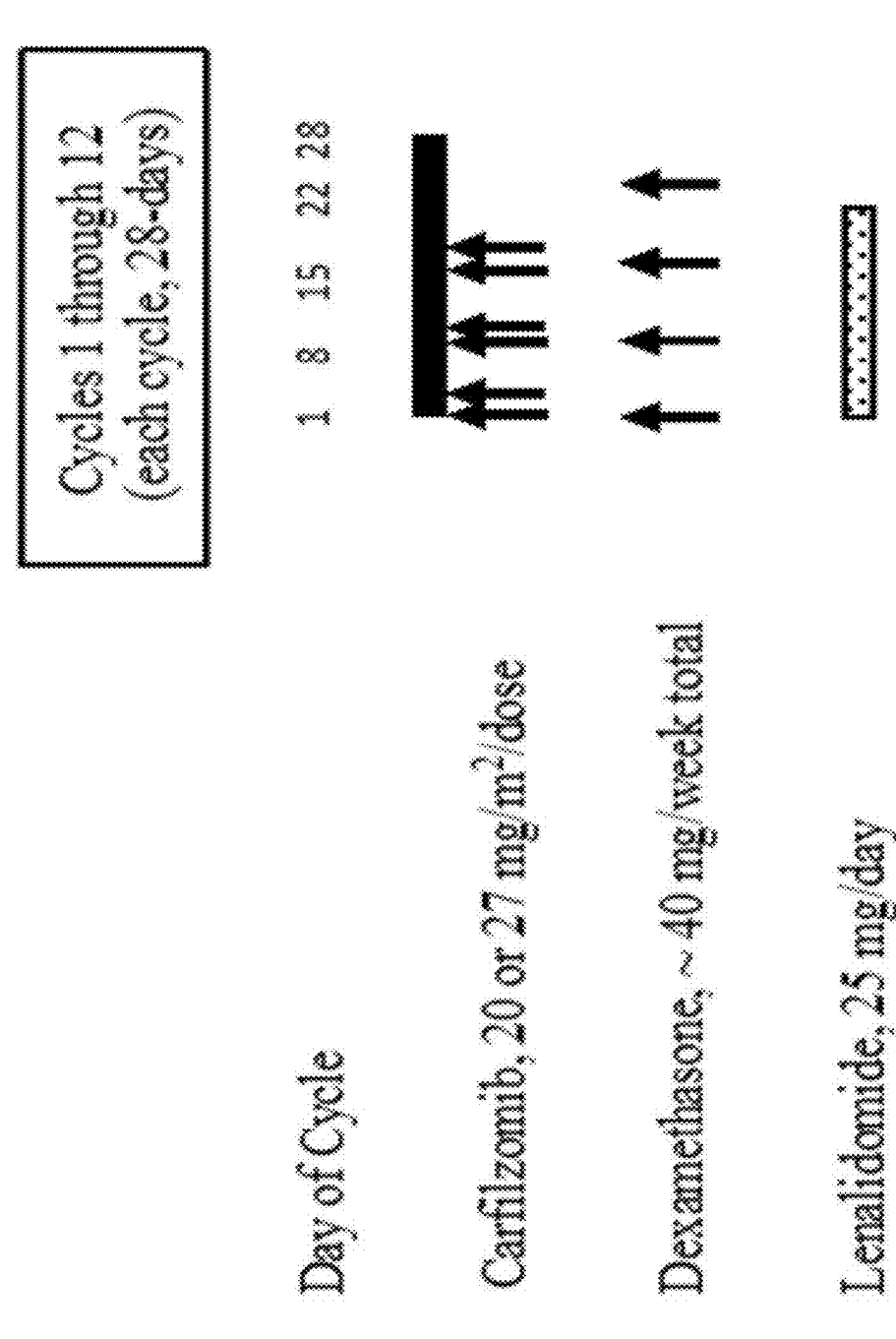
Figure 32C:
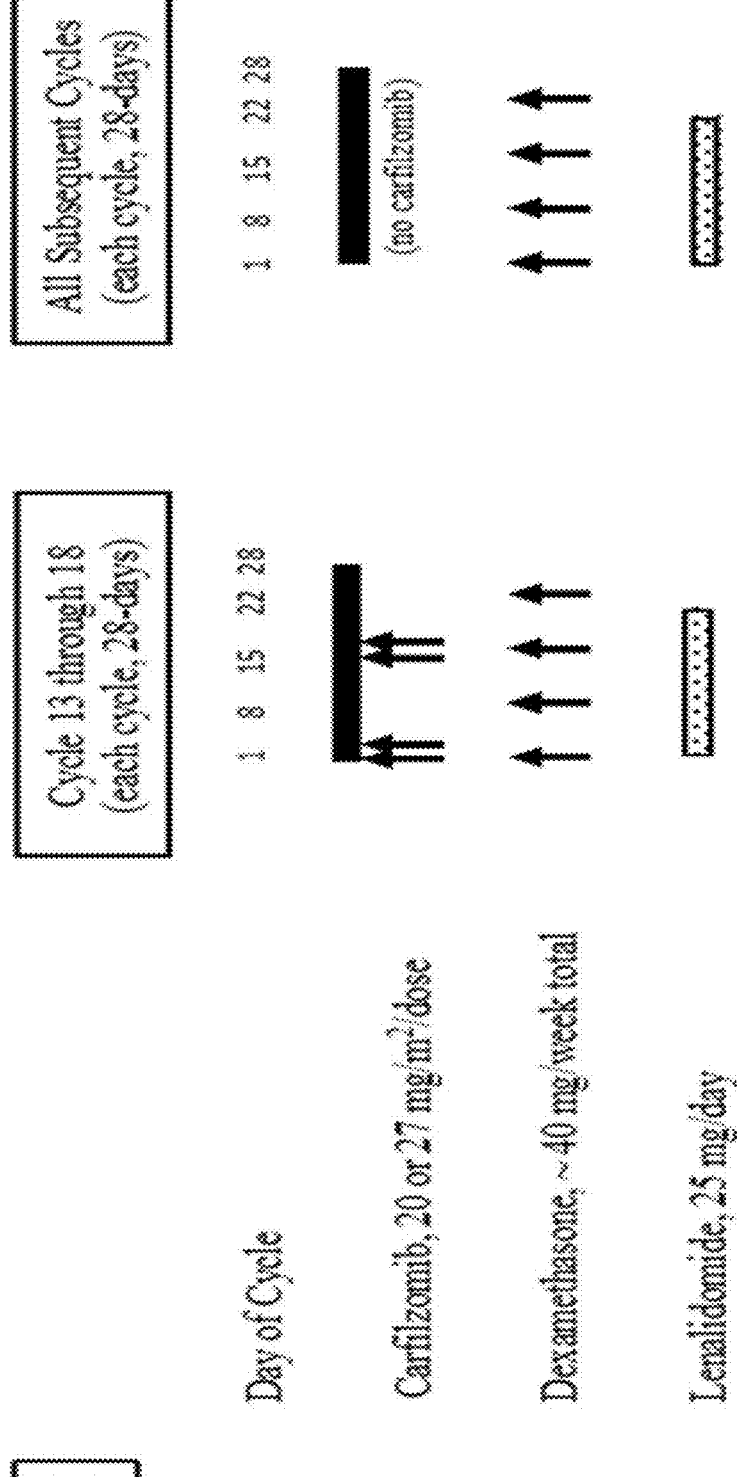

FIGS. 32A-32C detail the nature of the control arm, that is, subjects that are not randomized to the Rapa-T cell therapy will receive one of three FDA-approved triplet regimens suitable for subjects with MM in the second or third relapse, namely: the DPd regimen (FIG. 32A); the DRd regimen (FIG. 32B); or the KRd regimen (FIG. 32C).

For the control cohort depicted in FIGS. 32A-32C, patients will be enrolled and subsequently randomized at the time of second or third relapse of multiple myeloma (MM). Patients must be candidates to receive one of three FDA-approved regimens for treating this patient population. Patients randomized to the control cohort will receive either the DPd, DRd, or KRd regimen using the published standard regimens. Specific aspects of these standard regimens are indicated above in: [FIG. 32A] DPd Regimen; [FIG. 32B] DRd Regimen; and [FIG. 32C] KRd Regimen.

Statistical Evaluation of Manufactured T cell Efficacy The primary objective will be to compare the progression-free survival in recipients of the manufactured T cell therapy relative to recipients randomized to the standard-of-care therapy. By comparison, secondary objectives will be assessed in a preliminary manner using descriptive statistics. Eligible patients with MM in the second or third relapse will be randomized in a 1:1 manner to receive either standard-of-care therapy using an FDA-approved triplet regimen consisting of either DPd, DRd, or KRd or adoptive T cell therapy with ex vivo manufactured autologous, rapamycin-resistant Th1/Tc1 cells (manufactured T cell). N=65 evaluable patients will be accrued to each cohort. The primary study objective will be to determine whether patients treated on the manufactured T cell cohort have an increased progression-free-survival (PFS) relative to the patients treated on the standard-of-care cohort.

The progression-free survival (PFS) and overall survival of the patients will be estimated using the Kaplan-Meier method in both arms and presented with pointwise 95% confidence intervals. A non-parametric estimate of the median survival and its 95% confidence interval will be obtained by inverting the Kaplan-Meier estimate. The primary efficacy outcome (PFS) will be tested by a one-sided log-rank test. The final analysis will be performed when 130 PFS events have occurred in the study, or the recruitment goal has been reached and all patients have been followed for at least 12 months. Overall survival (OS) will be measured from the start of the treatment; death from any cause will be an event, and patients will be censored at the date of last contact.

Secondary endpoints will be evaluated in a descriptive manner such as mean, standard deviation, confidence interval, Kaplan-Meier analyses, or other methods of characterizing multiple myeloma remission status. Objective response rate (ORR) and minimum residual disease rate (MRD) will be estimated as the observed proportion of patients with the corresponding outcome, and presented with 95% confidence intervals.

Demographic and baseline data will be summarized in a descriptive manner. Categorical data will be presented as frequencies and percentages whereas continuous data will be presented using summary statistics such as mean, median, and standard deviation. Particular attention will be focused upon determination of prior therapies for multiple myeloma and degree of refractoriness to the individual agents utilized.

Two interim analyses with potential stopping for futility will be conducted when 28 and 55 PFS events have occurred overall (combining the two arms). A beta error-spending approach with a quadratic error-spending function will be used, which is a compromise between the O'Brien-Fleming and Pocock boundaries. The following table shows the null-hypothesis acceptance boundary for the two interim and one final analyses. These values would be modified using the error-spending function if the timing of the interim analyses is modified.

| Analysis | Number of PFS events | Expected number of patients randomized | Expected time from study start | P-value criterion for stopping for futility | P-value criterion for stopping for efficacy |
|---|---|---|---|---|---|
| $1^{st}$ interim | 28 | 80 | 19 months | p > 0.874 | — |
| $2^{nd}$ interim | 55 | 122 | 29 months | p > 0.425 | — |
| Final | 104 | 130 | 60 months | — | p < 0.026 |

The probability of stopping the trial early due to futility as a function of the true effect size is shown in the following table:

| True effect size as proportion of the design effect size | Probability of stopping for futility at $1^{st}$ interim analysis | Probability of stopping for futility at $1^{st}$ or $2^{nd}$ interim analysis |
|---|---|---|
| 0 | 12.6% | 58.3% |
| 0.5 | 3.8% | 22.6% |
| 1 | 0.8% | 4.4% |

Collection of Immune Cells to be Used as Substrate for Manufactured T Cell Manufacturing Collection and shipping of cells for manufactured T cell manufacturing will be required for patients randomized to the manufactured T cell therapy cohort.

In addition, in cases where the subject has the necessary value for immune cells in the bloodstream as defined by absolute lymphocyte count (ALC; value of at least 300 lymphocytes per microliter), steady-state apheresis will be performed and will consist of a 10- to 15-liter collection. The apheresis should be performed within 10 days of study entry. The apheresis product will be immediately shipped (without cryopreservation) to Rapa Therapeutics.

The first cycle of the PC regimen should be started within 10 days after study entry.

Subsequent iterations of manufactured T cell therapy may become more efficient, and as such, smaller numbers of input cells might be used to initiate manufacturing. Such improved methods will involve at least in part improved host preparation and improved manufacturing processes. In such methods, it will be possible to manufacture T cells with starting material obtained from a simple blood draw of 500 mL or less.

Manufactured T Cell Manufacturing

In the case of previously collected cellular products, such cryopreserved cells will be stored in the vapor phase of liquid nitrogen until thawing of cells and manufacture of manufactured T cells. In the case of freshly isolated cells by apheresis or in the future by simple blood collection, the cells will undergo immediate processing, and then may either be placed directly into culture or may be cryopreserved by controlled rate freezing technology and stored in the vapor phase of liquid nitrogen for subsequent use later.

T cell culture from cryopreserved cell substrates from freshly isolated cell populations requires some type of T cell enrichment. By way of example but not limitation, T cell enrichment can be achieved by use of monoclonal antibody and column technology (positive or negative selection). Enrichment of the raw cellular material used in manufactured T cell manufacturing does not require such antibody-based methodologies because T cells are efficiently enriched during the culture interval; as such, our method is consistent with recommendations for effective cell therapy on a global level. The initial processing steps for manufacture of manufactured T cells focuses on removal of di-methyl sulfoxide (DMSO) used in the cryopreservation steps (when applicable), lysis of red blood cells (RBCs), and centrifugal removal of contaminating granulocytes and to some extent, monocytes. These steps are performed in a relatively automated method using primarily closed-system technology. This procedure is advantageous as it reduces human error, provides detailed manufacturing data for batch records, improves consistency across manufacturing runs, and reduces the risk for infectious agent contamination of the final product. Processing for the manufactured T cell products incorporates the following steps: (1) thaw of cryopreserved products (when applicable) using solid-state, non-water based methods to reduce infectious agent contamination as in Triana E, Ortega S, Azqueta C, et al. Thawing of cryopreserved hematopoietic progenitor cells from apheresis will be with using a new dry-warming device. Transfusion. 2013; 53(1):85-90; (2) automated washing of the cellular product using the LOVO permeable membrane device as in Mfarrej B, Bouchet G, Couquiaud J, et al. Pre-clinical assessment of the Lovo device for dimethyl sulfoxide removal and cell concentration in thawed hematopoietic progenitor cell grafts. Cytotherapy. 2017; 19(12):1501-1508; (3) integration of lysis of RBCs using ammonium-chloride-potassium (ACK) buffer, described in Brown W E, Hu J C, Athanasiou K A. Ammonium-Chloride-Potassium Lysing Buffer Treatment of Fully Differentiated Cells Increases Cell Purity and Resulting Neotissue Functional Properties. Tissue engineering Part C, Methods. 2016; 22(9):895-903, during the LOVO washing steps; (4) volume reduction of cellular content using the LOVO method with subsequent plating of cells into the closed-system, counter-flow, centrifugal elutriation (CCE) device (Elutra; Terumo) as previously described in Stroncek D F, Fellowes V, Pham C, et al. Counter-flow elutriation of clinical peripheral blood mononuclear cell concentrates for the production of den-dritic and T cell therapies. J Transl Med. 2014; 12:241.(doi): 10.1186/s12967-12014-10241-y; and (5) pre-programmed operation of the Elutra device for efficient removal of granulocytes and monocytes by CCE.

After this lymphocyte enrichment and media purification, the cells are plated into specialized chambers that possess an enriched capacity for oxygen exchange (G-Rex vessels; Wilson-Wolf), described in Bajgain P, Mucharla R, Wilson J, et al. Optimizing the production of suspension cells using the G-Rex "M" series. Molecular Therapy Methods & Clinical Development. 2014; 1:14015. In addition to having enhanced gas permeability characteristics, the G-Rex ves-sels are closed system units and have the additional advan-tage of automated, closed system media volume reduction (GatheRex Liquid Handling Pump). The lymphocyte-en-riched cells are maintained in the G-Rex vessels for 6-days.

Several specific culture conditions are utilized to promote the manufacture of a mixture of CD4+ and CD8+ T cells in the G-Rex vessels with functional attributes of a manufac-tured T cell. These specific conditions include: (1) use of enriched media (including but not limited to X-Vivo 20; Lonza; mediate may also be supplemented with 5% AB serum), Zhang H D, Song Z L, Li W P. [In vitro cultivation of dendritic cells with serum-free medium]. Zhongguo shi yan xue ye xue za zhi. 2006; 14(5):985-989; Lonza) that is further supplemented with 5% human serum; (2) incorpo-ration of a 16-hour rest interval of cell plating into the G-Rex prior to co-stimulation (cells are plated at a relatively high density of 1.5×10⁶ T cells per ml); (3) during this initial rest interval, cells are optimally rested by addition of the mono-clonal antibody basiliximab (which blocks the IL-2 receptor and thereby prevents autonomous T cell activation by endogenously produced IL-2) and temsirolimus (which is a pharmacologic inhibitor of mTORC1); (4) after this 16-hour rest interval, cells are either not co-stimulated or co-stimu-lated with anti-CD3/anti-CD28 coated magnetic beads (3/28 beads) under sub-optimal conditions, as defined by a bead-to-T cell ratio of 1:3 (typically, most T cell expansion conditions utilize a 9-fold higher level of co-stimulation, a 3:1 bead-to-T cell ratio); (5) importantly, it is essential that the T cells are not washed after the initial rest interval; (6) after the rest interval, in addition to addition of 3/28 beads, it is essential to add the polarizing cytokine IFN-α at a high dose (10,000 IU/ml) to promote differentiation to CD4+ Th1 and CD8+ Tc1 phenotypes; (7) importantly, it is critical to avoid the addition of IL-2, which is a common additive to T cell cultures; and (8) after addition of the beads and IFN-α, it is important to leave the cells undisturbed until harvesting at day 6 of culture (no cell washing, no further culture additives).

Cryopreservation of Manufactured T Cell Products and Verification of Identity and Function After the 6-day cell culture in the G-Rex vessels, the volume of the culture will be reduced in a closed system manner by the GatheRex instrument. Subsequently, the cells will be harvested, 3/28 beads removed by hand-held magnet, and cells placed into the LOVO device for serial washing of the cells to remove >99% of culture additives (Temsiroli-mus, Basiliximab, IFN-α).

Washed cells will be reconstituted into cryopreservation media, which contains 5% DMSO and 5% pentastarch. The cryopreservation will be performed in multiple single use aliquots in 50 ml freezer bags. The manufactured T cell dose will be between 0.1 and 5×10⁶ T cells per kg of recipient body weight. Four single-use aliquots will be cryopreserved to allow four consecutive, approximate monthly infusions of manufactured T cells. Manufactured T cells will be cryo-preserved by GMP-compliant controlled rate freezing meth-odology, as previously described in Hunt C J. Cryopreser-vation of Human Stem Cells for Clinical Application: A Review. Transfusion medicine and hemotherapy: offizielles Organ der Deutschen Gesellschaft fur Transfusionsmedizin and Immunhamatologie. 2011; 38(2):107-123, and; cells will be shipped in the vapor phase of liquid nitrogen by certified cryo-shipper after the manufactured T cells have passed the specified release criteria testing.

Release criteria testing of the manufactured T cells will include standard tests such as content of CD3+, CD4+ and CD8+ T cell purity (final product must be >70% CD3+ T cell content by flow cytometry; CD4+ and CD8+ subsets must each be present at the 5% level). Cells must be >70% viable, as determined by flow cytometry annexin and 7-AAD assays. Furthermore, cells must be free of bacterial and fungal contamination upon a minimum of a 3-day culture interval (ideally, a 14-day culture interval); furthermore, the cell product must be below detection limit for bacterial LPS endotoxin and Mycoplasma.

In addition to these standard tests, specialized functional tests will constitute release criteria for the manufactured T cell products. Prior to release of product and cell therapy, a manufactured T cell can possess the following attributes relative to culture input T cells: (1) an enhanced T central memory phenotype, as defined by increased flow cytometric co-expression of CD62 ligand and CCR7; (2) low level expression of checkpoint inhibitory molecules, such as programmed death-1 (PD1); (3) a resting state, as defined by reduced levels of Th1/Tc1-type cytokine secretion upon maximal co-stimulation; (4) an autophagy signature, as evidenced by reduced mitochondrial mass by flow cytom-etry MitoTracker assay, see Xiao B, Deng X, Zhou W, Tan E K. Flow Cytometry-Based Assessment of Mitophagy Using MitoTracker. Frontiers in cellular neuroscience. 2016; 10:76; (5) a resistant phenotype, as evidenced by at least 50% inhibition of mTORC1 and mTORC2 downstream targets; and (6) a multi-faceted differential gene expression profile of n=80 key transcription factor and differentiation molecules.

Host Preparation Using PC Regimen

Patients on the manufactured T cell treatment receive a pentostatin plus cyclophosphamide (PC) regimen. Cycle 1 of the PC regimen will be administered during the interval of manufactured T cell manufacturing and will be thus administered without accompanying T cell infusion. Cycle 1 is advantageous on two levels: first, it will reduce the number and function of host regulatory T cells and end-stage senescent effector T cells, thereby potentiating futures cycles of manufactured T cell therapy; and second, it will directly mediate anti-tumor effects against the multiple myeloma, thereby controlling disease during the manufacturing inter-val. After cycle #1, subsequent cycles of the PC regimen will be followed by the adoptive transfer of manufactured T cells on the day after the two-week PC regimen interval (day 15). These cycles of the PC regimen are additionally advanta-geous because they will further modulate the host biology, including increasing T cell homeostatic cytokines such as IL-7 and IL-15, which will allow improved manufactured T cell expansion after adoptive transfer.

The PC regimen is followed by manufactured T cell infusion. Each cycle of PC therapy will consist of a 14-day course just prior to the manufactured T cell infusion on day 15 of the cycle. The manufactured T cell dose will be between 1 and $5\times10^6$ cells/kg, including T cell doses between $1\times10^5$ and $5\times10^6$ cells/kg. Pentostatin (P) will be administered (i.v.) at a dose of 4 mg/m2 on days 1, 4, 8, and 11; cyclophosphamide (Cy) will be administered at a dose of 200 mg per day on days 1 through 5 and days 8 through 12.

Premedications and prehydration will be required prior to pentostatin administration. Prehydration with 1 liter of 0.9% sodium chloride will be given 60 minutes prior to pentostatin. Premedications with an anti-emetic will be required. Anti-emetic regimen recommendations are as follows: (1) Dexamethasone, 12 mg by IV infusion 60 minutes prior to each pentostatin dose (that is, Days 1, 4, 8, and 11 of the cycle); (2) In addition, oral dexamethasone may be administered on other days on an as-needed basis at a dose of 4 mg per day; (3) Ondansetron will be administered at a dose of 8 mg by IV infusion 60 minutes prior to each dose of pentostatin; (4) For the remainder of treatment, ondansetron may be administered on an as-needed basis at an oral dose of 8 mg (tablets) every 12 hours on Days 1 through 14; and (5) Aprepitant may be added as-needed to the anti-emetic regimen in patients with uncontrolled nausea and vomiting. The pentostatin dose will be 4 mg/m$^2$; each dose of pentostatin will be administered intravenously over 30-60 minutes.

Pentostatin will be dose modified, with dosage of pentostatin administered to a patient being between 1-4 mg/m$^2$. Pentostatin will be dose modified based on creatine clearance (CrCl), which will be obtained either by 24-hour urine or calculated by the Cockcroft-Gault formula. If a subject experiences an increase in creatinine level during the pentostatin and cyclophosphamide therapy, subsequent dosing will be modified as follows: CrCl≥60 mL/min/1.73 m$^2$→administer 4 mg/m$^2$ of pentostatin (full-dose); CrCl<60 mL but ≥30 mL/min/1.73 m$^2$→administer pentostatin at a 50% dose reduction, to 2 mg/m$^2$; and CrCl<30 mL→hold pentostatin. Pentostatin is rarely associated with organ toxicity such as neurologic toxicity (seizure, coma) or cardiac toxicity (decreased ejection fraction). As such, special attention should be paid towards evaluating any organ toxicity that arises during PC therapy. In the event that pentostatin is associated with any organ toxicity of grade 2 or greater severity, the institutional PI should be contacted to discuss whether further pentostatin therapy and further protocol therapy is warranted.

Oral cyclophosphamide (Cy) will be used as a component of the PC regimen, wherein the dose of cyclophosphamide will be between 50-400 mg. The dose of Cy will be 200 mg daily on days 1-5 and 8-12 during cycles number one through five of the PC regimen. Cyclophosphamide 200 mg by intravenous infusion will be also permitted for tolerability issues or financial considerations. Due to cyclophosphamide bladder toxicity, adequate hydration must be maintained during the PC regimen. Patients should drink at least 2 to 4 liters of fluid per day to maintain a clear urine color.

Cyclophosphamide dosing will be adjusted, as necessary, according to the table below based on the complete blood count (CBC) and differential cell values (absolute lymphocyte count [ALC] and absolute neutrophil count [ANC]) obtained on days 1, 4, 8, and 11 of the cycle. The stated goal of the PC regimen is to attain immune depletion and immune suppression while minimizing myeloid cell suppression. To help ensure this goal, the cyclophosphamide dosing will be adjusted, as necessary, according to the following table based on the ALC and ANC values obtained on the days of pentostatin administration (that is, days 1, 4, 8, and 11 of the cycle). Notations in the table are as follows: [1] Pentostatin will not be dose-adjusted based on ALC/ANC values; [2] For ANC values <500, in addition to decrease in cyclophosphamide dosing, patient will receive G-CSF therapy until next ANC measurement; [3] Cyclophosphamide dose indicated will be continued daily until the next ALC/ANC measurements (performed on days 1, 4, 8, and 11 of the cycle).

Variations on the PC regimen are envisioned. First, pentostatin and cyclophosphamide are synergistic in terms of their immune depletion and immune suppression actions; such synergy also likely exists in terms of anti-tumor effects, although there is little information regarding this possibility. As such, we envision that the PC regimen might be used as a stand-alone therapy for cancer therapy, including solid tumors; in one prior example, patients with refractory mesothelioma who received a combination regimen that was comprised in part by the PC regimen had unprecedented anti-tumor benefits. Second, because of this synergy, we propose that it will be advantageous to administer the two drugs simultaneously by intravenous infusion, preferably by mixing the pentostatin and cyclophosphamide into the same intravenous infusion bag for ease of administration and to reduce pharmacy errors. In such an application, it would be important to offer options of the PC mixtures that would encompass the various clinically-relevant pentostatin-to-cyclophosphamide ratios.

| Cyclophosphamide Dose Adjustment Based on ALC and ANC Values | | | |
|---|---|---|---|
| Day of Cycle[1] | ALC Value at time of Evaluation | ANC Value at time of Evaluation[2] | Cyclophosphamide Dose[3] |
| 1 | Any | >1000 | 200 |
| 4 | ≥400 | >1000 | 200 |
| | 200-399 | 500-999 | 100 |
| | <200 | <500 | 0 |
| 8 | ≥200 | >1000 | 200 |
| | 101-199 | 500-999 | 100 |
| | <100 | <500 | 0 |
| 11 | ≥100 | >1000 | 200 |
| | 50-99 | 500-999 | 100 |
| | <50 | <500 | 0 |

Manufactured T Cell Infusion

Premedication will be required prior to all manufactured T cell administrations. Diphenhydramine (25 to 50 mg IV or PO) and acetaminophen (650 mg, PO) will be administered 30-60 minutes prior to manufactured T cell infusions.

Manufactured T cell infusions will occur on Day 15 of cycles two through five; however, up to a 3-day delay in manufactured T cell infusion may occur for logistic reasons. In addition, up to a 4-week delay between cycles will be allowed for logistic reasons and to allow for recovery of toxicities. The manufactured T cell dose will be $5\times10^6$ cells/kg; however, if sub-optimal cell yield occurs during manufacturing, doses of as low as $0.1\times10^6$ cells/kg will be allowed. The cryopreserved manufactured T cells will be thawed and immediately and rapidly administered intravenously (within 30 minutes) by gravity following the appropriate institutional SOP for blood product administration. This T cell infusion will be performed in the outpatient setting unless there is an unforeseen circumstance that requires inpatient administration. No steroids will be allowed in the management of DMSO-related toxicities (chills, muscle aches) that may occur immediately after cellular infusion unless the toxicity is deemed life threatening.

It is envisioned that smaller quantities of manufactured T cell infusion below $0.1 \times 10^6$ cells/kg may also be clinically-relevant (by way of example but not limitation, one-log lower, at $1 \times 10^5$ cells/kg). First, manufacturing will be optimized to yield manufactured T cells that mediate further heightened in vivo effects, thereby reducing the required T cell dose; this will be advantageous in part because T cell collection can occur by simple blood draw and in part because of an improved manufacturing feasibility. Second, with further improvements in the PC regimen, as detailed above, the adoptively transferred manufactured T cells will have a further improved in vivo selective advantage relative to host cells, thereby effectively reducing the required manufactured T cell dose.

Specialized Immune Monitoring During and after Therapy

Peripheral blood mononuclear cells and bone marrow cells will be sent to Rapa Therapeutics such that immune monitoring tests can be performed; the purpose of these tests will be to explore the mechanism of action of the manufactured T cell therapy and to develop biomarkers that will predict manufactured T cell efficacy. In one effort, we will evaluate manufactured T cell recipients for their capacity to produce various Th1- and Th2-type cytokines in response to various stimulations, including autologous multiple myeloma tumor cells or known or suspected tumor antigens, such as molecules in the cancer-testis-antigen (CTA) family. The CTA family of genes is extensive in number, and has been shown to be relevant in multiple myeloma; because the sequences of CTA genes are known and the relevance of specific CTA genes has been characterized in multiple myeloma, manufactured T cell therapy can be demonstrated to specifically induce T cell-mediated immunity against a range of CTA antigens. Measurement of such cytokine responses can be performed using RNA expression analysis, secretion analysis by ELISA or Luminex multi-analyte method, flow cytometry, or ELISPOT assay. Antigen-specific immunity can also be quantified by use of antibody production assays or cytolytic assays.

We will evaluate whether T cells obtained after manufactured T cell therapy have increased reactivity to autologous multiple myeloma cells relative to T cells obtained before manufactured T cell therapy. One obstacle to this effort is that propagation of patient-specific multiple myeloma cell lines is typically not successful. To overcome this obstacle, we will propagate myeloma cells using: specialized vessels, as in Zhang W, Gu Y, Sun Q, et al. Ex Vivo Maintenance of Primary Human Multiple Myeloma Cells through the Optimization of the Osteoblastic Niche. PLoS One. 2015; 10(5), and media supplemented with combinations of factors known to enhance multiple myeloma proliferation and survival, including IL-6, CD40 ligand, and acquisition of resistance to carfilzomib. Patient-specific multiple myeloma cells can be used alone as stimulators in the assessment of immune T cell anti-tumor reactivity; alternatively, such tumor cells can be rendered into the apoptotic state, with the contents loaded into professional antigen-presenting-cells, which can be manufactured from patient specific monocytes collected from the elutriation procedure during manufactured T cell manufacturing.

In addition, we envision that T cell receptor (TCR) immune repertoire analysis will be useful as a biomarker for manufactured T cell therapy. Preferably, such repertoire analysis will be performed by RNA sequencing rather than the more commonly employed DNA sequencing. Unlike the majority of T cell therapies, which are targeted, manufactured T cell therapy is a polyclonal method as the manufacturing process does not preferentially shift T cell reactivity towards any particular tumor antigen. As such, any beneficial anti-tumor effect after manufactured T cell therapy is expected to be derived from in vivo clonal expansion to a diversity of tumor antigens; given this biology, successful manufactured T cell therapy will result in a differential TCR repertoire when comparing the patient pre-treatment repertoire to the post-treatment repertoire. In other cancer therapy settings, such as monoclonal antibody therapy to disengage checkpoint inhibition, successful therapy is associated with emergence of new TCR clonal specificities, known as skewing of the TCR repertoire that can be ascertained by quantification of the Morisito Index, Robert L, Harview C, Emerson R, et al. Distinct immunological mechanisms of CTLA-4 and PD-1 blockade revealed by analyzing TCR usage in blood lymphocytes. Oncoimmunology. 2014; 3:e29244. In a similar manner, with successful manufactured T cell therapy, there will be skewing of the TCR repertoire; persistence of the TCR skewing beyond the interval of manufactured T cell therapy will be consistent with long-term T cell immunity to malignancy. With manufacturing advances, improved forms of manufactured T cells will be generated; in such a case, the TCR skewing will be more extensive, will occur at reduced numbers of treatment cycles, and will be more durable in the post-therapy interval.

Protocol Inclusion Criteria for Therapy of Multiple Myeloma

Male or female patients ≥18 years of age are potentially eligible for manufactured T cell therapy. There will be no formal upper age limit. However, for patients over the age of 65 years who have a history of cardio-vascular pathology or symptoms (even if not clearly fitting the exclusion criteria detailed below), there should be evaluation by a cardiologist at the multi-center site. Such a subject will then be considered on a case-by-case basis. Overall patient performance status should be at least of moderately good health, as quantified by an ECOG Performance Status of ≤2.

Patients must have a confirmed diagnosis of multiple myeloma by histology or cytology studies. In addition, the disease must be symptomatic and the patient must be in the second or third relapse of disease after having received drugs from the following classes of agents: proteasome inhibitors, immune modulatory drugs, alkylators, CD38 monoclonal antibodies, and glucocorticoids.

Patients in the second or third relapse of disease are in a relatively advanced stage of disease. However, with demonstration of the safety and efficacy of manufactured T cell therapy, we envision that multiple myeloma patients earlier in the treatment algorithm will benefit from manufactured T cell therapy. By way of example but not limitation, manufactured T cell therapy may be used as an alternative to high-dose chemotherapy combined with autologous hematopoietic cell transplantation or may be used for the substantial number of patients who are transplant ineligible. Furthermore, manufactured T cell therapy can be envisioned at the earliest point in multiple myeloma progression prior to clinical symptoms, that is, during early detection at the phase of smoldering disease.

On the other hand, it is envisioned that the Rapa-T cell therapy described here will be applicable to the treatment of patients in more advanced stages of multiple myeloma and in patients with highly refractory disease. Specifically, Rapa-T cell therapy can be utilized to treat penta-refractory MM, which is defined as patients who have relapsed MM and resistance to five of the top drugs used to treat MM, namely: lenalidomide, pomalidomide, bortezomib, carfilzomib, and daratumumab.

Because patients with penta-refractory MM do not have a standard-of-care option for therapy, the clinical protocol to assess Rapa-T cell therapy in this setting will be a single-arm phase II study similar to that previously performed in Chen C, Siegel D, Gutierrez M, et al. Safety and efficacy of selinexor in relapsed or refractory multiple myeloma and Waldenstrom macroglobulinemia. Blood. 2018; 131(8):855-863 to evaluate a novel anti-cancer drug. For this phase II study, the Rapa-T cell therapy will be administered, as described in FIGS. 30, 31, and 32A-32C. The statistical goal of the study will be to determine whether the Rapa-T cell therapy can induce a significant rate of at least partial remission of the penta-refractory MM, as defined by a rate that is at least consistent with 30%.

Must have a potential source of autologous T cells potentially sufficient to manufacture manufactured T cells. Specifically, the patient must have either a sufficient number of previously cryopreserved PBSC units available for manufacturing (defined by total $CD34^+$ content of >2 million cells/kg) or a sufficient number of circulating T cells that can be harvested by steady-state apheresis (defined by an ALC of greater than 300 cells per microliter).

Patients must be at least two weeks from myeloma therapy, major surgery, radiation therapy, participation in other investigational trials and have recovered from clinically significant toxicities of these prior treatments (resolution of CTCAE toxicity to value of 2 or less). Cardiac ejection fraction (EF) by MUGA or 2-D echocardiogram must be within institution normal limits, with an EF level of at least 40%. Kidney function as measured by serum creatinine must be less than or equal to 2.5 mg/dl. Liver function must be adequate, as measured by AST and ALT less than or equal to 3× upper limit of normal and Total Bilirubin less than or equal to 1.5 (except if due to Gilbert's disease). Lung function must be adequate, as defined by corrected DLCO greater than or equal to 50% of expected on Pulmonary Function Tests. There must be no history of abnormal bleeding tendency. Voluntary written consent must be given before performance of any study related procedure not part of standard medical care, with the understanding that consent may be withdrawn by the patient at any time without prejudice to future medical care.

Randomized Phase III Trial: Standard of Care Therapy

To prove the benefit of the manufactured T cell therapy, a randomized study will be performed to formally compare the results of manufactured T cell therapy with standard-of-care therapy, which will consist of either the DPd, DRd, or KRd regimens; the regimens will be administered as prescribed in the literature, according to their FDA approved status for MM patients in the second or third relapse.

Example 7

Figure 34A:
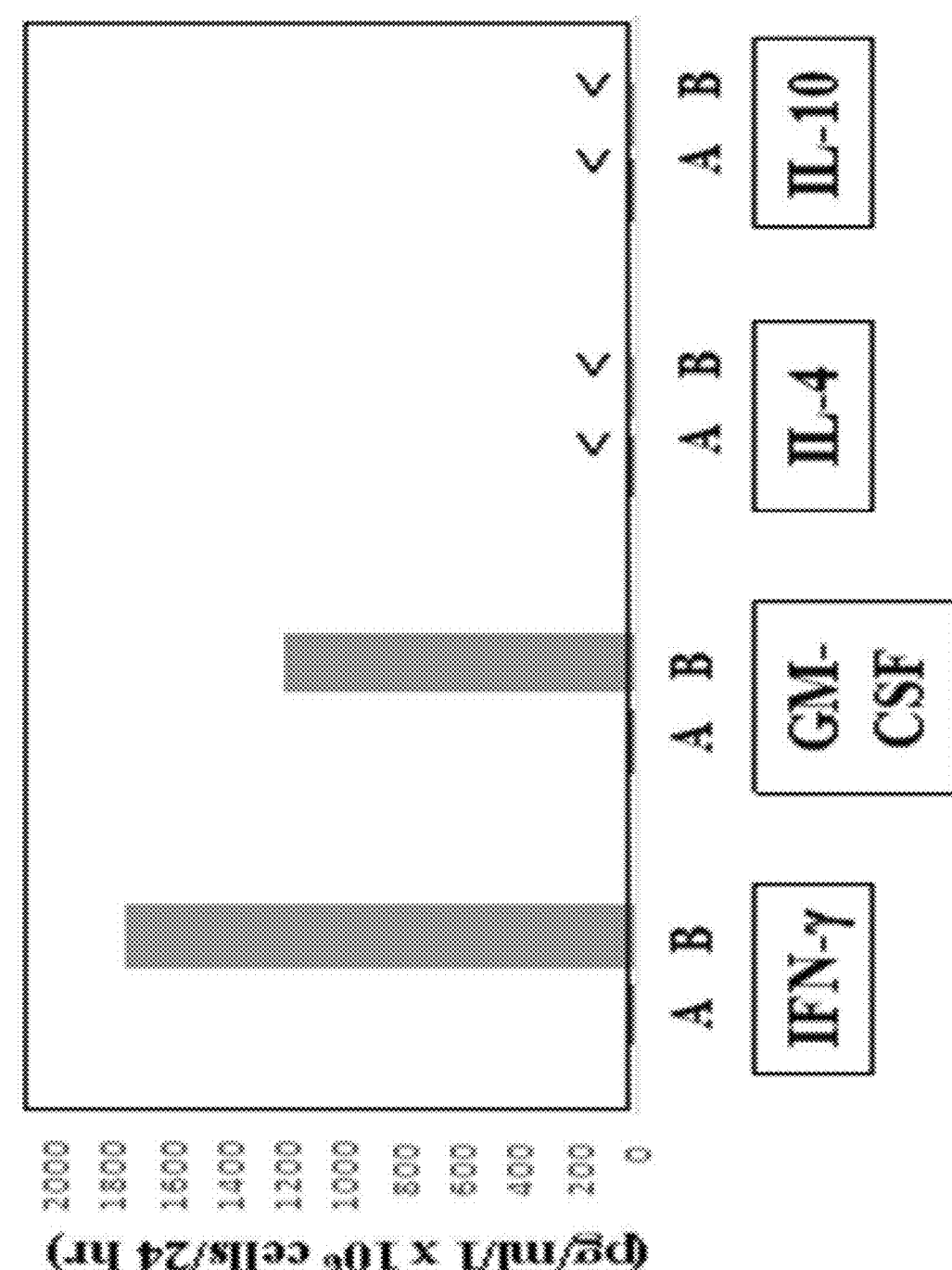
FIG. 34A depicts cytokine secretion by RAPA-T cells after exposure to pancreatic cancer cells.
Figure 34B:
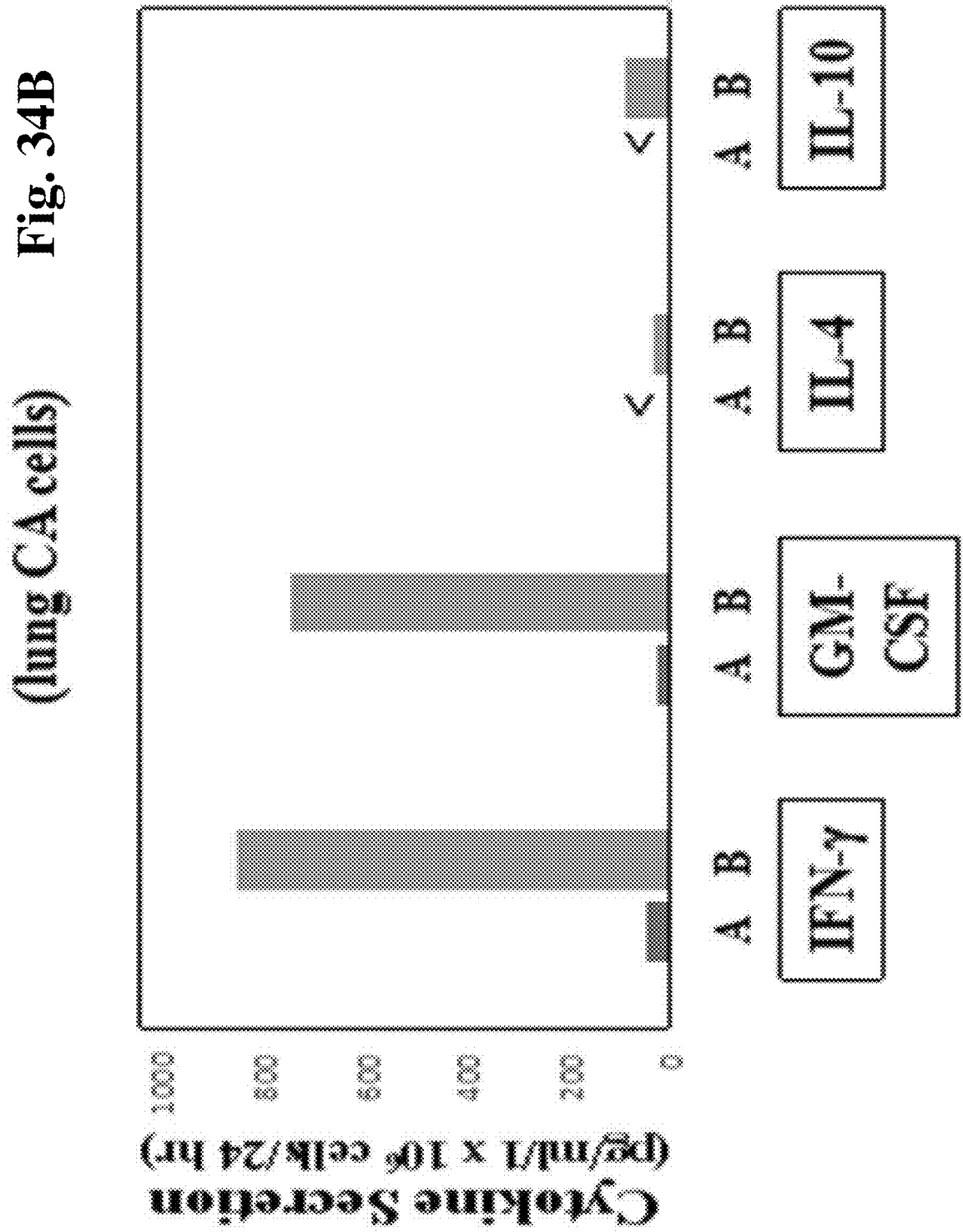
FIG. 34B depicts cytokine secretion by RAPA-T cells after exposure to lung cancer cells.

Steady-state apheresis was performed to obtain patient samples containing PBMCs Lymphocytes in the samples were enriched by using an automated Ficoll procedure on a Sepax® instrument by GE The lymphocyte-enriched cell populations were then plated in G-REX culture vessels and cultured for 6 days in TexMACS media (without serum supplementation; no IL-2 supplementation) and containing IFN-α, temsirolimus and basiliximab. At the end of manufacturing, the resulting Th1/Tc1 cells were exposed to either pancreatic cancer cells (MIA-Paca2 cell line) or lung cancer cells (H23 cell line) that were rendered apoptotic by exposure to etoposide. Pulsing with this tumor lysate was followed by 7 days in culture in IL-2 (200 IU/mL), at which time a secondary exposure to tumor lysate was performed. After an additional 7 day culture interval in IL-2 containing media, a tertiary tumor lysate exposure was performed and the resultant 24-hour supernatant was tested for cytokine content by Luminex assay (results shown are in pg/mL per $1\times10^6$ cells per 24 hours). Results for the cytokine assay are shown in FIGS. 34A-B. Condition A indicates pulsing with a sub-optimal formulation of the tumor lysate; condition B represents the optimal formulation of the tumor lysate. "<" indicates that the value was below the detection limit.

As shown in FIGS. 34A-B, RAPA-T cells can be further characterized by their capacity to respond to lysate harvested from etoposide-treated tumor cells, including solid tumors such as pancreatic cancer cells and lung cancer cells. As further shown in FIGS. 34A-B, the RAPA-T cells can maintain the characteristic Th1 cytokine phenotypes, as evidenced by high level secretion of IFN-γ and GM-CSF, and a reduced secretion of Th2 cytokines IL-4 and IL-10.

In another experiment, at the end of manufacturing, the resulting Th1/Tc1 cells were exposed to lysate harvested from either pancreatic cancer cells (MIA-Paca2 cell line) or lung cancer cells (H23 cell line) that were rendered apoptotic by exposure to etoposide. Pulsing with this tumor lysate was followed by 7 days in culture in IL-7 (20 ng/mL) and IL-15 (10 ng/mL), at which time a secondary exposure to tumor lysate was performed. After an additional 7 day culture interval in IL-7 and IL-15 containing media, a tertiary tumor lysate exposure was performed and the resultant 24-hour supernatant was tested for cytokine content by Luminex assay (results shown are in pg/mL per $1\times10^6$ cells per 24 hours). A control culture ("RAPA-201, No Tumor") consisted of the manufactured resistant Th1/Tc1 cells that were propagated in IL-7 and IL-15 containing media but did not receive pulsing with the tumor lysate. Results for the cytokine assay are shown in FIG. 35.

Figure 35:
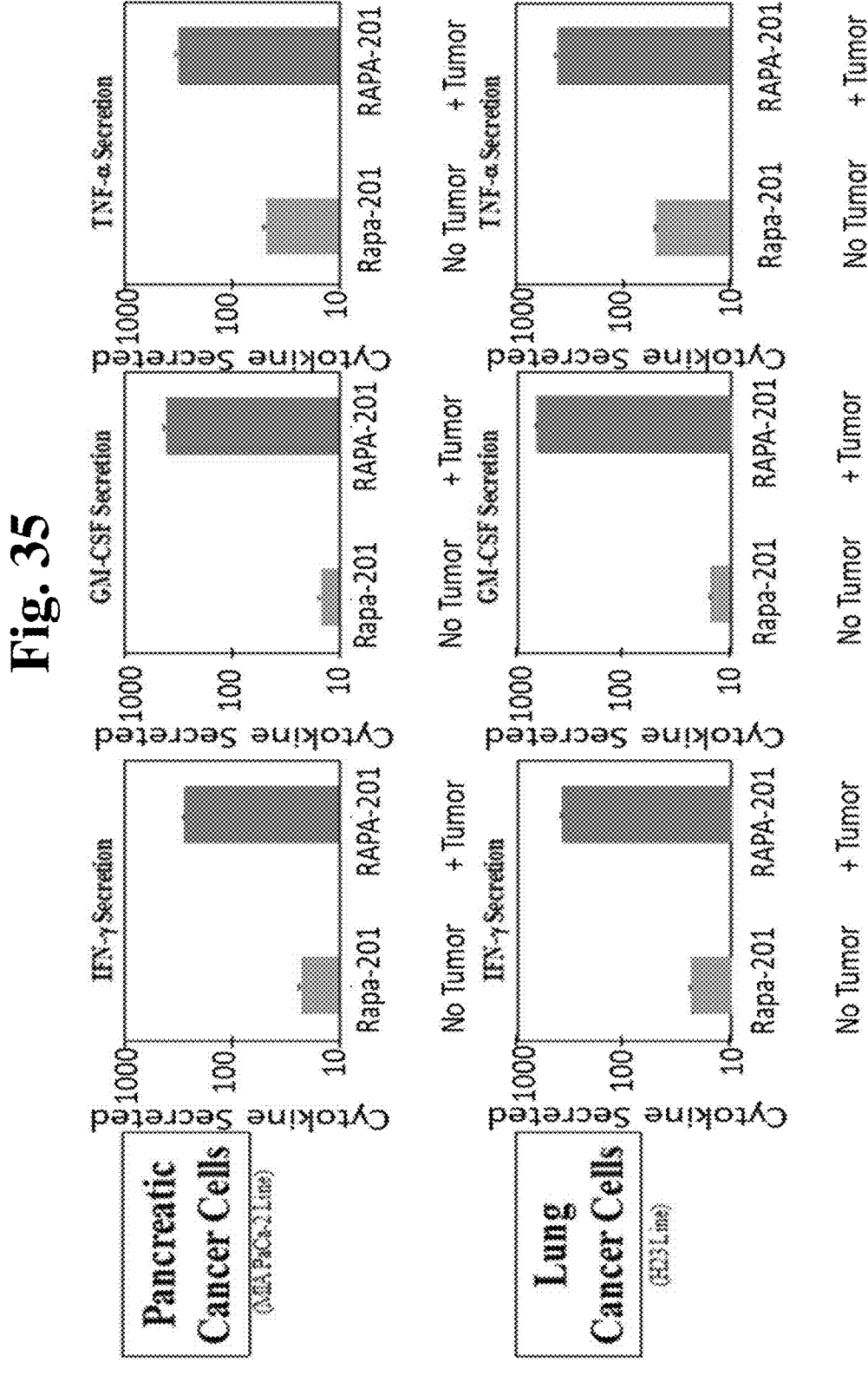
FIG. 35 depicts cytokine secretion by RAPA-T cells with or without exposure to pancreatic or lung cancer cells.

As shown in FIG. 35, RAPA-T cells can be further characterized by their capacity to respond to tumor cells, including solid tumors such as pancreatic cancer cells and lung cancer cells. This in vitro sensitization to solid tumor cell lines can be readily demonstrated by culture expansion in media supplemented with IL-7 and IL-15, which are two homeostatic cytokines that have been shown to selectively drive the effector function of RAPA-T cells. RAPA-T cell cytokine secretion to the tumor cells can maintain the characteristic Th1 cytokine phenotype, as evidenced by high level secretion of IFN-γ, GM-CSF and TNF-α.

Figure 36:
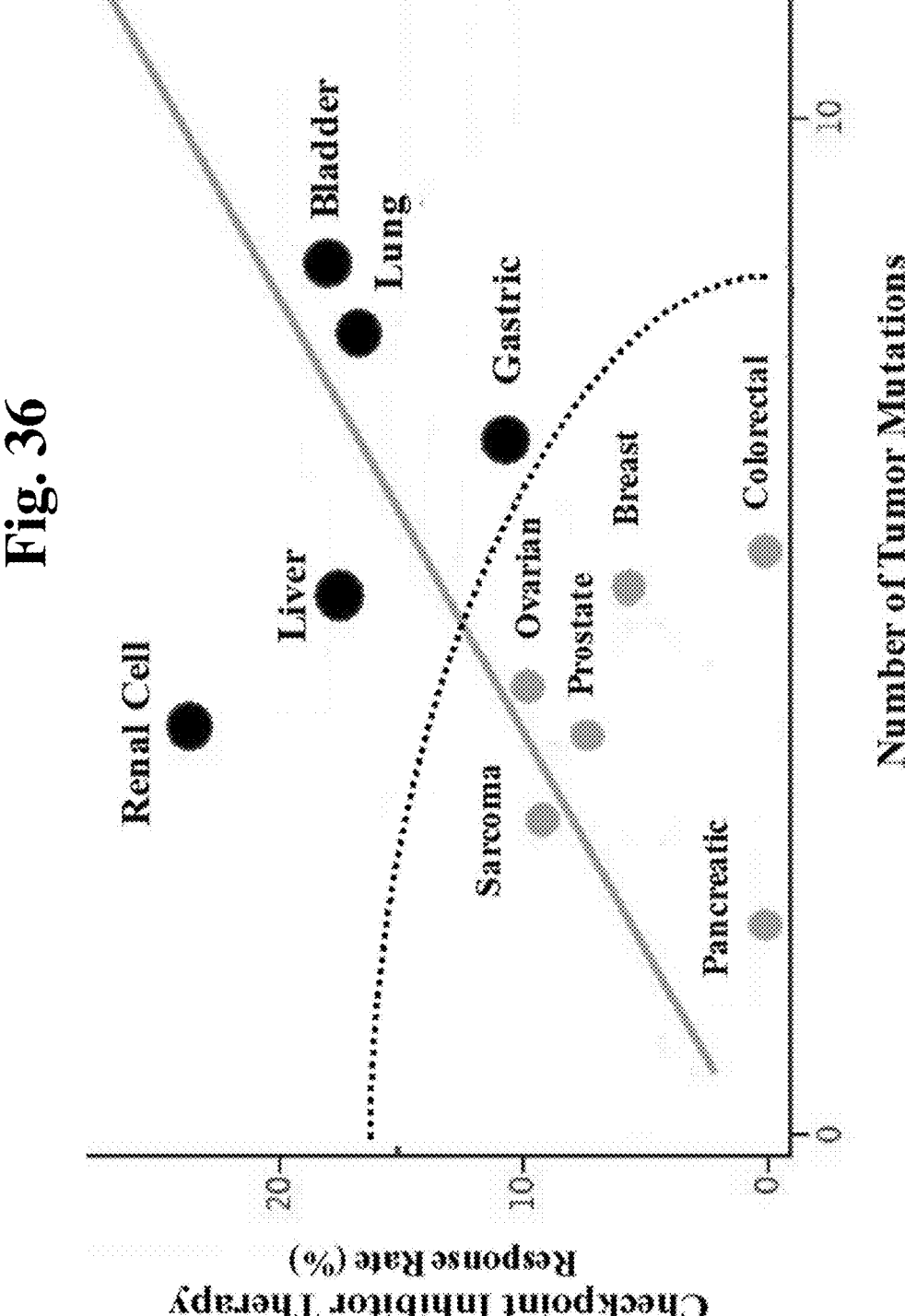
FIG. 36 depicts a correlation between checkpoint inhibitor therapy response and the number of tumor mutations in various cancer types.

As shown in FIG. 36, numerous cancers, such as renal cell carcinoma, liver cancer, lung cancer, bladder cancer and gastric cancer have been shown to be responsive to checkpoint inhibitor therapy such as monoclonal therapy against checkpoint inhibitor molecules such as PD-1 and CTLA4 which can induce remission in solid tumors. In a further experiment, under a Simon's 2-stage Design, patients (n=7) with renal cancer, lung cancer, liver cancer, gastric cancer, bladder cancer and low mutation PDL1-negative or low mutation rate cancers will be administered manufactured T cell therapy. If any cohort has at least one responsive patient, the cohort will be expanded to a 20 patient cohort.

Without being bound to theory, it is expected that the Rapa-T cells can provide therapeutic benefit in cancer because the cells have reduced or no checkpoint inhibitor receptors. It is suspected that certain cancers may be non-responsive to certain treatment because of checkpoint inhibitor receptors other than PD1 and CTLA4. Thus, it is expected, without being bound to theory that the Rapa-T cells, due to the lack of additional checkpoint inhibitor receptors may be effective in treating other cancers.

Example 8

Rapa-T cells were manufactured by a 6-day culture, with the post-Ficoll cell population cultured in media containing temsirolimus (2 μM) and the anti-IL-2 receptor monoclonal antibody, basiliximab (30 μg/mL). After 24 hours, the culture was supplemented with IFN-α (20,000 IU/mL) there was no IL-2 supplementation of culture. There was no form of anti-CD3/anti-CD28 co-stimulation used in the culture.

In contrast, for the "control": the post-Ficoll cell population was cultured in media without temsirolimus and without basiliximab. The cells were co-stimulated on the day of culture initiation with anti-CD3/anti-CD28 coated beads at a bead-to-T cell ratio of 3:1. The media was supplemented on the day of culture initiation with IL-2 (20 IU/mL) and IFN-α (20,000 IU/mL). Mean fluorescence intensity (MFI) for BTLA, CTLA4, PD1 and TIM3 was measured by flow cytometry for the CD4+ and CD8+ T cells subsets for the culture input population, the Rapa-T cells and the control cells. Data are shown in Table 2 below. A reduction in checkpoint inhibitor receptor expression was seen as between the Rapa-T and control cells with the MFI for each checkpoint being approximately the same for the Rapa-T cells and the culture input cells.

TABLE 2

| Mean Fluorescence Intensities | | | | |
| --- | --- | --- | --- | --- |
| Checkpoint | Day 0 Culture Input | Day 6 Rapa-T | Day 6 T-Rapa | Percent Reduction (Rapa-T v. T-Rapa) |
| BTLA | CD4+ | 3.59 | 3.70 | 92% |
| | CD8+ | 3.02 | 3.89 | 79% |
| CTLA4 | CD4+ | 3.13 | 2.93 | 100% |
| | CD8+ | 3.10 | 3.04 | 100% |
| PD1 | CD4+ | 2.92 | 3.10 | 90% |
| | CD8+ | 3.13 | 3.03 | 100% |
| TIM3 | CD4+ | 3.80 | 3.57 | 100% |
| | CD8+ | 3.03 | 3.10 | 96% |

Example 9: Sensitized, Manufactured T Cells Produced from Manufactured T Cells Exposed to an Immunogenic Composition of Tumor Lysate Manufactured T cells for this and all of the following examples were produced by the following procedure: peripheral blood apheresis PBMC product was subjected to Ficoll gradient centrifugation and the resultant cells were plated at $15 \times 10^6$ cells/mL; at culture initiation, temsirolimus was added at a final concentration of 2 μM and basiliximab was added at a final concentration of 30 μg/mL; after 24 hours of culture, IFN-α was added to achieve a final concentration of 20,000 IU/mL; no other cytokines were added; no co-stimulation was provided; the manufactured T cells were harvested on day 6 of culture for further use.

The pancreatic cancer cell line MIA PaCa-2 and the lung cancer cell line H23 were treated for 72-hours with etoposide, an inducer of immunogenic cell death, at concentrations of 0.5, 5.0 and 50 μM. Briefly, a cell concentration of $5 \times 10^6$ tumor cells/mL was utilized to generate 100 μL of lysate, which was then used to directly stimulate manufactured T cells. That is, there was no separate T cell APC manufacturing step used for this experiment (lysate added directly to effector T cells). The tumor cell lysate was then added to manufactured T cells which were expanded in X-Vivo 20 media containing IL-2 (100 IU/mL), IL-7 (10 ng/mL), and IL-15 (10 ng/mL). After 10-days of culture, the resultant T cells were harvested and re-stimulated at a cell concentration of $1 \times 10^6$ cells/mL with 100 μL of the tumor lysate utilized at the initiation of culture; the resultant 24-hour supernatant was then tested for cytokine content by Luminex assay with results shown as cytokine content in pg per mL per 24-hours per $1 \times 10^6$ cells/mL as shown in FIG. 37.

Figure 37:
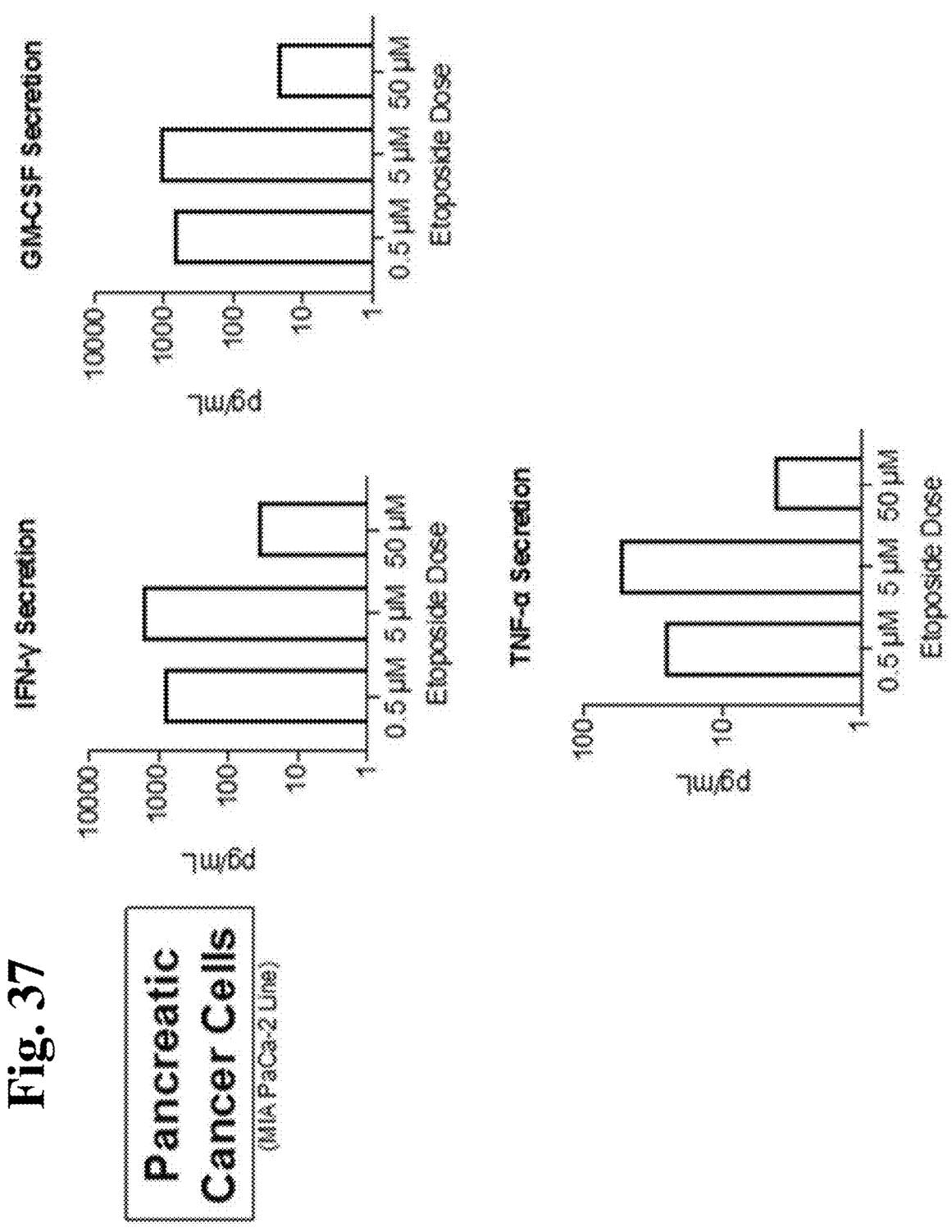
FIG. 37 depicts cytokine secretion by sensitized, manufactured T cells after re-stimulation with tumor lysate.

The results of this experiment, which are shown in FIG. 37, demonstrate that 72-hour incubation of the pancreatic cancer cell line MIA PaCa-2 or the lung cancer cell line H23 with etoposide at a concentration ranging from 0.5 to 5.0 μM was effective for sensitizing manufactured T cells to cytokine secretion in response to repeat exposure to lysate. In marked contrast, use of etoposide at the higher concentration of 50 μM was not effective for T cell sensitization. Therefore, in this system, use of etoposide at a concentration between 0.5 and 5.0 μM (and possibly higher, but below 50 μM) can be utilized to induce an immunogenic cell death; use of higher concentrations (50 μM or more), without being bound to theory, likely induces a necrotic-type of cell death that is not effective for T cell sensitization.

Example 10: Production of Loaded-Antigen Presenting T Cells by Exposure to Tumor Lysates and Anti-CD3/Anti-CD28 Co-Stimulation It was hypothesized, without being bound to theory, that anti-CD3/anti-CD28 co-stimulation might up-regulate APC function in the manufactured T cell population. To address this, during a 48 hour T cell APC generation step, anti-CD3/anti-CD28 coated magnetic beads were added to the T cells at a 1:1 bead-to-T cell ratio either on day 0 or day 1 of the 48 hour culture. If co-stimulation was provided at day 0, then the tumor lysate was added at day 1; conversely, if co-stimulation was provided at day 1, then the tumor lysate was added at day 0. For APC generation in this and all subsequent examples, a starting cell density of $2.5 \times 10^6$ cells/mL was used.

Figure 38A:
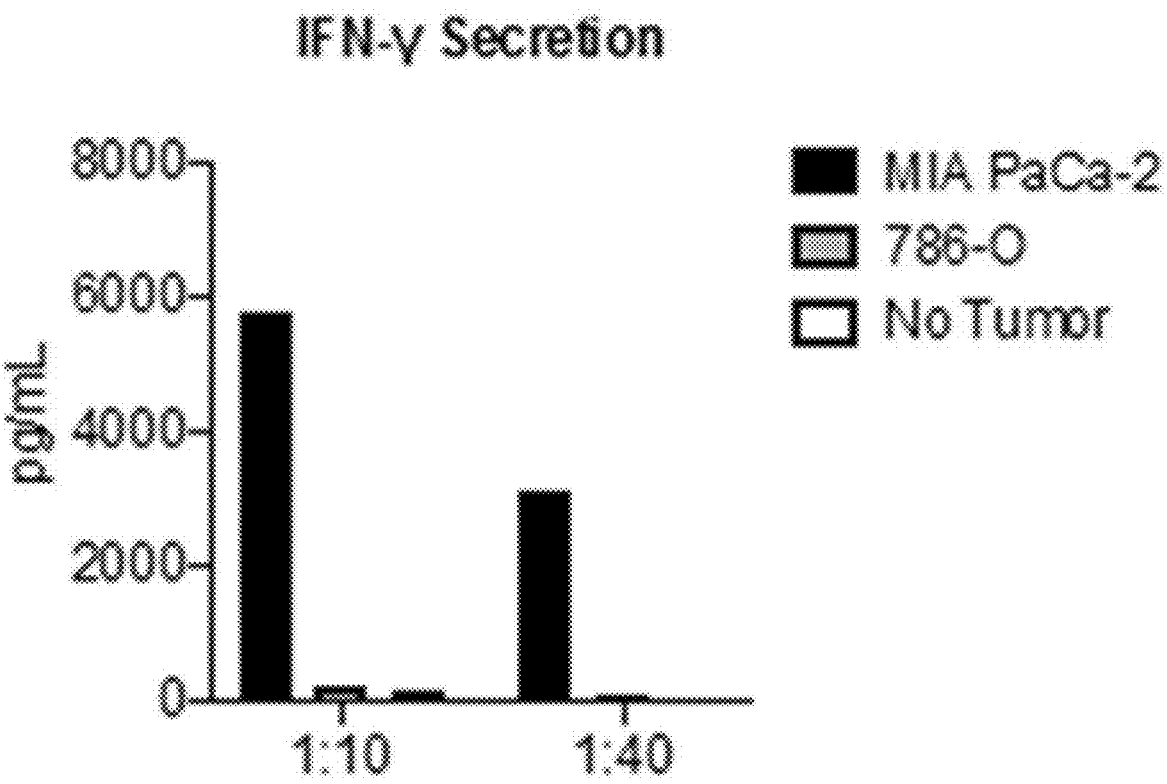
FIG. 38A depicts 24-hour IFN-γ secretion from responder T cells after re-stimulation with lysate-loaded, antigen-presenting T cells or no re-stimulation.
Figure 38B:
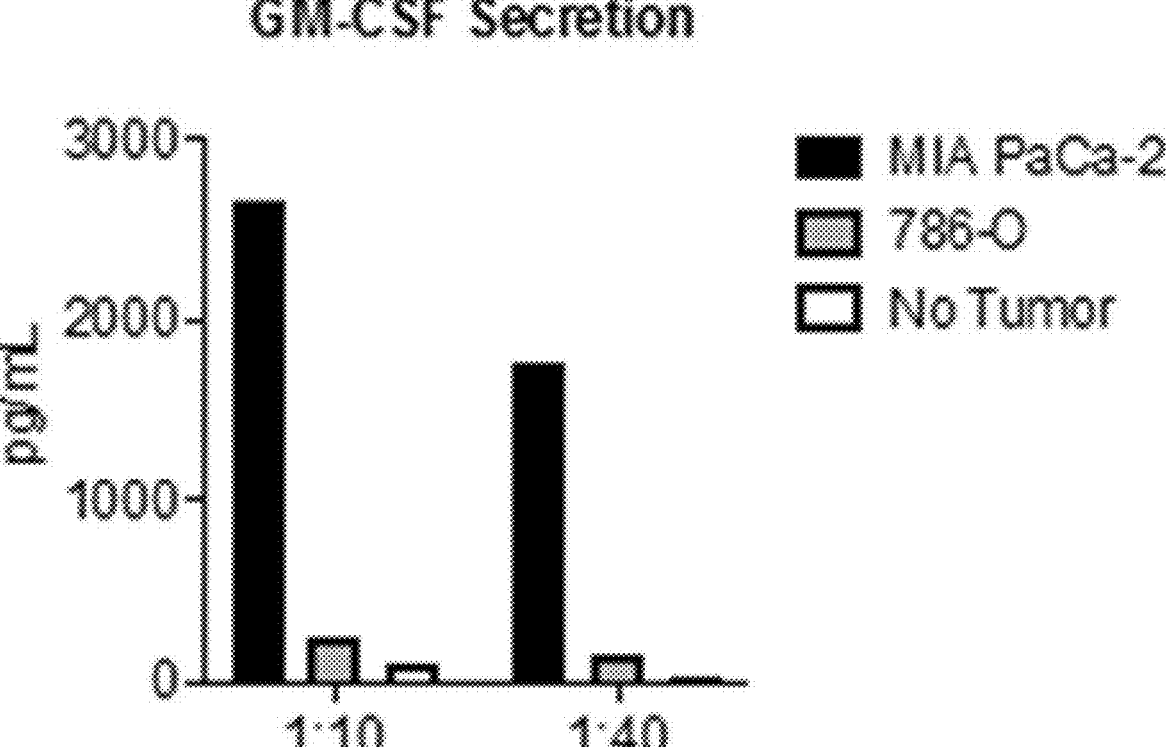
FIG. 38B depicts 24-hour GM-CSF secretion from responder T cells after re-stimulation with lysate-loaded, antigen-presenting T cells or no re-stimulation.
Figure 38C:
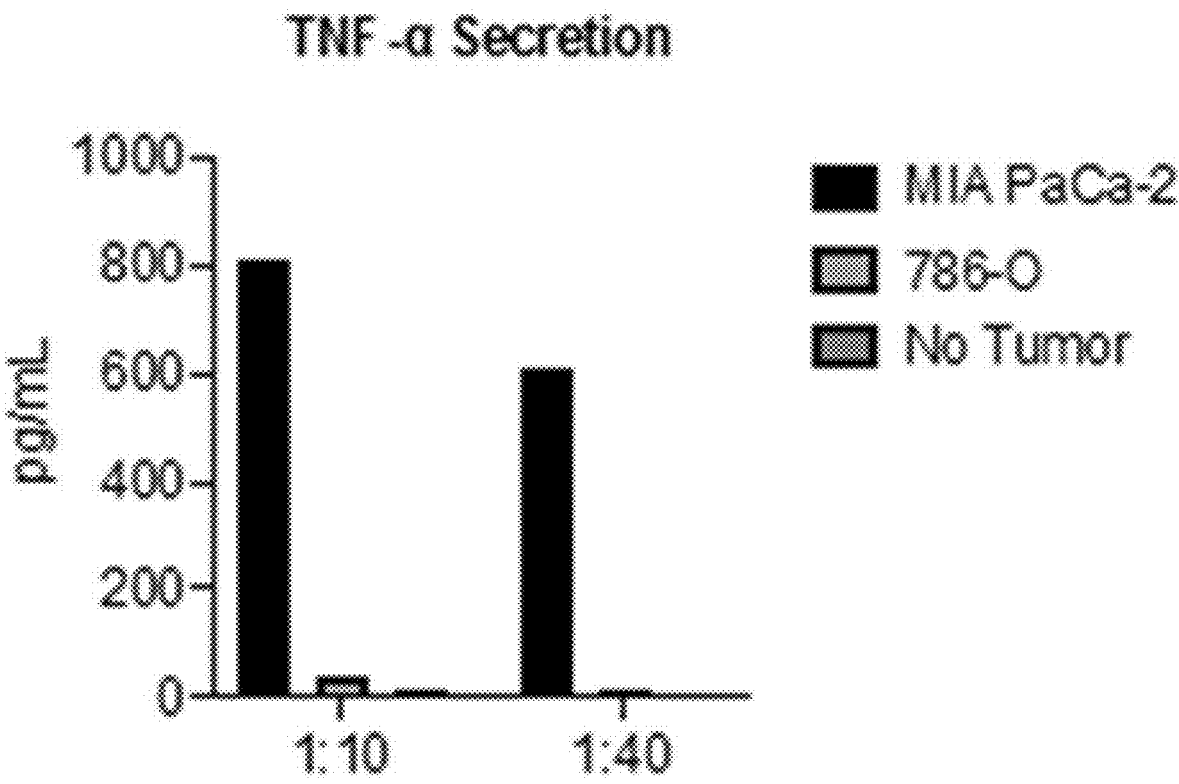
FIG. 38C depicts 24-hour TNF-α secretion from responder T cells after re-stimulation with lysate-loaded, antigen-presenting T cells or no re-stimulation.
Figure 38D:
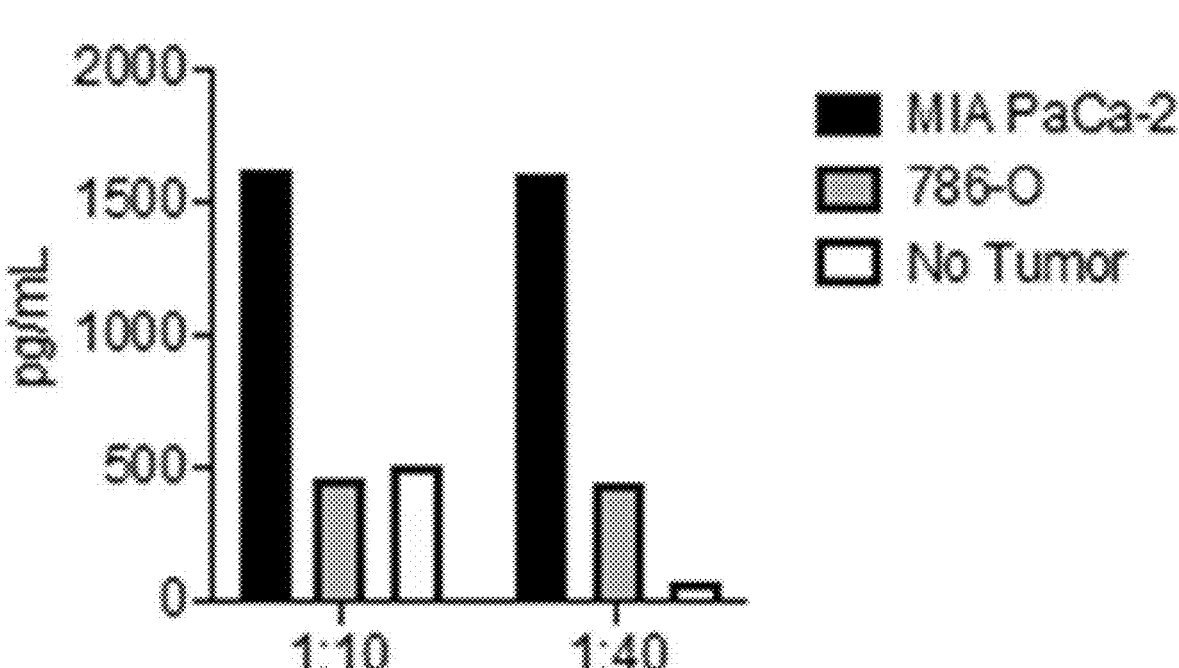
FIG. 38D depicts 24-hour IFN-γ secretion from responder T cells after re-stimulation with lysate-loaded, antigen-presenting T cells or no re-stimulation.
Figure 38E:
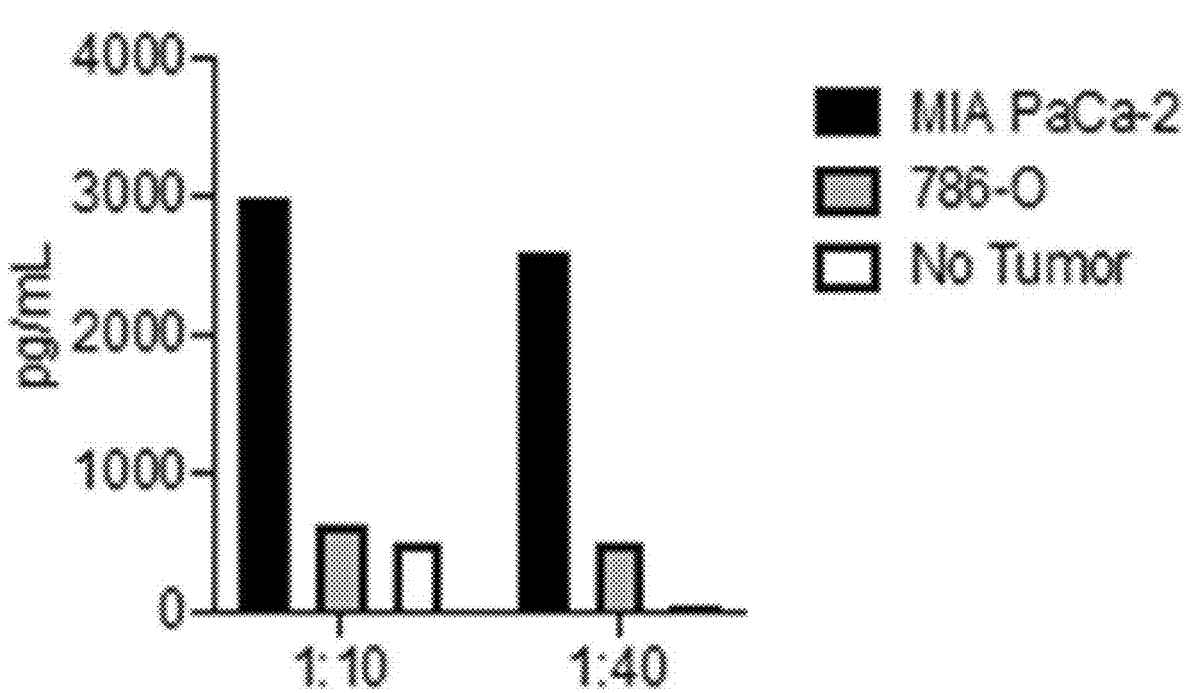
FIG. 38E depicts 24-hour GM-CSF secretion from responder T cells after re-stimulation with lysate-loaded, antigen-presenting T cells or no re-stimulation.
Figure 38F:
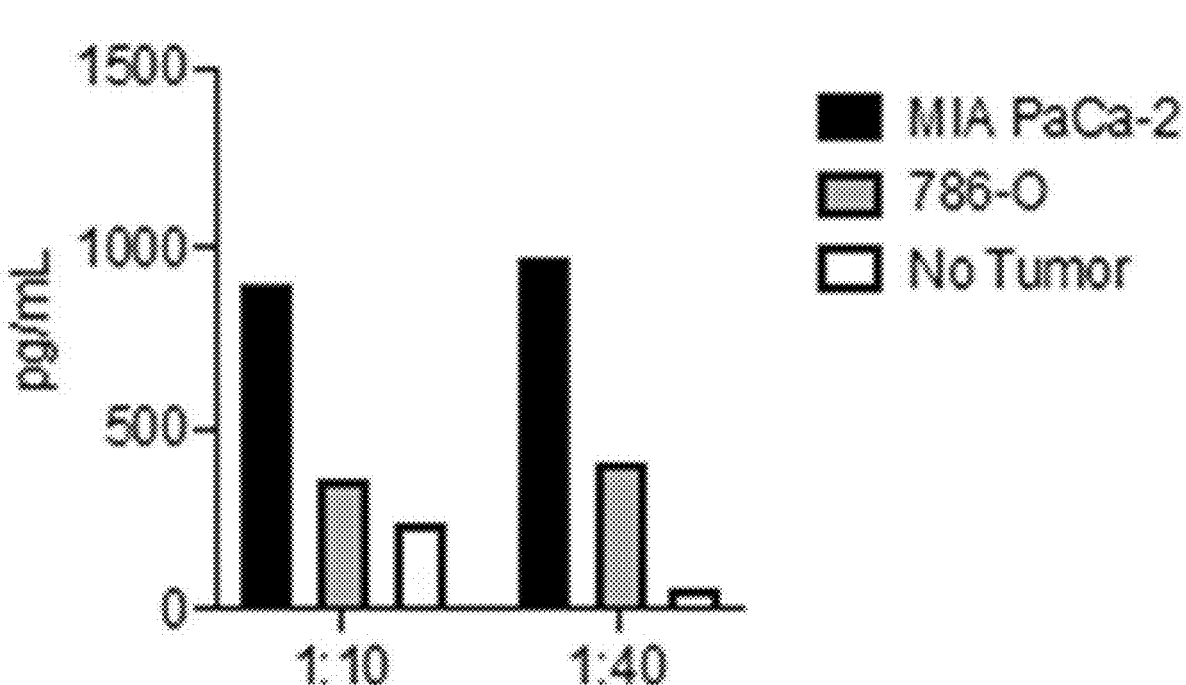
FIG. 38F depicts 24-hour TNF-α secretion from responder T cells after re-stimulation with lysate-loaded, antigen-presenting T cells or no re-stimulation.

As detailed above, T cells manufactured according to the present disclosure were utilized as the responder T cell population and a modified population of such T cells were utilized to serve as APC for presentation of tumor lysate from the pancreatic cancer cell line, MIA PaCa-2. For APC generation, the manufactured T cells were cultured for 48 hours in media containing cytokines (IL-7 [10 ng/mL], IL-15 [10 ng/mL], GM-CSF [100 ng/mL], and IL-4[1000 IU/mL]). A lysate derived from etoposide-treated MIA PaCa-2 pancreatic cancer cells, prepared as described below, was added either on day 0 [FIGS. 38A-38C] or on day 1 [FIGS. 38D-38F]. Co-stimulation (1:1 ratio of beads-to-T cells) was provided on either day 1 [FIGS. 38A-38C] or day 0 [FIGS. 38D-38F] of the 48 hour APC generation interval. For etoposide incubation of tumor cell lines (for all experiments), a cell concentration of $5 \times 10^6$ tumor cells/mL was utilized to generate 100 μL of lysate, with this amount of lysate used to pulse $2.5 \times 10^6$ T cells for APC generation. After 10 days of APC T cell-to-responder T cell co-culture at the indicated ratios (1:10 and 1:40) starting with $1 \times 10^6$ responder T cells/mL on both day 0 and day 5 of co-culture, the resultant responder T cells were re-stimulated with further APC for 24 hours (APC pulsed with either the relevant MIA PaCa-2 lysate ["MIA PaCA-2"] or a control lysate from 786-0 renal cell carcinoma cells ["786-0"]); the resultant supernatant was then tested for cytokine content by Luminex assay, with results presented as pg/mL per 24-hours per $1\times10^6$ cells/mL. As an additional control, resultant T cells were plated for 24-hour supernatant generation alone, without any tumor lysate or APC stimulation ("No Tumor").

The results from this experiment are shown in FIGS. 38A-38F. In this experiment, the responder T cells manufactured according to the present disclosure (manufactured T cells), when co-cultured ex vivo with T cells that were modified for APC characteristics, developed increased reactivity to lysate-pulsed APC (lysate from MIA PaCa-2 pancreatic cell line). Importantly, T cell response to the lysate-pulsed APC was observed at an APC-to-responder ratio of both 1:10 and 1:40, thereby suggesting a relatively potent APC function. In addition, T cell response was observed with both forms of T cell APC (provision of co-stimulation at day 0 or day 1 of the 48-hour culture); therefore, T cell APC generation can be performed with either sequence (tumor lysate 4 co-stimulation [result shown in FIGS. 38A-38C] or co-stimulation 4 tumor lysate [result shown in FIGS. 38D-38F]). We also envision that tumor lysate and co-stimulation can be performed concomitantly during various points of the 48-hour APC generation interval. However, it should be noted that the sequence of tumor lysate followed by co-stimulation (FIGS. 38A-38C) resulted in the highest levels of specific secretion of IFN-γ and resulted in the lowest background levels of cytokine secretion in the control re-stimulation conditions. Therefore, the APC generation sequence that utilizes lysate exposure followed by co-stimulation may, without being bound to theory, be favorable and was therefore selected for further experiments.

Figure 39:
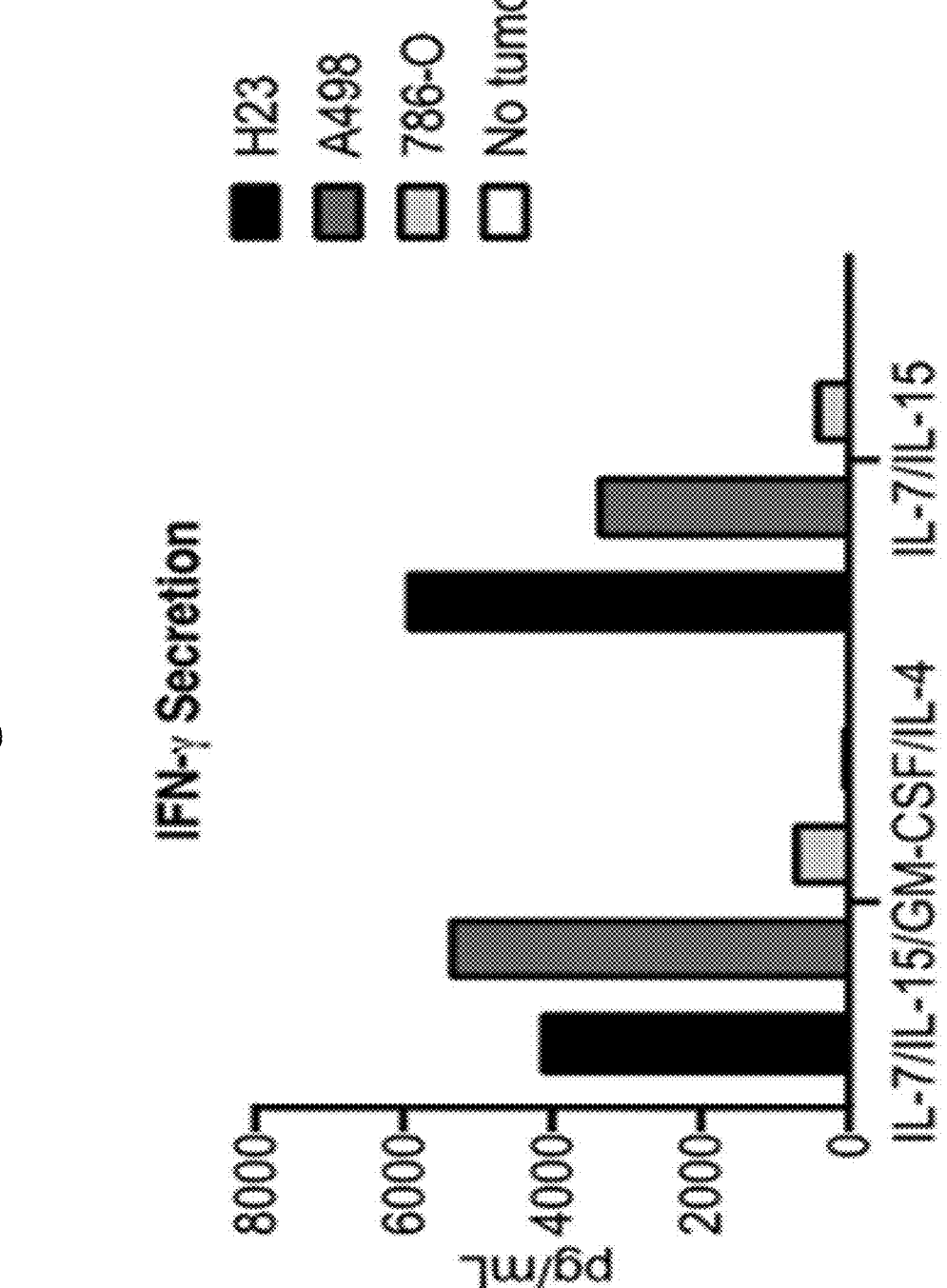
FIG. 39 depicts 24-hour IFN-γ, GM-CSF and TNF-α secretion from responder T cells after re-stimulation with lysate-loaded, antigen-presenting T cells or no re-stimulation.
Figure 39:
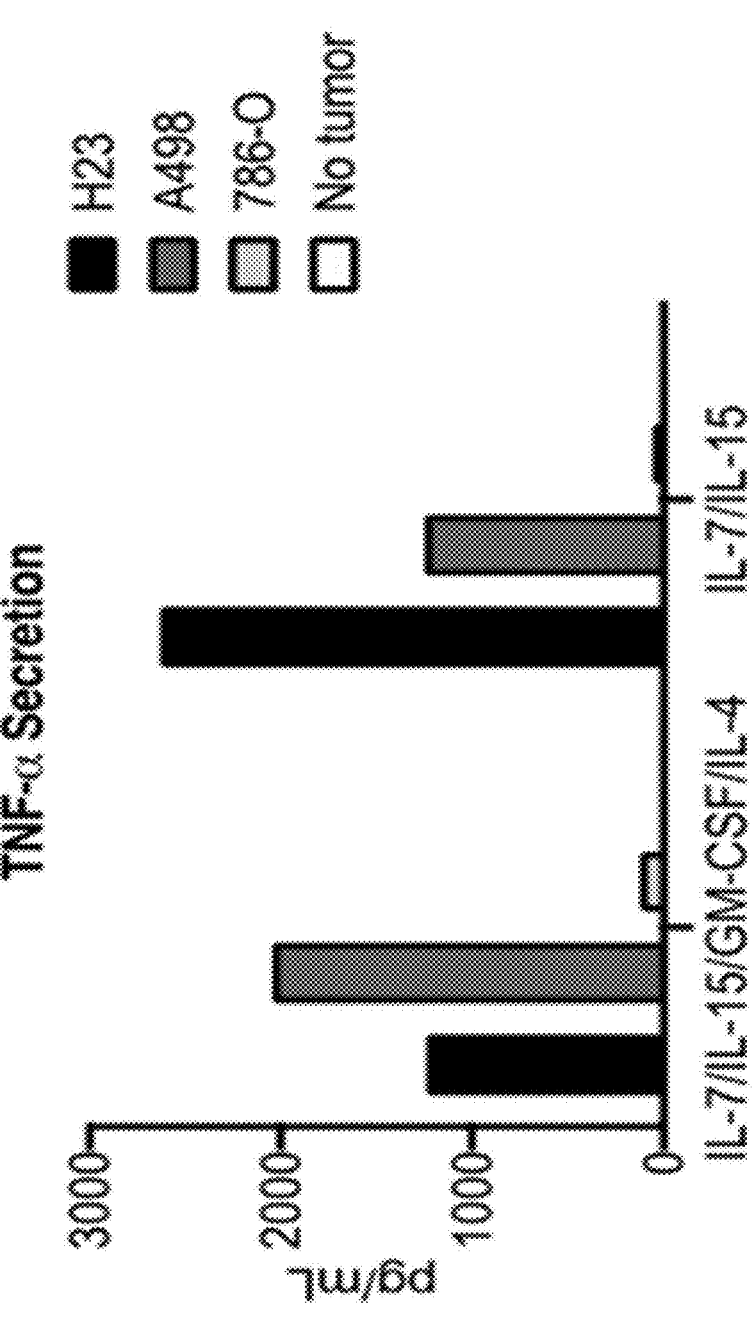
Figure 39:
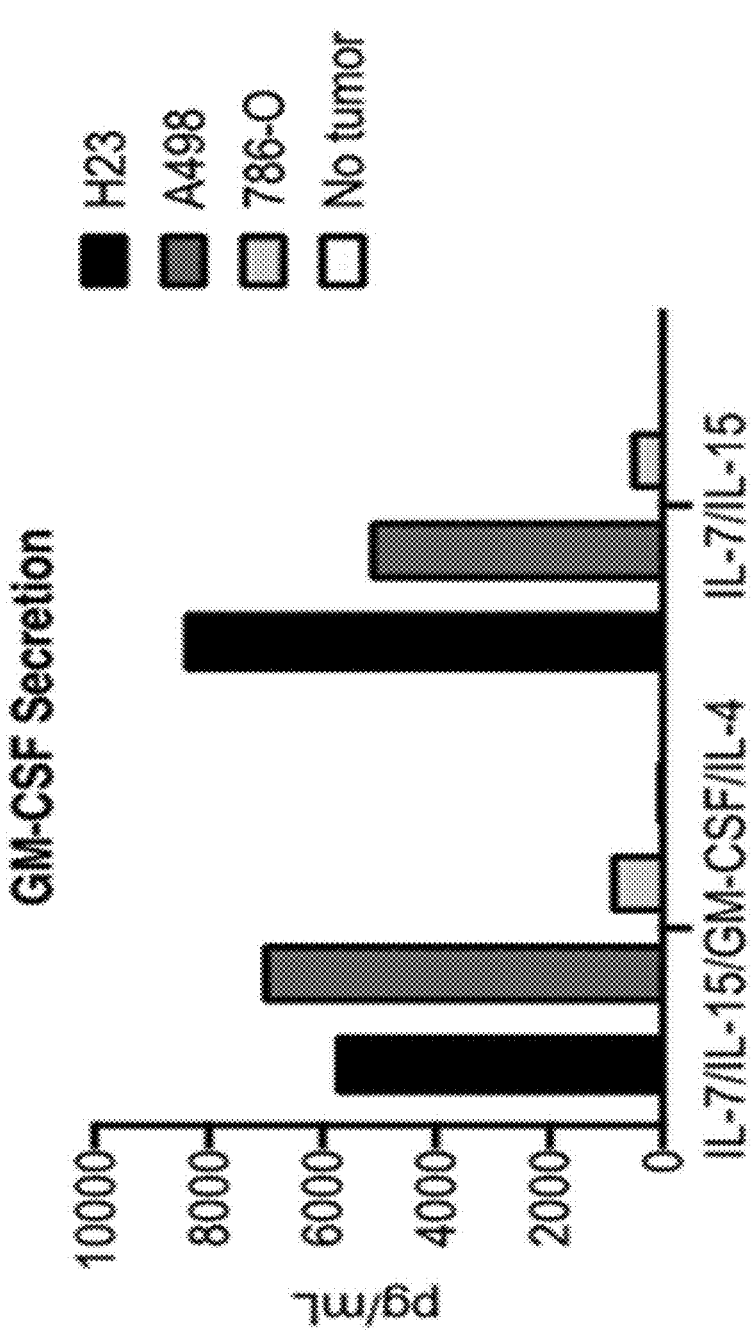

Example 11: Evaluation of Culture Conditions for Antigen-Presenting T Cell Production An additional experiment was performed to better characterize the necessary cytokine environment for generation of the T cell APC population (antigen-presenting T cell population). Specifically, without being bound to theory, it was hypothesized that GM-CSF and IL-4, which are utilized for generation of APC derived from cells of myeloid lineage, may not be required for T cell APC generation. To address this, T cell APC (antigen-presenting T cells) manufactured using IL-7, IL-15, GM-CSF, and IL-4 were compared versus T cell APC (antigen-presenting T cells) manufactured using only IL-7 and IL-15 (this experiment utilized the lung cancer cell line H23 lysate for APC generation). The results of this experiment, which are shown in FIG. 39, indicate that IL-7 and IL-15 are sufficient for T cell APC generation, as both cytokine conditions resulted in T cells with the capacity for cytokine secretion in response to APC-loaded with H23 lysate and a separate lung cancer lysate (A498 cell line); cytokine secretion in response to APC loaded with a lysate from the renal cell carcinoma cell line 786-0 was nominal, as was autonomous cytokine secretion (no APC addition; media alone at re-stimulation).

As detailed above, T cells manufactured according to the present disclosure were utilized as the responder T cell population and a modified population of such T cells were utilized to serve as APC by presentation of tumor lysate from the lung cancer cell line, H23. For APC generation, the T cells were cultured for 48 hours in media containing two different cytokine conditions (IL-7, IL-15, GM-CSF (100 ng/mL), and IL-4 (1000 IU/mL) versus IL-7, IL-15; cytokines utilized at same concentrations as previously detailed) and a lysate derived from etoposide-treated H23 cancer cells. Co-stimulation (1:1 ratio of beads-to-T cells) was provided on day 1 of the 48-hour APC generation interval. After 10 days of APC T cell-to-responder T cell co-culture at the ratio of 1:40, the resultant responder T cells were re-stimulated with further APC for 24-hours; the resultant supernatant was then tested for cytokine content by Luminex assay, with results presented as pg/mL per 24-hours per $1\times10^6$ cells/mL. APC pulsed with A498 and 786-0 tumor cell lysates and a non-stimulated condition (no tumor cells, no APC) were used as controls during re-stimulation.

Example 12: Evaluation of Checkpoint Inhibitor on Antigen-Presenting T Cells An additional experiment was performed to determine whether blockade of the checkpoint inhibitor receptor PD1 can enhance the ability of the APC T cell population to sensitize responder T cells to the tumor lysate. It was hypothesized, without being bound to theory, that PD1 blockade, which is z successful strategy for improving anti-tumor responses in solid tumors, may not be contributory in the manufacturing method because the T cells generated according to present disclosure are checkpoint-deficient, including down-regulated PD1 expression. As detailed below, the T cell APC incubated with the lysate from the pancreatic cancer cell line MIA PaCa-2 successfully sensitized responder T cells to the lysate-exposed T cell APC; however, inclusion of an anti-PD1 monoclonal antibody (R&D Systems; Clone #913429; 1.0 ng/mL) during T cell co-culture did not increase this response. These results add further support to the conclusion that T cells manufactured according to the methods detailed in the present disclosure may have a functional advantage in terms of responding to solid tumors because of down-regulation of checkpoint inhibitory receptors.

Figure 40:
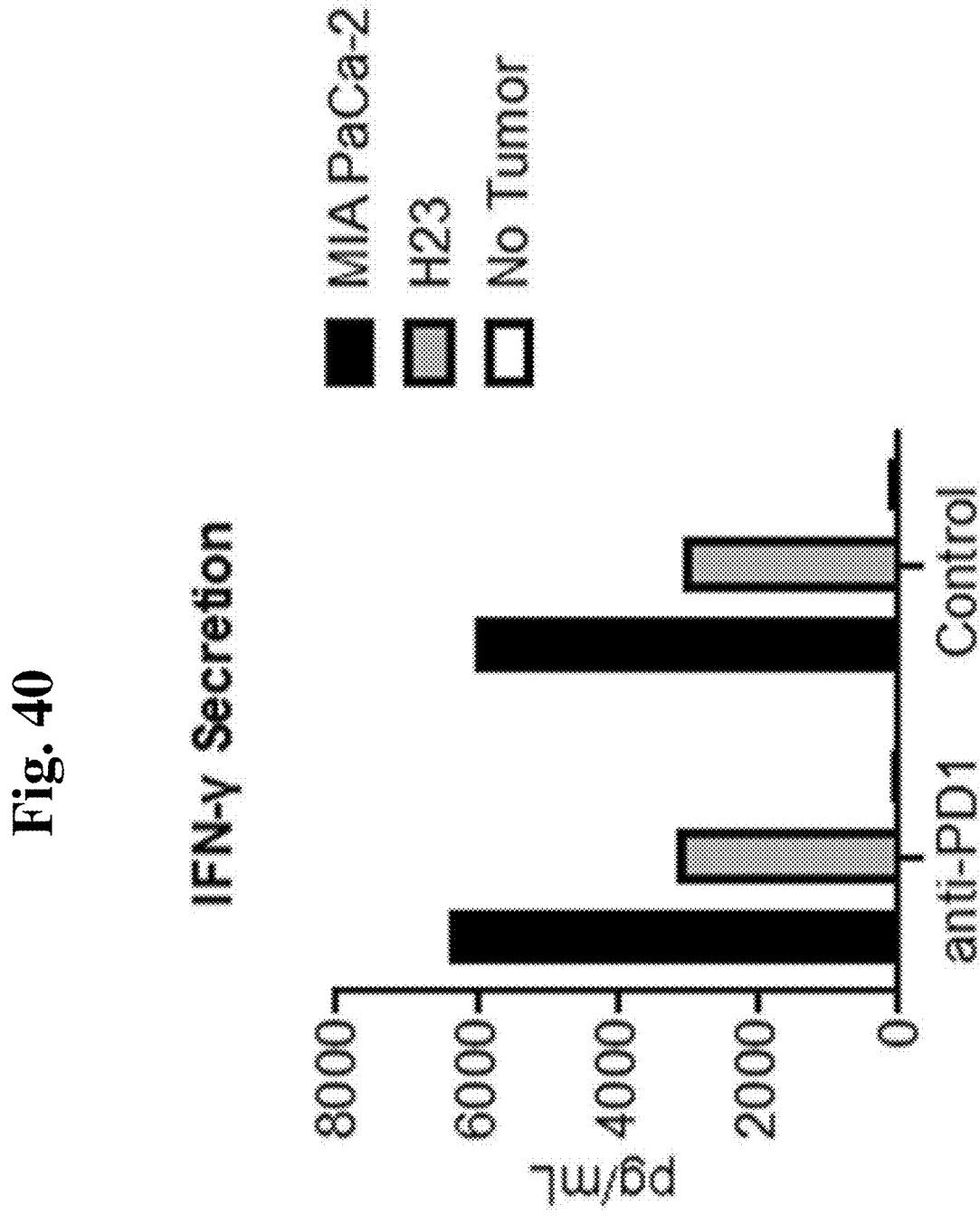
FIG. 40 depicts 24-hour IFN-γ, GM-CSF, TNF-α, and IL-2 secretion from responder T cells after re-stimulation with lysate-loaded, antigen-presenting T cells or no re-stimulation with or without anti-PD1 antibody.
Figure 40:
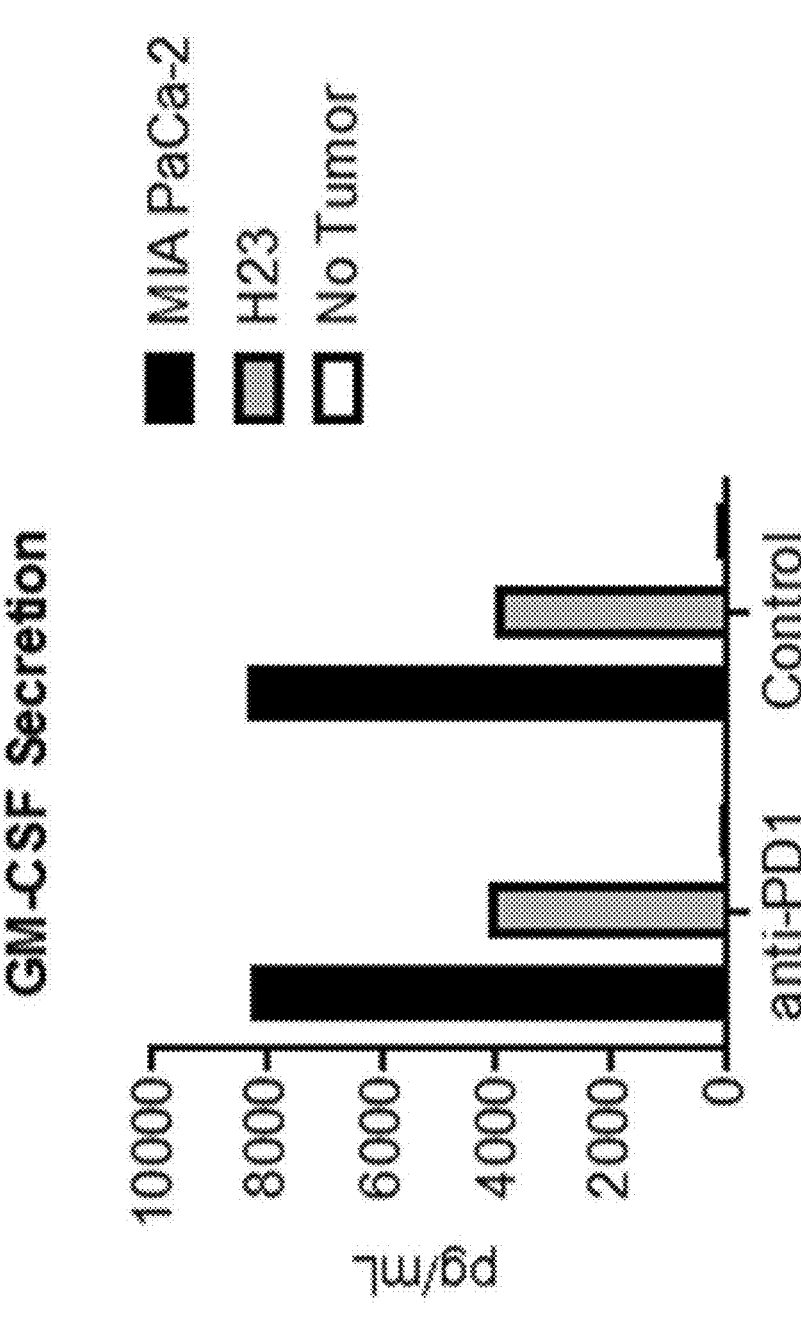
Figure 40:
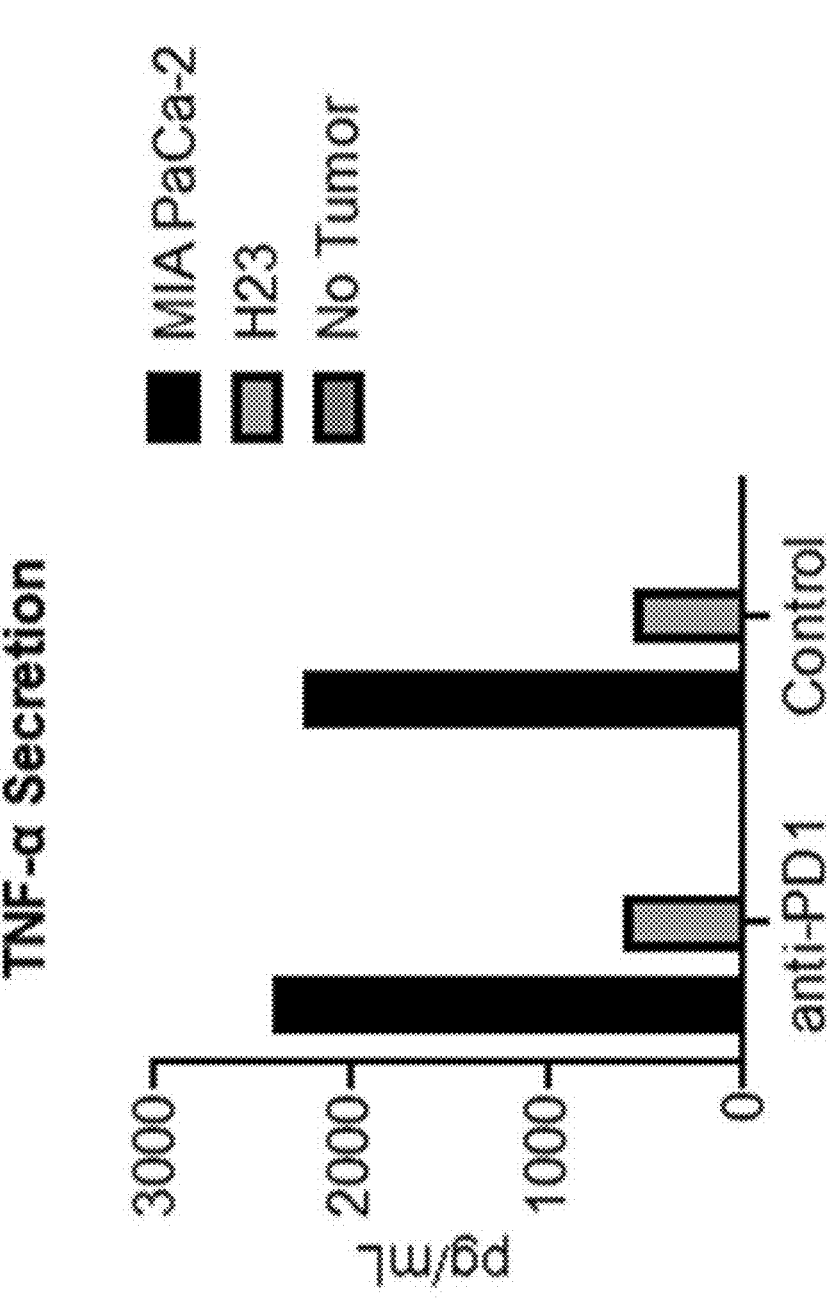
Figure 40:
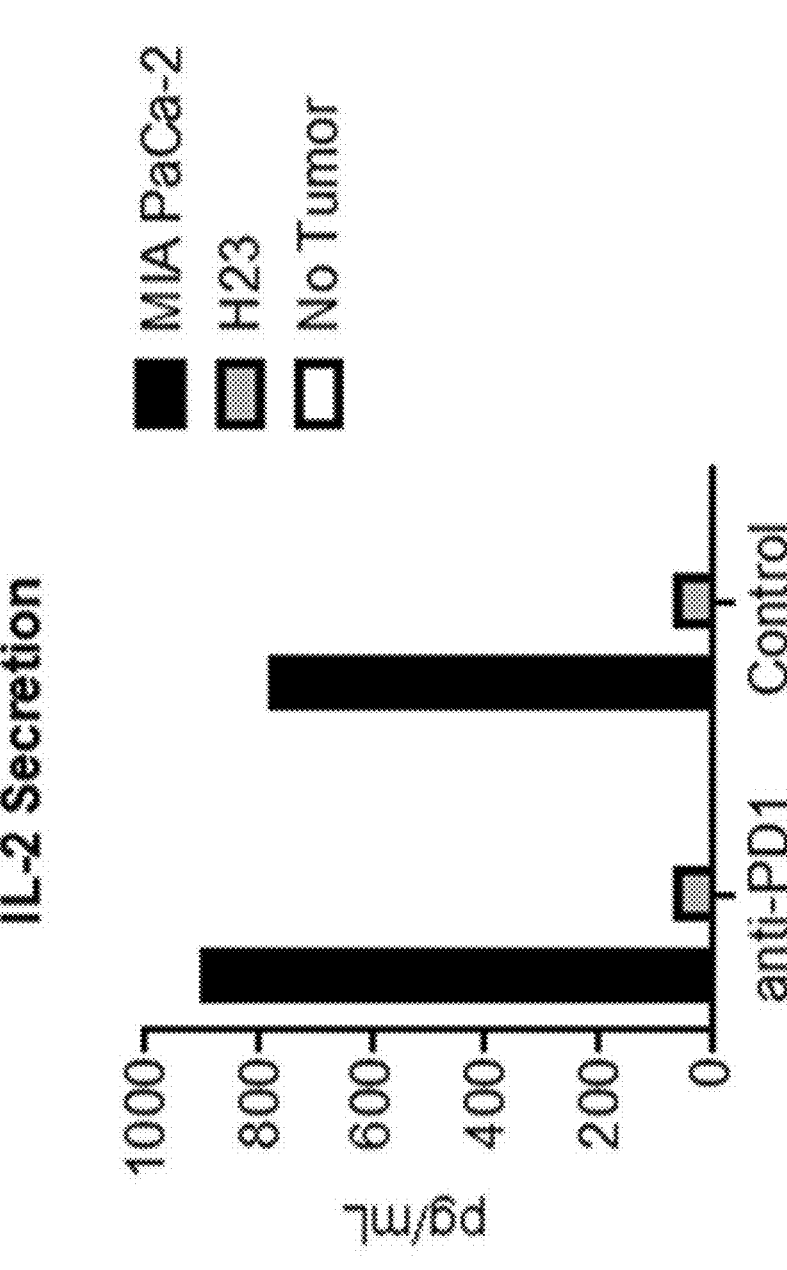

As detailed above, T cells manufactured according to the present disclosure were utilized as the responder T cell population and a modified population of such T cells were utilized to serve as APC by presentation of tumor lysate from the lung cancer cell line, H23. For APC generation, the T cells were cultured for 48-hours in cytokine-contained media (IL-7 and IL-15 at the same levels as previously noted) with further supplementation with a lysate derived from etoposide-treated MIA PaCa-2 cancer cells. Co-stimulation (1:1 ratio of beads-to-T cells) was provided on day 1 of the 48-hour APC generation interval. After 10-days of APC T cell-to-responder T cell co-culture at the indicated ratio on 1:40 in the presence ("anti-PD1", at 1 ng/mL) or absence ("Control") of anti-PD1 monoclonal antibody, the resultant responder T cells were stimulated with further APC in a tertiary stimulation for 24-hours. The resultant supernatant was then tested for cytokine content by Luminex assay, with results presented as pg/mL per 24-hours per $1\times10^6$ cells/mL in FIG. 40. APC pulsed with a control H23 lysate and a non-stimulated condition (no tumor cells, no APC) were used as controls during re-stimulation.

It is believed, without being bound to theory, that the T cells manufactured according to the present disclosure possess substantial APC function, which can be realized in a reproducible manner through 48-hour culture of the T cell product in the following conditions: use of media supplemented with 5% human AB serum; supplementation of media on day 0 of culture with IL-7 and IL-15; supplementation of media with tumor lysate generated from etoposide-exposed tumor cells of various tissue origins (all tumor types can be envisioned); and provision of T cell co-stimulation via anti-CD3, anti-CD28 coated magnetic beads (other methods of co-stimulation and T cell activation can be envisioned). It is important to note that the T cells manufactured according to the present disclosure are comprised of both CD4$^+$ and CD8$^+$ subsets. An additional experiment was also performed to evaluate whether the CD4$^+$ and CD8$^+$ T cells contributed equally to the observed T cell APC function in our manufacturing method.

Example 13: Evaluation of CD4$^+$ and CD8$^+$ Enrichment on Antigen-Presenting T Cell Production To address the role of CD4$^+$ and CD8$^+$ T cell subsets, the T cell APC was generated as previously described, namely, 48-hour culture of the manufactured T cell product using: media supplemented with 5% human AB serum; media supplementation with IL-7 and IL-15; addition of etoposide-exposed tumor cell lysate (day 0 of APC culture); and provision of co-stimulation (addition of anti-CD3, anti-CD28 coated beads on day 1 of APC culture at bead-to-T cell ratio of 1:1). However, prior to APC culture, the T cells were separated into three fractions, namely: unseparated ("CD4$^+$, CD8$^{+"}$"); CD4-enriched T cells ("CD4$^{+"}$"); and CD8-enriched T cells ("CD8$^{+"}$"); purification of fractions was performed by standard methods in the field (commercial antibody-bead purification), These three candidate APC populations were then tested for their ability to sensitize responder T cells to the tumor lysate.

Figure 41:
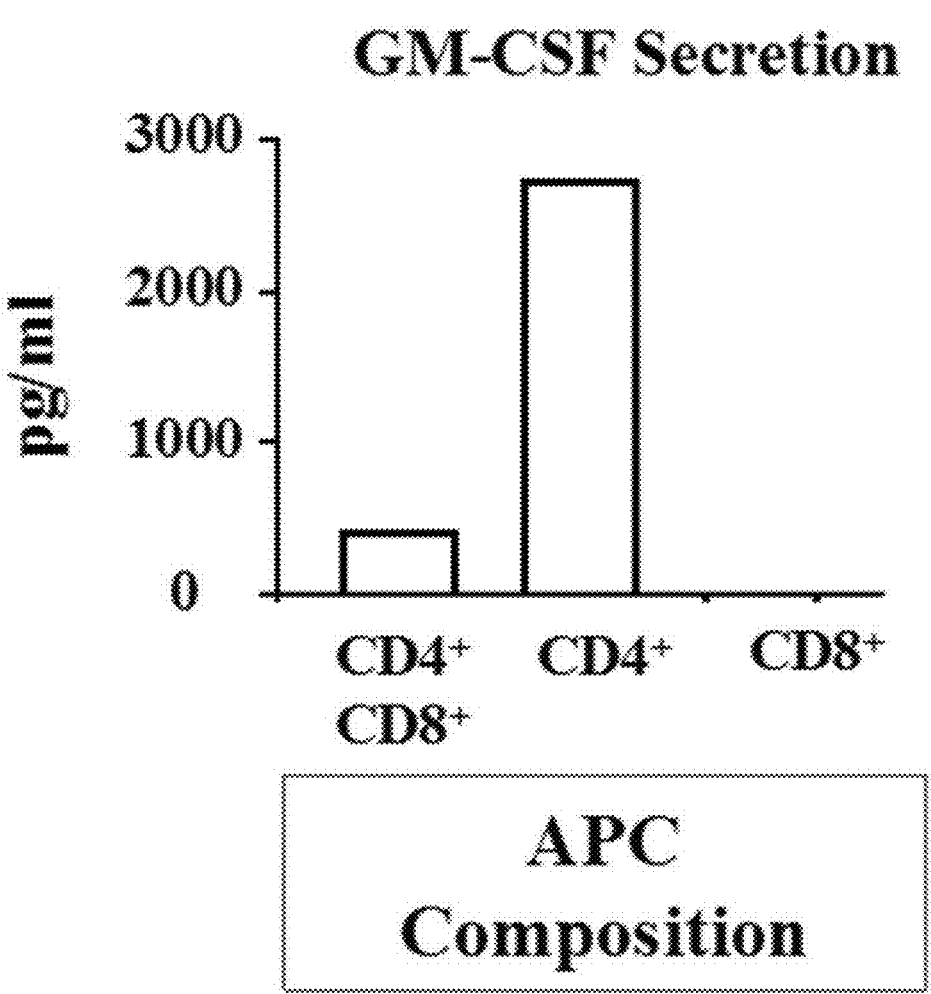
FIG. 41 depicts 24-hour GM-CSF and IFN-γ secretion from responder T cells after re-stimulation with lysate-loaded, antigen-presenting T cells for mixed loaded, antigen-presenting T cells, CD4⁺-enriched loaded, antigen-presenting T cells or CD8⁺-enriched loaded, antigen-presenting T cells.
Figure 41:
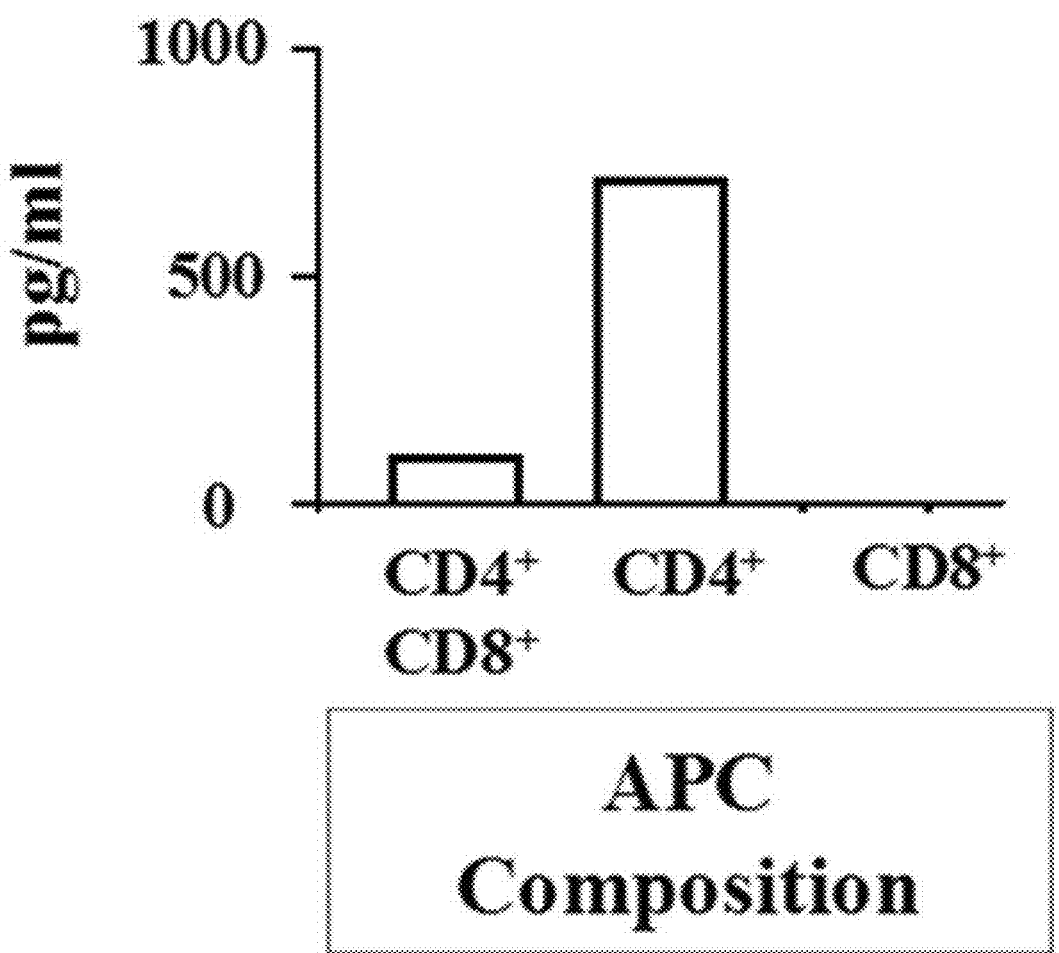

The results of this experiment, which are shown in FIG. 41, demonstrate that the CD4$^+$-enriched population of APC was indeed enriched for an ability to sensitize responder T cells to tumor lysate.

As detailed above, T cells manufactured according to the present disclosure were utilized as the responder T cell population and a modified population of such T cells were utilized to serve as APC by presentation of tumor lysate from the lung cancer cell line, H23. For APC generation, three populations of T cells (unseparated [CD4$^+$CD8$^+$]; CD4-enriched [CD4$^+$]; and CD8-enriched [CD8$^+$]) were cultured for 48-hours in media containing IL-7 (same amount as in the previous example), IL-15 (same amount as in previous example), and a lysate derived from etoposide-treated H23 cancer cells (same amount as in previous example). Co-stimulation (1:1 ratio of beads-to-T cells) was provided on day 1 of the 48-hour APC generation interval. After 10-days of APC T cell-to-responder T cell co-culture at the ratio of 1:10, the resultant responder T cells were stimulated with further APC for 24-hours; the resultant supernatant was then tested for cytokine content by Luminex assay, with results presented as pg/mL per 24-hours per $1 \times 10^6$ cells/mL. The result shown represents normalized cytokine secretion in response to H23-lysate pulsed APC (spontaneous cytokine secretion detected in media alone control subtracted).

In summary, T cells manufactured according to the present disclosure can have some APC function, as evidenced by the ability of tumor lysate addition directly to the T cell product to induce reactivity to tumor lysate presented on an APC. We have extended this prior observation by directly demonstrating the ability of such T cells to serve as an APC in a T cell-to-T cell co-culture.

T cells manufactured according to the present disclosure can be efficiently and reproducibly optimized for APC function by a short, 48-hour culture interval that incorporates the following interventions: cytokine exposure (IL-7 and IL-15); anti-CD3, anti-CD28 co-stimulation; optionally, addition of immunogenic tumor lysate or other immunogenic composition; and, optionally, enrichment for the CD4+ T cell component of the APC culture.

We envision that the APC population derived from the manufactured T cells according to the present disclosure can be generated at various time points of the T cell culture. For example, a fraction of the primary T cell culture can be harvested either at day 2, day 3, day 4, day 5, or day 6 to initiate the 48-hour APC generation.

We envision that the immunogenic tumor lysate aspect of the methods of the present disclosure can be further optimized by previously described interventions, including: generation of tumor cell immunogenic cell death by methods that are alternative relative to etoposide, including chemotherapy agents such as bleomycin, bortezomib, cyclophosphamide, doxorubicin, and oxaliplatin and other non-chemotherapy methods, including radiation therapy and cryotherapy; and purification of lysate into fractions, such as heat-shock-protein fractions. It should be understood that such interventions can also be used to induce immunogenic cell death in vivo and, in the context of infectious diseases that treatment other than purely pharmacologic treatments can also be employed to make antigens of the pathogen available to the T cells.

It should be understood that the below cancer treatment embodiments can be modified to incorporate administration of manufactured T cells with concurrent chemotherapeutic treatment to induce immunogenic cancer cell death or an anti-infectious agent to induce production of an antigen from the infectious agent (in the case of treating infectious disease), agents that increase expression of IL-7 or IL-15, exogenous IL-7 or IL-15, and combinations thereof, as well as with antigen-presenting T cells as described herein, loaded, antigen-presenting T cells as described herein and sensitized, manufactured T cells as described herein, instead of or in addition to the manufactured T cells alone. By way of example, but not limitation, the cells administered to the subject can be manufactured T cells, antigen-presenting T cells, loaded, antigen-presenting T cells, sensitized, manufactured T cells or a combination thereof. By way of further example, but not limitation, the T cells can be autologous to the subject. By way of still further example, the sensitized, manufactured T cells can be sensitized to a tumor lysate from the subject if generated ex vivo, likewise, the loaded, antigen-presenting T cells can include an antigen or portion thereof from a tumor lysate from the subject. In the case of infectious disease, the sensitized, manufactured T cells or sensitized T cells can be sensitized to an antigen associated with the infectious agent and the loaded, antigen-presenting T cells can include an antigen or portion thereof from the infectious agent. Alternatively, the cells can be allogenic. It should likewise be understood that in the following cancer/infectious disease treatment embodiments, the aspects of the methods for treating infectious disease throughout this disclose can be incorporated, e.g. rather than the cancer being from a certain group, the infectious disease can be as described herein.

Cancer/Infectious Disease Treatment Embodiments:

1. A method for treating cancer in a subject in need thereof, comprising:
   administering to said subject a composition comprising manufactured T cells at a therapeutically effective dose.

2. The method of embodiment 1, further comprising:
   subjecting said subject to an immune depletion regimen to reduce at least a portion of regulatory T cells and/or end-stage senescent effector T cells or to reduce at least a portion of the function of regulatory T cells and/or end-stage senescent effector T cells, prior to administering to said subject the composition comprising manufactured T cells at a therapeutically effective dose.

3. The method of embodiment 2, further comprising:
harvesting autologous cells from said subject, prior to subjecting said subject to said immune depletion regimen.

4. The method of embodiment 1, further comprising:
harvesting autologous cells from said subject prior to administering said composition comprising manufactured T cells to said subject.

5. The method of embodiment 2, wherein said immune depletion regimen comprises:
administering to said subject at least one of pentostatin and cyclophosphamide.

6. The method of embodiment 2, wherein said immune depletion regimen comprises:
administering to said subject a first composition comprising pentostatin; and
administering to said subject a second composition comprising cyclophosphamide.

7. The method of embodiment 5, wherein pentostatin is administered to said subject, and wherein a dose of said pentostatin is between 0.5-4 mg/m$^2$.

8. The method of embodiment 5, wherein cyclophosphamide is administered to said subject, and wherein a dose of said cyclophosphamide is between 50-400 mg.

9. The method of embodiment 5, wherein both pentostatin and cyclophosphamide are administered to said subject.

10. The method of embodiment 9, wherein said pentostatin and cyclophosphamide are administered to said subject in a single composition.

12. The method of embodiment 10, wherein said single composition is administered intravenously to said subject.

13. The method of embodiment 6, wherein said first composition is administered at a dose of 0.5-4 mg/m$^2$ of pentostatin.

14. The method of embodiment 6, wherein said second composition comprises cyclophosphamide, and wherein said composition is administered at a dose of said cyclophosphamide between 50-400 mg.

15. The method of embodiment 1, wherein said therapeutically effective dose is 1×10$^5$ to 5×10$^6$ manufactured T cells per kg of the subject's body weight.

16. The method of embodiment 15, wherein said composition is administered to said subject by infusion.

17. The method of any of the preceding embodiments, wherein said subject is suffering from smoldering multiple myeloma.

18. The method of any one of embodiments 1-16, wherein the said subject is suffering from relapsed, refractory multiple myeloma.

19. The method of any one of embodiments 1-16, wherein said subject is suffering from quad- or penta-refractory multiple myeloma.

20. The method of any one of embodiments 1-16, wherein said subject has previously been treated with three of more different lines of treatment selected from the group consisting of administration of a proteasome inhibitor, administration of immune modulatory drugs, administration of alkylators, administration of CD38 monoclonal antibodies, and administration of glucocorticoids, and wherein said subject is refractory to at least one proteasome inhibitor and at least one immune modulatory drug.

21. The method of any one of embodiments 1-16, wherein said subject has less than a 25% reduction in M-protein/free light chain difference or progression of disease during treatment or within 60 days after treatment cessation for previous treatments.

22. A method for the treatment of cancer in a subject in need thereof, comprising:
a first treatment cycle and one or more additional treatment cycles,
said first treatment cycle comprising:
subjecting said subject to a first immune depletion regimen to reduce at least a portion of regulatory T cells and/or end-stage senescent effector T cells or to reduce at least a portion of the function of regulatory T cells and/or end-stage senescent effector T cells;
each of said one or more additional treatment cycles comprising:
subjecting said subject to a second immune depletion regimen to reduce at least a portion of regulatory T cells and/or end-stage senescent effector T cells or to reduce at least a portion of the function of regulatory T cells and/or end-stage senescent effector T cells; and
administering to said subject a composition comprising manufactured T cells at a therapeutically effective dose.

23. The method of embodiment 22, wherein the first treatment cycle is a minimum of 28 days in duration.

24. The method of embodiment 22, wherein each of said one or more additional treatment cycles is a minimum of 35 days in duration.

25. The method of embodiment 22, wherein said first immune depletion regimen comprises:
administering pentostatin to said subject; and
administering cyclophosphamide to said subject.

26. The method of embodiment 25, wherein said step of administering pentostatin to said subject is repeated during the first treatment cycle.

27. The method of embodiment 26, wherein said step of administering pentostatin to said subject is performed on days 1, 4, 8, and/or 11 of said first treatment cycle.

28. The method of embodiment 27, wherein pentostatin is administered to said subject at a dose between 0.5-4 mg/m$^2$.

28. The method of any one of embodiments 26-28, wherein said step of administering cyclophosphamide to said subject is repeated during the first treatment cycle.

29. The method of embodiment 28, wherein said step of administering cyclophosphamide to said subject is performed on days 1, 2, 3, 4, 5, 8, 9, 10, 11 and/or 12 of the first treatment cycle.

30. The method of embodiment 29, wherein cyclophosphamide is administered to said subject at a dose of 50-400 mg.

31. The method of any one of embodiments 22-30, wherein said second immune depletion regimen comprises:
administering pentostatin to said subject; and
administering cyclophosphamide to said subject.

32. The method of embodiment 31, wherein said step of administering pentostatin to said subject is repeated during the each of said one or more additional treatment cycles.

33. The method of embodiment 32, wherein said step of administering pentostatin to said subject is performed on days 1, 4, 8, and/or 11 of each of said one or more additional treatment cycles.

34. The method of embodiment 33, wherein pentostatin is administered to said subject at a dose between 1-4 mg/m$^2$.

35. The method of any one of embodiments 32-33, wherein said step of administering cyclophosphamide to said subject is repeated during each of said one or more additional treatment cycles.

36. The method of embodiment 35, wherein said step of administering cyclophosphamide to said subject is performed on days 1, 2, 3, 4, 5, 8, 9, 10, 11 and/or 12 of each of said one or more additional treatment cycles.

37. The method of embodiment 36, wherein cyclophosphamide is administered to said subject at a dose of 50-400 mg.

38. The method of any one of embodiments 22-37, wherein each of said one or more additional treatment cycles are separated by 0 to 4 weeks.

39. The method of any one of embodiments 22-37, wherein said first treatment cycle and a first of said one or more additional treatment cycles are separated by 0 to 4 weeks.

40. The method of any one of embodiments 22-40, wherein said step of administering to said subject a composition comprising manufactured T cells at a therapeutically effective dose is performed on day 15, 16, 17 or 18 of each of said one or more additional treatment cycles.

41. The method of embodiment 40, wherein said therapeutically effective dose is between $1\times10^5$ to $5\times10^6$ manufactured T cells per kg of the subject's body weight.

42. The method of embodiment 41, wherein said composition comprising manufactured T cells is administered by infusion.

43. The method of any one of embodiments 22-42, wherein said subject is suffering from smoldering multiple myeloma.

44. The method of any one of embodiments 22-42, wherein the said subject is suffering from relapsed, refractory multiple myeloma.

45. The method of any one of embodiments 22-42, wherein said subject is suffering from quad- or penta-refractory multiple myeloma 46. The method of any one of embodiments 22-42, wherein said subject has previously been treated with three of more different lines of treatment selected from the group consisting of administration of a proteasome inhibitor, administration of immune modulatory drugs, administration of alkylators, administration of CD38 monoclonal antibodies, and administration of glucocorticoids, and wherein said subject is refractory to at least one proteasome inhibitor and at least one immune modulatory drug.

47. The method of any one of embodiments 22-42, wherein said subject has less than a 25% reduction in M-protein/free light chain difference or progression of disease during treatment or within 60 days after treatment cessation for previous treatments.

48. A method for treating cancer in a subject in need thereof, comprising:
subjecting said subject to an immune depletion regimen to reduce at least a portion of regulatory T cells and/or end-stage senescent effector T cells or to reduce at least a portion of the function of regulatory T cells and/or end-stage senescent effector T cells; and administering to said subject a composition comprising manufactured T cells at a therapeutically effective dose after said immune depletion regimen.

49. The method of embodiment 48, wherein said immune depletion regimen comprises:
administering pentostatin to said subject; and
administering cyclophosphamide to said subject;
administering one or more additional doses of pentostatin to said subject if said subject's creatine clearance is >30 mL/min/1.73 m$^2$.
administering one or more additional doses of cyclophosphamide to said subject if said subject's absolute lymphocyte count is 50 or greater and said subject's absolute neutrophil count is 500 or greater.

50. The method of embodiment 49, further comprising prior to administering one or more additional doses of pentostatin to said subject, measuring the creatine clearance (CrCl) of said subject and adjusting a dose of pentostatin to be administered to said subject based on the CrCl, wherein pentostatin is administered at 4 mg/m$^2$ when CrCl>60 mL/min/1.73 m$^2$, wherein pentostatin is administered at 2 mg/m$^2$ when 60 mL/min/1.73 m$^2$>CrCl>30 mL/min/1.73 m$^2$, and wherein pentostatin is not administered when CrCl<30 mL/min/1.73 m$^2$.

51. The method of any one of embodiments 48-49, further comprising, prior to administering one or more additional doses of cyclophosphamide, measuring absolute lymphocyte count (ALC) and absolute neutrophil count (ANC) and adjusting a dose of cyclophosphamide to be administered to said subject based on the ALC and ANC, wherein cyclophosphamide is administered at a dose of 200 mg when ANC>1000 per microliter, wherein cyclophosphamide is administered at a dose of 100 mg when ANC is 500-999 per microliter and ALC>50 per microliter, and wherein cyclophosphamide is not administered when ALC<50 per microliter or ANC<500 per microliter.

52. The method of embodiment 50, wherein said step of measuring the CrCl of said subject and adjusting a dose of pentostatin to be administered is performed on days 1, 4, 8, and/or 11 of said immune depletion regimen.

53. The method of embodiment 51, wherein said step of measuring ALC and ANC and adjusting a dose of cyclophosphamide to be administered is performed on days 1, 2, 3, 4, 5, 8, 9, 10, 11 and/or 12 of the immune depletion regimen.

54. The method of any one of embodiments 48-53, wherein said step of administering to said subject a composition comprising manufactured T cells at a therapeutically effective dose after said immune depletion regimen is performed 15-18 days after the start of the immune depletion regimen.

55. The method of any one of embodiments 48-53, wherein the steps subjecting said subject to an immune depletion regimen to reduce at least a portion of regulatory T cells and/or end-stage senescent effector T cells or to reduce at least a portion of the function of regulatory T cells and/or end-stage senescent effector T cells and administering to said subject a composition comprising manufactured T cells at a therapeutically effective dose after said immune depletion regimen are repeated at least twice.

56. The method of embodiment 55, wherein the steps subjecting said subject to an immune depletion regimen to reduce at least a portion of regulatory T cells and/or end-stage senescent effector T cells or to reduce at least a portion of the function of regulatory T cells and/or end-stage senescent effector T cells and administering to said subject a composition comprising manufactured T cells at a therapeutically effective dose after said immune depletion regimen are repeated up to 5 times.

57. The method of any one of embodiments 55-56, wherein each step of administering to said subject a composition comprising manufactured T cells at a therapeutically effective dose after said immune depletion regimen is separated by 0 to 9 weeks.

58. The method of any one of embodiments 48-57, wherein said therapeutically effective dose is between $1 \times 10^5$ to $5 \times 10^6$ manufactured T cells per kg of the subject's body weight.

59. The method of embodiment 58, wherein said composition comprising manufactured T cells is administered by infusion.

60. The method of any one of embodiments 48-59, wherein said subject is suffering from smoldering multiple myeloma.

61. The method of any one of embodiments 48-59, wherein the said subject is suffering from relapsed, refractory multiple myeloma.

62. The method of any one of embodiments 48-59, wherein said subject is suffering from quad- or penta-refractory multiple myeloma.

63. The method of any one of embodiments 48-59, wherein said subject has previously been treated with three of more different lines of treatment selected from the group consisting of administration of a proteasome inhibitor, administration of immune modulatory drugs, administration of alkylators, administration of CD38 monoclonal antibodies, and administration of glucocorticoids, and wherein said subject is refractory to at least one proteasome inhibitor and at least one immune modulatory drug.

64. The method of any one of embodiments 48-59, wherein said subject has less than a 25% reduction in M-protein/free light chain difference or progression of disease during treatment or within 60 days after treatment cessation for previous treatments.

65. The method of any one of embodiments 1-16, 20-42, 46-59 and 63-64, wherein the cancer is selected from the group consisting of multiple myeloma, renal cell carcinoma, bladder cancer, lung cancer, liver cancer, lymphoma, gastric cancer, colon cancer, sarcoma, pancreatic cancer, prostate cancer, ovarian cancer, breast cancer and colorectal cancer.

66. The method of any one of embodiments 1-65, wherein the manufactured T cells are a population of manufactured T cells having one or more of the following properties:

at least a 50% increase in secretion of IFN-γ relative to T-Rapa cells after one week of incubation using stimulation with anti-CD3/anti-CD28 magnetic beads at bead:T cell ratio of 3:1;

at least a 50% increase in secretion of TNF-α relative to T-Rapa cells after one week of incubation using stimulation with anti-CD3/anti-CD28 magnetic beads at bead:T cell ratio of 3:1;

at least a 50% increase in secretion of GM-CSF relative to T-Rapa cells after one week of incubation using stimulation with anti-CD3/anti-CD28 magnetic beads at bead:T cell ratio of 3:1;

at least a 50% increase in secretion of IL-2 relative to T-Rapa cells after one week of incubation using stimulation with anti-CD3/anti-CD28 magnetic beads at bead:T cell ratio of 3:1;

an increased percentage of cells of at least 50% positive for CD4, CD62L, CCR7 and CD127 relative to a control population of T cells characteristic of the T cells from which the population of manufactured T cells was produced;

an increase in 4EBP1 phosphorylation of no more than 50% relative to a control population of T cells characteristic of the T cells from which the population of T cells was produced;

at least 50% reduced expression of p70S6K or Raptor relative to a population of T-Rapa cells cultured under the same conditions;

at least 50% reduced expression of p-STAT5 relative to a population of T-Rapa cells cultured under the same conditions;

a detectable level of STAT1 and p-STAT1 expression;

at least 10% increased expression of p70S6K relative to a control population of T cells characteristic of the cells from which the population of manufactured T cells was produced;

at least 50% reduced expression of CD25 relative to a population of T-Rapa cells;

10% or less of CD4$^+$ or CD8$^+$ T cells expressing CTLA4 as measured by flow cytometry;

10% or less of CD4$^+$ or CD8$^+$ T cells expressing TIM3 as measured by flow cytometry;

5% or less of CD4$^+$ or CD8$^+$ T cells expressing PD1 as measured by flow cytometry;

5% or less of CD4$^+$ or CD8$^+$ T cells expressing 2B4 as measured by flow cytometry;

10% or less of CD4$^+$ or CD8$^+$ T cells expressing LAIR1 as measured by flow cytometry;

10% or less of CD4$^+$ or CD8$^+$ T cells expressing TIGIT as measured by flow cytometry;

10% or less of CD4$^+$ or CD8$^+$ T cells expressing LAGS as measured by flow cytometry;

5% or less of CD4$^+$ or CD8$^+$ T cells expressing CD25 as measured by flow cytometry;

5% or less of CD4$^+$ or CD8$^+$ T cells expressing KLRG1 as measured by flow cytometry;

20% or less of CD4$^+$ or CD8$^+$ T cells expressing CD39 as measured by flow cytometry;

20% or less of CD4$^+$ or CD8$^+$ T cells expressing CD73 as measured by flow cytometry;

5% or less of CD4$^+$ or CD8$^+$ T cells expressing GITR as measured by flow cytometry;

an expression level of CD28 within about 20% of a control population of T cells characteristic of T cells from which the population of manufactured T cells was produced;

an expression level of ICOS within about 20% of a control population of T cells characteristic of T cells from which the population of manufactured T cells was produced;

an expression level of CD45RA within about 20% of a control population of T cells characteristic of T cells from which the population of manufactured T cells was produced;

an increase of at least 50% of CD4$^+$ T cells positive for CD45RA as measured by flow cytometry;

at least a 1.1-fold increase in IL-2 secretion relative to a T-Rapa culture incubated under the same conditions;

secretion of at least 500 pg/mL/$1\times10^6$ cells/day of IL-2 after co-stimulation with anti-CD3/anti-CD28 coated magnetic beads at a ratio of between 3:1 and 1:3 beads:T cell;

at least a 1.1-fold increase in IL-2 secretion relative when incubated in the presence of IL-7, IL-15 or a combination of IL-7 and IL-15, wherein the IL-7 and IL-15, when present, are added at 10 ng/mL each;

secretion of at least 1000 pg/mL/$1\times10^6$ cells/day of IL-2 after incubation in the presence of IL-7, IL-15 or a combination of IL-7 and IL-15, wherein the IL-7 and IL-15, when present, are added at 10 ng/mL each;

at least a 25% reduction in expression of one or more checkpoint inhibitors selected from: CD39, CD73, GITR, LAG3, PD1, 2B4, LAIR1, CTLA4, KLRG1, TIGIT, TIM3 and combinations thereof, relative to a corresponding expression level of a population of T-Rapa cells;

an expression level of one or more checkpoint inhibitors selected from: CD39, CD73, GITR, LAG3, PD1, 2B4, LAIR1, CTLA4, KLRG1, TIGIT, TIM3 and combinations thereof, that is within 25% of a corresponding expression level in a control population of T cells characteristic of the cells from which the population of manufactured T cells was produced;

at least 5% of CD4$^+$ T cells expressing CD127;

an increase of at least 50% in the frequency of CD4$^+$ T cells expressing CD127 relative to a control T cell population characteristic of the cells from which the population of manufactured T cells was produced;

at least a 25% increase in the frequency of T cells that co-express CD62L and CCR7 relative to the culture input T cells;

a frequency of CD4$^+$ and CD8$^+$ T cells that co-express the IL-2 receptor CD25 at less than a 5% rate and more preferably at less than a 1% rate;

secretion of low levels of the inflammatory cytokines IFN-$\gamma$ and TNF-$\alpha$ at the end of manufacturing, as defined by <100 pg/ml per $1\times10^6$ cells per 24 hours contained in a culture supernatant after a stimulation procedure using a high level of co-stimulation (3:1 bead-to-T cell ratio);

an increase in IFN-$\gamma$ and TNF-$\alpha$ secretion after a 6-day period of expansion in the absence of inhibitors that is at least 5-fold and more preferably 20-fold increased relative to the day 6 secretion levels; and combinations thereof.

67. A manufactured T cell having one or more of the following properties:

at least a 50% increase in secretion of IFN-$\gamma$ relative to T-Rapa cells after one week of incubation using stimulation with anti-CD3/anti-CD28 magnetic beads at bead:T cell ratio of 3:1;

at least a 50% increase in secretion of TNF-$\alpha$ relative to T-Rapa cells after one week of incubation using stimulation with anti-CD3/anti-CD28 magnetic beads at bead:T cell ratio of 3:1;

at least a 50% increase in secretion of GM-CSF relative to T-Rapa cells after one week of incubation using stimulation with anti-CD3/anti-CD28 magnetic beads at bead:T cell ratio of 3:1;

at least a 50% increase in secretion of IL-2 relative to T-Rapa cells after one week of incubation using stimulation with anti-CD3/anti-CD28 magnetic beads at bead:T cell ratio of 3:1;

an increase in 4EBP1 phosphorylation of no more than 50% relative to a control population of T cells characteristic of the T cells from which the population of T cells was produced;

at least 50% reduced expression of p70S6K or Raptor relative to a population of T-Rapa cells cultured under the same conditions;

at least 50% reduced expression of p-STAT5 relative to a population of T-Rapa cells cultured under the same conditions;

a detectable level of STAT1 and p-STAT1 expression;

at least 10% increased expression of p70S6K relative to a control population of T cells characteristic of the cells from which the population of manufactured T cells was produced;

at least 50% reduced expression of CD25 relative to a population of T-Rapa cells;

an expression level of CD28 within about 20% of a control population of T cells characteristic of T cells from which the population of manufactured T cells was produced;

an expression level of ICOS within about 20% of a control population of T cells characteristic of T cells from which the population of manufactured T cells was produced;

an expression level of CD45RA within about 20% of a control population of T cells characteristic of T cells from which the population of manufactured T cells was produced;

an increase of at least 50% of CD4$^+$ T cells positive for CD45RA as measured by flow cytometry;

at least a 1.1-fold increase in IL-2 secretion relative to a T-Rapa culture incubated under the same conditions;

secretion of at least 500 pg/mL/$1\times10^6$ cells/day of IL-2 after co-stimulation with anti-CD3/anti-CD28 coated magnetic beads at a ratio of between 3:1 and 1:3 beads:T cell;

at least a 1.1-fold increase in IL-2 secretion relative when incubated in the presence of IL-7, IL-15 or a combination of IL-7 and IL-15, wherein the IL-7 and IL-15, when present, are added at 10 ng/mL each;

secretion of at least 1000 pg/mL/$1\times10^6$ cells/day of IL-2 after incubation in the presence of IL-7, IL-15 or a combination of IL-7 and IL-15, wherein the IL-7 and IL-15, when present, are added at 10 ng/mL each;

at least a 25% reduction in expression of one or more checkpoint inhibitors selected from: CD39, CD73, GITR, LAG3, PD1, 2B4, LAIR1, CTLA4, KLRG1, TIGIT, TIM3 and combinations thereof, relative to a corresponding expression level of a population of T-Rapa cells;

an expression level of one or more checkpoint inhibitors selected from: CD39, CD73, GITR, LAG3, PD1, 2B4, LAIR1, CTLA4, KLRG1, TIGIT, TIM3 and combinations thereof, that is within 25% of a corresponding expression level in a control population of T cells characteristic of the cells from which the population of manufactured T cells was produced;

expressing CD127;

secretion of low levels of the inflammatory cytokines IFN-$\gamma$ and TNF-$\alpha$ at the end of manufacturing, as defined by <100 pg/ml per $1\times10^6$ cells per 24 hours contained in a culture supernatant after a stimulation procedure using a high level of co-stimulation (3:1 bead-to-T cell ratio);

an increase in IFN-γ and TNF-α secretion after a 6-day period of expansion in the absence of inhibitors that is at least 5-fold and more preferably 20-fold increased relative to the day 6 secretion levels; and combinations thereof.

68. The method of any one of embodiments 1-65, wherein the manufactured T cells have at least one of the following properties:

at least a 50% increase in secretion of IFN-γ relative to T-Rapa cells after one week of incubation using stimulation with anti-CD3/anti-CD28 magnetic beads at bead:T cell ratio of 3:1;

at least a 50% increase in secretion of TNF-α relative to T-Rapa cells after one week of incubation using stimulation with anti-CD3/anti-CD28 magnetic beads at bead:T cell ratio of 3:1;

at least a 50% increase in secretion of GM-CSF relative to T-Rapa cells after one week of incubation using stimulation with anti-CD3/anti-CD28 magnetic beads at bead:T cell ratio of 3:1;

at least a 50% increase in secretion of IL-2 relative to T-Rapa cells after one week of incubation using stimulation with anti-CD3/anti-CD28 magnetic beads at bead:T cell ratio of 3:1;

an increase in 4EBP1 phosphorylation of no more than 50% relative to a control population of T cells characteristic of the T cells from which the population of T cells was produced;

at least 50% reduced expression of p70S6K or Raptor relative to a population of T-Rapa cells cultured under the same conditions;

at least 50% reduced expression of p-STAT5 relative to a population of T-Rapa cells cultured under the same conditions;

a detectable level of STAT1 and p-STAT1 expression;

at least 10% increased expression of p70S6K relative to a control population of T cells characteristic of the cells from which the population of manufactured T cells was produced;

at least 50% reduced expression of CD25 relative to a population of T-Rapa cells;

an expression level of CD28 within about 20% of a control population of T cells characteristic of T cells from which the population of manufactured T cells was produced;

an expression level of ICOS within about 20% of a control population of T cells characteristic of T cells from which the population of manufactured T cells was produced;

an expression level of CD45RA within about 20% of a control population of T cells characteristic of T cells from which the population of manufactured T cells was produced;

an increase of at least 50% of CD4$^+$ T cells positive for CD45RA as measured by flow cytometry;

at least a 1.1-fold increase in IL-2 secretion relative to a T-Rapa culture incubated under the same conditions;

secretion of at least 500 pg/mL/1×10$^6$ cells/day of IL-2 after co-stimulation with anti-CD3/anti-CD28 coated magnetic beads at a ratio of between 3:1 and 1:3 beads:T cell;

at least a 1.1-fold increase in IL-2 secretion relative when incubated in the presence of IL-7, IL-15 or a combination of IL-7 and IL-15, wherein the IL-7 and IL-15, when present, are added at 10 ng/mL each;

secretion of at least 1000 pg/mL/1×10$^6$ cells/day of IL-2 after incubation in the presence of IL-7, IL-15 or a combination of IL-7 and IL-15, wherein the IL-7 and IL-15, when present, are added at 10 ng/mL each;

at least a 25% reduction in expression of one or more checkpoint inhibitors selected from: CD39, CD73, GITR, LAG3, PD1, 2B4, LAIR1, CTLA4, KLRG1, TIGIT, TIM3 and combinations thereof, relative to a corresponding expression level of a population of T-Rapa cells;

an expression level of one or more checkpoint inhibitors selected from: CD39, CD73, GITR, LAG3, PD1, 2B4, LAIR1, CTLA4, KLRG1, TIGIT, TIM3 and combinations thereof, that is within 25% of a corresponding expression level in a control population of T cells characteristic of the cells from which the population of manufactured T cells was produced;

expressing CD127;

secretion of low levels of the inflammatory cytokines IFN-γ and TNF-α at the end of manufacturing, as defined by <100 pg/ml per 1×10$^6$ cells per 24 hours contained in a culture supernatant after a stimulation procedure using a high level of co-stimulation (3:1 bead-to-T cell ratio);

an increase in IFN-γ and TNF-α secretion after a 6-day period of expansion in the absence of inhibitors that is at least 5-fold and more preferably 20-fold increased relative to the day 6 secretion levels; and combinations thereof.

What is claimed is:

1. A method for producing manufactured T cells, comprising:

inoculating a culture input population of cells from a subject at a cell density of at least 1.5×10$^6$ cells per mL in a culture medium comprising temsirolimus and an IL-2 signaling inhibitor, wherein said temsirolimus is present in said culture medium at a concentration of at least 1 µM, wherein the culture input population of cells comprises T cells;

incubating said culture input population of cells in the culture medium for a first period of time, wherein said first period of time is at least 16 hours;

adding IFN-α, IL-7, and IL-15 to the culture medium after the first period of time, wherein said IFN-α is added to said culture medium to a concentration of at least 10,000 IU/mL;

incubating said culture input population of cells in the culture medium for a second period of time following addition of IFN-α, IL-7, and IL-15 to yield manufactured T cells, wherein IL-2 is not added to the culture medium at any time during the method, and wherein no anti-CD3/anti-CD28 co-stimulation is performed at any time during the method; and harvesting said manufactured T cells, wherein 5% or less of the manufactured T cells that are CD4+ or CD8+ express CD25 as measured by flow cytometry.

2. The method of claim 1, further comprising, after harvesting said manufactured T cells:

packaging at least a portion of said manufactured T cells in a package; and freezing said package containing said portion of said manufactured T cells.

3. The method of claim 1, wherein said IL-2 signaling inhibitor is an anti-IL-2 receptor antibody or fragment thereof.

4. The method of claim 3, wherein said anti-IL-2 receptor antibody is basiliximab or daclizumab.

5. The method of claim 1, wherein said IL-2 signaling inhibitor is present in said culture medium at a concentration of 5 to 50 µg/mL.

6. The method of claim 1, wherein said first and second period of time is a total of 6 days.

7. The method of claim 1, wherein the culture medium is free of serum.

8. The method of claim 1, wherein said culture input population of cells comprises about 99% or more T cells out of the total number of cells in said culture input population of cells.

9. A method for treating a solid tumor in a subject comprising:

obtaining a sample of immune cells harvested from the subject, wherein the sample of immune cells comprises T cells;

adding the sample of immune cells to a culture medium at a cell density of at least $1.5 \times 10^6$ cells per mL, wherein the culture medium comprises temsirolimus and an IL-2 signaling inhibitor, wherein said temsirolimus is present in said culture medium at a concentration of at least 1 UM;

incubating said sample of immune cells in the culture medium for a first period of time, wherein said first period of time is at least 16 hours;

adding IFN-α, IL-7, and IL-15 to the culture medium after the first period of time, wherein said IFN-α is added to said culture medium to a concentration of at least 10,000 IU/mL;

incubating said sample of immune cells in the culture medium for a second period of time following addition of IFN-α, IL-7, and IL-15 to yield manufactured T cells, wherein IL-2 is not added to the culture medium at any time during the production of manufactured T cells, and wherein no anti-CD3/anti-CD28 co-stimulation is performed at any time during the method production of manufactured T cells; and harvesting said manufactured T cells, wherein 5% or less of the manufactured T cells that are CD4+ or CD8+ express CD25 as measured by flow cytometry; and administering a therapeutically effective amount of the manufactured T cells to the subject.

10. The method of claim 9, wherein the method further comprises administering to the subject a chemotherapeutic agent in an amount sufficient to induce immunogenic cell death of at least a portion of cancer cells in the solid tumor.

11. The method of claim 10, wherein the chemotherapeutic agent sufficient to induce immunogenic cell death is selected from the group consisting of etoposide, bortezomib, doxorubicin, epirubicin, cyclophosphamide, oxaliplatin, 5-fluorouracil, gemcitabine, mitoxantrone, bleomycin, dactinomycin, lubrinectedin, teniposide, radiation, cryotherapy, and combinations thereof.

12. The method of claim 9, wherein the therapeutically effective amount of manufactured T cells is about $0.1 \times 10^6$ cells/kg to about $5 \times 10^6$ cells/kg of subject body weight.

13. The method of claim 9, wherein the solid tumor is selected from the group consisting of renal cell carcinoma, bladder cancer, lung cancer, small-cell lung cancer, non-small cell lung cancer, liver cancer, gastric cancer, colon cancer, sarcoma, pancreatic cancer, prostate cancer, ovarian cancer, breast cancer, rectal cancer, endometrial cancer, kidney cancer, bile duct cancer, thyroid cancer, melanoma, non-melanoma skin cancer, esophageal cancer, cervical cancer, oral cavity cancer, pharyngeal cancer, stomach cancer, brain cancer, and colorectal cancer.

\* \* \* \* \*